(12) United States Patent
Aldrich et al.

(10) Patent No.: US 6,342,503 B1
(45) Date of Patent: Jan. 29, 2002

(54) 1N-ALKYL-N-ARYLPYRIMIDINAMINES AND DERIVATIVES THEREOF

(75) Inventors: Paul Edward Aldrich, Wilmington, DE (US); Argyrios Georgios Arvanitis, Kennett Square, PA (US); Robert Scott Cheeseman, Phoenixville, PA (US); Robert John Chorvat, West Chester, PA (US); Thomas Eugene Christos, Oxford, PA (US); Paul Joseph Gilligan, Wilmington, DE (US); Dimitri Emil Grigoriadis, Carlsbad, CA (US); Carl Nicholas Hodge, Wilmington, DE (US); Paul John Krenitsky, Newark, DE (US); Everett Latham Scholfield, New Castle, DE (US); Sang William Tam, Boston, MA (US); Zelda Rakowitz Wasserman, Wilmington, DE (US)

(73) Assignee: DuPont Pharmaceuticals Company, Wilmington, DE (US)

(*) Notice: Subject to any disclaimer, the term of this patent is extended or adjusted under 35 U.S.C. 154(b) by 0 days.

(21) Appl. No.: 09/004,150

(22) Filed: Jan. 7, 1998

Related U.S. Application Data

(63) Continuation of application No. 08/315,660, filed on Sep. 29, 1994, now abandoned, which is a continuation-in-part of application No. 08/297,274, filed on Aug. 26, 1994, now abandoned, which is a continuation-in-part of application No. 08/134,209, filed on Oct. 12, 1993, now abandoned.

(51) Int. Cl.[7] .................. C07D 239/42; C07D 239/48; A61K 31/505
(52) U.S. Cl. ................. 514/272; 514/275; 544/323; 544/324; 544/330; 544/331; 544/332
(58) Field of Search ................ 514/272, 275; 544/323, 324, 330, 331, 332

(56) References Cited

U.S. PATENT DOCUMENTS

| | | | | |
|---|---|---|---|---|
| 3,669,936 A | | 6/1972 | Regenass et al. | 260/77.5 |
| 4,229,453 A | | 10/1980 | Roth et al. | 544/280 |
| 4,783,459 A | * | 11/1988 | Buhmann et al. | 544/331 |
| 4,788,195 A | * | 11/1988 | Torley et al. | 544/331 |
| 4,876,252 A | * | 10/1989 | Torley et al. | 544/331 |
| 4,992,438 A | * | 2/1991 | Ito | 544/321 |
| 5,063,245 A | | 11/1991 | Abreau et al. | 514/424 |
| 5,516,775 A | * | 5/1996 | Zimmermann | 544/331 |
| 5,612,340 A | | 3/1997 | Zimmermann | 514/252 |

FOREIGN PATENT DOCUMENTS

| | | |
|---|---|---|
| DE | A 1944106 | 5/1970 |
| EP | A 0005205 | 11/1979 |
| EP | 0013143 A2 | 12/1979 |
| EP | A 0061056 | 9/1982 |
| EP | A 0155911 | 9/1985 |
| EP | A 0270111 | 6/1988 |
| EP | A 0336494 | 10/1989 |
| EP | A 0563001 | 9/1993 |
| EP | 0588762 A1 | 3/1994 |
| WO | WO 8901938 | 3/1989 |
| WO | WO 9118887 A | 12/1991 |
| WO | WO 9413643 | 6/1994 |
| WO | WO 9413644 | 6/1994 |
| WO | WO 9413661 | 6/1994 |
| WO | WO 9413676 | 6/1994 |
| WO | WO 9413677 | 6/1994 |

OTHER PUBLICATIONS

Dunn and Berridge, Physiological and behavioral responses to corticotropin–releasing factor administration: is CRF a mediator of anxiety or stress responses?, *Brain Research Reviews*, 15, 71–100, 1990.

R. Chambers et al., Polyhalogenoheterocyclic compounds Part 40. Tertiary Aromatic Amines as Carbon Nucleophiles, *Tetrahedron*, 48, 7939–7950, 1992.

R.C. Young Et Al, Purine Derivatives as Competitive Inhibitors of Human Erythrocyte Membrane Phosphatidylinositol 4–Kinase, *Journal of Medicinal Chemistry*, 33, 2073–2080, 1990.

* cited by examiner

*Primary Examiner*—Mukund J. Shah
*Assistant Examiner*—Deepak R. Rao
(74) *Attorney, Agent, or Firm*—Robert W. Black; Kenneth B. Rubin; Kalim S. Fuzail

(57) ABSTRACT

The present invention provides novel compounds, compounds and pharmaceutical compositions thereof, and methods of using same in the treatment of affective disorders, anxiety, depression, post-traumatic stress disorders, eating disorders, supranuclear palsy, irritable bowel syndrome, immune suppression, Alzheimer'disease, gastrointestinal diseases, anorexia nervosa, drug and alcohol withdrawal symptoms, drug addiction, inflammatory disorders, or fertility problems. The novel compounds provided by this invention are those of formula:

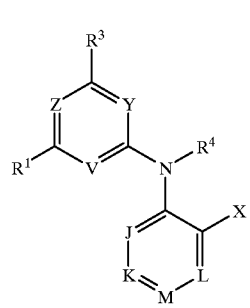

(I)

wherein $R^1$, $R^3$, $R^4$, $R^5$, Z, Y, V, X, X', J, K, L, and M are as defined herein.

7 Claims, No Drawings

1N-ALKYL-N-ARYLPYRIMIDINAMINES AND DERIVATIVES THEREOF

CROSS-REFERENCE TO EARLIER FILED APPLICATIONS

This is a continuation, of application Ser. No. 08/315,660 filed Sep. 29, 1994 now abandoned which is a continuation-in-part of U.S. patent application Ser. No. 08/297,274 filed, Aug. 26, 1994, now abandoned, which is a continuation-in-part of U.S. patent application Ser. No. 08/134,209, filed Oct. 12, 1993 now abandoned. The disclosures of these earlier filed applications are hereby incorporated herein by reference.

BACKGROUND OF THE INVENTION

1. Field of the Invention

The present invention relates to novel compounds, compounds and pharmaceutical compositions thereof, and to methods of using same in the treatment of psychiatric disorders and neurological diseases including major depression, anxiety-related disorders, post-traumatic stress disorder, supranuclear palsy eating feeding disorders, irritable bowel syndrome, immune suppression, Alzheimer's disease, gastrointestinal diseases, anorexia nervosa, drug and alcohol withdrawal symptoms, drug addiction, inflammatory disorders, and fertility problems.

2. Description of the Related Art

Corticotropin releasing factor (herein referred to as CRF), a 41 amino acid peptide, is the primary physiological regulator of proopiomelanocortin (POMC)-derived peptide secretion from the anterior pituitary gland (J. Rivier et al., *Proc. Nat. Acad. Sci. (USA)* 80:4851 (1983); W. Vale et al., *Science* 213:1394 (1981)). In addition to its endocrine role at the pituitary gland, immunohistochemical localization of CRF has demonstrated that the hormone has a broad extra-hypothalamic distribution in the central nervous system and produces a wide spectrum of autonomic, electrophysiological and behavioral effects consistent with a neurotransmitter or neuromodulator role in brain (W. Vale et al., *Rec. Prog. Horm. Res.* 39:245 (1983); G. F. Koob, *Persp. Behav. Med.* 2:39 (1985); E. B. De Souza et al., *J. Neurosci.* 5:3189 (1985)). There is also evidence demonstrating that CRF may also play a significant role in integrating the response of the immune system to physiological, psychological, and immunological stressors (J. E. Blalock, *Physiological Reviews* 69:1 (1989); J. E. Morley, *Life Sci.* 41:527 (1987)).

Clinical data have demonstrated that CRF may have implications in psychiatric disorders and neurological diseases including depression, anxiety-related disorders and eating disorders. A role for CRF has also been postulated in the etiology and pathophysiology of Alzheimer's disease, Parkinson's disease, Huntington's disease, progressive supranuclear palsy and amyotrophic lateral sclerosis as they relate to the dysfunction of CRF neurons in the central nervous system (for review see E. B. De Souza, *Hosp. Practice* 23:59 (1988)).

In affective disorder, or major depression, the concentration of CRF is significantly increased in the cerebral spinal fluid (CSF) of drug-free individuals (C. B. Nemeroff et al., *Science* 226:1342 (1984); C. M. Banki et al. *Am. J. Psychiatry* 144:873 (1987); R. D. France et al., *Biol. Psychiatry* 28:86 (1988); M. Arato et al., *Biol. Psychiatry* 25:355 (1989)). Furthermore, the density of CRF receptors is significantly decreased in the frontal cortex of suicide victims, consistent with a hypersecretion of CRF (C. B. Nemeroff et al., *Arch. Gen. Psychiatry* 45:577 (1988)). In addition, there is a blunted adrenocorticotropin (ACTH) response to CRF (i.v. administered) observed in depressed patients (P. W. Gold et al., *Am J. Psychiatry* 141:619 (1984); F. Holsboer et al., *Psychoneuroendocrinology* 9:147 (1984); P. W. Gold et al., *New Eng. J. Med.* 314:1129 (1986)). Preclinical studies in rats and non-human primates provide additional support for the hypothesis that hypersecretion of CRF may be involved in the symptoms seen in human depression (R. M. Sapolsky, *Arch. Gen. Psychiatry* 46:1047 (1989)). There is preliminary evidence that tricyclic antidepressants can alter CRF levels and thus modulate the number of CRF receptors in brain (Grigoriadis et al., *Neuropsychopharmacology* 2:53 (1989)).

There has also been a role postulated for CRF in the etiology of anxiety-related disorders. CRF produces anxiogenic effects in animals and interactions between benzodiazepine/non-benzodiazepine anxiolytics and CRF have been demonstrated in a variety of behavioral anxiety models (D. R. Britton et al., *Life Sci.* 31:363 (1982); C. W. Berridge and A. J. Dunn *Regul. Peptides* 16:83 (1986)). Preliminary studies using the putative CRF receptor antagonist α-helical ovine CRF (9-41) in a variety of behavioral paradigms demonstrate that the antagonist produces "anxiolytic-like" effects that are qualitatively similar to the benzodiazepines (C. W. Berridge and A. J. Dunn *Horm. Behav.* 21:393 (1987), *Brain Research Reviews* 15:71 (1990)). Neurochemical, endocrine and receptor binding studies have all demonstrated interactions between CRF and benzodiazepine anxiolytics providing further evidence for the involvement of CRF in these disorders. Chlordiazepoxide attenuates the "anxiogenic" effects of CRF in both the conflict test (K. T. Britton et al., *Psychopharmacology* 86:170 (1985); K. T. Britton et al., *Psychopharmacology* 94:306 (1988)) and in the acoustic startle test (N. R. Swerdlow et al., *Psychopharmacology* 88:147 (1986)) in rats. The benzodiazepine receptor antagonist (Ro15-1788), which was without behavioral activity alone in the operant conflict test, reversed the effects of CRF in a dose-dependent manner while the benzodiazepine inverse agonist (FG7142) enhanced the actions of CRF (K. T. Britton et al., *Psychopharmacology* 94:306 (1988)).

The mechanisms and sites of action through which the standard anxiolytics and antidepressants produce their therapeutic effects remain to be elucidated. It has been hypothesized, however, that they are involved in the suppression of the CRF hypersecretion that is observed in these disorders. Of particular interest is that preliminary studies examining the effects of a CRF receptor antagonist (α-helical $CRF_{9-41}$) in a variety of behavioral paradigms have demonstrated that the CRF antagonist produces "anxiolytic-like" effects qualitatively similar to the benzodiazepines (for review, see G. F. Koob and K. T. Britton, In: *Corticotropin-Releasing Factor: Basic and Clinical Studies of a Neuropeptide*, E. B. De Souza and C. B. Nemeroff eds., CRC Press p.221 (1990)).

In order to study these specific cell-surface receptor proteins, compounds must be identified that can interact with the CRF receptor in a specific manner dictated by the pharmacological profile of the characterized receptor. Toward that end, there is evidence that the direct CRF antagonist compounds and compositions of this invention, which can attenuate the physiological responses to stress-related disorders, will have potential therapeutic utility for the treatment of depression and anxiety-related disorders. All of the aforementioned references are hereby incorporated by reference.

U.S. Pat. Nos. 4,788,195 and 4,876,252 teach the synthesis of compounds with the general formula (A):

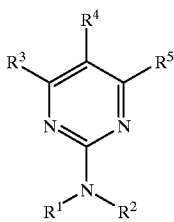

(A)

The utility of these compounds is described as treatment of asthma, allergic diseases, inflammation, and diabetes in mammals.

PCT application WO 89/01938 describes the synthesis and utility of compounds with the formula (B):

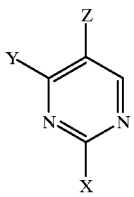

(B)

These compounds can be utilized in the treatment of neurologic diseases, having an effect of regenerating and repairing nerve cells and improving and restoring learning and memory.

U.S. Pat. No. 4,783,459 describes the utility and synthesis of compounds with the following general formula (C):

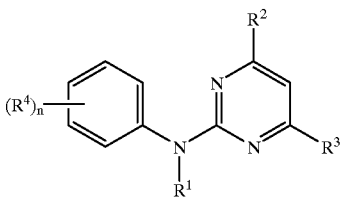

The compounds have activity as fungicides, especially against fungal diseases of plants.

U.S. Pat. No. 4,992,438 discloses the utility and synthesis of compounds with the following general formula:

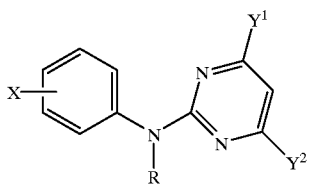

The utility of these compounds is described as fungicides with a broad spectrum activity against plant pathogenic fungi.

European Patent Application 0 013 143 A2 discloses the utility and synthesis of compounds with the following general formula:

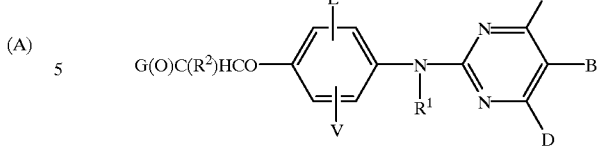

These compounds are described as pre- and post-emergence herbicides.

U.S. Pat. No. 5,063,245 discloses a method of producing CRF antagonism with compounds with the general formulae:

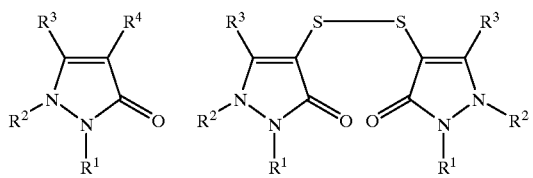

PCT application WO 91/18887 discloses compounds of the general formula:

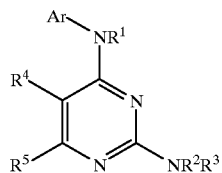

wherein $R^2$ may be $C_1-C_4$ alkyl and $R^3$ may be substituted phenyl, said compounds being useful for the inhibition of gastric acid secretion.

European patent application EP 0588762 A1 discloses compounds of the general formula:

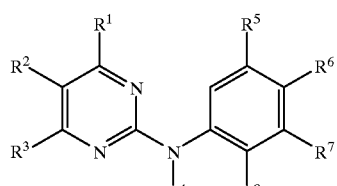

wherein $R^4$ may be $C_1-C_3$ alkyl, said compounds being useful as protein kinase C inhibitors and antitumor agents. The application also generally discloses the use of these compounds for the treatment of AIDS, atherosclerosis, and cardiovascular and central nervous system disorders.

European patent application EP 336494 A2 discloses compounds of the general formula:

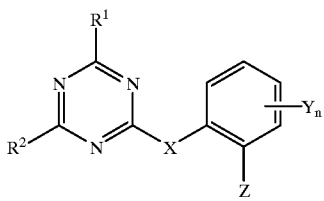

wherein X may be N—R⁴ and R⁴ may be (un)substituted alkyl, said compounds being useful as herbicides.

U.S. Pat. No. 3,988,338 discloses compounds of the general formula:

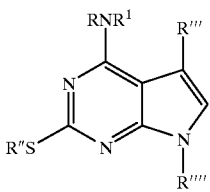

wherein R'''' may be an optionally substituted phenyl, said compounds having anticytokinin activity.

European patent application EP 0563001 A1 discloses compounds of the general formula:

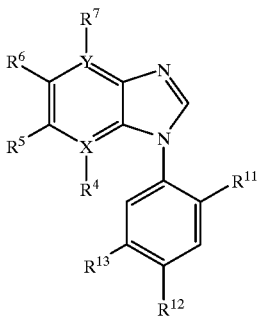

said compounds having claimed utility for the treatment of psychosis, depression, and convulsive disorders.

European patent application EP 0155911 A1 discloses compounds of the general formula:

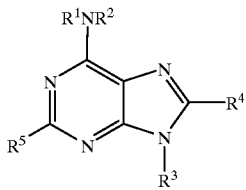

wherein R³ may be substituted phenyl, said compounds being useful as herbicides.

Australian patent AU 8425873 A discloses compounds of the general formula:

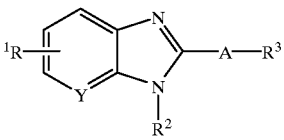

wherein R² may be a substituted phenyl group, said compounds being useful as antiulcer agents.

Eswaran et al, *Org. Prep. Proced. Int.* 24(1):71–3, (1992), discloses the use of related 5,7-diazaindoles as synthetic intermediates. El-Bayouki et al, *J. Heterocycl. Chem.* 22(3): 853–6, (1985) discloses the use of related 5,7-diazaisoindazoles as synthetic intermediates.

The compounds and methods of the present invention provide the methodology for the production of specific high-affinity compounds capable of inhibiting the action of CRF at its receptor protein in the brain. These compounds should be useful in the treatment of a variety of neurodegenerative, neuropsychiatric and stress-related disorders such as irritable bowel syndrome, immune suppression. Alzheimer's disease, gastrointestinal diseases, anorexia nervosa, drug and alcohol withdrawal symptoms, drug addiction, inflammatory disorders, and fertility problems. It is further asserted that this invention may provide compounds and pharmaceutical compositions suitable for use in such a method. Further advantages of this invention will be clear to one skilled in the art from the reading of the description that follows.

SUMMARY OF THE INVENTION

The present invention relates to compositions and methods of use and preparation of N-alkyl-N-aryl-pyrimidinamines and derivatives thereof. These compounds interact with and have antagonist activity at the CRF receptor and would thus have some therapeutic effect on psychiatric disorders and neurological diseases including major depression, anxiety-related disorders, post-traumatic stress and eating disorders, supranuclear palsy, irritable bowel syndrome, immune suppression, Alzheimer's disease, gastrointestinal diseases, anorexia nervosa, drug and alcohol withdrawal symptoms, drug addiction, inflammatory disorders, and fertility problems.

Novel compounds of this invention include compounds of formula:

(I)

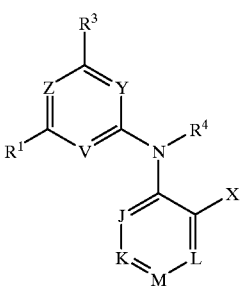

or a pharmaceutically acceptable salt or prodrug thereof, wherein Y is $CR^{3a}$, N, or $CR^{29}$;

when Y is $CR^{3a}$ or N:

$R^1$ is independently selected at each occurrence from the group consisting of $C_1$–$C_4$ alkyl, $C_2$–$C_4$ alkenyl, $C_2$–$C_4$ alkynyl, halogen, $C_1$–$C_2$ haloalkyl, $NR^6R^7$, $OR^8$, and $S(O)_n R^8$;

$R^3$ is $C_1$–$C_4$ alkyl, aryl, $C_3$–$C_6$ cycloalkyl, $C_1$–$C_2$ haloalkyl, halogen, nitro, $NR^6R^7$, $OR^8$, $S(O)_nR^8$, $C(=O)R^9$, $C(=O)NR^6R^7$, $C(=S)NR^6R^7$, —$(CHR^{16})_k NR^6R^7$, $(CH_2)_kOR^8$, $C(=O)NR^{10}CH(R^{11})CO_2R^{12}$, —$C(OH)(R^{25})(R^{25a})$, —$(CH_2)_pS(O)_n$-alkyl, —$(CHR^{16})R^{25}$, —$C(CN)(R^{25})(R^{16})$ provided that $R^{25}$ is not —NH-containing rings, —$C(=O)R^{25}$, —CH $(CO_2R^{16})_2$, $NR^{10}C(=O)CH(R^{11})NR^{10}R^{12}$, $NR^{10}CH (R^{11})CO_2R^{12}$; substituted $C_1$–$C_4$ alkyl, substituted $C_2$–$C_4$ alkenyl, substituted $C_2$–$C_4$ alkynyl, substituted $C_1$–$C_4$ alkoxy, aryl-(substituted $C_1$–$C_4$) alkyl, aryl-(substituted $C_1$–$C_4$) alkoxy, substituted $C_3$–$C_6$ cycloalkyl, amino-(substituted $C_1$–$C_4$) alkyl, substituted $C_1$–$C_4$ alkylamino, where substitution by $R^{27}$ can occur on any carbon containing substituent; 2-pyridinyl, imidazolyl, 3-pyridinyl, 4-pyridinyl, 2-methyl-3-pyridinyl, 4-methyl-3-pyridinyl, furanyl, 5-methyl-2-furanyl, 2,5-dimethyl-3-furanyl, 2-thienyl, 3-thienyl, 5-methyl-2-thienyl, 2-pheno-thiazinyl, 4-pyrazinyl, azetidinyl, phenyl, 1H-indazolyl, 2-pyrrolidonyl, 2H,6H-1,5,2-dithiazinyl, 2H-pyrrolyl, 3H-indolyl, 4-piperidonyl, 4aH-carbazolyl, 4H-quinolizinyl, 6H-1,2,5-thiadiazinyl, acridinyl, azocinyl, azepinyl, benzofuranyl, benzothiophenyl, carbazolyl, chromanyl, chromenyl, cinnolinyl, decahydroquinolinyl, furazanyl, imidazolidinyl, indolinyl, indolizinyl, indolyl, isobenzofuranyl, isochromanyl, isoindolinyl, isoindolyl, isoquinolinyl benzimidazolyl, isothiazolyl, isoxazolyl, morpholinyl, naphthyridinyl, octahydroisoquinolinyl, oxazolidinyl, oxazolyl, phenanthridinyl, phenanthrolinyl, phenazinyl, phenoxathiinyl, phenoxazinyl, phthalazinyl, piperazinyl, piperidinyl, pteridinyl, purinyl, pyranyl, pyrazolidinyl, pyrazolinyl, pyrazolyl, pyridazinyl, pyrimidinyl, pyrrolidinyl, pyrrolinyl, pyrrolyl, quinazolinyl, quinolinyl, quinoxalinyl, quinuclidinyl, β-carbolinyl, tetrahydrofuranyl, tetrahydroisoquinolinyl, tetrahydroquinolinyl, tetrazolyl, thianthrenyl, thiazolyl, thiophenyl, triazinyl, xanthenyl; or 1-tetrahydroquinolinyl or 2-tetrahydroisoquinolinyl either of which can be substituted with 0–3 groups chosen from keto and $C_1$–$C_4$ alkyl;

J, K, and L are independently selected at each occurrence from the group of N, CH, and CX';

M is $CR^5$ or N;

V is $CR^{1a}$ or N;

Z is $CR^2$ or N;

$R^{1a}$, $R^2$, and $R^{3a}$ are independently selected at each occurrence from the group consisting of hydrogen, halo, halomethyl, $C_1$–$C_3$ alkyl, and cyano;

$R^4$ is $(CH_2)_mOR^{16}$, $C_1$–$C_4$ alkyl, allyl, propargyl, $(CH_2)_m R^{13}$, or —$(CH_2)_mOC(O)R^{16}$;

X is halogen, $S(O)_2R^8$, $SR^8$, halomethyl, —$(CH_2)_pOR^8$, —$OR^8$, cyano, —$(CHR^{16})_pNR^{14}R^{15}$, —$C(=O)R^8$, $C_1$–$C_6$ alkyl, $C_4$–$C_{10}$ cycloalkylalkyl, $C_1$–$C_{10}$alkenyl, $C_2$–$C_{10}$alkynyl, $C_1$–$C_{10}$alkoxy, aryl-($C_2$–$C_{10}$)-alkyl, $C_3$–$C_6$ cycloalkyl, aryl-($C_1$–$C_{10}$)-alkoxy, nitro, thio-($C_1$–$C_{10}$)-alkyl, —$C(=NOR^{16})$—$C_1$–$C_4$-alkyl, —$C(=NOR^{16})H$, or —$C(=O)NR^{14}R^{15}$ where substitution by $R^{18}$ can occur on any carbon containing substituents;

X' is independently selected at each occurrence from the group consisting of hydrogen, halogen, $S(O)_nR^8$, halomethyl, —$(CHR^{16})_pOR^8$, cyano, —$(CHR^{16})_p NR^{14}R^{15}$, $C(=O)R^8$, $C_1$–$C_6$ alkyl, $C_2$–$C_{10}$ alkenyl, $C_2$–$C_{10}$ alkynyl, $C_1$–$C_{10}$ alkoxy, aryl-($C_1$–$C_{10}$)-alkyl, $C_3$–$C_6$ cycloalkyl, aryl-($C_1$–$C_{10}$)-alkoxy, nitro, thio-($C_1$–$C_{10}$)-alkyl, —$C(=NOR^{16})$—$C_1$–$C_4$-alkyl, —$C(=NOR^{16})H$, and —$C(=O)NR^{14}R^{15}$, where substitution by $R^{18}$ can occur on any carbon containing substituents;

$R^5$ is halo, —$C(=NOR^{16})$—$C_1$–$C_4$-alkyl, $C_1$–$C_6$ alkyl, $C_1$–$C_3$ haloalkyl, —$(CHR^{16})_pOR^8$, —$(CHR^{16})_pS(O)_n R^8$, —$(CHR^{16})_pNR^{14}R^{15}$, $C_3$–$C_6$ cycloalkyl, $C_2$–$C_{10}$ alkenyl, $C_2$–$C_{10}$ alkynyl, aryl-($C_2$–$C_{10}$)-alkyl, aryl-($C_1$–$C_{10}$)-alkoxy, cyano, $C_3$–$C_6$ cycloalkoxy, nitro, amino-($C_1$–$C_{10}$)-alkyl, thio-($C_2$–$C_{10}$)-alkyl, $SO_n(R^8)$, $C(=O)R^8$, —$C(=NOR^{16})H$, or —$C(=O)NR^{14}R^{15}$, where substitution by $R^{18}$ can occur on any carbon containing substituents;

$R^6$ and $R^7$ are independently selected at each occurrence from the group consisting of hydrogen, $C_1$–$C_6$ alkyl, $C_3$–$C_{10}$ cycloalkyl, $C_1$–$C_6$ alkoxy, $(C_4$–$C_{12})$-cycloalkylalkyl, —$(CH_2)_kR^{13}$, $(CHR^{16})_pOR^8$, —($C_1$–$C_6$alkyl)-aryl, heteroaryl, aryl, —$S(O)_2$-aryl or —($C_1$–$C_6$ alkyl)-heteroaryl or aryl wherein the aryl or heteroaryl groups are optionally substituted with 1–3 groups selected from the group consisting of hydrogen, halogen, $C_1$–$C_6$ alkyl, $C_1$–$C_6$ alkoxy, amino, NHC $(=O)(C_1$–$C_6$ alkyl), $NH(C_1$–$C_6$ alkyl), $N(C_1$–$C_6$ alkyl)$_2$, nitro, carboxy, $CO_2(C_1$–$C_6$ alkyl), cyano, and $S(O)_z$—($C_1$–$C_6$-alkyl); or can be taken together to form —$(CH_2)_qA(CH_2)_r$—, optionally substituted with 0–3 $R^{17}$; or, when considered with the commonly attached nitrogen, can be taken together to form a heterocycle, said heterocycle being substituted on carbon with 1–3 groups consisting of hydrogen, $C_1$–$C_6$ alkyl, hydroxy, or $C_1$–$C_6$ alkoxy;

A is $CH_2$, O, $NR^{25}$, $C(=O)$, $S(O)_n$, $N(C(=O)R^{17})$, $N(R^{19})$, $C(H)(NR^{14}R^{15})$, $C(H)(OR^{20})$, $C(H)(C(=O) R^{21})$, or $N(S(O)_nR^{21})$;

$R^8$ is independently selected at each occurrence from the group consisting of hydrogen; $C_1$–$C_6$ alkyl; —($C_4$–$C_{12}$) cycloalkylalkyl; $(CH_2)_kR^{22}$; $C_3$–$C_{10}$ cycloalkyl; —$NR^6R^7$; aryl; —$NR^{16}(CH_2)_nNR^6R^7$; —$(CH_2)_kR^{25}$; and $(CH_2)_t$heteroaryl or $(CH_2)_t$aryl, either of which can optionally be substituted with 1–3 groups selected from the group consisting of hydrogen, halogen, $C_1$–$C_6$ alkyl, $C_1$–$C_6$ alkoxy, amino, NHC $(=O)(C_1$–$C_6$ alkyl), $NH(C_1$–$C_6$ alkyl), $N(C_1$–$C_6$ alkyl)$_2$, nitro, carboxy, $CO_2(C_1$–$C_6$ alkyl), cyano, and $S(O)_z(C_1$–$C_6$-alkyl);

$R^9$ is independently selected at each occurrence from $R^{10}$, hydroxy, $C_1$–$C_4$ alkoxy, $C_3$–$C_6$ cycloalkyl, $C_2$–$C_4$ alkenyl, aryl substituted with 0–3 $R^{18}$, and —($C_1$–$C_6$ alkyl)-aryl substituted with 0–3 $R^{18}$;

$R^{10}$, $R^{16}$, $R^{23}$, and $R^{24}$ are independently selected at each occurrence from hydrogen or $C_1$–$C_4$ alkyl;

$R^{11}$ is $C_1$–$C_4$ alkyl substituted with 0–3 groups chosen from the following: keto, amino, sulfhydryl, hydroxyl, guanidinyl, p-hydroxyphenyl, imidazolyl, phenyl, indolyl, indolinyl, or, when taken together with an adjacent $R^{10}$, are $(CH_2)_i$;

$R^{12}$ is hydrogen or an appropriate amine protecting group for nitrogen or an appropriate carboxylic acid protecting group for carboxyl;

$R^{13}$ is independently selected at each occurrence from the group consisting of CN, $OR^{19}$, $SR^{19}$, and $C_3$–$C_6$ cycloalkyl;

$R^{14}$ and $R^{15}$ are independently selected at each occurrence from the group consisting of hydrogen, $C_4$–$C_{10}$ cycloalkyl-alkyl, and $R^{19}$;

$R^{17}$ is independently selected at each occurrence from the group consisting of $R^{10}$, $C_1$–$C_4$ alkoxy, halo, $OR^{23}$, $SR^{23}$, $NR^{23}R^{24}$, and ($C_1$–$C_6$) alkyl ($C_1$–$C_4$) alkoxy;

$R^{18}$ is independently selected at each occurrence from the group consisting of $R^{10}$, hydroxy, halogen, $C_1$–$C_2$ haloalkyl, $C_1$–$C_4$ alkoxy, $C(=O)R^{24}$, and cyano;

$R^{19}$ is independently selected at each occurrence from the group consisting of $C_1$–$C_6$ alkyl, $C_3$–$C_6$ cycloalkyl, $(CH_2)_w R^{22}$, and aryl substituted with 0–3 $R^{18}$;

$R^{20}$ is independently selected at each occurrence from the group consisting of $R^{10}$, $C(=O)R^{31}$, and $C_2$–$C_4$ alkenyl;

$R^{21}$ is independently selected at each occurrence from the group consisting of $R^{10}$, $C_1$–$C_4$ alkoxy, $NR^{23}R^{24}$, and hydroxyl;

$R^{22}$ is independently selected at each occurrence from the group consisting of cyano, $OR^{24}$, $SR^{24}$, $NR^{23}R^{24}$, $C_1$–$C_6$ alkyl, $C_3$–$C_6$ cycloalkyl, $-S(O)_n R^{31}$, and $-C(=O)R^{25}$;

$R^{25}$, which can be optionally substituted with 0–3 $R^{17}$, is independently selected at each occurrence from the group consisting of phenyl, pyrazolyl, imidazolyl, 2-methyl-3-pyridinyl, 4-methyl-3-pyridinyl, furanyl, 5-methyl-2-furanyl, 2,5-dimethyl-3-furanyl, 2-thienyl, 3-thienyl, 5-methyl-2-thienyl, 2-pheno-thiazinyl, 4-pyrazinyl, azetidinyl, 1H-indazolyl, 2-pyrrolidonyl, 2H,6H-1,5,2-dithiazinyl, 2H-pyrrolyl, 3H-indolyl, 4-piperidonyl, 4aH-carbazolyl, 4H-quinolizinyl, 6H-1,2,5-thiadiazinyl, acridinyl, azocinyl, azepinyl, benzofuranyl, benzothiophenyl, carbazolyl, chromanyl, chromenyl, cinnolinyl, decahydroquinolinyl, furazanyl, indolinyl, indolizinyl, indolyl, isobenzofuranyl, isochromanyl, isoindolinyl, isoindolyl, isoquinolinyl benzimidazolyl, isothiazolyl, isoxazolyl, morpholinyl, naphthyridinyl, octahydroisoquinolinyl, oxazolidinyl, oxazolyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazolidinyl, pyridazinyl, pyridyl, pyrimidinyl, pyrrolidinyl, pyrrolinyl, pyrrolyl, quinazolinyl, quinolinyl, quinoxalinyl, quinuclidinyl, β-carbolinyl, tetrahydrofuranyl, tetrazolyl, thianthrenyl, thiazolyl, thiophenyl, triazinyl, xanthenyl; and 1-tetrahydroquinolinyl or 2-tetrahydroisoquinolinyl either of which can be substituted with 0–3 groups chosen from keto and $C_1$–$C_4$ alkyl;

$R^{25a}$, which can be optionally substituted with 0–3 $R^{17}$, is independently selected at each occurrence from the group consisting of H and $R^{25}$;

$R^{27}$ is independently selected at each occurrence from the group consisting of $C_1$–$C_3$ alkyl, $C_2$–$C_4$ alkenyl, $C_2$–$C_4$ alkynyl, $C_2$–$C_4$ alkoxy, aryl, nitro, cyano, halogen, aryloxy, and heterocycle optionally linked through O;

$R^{31}$ is independently selected at each occurrence from the group consisting of $C_1$–$C_4$ alkyl, $C_3$–$C_7$ cycloalkyl, $C_4$–$C_{10}$ cycloalkyl-alkyl, and aryl-($C_1$–$C_4$) alkyl;

k, m, and r are independently selected at each occurrence from 1–4;

n is independently selected at each occurrence from 0–2;

p, q, and z are independently selected at each occurrence from 0–3;

t and w are independently selected at each occurrence from 1–6, provided that when J is CX' and K and L are both CH, and M is $CR^5$, then (A) when V and Y are N and Z is CH and $R^1$ and $R^3$ are methyl,
(1) and $R^4$ is methyl, then
(a) $R^5$ can not be methyl when X is OH and X' is H;
(b) $R^5$ can not be $-NHCH_3$ or $-N(CH_3)_2$ when X and X' are $-OCH_3$; and
(c) $R^5$ can not be $-N(CH_3)_2$ when X and X' are $-OCH_2CH_3$;
(2) and $R^4$ is ethyl, then
(a) then $R^5$ can not be methylamine when X and X' are $-OCH_3$;
(b) $R^5$ can not be OH when X is Br and X' is OH; and
(c) $R^5$ can not be $-CH_2OH$ or $-CH_2N(CH_3)_2$ when X is $-SCH3$ and X' is H;

(B) when V and Y are N, Z is CH, $R^4$ is ethyl, $R^5$ is iso-propyl, X is Br, X' is H, and
(1) $R^1$ is $CH_3$, then
(a) $R^3$ can not be OH, piperazin-1-yl, $-CH_2$-piperidin-1-yl, $-CH_2-(N-4-methylpiperazin-1-yl)$, $-C(O)NH$-phenyl, $-CO_2H$, $-CH_2O$-(4-pyridyl), $-C(O)NH_2$, 2-indolyl, $-CH_2O$-(4-carboxyphenyl), $-N(CH_2CH_3)$(2-bromo-4-isopropylphenyl);
(2) $R^1$ is $-CH_2CH_2CH_3$ then $R^3$ can not be $-CH_2CH_2CH_3$;

(C) when V, Y and Z are N, $R^4$ is ethyl, and
(1) $R^5$ is iso-propyl, X is bromo, and X' is H, then
(a) $R^3$ can not be OH or $-OCH_2CN$ when $R^1$ is $CH_3$; and
(b) $R^3$ can not be $-N(CH_3)_2$ when $R^1$ is $-N(CH_3)_2$;
(2) $R^5$ is $-OCH-$, X is $-OCH_3$, and X' is H, then $R^3$ and $R^1$ can not both be chloro;

further provided that when J, K, and L are all CH and M is $CR^5$, then
(D) at least one of V, Y, and Z must be N;
(E) when V is $CR^{1a}$, Z and Y can not both be N;
(F) when Y is $CR^{3a}$, Z and V can not both be N;
(G) when Z is $CR^2$, V and Y must both be N;
(H) Z can be N only when both V and Y are N or when V is $CR^{1a}$ and Y is $CR^{3a}$;
(I) when V and Y are N, Z is $CR^2$, and $R^2$ is H or $C_1$–$C_3$ alkyl, and $R^4$ is $C_1$–$C_3$ alkyl, $R^3$ can not be 2-pyridinyl, indolyl, indolinyl, imidazolyl, 3-pyridinyl, 4-pyridinyl, 2-methyl-3-pyridinyl, 4-methyl-3-pyridinyl, furanyl, 5-methyl-2-furanyl, 2,5-dimethyl-3-furanyl, 2-thienyl, 3-thienyl, 5-methyl-2-thienyl, 2-phenothiazinyl, or 4-pyrazinyl;
(J) when V and Y are N; Z is $CR^2$; $R^2$ is H or $C_1$–$C_3$ alkyl; $R^4$ is $C_1$–$C_4$ alkyl; $R^5$, X, and/or X' are OH, halo, $CF_3$, $C_1$–$C_4$ alkyl, $C_1$–$C_4$ alkoxy, $C_1$–$C_4$ alkylthio, cyano, amino, carbamoyl, or $C_1$–$C_4$ alkanoyl; and $R^1$ is $C_1$–$C_4$ alkyl, then $R^3$ can not be $-NH$(substituted phenyl) or $-N(C_1$–$C_4$ alkyl)(substituted phenyl);

and wherein, when Y is $CR^{29}$:
J, K, L, M, Z, A, k, m, n, p, q, r, t, w, $R^3$, $R^{10}$, $R^{11}$, $R^{12}$, $R^{13}$, $R^{16}$, $R^{18}$, $R^{19}$, $R^{21}$, $R^{23}$, $R^{24}$, $R^{25}$, and $R^{27}$ are as defined above and $R^{25a}$, in addition to being as defined above, can also be $C_1$–$C_4$ alkyl, but
V is N;
$R^1$ is $C_1$–$C_2$ alkyl, $C_2$–$C_4$ alkenyl, $C_2$–$C_4$ alkynyl, $C_2$–$C_4$ alkoxy, halogen, amino, methylamino, dimethylamino, aminomethyl, or N-methylaminomethyl;

$R^2$ is independently selected at each occurrence from the group consisting of hydrogen, halo, $C_1$–$C_3$ alkyl, nitro, amino, and —$CO_2R^{10}$;

$R^4$ is taken together with $R^{29}$ to form a 5-membered ring and is —$C(R^{28})$= or —N= when $R^{29}$ is —$C(R^{30})$= or —N=, or —$CH(R^{28})$— when $R^{29}$ is —$CH(R^{30})$—;

X is Cl, Br, I, $S(O)_nR^8$, $OR^8$, halomethyl, —$(CHR^{16})_pOR^8$, cyano, —$(CHR^{16})_pNR^{14}R^{15}$, $C(=O)R^8$, $C_1$–$C_6$ alkyl, $C_2$–$C_{10}$ alkenyl, $C_2$–$C_{10}$ alkynyl, $C_1$–$C_{10}$ alkoxy, aryl-($C_1$–$C_{10}$)-alkyl, $C_3$–$C_6$ cycloalkyl, aryl-($C_1$–$C_{10}$)-alkoxy, nitro, thio-($C_1$–$C_{10}$)-alkyl, —$C(=NOR^{16})$—$C_1$–$C_4$-alkyl, —$C(=NOR^{16})H$, or $C(=O)NR^{14}R^{15}$ where substitution by $R^{18}$ can occur on any carbon containing substituents;

X' is hydrogen, Cl, Br, I, $S(O)_nR^8$, —$(CHR^{16})_pOR^8$, halomethyl, cyano, —$(CHR^{16})_pNR^{14}R^{15}$, $C(=O)R^8$, $C_1$–$C_6$ alkyl, $C_2$–$C_{10}$ alkenyl, $C_2$–$C_{10}$ alkynyl, $C_1$–$C_{10}$, alkoxy, aryl-($C_1$–$C_{10}$)-alkyl, $C_3$–$C_6$ cycloalkyl, aryl-($C_2$–$C_{10}$)-alkoxy, nitro, thio-($C_2$–$C_{10}$)-alkyl, —$C(=NOR^{16})$—$C_1$–$C_4$-alkyl, —$C(=NOR^{16})H$, or $C(=O)NR^8R^{15}$ where substitution by $R^{18}$ can occur on any carbon containing substituents;

$R^5$ is halo, —$C(=NOR^{16})$—$C_1$–$C_4$-alkyl, $C_1$–$C_6$ alkyl, C1–C3 haloalkyl, $C_1$–$C_6$ alkoxy, $(CHR^{16})_pOR^8$, $(CHR^{16})_pS(O)_nR^8$, $(CHR^{16})_pNR^{14}R^{15}$, $C_3$–$C_6$ cycloalkyl, $C_2$–$C_{10}$ alkenyl, $C_2$–$C_{10}$ alkynyl, aryl-($C_2$–$C_{10}$)-alkyl, aryl-($C_1$–$C_{10}$)-alkoxy, cyano, $C_3$–$C_6$ cycloalkoxy, nitro, amino-($C_1$–$C_{10}$)-alkyl, thio-($C_1$–$C_{10}$)-alkyl, $SO_n(R^8)$, $C(=O)R^8$, —$C(=NOR^{16})H$, or $C(=O)NR^8R^{15}$ where substitution by $R^{18}$ can occur on any carbon containing substituents;

$R^6$ and $R^7$ are independently selected at each occurrence from the group consisting of hydrogen, $C_1$–$C_6$ alkyl, $C_3$–$C_{10}$ cycloalkyl, —$(CH_2)_kR^{13}$, ($C_4$–$C_{12}$)-cycloalkylalkyl, $C_1$–$C_6$ alkoxy, —($C_1$–$C_6$ alkyl)-aryl, heteroaryl, aryl, —$S(O)_z$-aryl or —($C_1$–$C_6$ alkyl)-heteroaryl or aryl wherein the aryl or heteroaryl groups are optionally substituted with 1–3 groups selected from hydrogen, halogen, $C_1$–$C_6$ alkyl, $C_1$–$C_6$ alkoxy, amino, $NHC(=O)(C_1$–$C_6$ alkyl), $NH(C_1$–$C_6$ alkyl), $N(C_1$–$C_6$ alkyl)$_2$, nitro, carboxy, $CO_2(C_1$–$C_6$ alkyl), and cyano; or can be taken together to form —$(CH_2)_qA(CH_2)_r$—, optionally substituted with 0–3 $R^{17}$; or, when considered with the commonly attached nitrogen, can be taken together to form a heterocycle, said heterocycle being substituted on carbon with 1–3 groups consisting of hydrogen, $C_1$–$C_6$ alkyl, hydroxy, or $C_1$–$C_6$ alkoxy;

$R^8$ is independently selected at each occurrence from the group consisting of hydrogen, $C_1$–$C_6$ alkyl, —($C_4$–$C_{12}$) cycloalkylalkyl, $(CH_2)_kR^{22}$, $C_3$–$C_{10}$ cycloalkyl, —($C_1$–$C_6$ alkyl)-aryl, heteroaryl, —$NR^{16}$, —$N(CH_2)_nNR^6R^7$; —$(CH_2)_kR^{25}$, —($C_1$–$C_6$ alkyl)-heteroaryl or aryl optionally substituted with 1–3 groups selected from hydrogen, halogen, $C_1$–$C_6$ alkyl, $C_1$–$C_6$ alkoxy, amino, $NHC(=O)(C_1$–$C_6$ alkyl), $NH(C_1$–$C_6$ alkyl), $N(C_1$–$C_6$ alkyl)$_2$, nitro, carboxy, $CO_2(C_1$–$C_6$ alkyl), and cyano;

$R^9$ is independently selected at each occurrence from $R^{10}$, hydroxy, $C_1$–$C_4$ alkoxy, $C_3$–$C_6$ cycloalkyl, $C_2$–$C_4$ alkenyl, and aryl substituted with 0–3 $R^{18}$;

$R^{14}$ and $R^{15}$ are independently selected at each occurrence from the group consisting of hydrogen, $C_1$–$C_6$ alkyl, $C_3$–$C_6$ cycloalkyl, $(CH_2)_kR^{22}$, and aryl substituted with 0–3 $R^{18}$;

$R^{17}$ is independently selected at each occurrence from the group consisting of $R^{10}$, $C_1$–$C_4$ alkoxy, halo, $OR^{23}$, $SR^{23}$, and $NR^{23}R^{24}$;

$R^{20}$ is independently selected at each occurrence from the group consisting of $R^{10}$ and $C(=O)R^{31}$;

$R^{22}$ is independently selected at each occurrence from the group consisting of cyano, $OR^{24}$, $SR^{24}$, $NR^{23}R^{24}$, $C_3$–$C_6$ cycloalkyl, —$S(O)_nR^{31}$, and —$C(=O)R^{25}$;

$R^{26}$ is hydrogen or halogen:

$R^{28}$ is $C_1$–$C_2$ alkyl, $C_2$–$C_4$ alkenyl, $C_2$–$C_4$ alkynyl, hydrogen, $C_1$–$C_2$ alkoxy, halogen, or $C_2$–$C_4$ alkylamino;

$R^{29}$ is taken together with $R^4$ to form a five membered ring and is: —$CH(R^{30})$— when $R^4$ is —$CH(R^{28})$—, —$C(R^{30})$= or —N= when $R^4$ is —$C(R^{28})$= or —N=;

$R^{30}$ is hydrogen, cyano, $C_1$–$C_2$ alkyl, $C_1$–$C_2$ alkoxy, halogen, $C_1$–$C_2$ alkenyl, nitro, amido, carboxy, or amino;

$R^{31}$ is $C_1$–$C_4$ alkyl, $C_3$–$C_7$ cycloalkyl, or aryl-($C_1$–$C_4$) alkyl;

provided that when J, K, and L are all CH, M is $CR^5$, Z is CH, $R^3$ is $CH_3$, $R^{28}$ is H, $R^5$ is iso-propyl, X is Br, X' is H, and $R^1$ is $CH_3$, then $R^{30}$ can not be H, —$CO_2H$, or —$CH_2NH_2$;

and further provided that when J, K and L are all CH; M is $CR^5$; Z is N; and (A) $R^{29}$ is —$C(R^1)$=; then one of $R^{28}$ or $R^{30}$ is hydrogen;

(B) $R^{29}$ is N; then $R^3$ is not halo, $NH_2$, $NO_2$, $CF_3$, $CO_2H$, $CO_2$-alkyl, alkyl, acyl, alkoxy, OH, or —$(CH_2)_mOalkyl$;

(C) $R^{29}$ is N; then $R^{28}$ is not methyl if X or X' are bromo or methyl and $R^5$ is nitro; or (D) $R^{29}$ is N, and $R^1$ is $CH_3$ and $R^3$ is amino; then $R^5$ is not halogen or methyl.

Preferred compounds of this invention are those compounds of Formula I wherein,

Y is $CR^{3a}$ or N:

$R^3$ is $C_1$–$C_4$ alkyl, aryl, halogen, $C_1$–$C_2$ haloalkyl, nitro, $NR^6R^7$, $OR^8$, $SR^8$, $C(=O)R^9$, $C(=O)NR^6R^7$, $C(=S)NR^6R^7$, $(CH_2)_kNR^6R^7$, $(CH_2)_kOR^8$, $C(=O)NR^{10}CH(R^{11})CO_2R^{12}$, —$(CHR^{16})_pOR^8$, —$C(OH)(R^{25})(R^{25a})$, —$(CH_2)_pS(O)_n$-alkyl, —$C(CN)(R^{25})(R^{16})$ provided that $R^{25}$ is not an —NH— containing ring, —$C(=O)R^{25}$, —$CH(CO_2R^{16})_2$, $NR^{10}C(=O)CH(R^{11})NR^{10}R^{12}$; substituted $C_1$–$C_4$alkyl, substituted $C_2$–$C_4$ alkenyl, substituted $C_2$–$C_4$ alkynyl, $C_3$–$C_6$ cycloalkyl, substituted $C_1$–$C_4$ alkoxy, aryl-(substituted $C_1$–$C_4$) alkyl, aryl-(substituted $C_1$–$C_4$) alkoxy, substituted $C_3$–$C_6$ cycloalkyl, amino-(substituted $C_1$–$C_4$)alkyl, substituted $C_1$–$C_4$ alkylamino, where substitution by $R^{27}$ can occur on any carbon containing substituent; 2-pyridinyl, indolinyl, indolyl, pyrazoyl, imidazolyl, 3-pyridinyl, 4-pyridinyl, furanyl, 2,5-dimethyl-3-furanyl, 2-thienyl, 3-thienyl, or 5-methyl-2-thienyl, azetidinyl, 2-pyrrolidonyl, 2H-pyrrolyl, 3H-indolyl, 4-piperidonyl, 4aH-carbazolyl, 4H-quinolizinyl, azocinyl, azepinyl, benzofuranyl, benzothiophenyl, carbazolyl, chromanyl, chromenyl, cinnolinyl, decahydroquinolinyl, furazanyl, imidazolidinyl, indolinyl, indolizinyl, indolyl, isobenzofuranyl, isochromanyl, isoindolinyl, isoindolyl, isoquinolinyl (benzimidazolyl), isothiazolyl, isoxazolyl, morpholinyl, naphthyridinyl, octahydroisoquinolinyl, oxazolidinyl, oxazolyl, phthalazinyl, piperazinyl, piperidinyl, pteridinyl, purinyl, pyranyl, pyrazolidinyl, pyrazolinyl, pyrazolyl, pyridazinyl, pyrimidinyl, pyrrolidinyl, pyrrolinyl, pyrrolyl, quinazolinyl, quinolinyl, quinoxalinyl, quinuclidinyl, β-carbolinyl, tetrahydrofuranyl, tetrahydroisoquinolinyl, tetrahydroquinolinyl, tetrazolyl, thiazolyl, triazinyl; or 1-tetrahydroquinolinyl or 2-tetrahydroisoquinolinyl either of which can be substituted with 0–3 groups chosen from keto and $C_1$–$C_4$ alkyl;

J, K, and L are independently selected at each occurrence from the group consisting of CH and CX';

M is $CR^5$;

$R^{1a}$, $R^2$, and $R^{3a}$ are independently selected at each occurrence from the group consisting of hydrogen, halo, methyl, or cyano;

X is halogen, $S(O)_2R^8$, $SR^8$ halomethyl, $(CH_2)_pOR^8$, cyano, —$(CHR^{16})_pNR^{14}R^{15}$, $C(=O)R^8$, $C_1$–$C_6$ alkyl, $C_2$–$C_{10}$ alkenyl, $C_2$–$C_{10}$ alkynyl, $C_1$–$C_{10}$ alkoxy, aryl-($C_1$–$C_{10}$)-alkyl, $C_3$–$C_6$ cycloalkyl, aryl-($C_1$–$C_{10}$)-alkoxy, nitro, thio-($C_1$–$C_{10}$)-alkyl, —$C(=NOR^{16})$—$C_1$–$C_4$-alkyl, –$C(=NOR^{16})H$, or —$C(=O)NR^{14}R^{15}$ where substitution by $R^{18}$ can occur on any carbon containing substituents;

X' is hydrogen, halogen, $S(O)_nR^8$, halomethyl, $(CH_2)_pOR^8$, cyano, —$(CHR^{16})_pNR^{14}R^{15}$, $C(=O)R^8$, $C_1$–$C_6$ alkyl, $C_2$–$C_{10}$ alkenyl, $C_2$–$C_{10}$ alkynyl, $C_1$–$C_{10}$ alkoxy, aryl-($C_1$–$C_{10}$-alkyl, $C_3$–$C_6$ cycloalkyl, aryl-($C_1$–$C_{10}$)-alkoxy, nitro, thio-($C_1$–$C_{10}$)-alkyl, —$C(=NOR^{16})$—$C_1$–$C_4$-alkyl, —$C(=NOR^{16})H$, or —$C(=O)NR^{14}R^{15}$ where substitution by $R^{18}$ can occur on any carbon containing substituents;

$R^5$ is halo, —$C(=NOR^{16})$—$C_1$–$C_4$-alkyl, $C_1$–$C_6$ alkyl, $C_1$–$C_3$ haloalkyl, $C_1$–$C_6$ alkoxy, $(CHR^{16})_pOR^8$, $(CHR^{16})_pS(O)_nR^8$, $(CHR^{16})_pNR^{14}R^{15}$, $C_3$–$C_6$ cycloalkyl, $C_2$–$C_{10}$ alkenyl, $C_2$–$C_{10}$ alkynyl, aryl-($C_2$–$C_{10}$)-akyl, aryl-($C_2$–$C_{10}$)-alkoxy, cyano, $C_3$–$C_6$ cycloalkoxy, nitro, amino-($C_2$–$C_{10}$)-alkyl, thio-($C_2$–$C_{10}$)-alkyl, $SO_n(R^8)$, $C(=O)R^8$, —$C(=NOR^{16})H$, or $C(=O)NR^{14}R^{15}$ where substitution by $R^{18}$ can occur on any carbon containing substituents;

$R^6$ and $R^7$ are independently selected at each occurrence from the group consisting of hydrogen, $C_1$–$C_6$ alkyl, $C_3$–$C_{10}$ cycloalkyl, cycloalkylalkyl, —$(CH_2)_kR^{13}$, $C_1$–$C_6$ alkoxy, —$(CHR^{16})_pOR^8$, —($C_1$–$C_6$ alkyl)-aryl, aryl, heteroaryl, —($C_1$–$C_6$ alkyl)-heteroaryl or aryl, wherein the aryl or heteroaryl groups are optionally substituted with 1–3 groups selected from hydrogen, halogen, $C_1$–$C_6$ alkyl, $C_1$–$C_6$ alkoxy, NHC(=O)($C_1$–$C_6$ alkyl), NH($C_1$–$C_6$ alkyl), N($C_1$–$C_6$ alkyl)$_2$, carboxy, $CO_2$($C_1$–$C_6$ alkyl), cyano, or can be taken together to form —$(CH_2)_qA(CH_2)_r$—, optionally substituted with 0–3 $R^{17}$, or, when considered with the commonly attached nitrogen, can be taken together to form a heterocycle, said heterocycle being substituted on carbon with 1–3 groups consisting of hydrogen, $C_1$–$C_6$ alkyl, ($C_1$–$C_6$)alkyl($C_1$–$C_4$)alkoxy, and $C_1$–$C_6$ alkoxy;

$R^8$ is independently selected at each occurrence from the group consisting of hydrogen; $C_1$–$C_6$ alkyl; —($C_4$–$C_{12}$) cycloalkylalkyl; $(CH_2)_tR^{22}$; $C_3$–$C_{10}$ cycloalkyl; —$NR^6R^7$; aryl; —$NR^{16}(CH_2)_nNR^6R^7$; —$(CH_2)_kR^{25}$; and $CH_2)_t$heteroaryl or $(CH_2)_t$aryl, either of which can optionally be substituted with 1–3 groups selected from the group consisting of hydrogen, halogen, $C_1$–$C_6$ alkyl, $C_1$–$C_6$ alkoxy, NHC(=O)($C_1$–$C_6$ alkyl), NH($C_1$–$C_6$ alkyl), N($C_1$–$C_6$ alkyl)$_2$, carboxy, and $CO_2$($C_1$–$C_6$ alkyl);

$R^{10}$ is hydrogen;

$R^{13}$ is independently selected at each occurrence from the group consisting of $OR^{19}$, $SR^{19}$, and $C_3$–$C_6$ cycloalkyl;

$R^{14}$ and $R^{15}$ are independently selected at each occurrence from the group consisting of hydrogen, $C_1$–$C_6$ alkyl, $C_3$–$C_6$ cycloalkyl, and $C_4$–$C_{10}$ cycloalkyl-alkyl;

$R^{17}$ is independently selected at each occurrence from the group consisting of hydrogen, $C_1$–$C_4$ alkyl, $C_1$–$C_4$ alkoxy, and ($C_1$–$C_6$)alkyl($C_1$–$C_4$)alkoxy;

$R^{19}$ is independently selected at each occurrence from the group consisting of $C_1$–$C_6$ alkyl, $C_3$–$C_6$ cycloalkyl, and aryl substituted with 0–3 $R^{18}$;

$R^{22}$ is independently selected at each occurrence from the group consisting of cyano, $OR^{24}$ $SR^{24}$, $NR^{23}R^{24}$, $C_3$–$C_6$ cycloalkyl, —$S(O)_nR^{31}$, and —$C(=O)R^{25}$;

$R^{25}$, which can be optionally substituted with 0–3 $R^{17}$, is independently selected at each occurrence from the group consisting of phenyl, pyrazolyl, imidazolyl, 2-methyl-3-pyridinyl, 4-methyl-3-pyridinyl, furanyl, 5-methyl-2-furanyl, 2,5-dimethyl-3-furanyl, 2-thienyl, 3-thienyl, 5-methyl-2-thienyl, 2-pheno-thiazinyl, 4-pyrazinyl, 1H-indazolyl, 2-pyrrolidonyl, 2H-pyrrolyl, 3H-indolyl, 4-piperidonyl, 4aH-carbazolyl, 4H-quinolizinyl, azocinyl, benzofuranyl, carbazolyl, chromanyl, chromenyl, cinnolinyl, decahydroquinolinyl, furazanyl, indolinyl, indolizinyl, indolyl, isobenzofuranyl, isochromanyl, isoindolinyl, isoindolyl, isoquinolinyl (benzimidazolyl), isothiazolyl, isoxazolyl, morpholinyl, naphthyridinyl, octahydroisoquinolinyl, oxazolidinyl, oxazolyl, piperazinyl, piperidinyl, pteridinyl, purinyl, pyranyl, pyrazolidinyl, pyridazinyl, pyridyl, pyrimidinyl, pyrrolidinyl, pyrrolinyl, pyrrolyl, quinazolinyl, quinolinyl, quinoxalinyl, quinuclidinyl, β-carbolinyl, tetrahydrofuranyl, tetrazolyl, thiazolyl, triazinyl; and 1-tetrahydroquinolinyl or 2-tetrahydroisoquinolinyl either of which can be substituted with 0–3 groups chosen from keto and $C_1$–$C_4$ alkyl;

$R^{25a}$, which can be optionally substituted with 0–3 $R^{17}$, is independently selected at each occurrence from the group consisting of H, phenyl, pyrazolyl, imidazolyl, 2-methyl-3-pyridinyl, 4-methyl-3-pyridinyl, furanyl, 5-methyl-2-furanyl, 2,5-dimethyl-3-furanyl, 2-thienyl, 3-thienyl, 5-methyl-2-thienyl, 4-pyrazinyl, 1H-indazolyl, 2-pyrrolidonyl, 2H-pyrrolyl, 3H-indolyl, 4-piperidonyl, 4aH-carbazolyl, 4H-quinolizinyl, azocinyl, benzofuranyl, benzothiophenyl, carbazolyl, chromanyl, chromenyl, cinnolinyl, decahydroquinolinyl, furazanyl, indolinyl, indolizinyl, indolyl, isobenzofuranyl, isochromanyl, isoindolinyl, isoindolyl, isoquinolinyl (benzimidazolyl), isothiazolyl, isoxazolyl, morpholinyl, naphthyridinyl, octahydroisoquinolinyl, oxazolidinyl, oxazolyl, piperazinyl, piperidinyl, pteridinyl, purinyl, pyranyl, pyrazolidinyl, pyridazinyl, pyridyl, pyrimidinyl, pyrrolidinyl, pyrrolinyl, pyrrolyl, quinazolinyl, quinolinyl, quinoxalinyl, quinuclidinyl, β-carbolinyl, tetrahydrofuranyl, tetrazolyl, thiazolyl, thiophenyl, triazinyl; and 1-tetrahydroquinolinyl or 2-tetrahydroisoquinolinyl either of which can be substituted with 0–3 groups chosen from keto and $C_1$–$C_4$ alkyl;

t is independently selected at each occurrence from 1–3; and w is 1–3.

Other preferred compounds of this invention are those compounds of Formula I wherein, Y is $CR^{29}$;

Z is $CR^2$;

$R^1$ is methyl, amino, chloro, or methylamino;

$R^2$ is hydrogen;

$R^3$ is $C_1$–$C_4$ alkyl, aryl, halogen, nitro, $NR^6R^7$, $OR^8$, $SR^8$, $C(=O)R^9$, $C(=O)NR^6R^7$, $(CH_2)_kNR^6R^7$, $(CH_2)_kOR^8$, —$C(OH)(R^{25})(R^{25a})$, —$(CH_2)_pS(O)_n$-alkyl, —$C(=O)R^{25}$, —$CH(CO_2R^{16})_2$; substituted $C_1$–$C_4$ alkyl, substituted $C_2$–$C_4$ alkenyl, substituted $C_2$–$C_4$ alkynyl, $C_3$–$C_6$ cycloalkyl, substituted $C_1$–$C_4$ alkoxy, aryl-(substituted $C_1$–$C_4$) alkyl, aryl-(substituted $C_1$–$C_4$) alkoxy, substituted $C_3$–$C_6$ cycloalkyl, amino-(substituted $C_1$–$C_4$) alkyl, substituted $C_1$–$C_4$ alkylamino, or is N-linked piperidinyl, piperazinyl, morpholino, thiomorpholino, imidazolyl, 2-pyridinyl, 3-pyridinyl, 4-pyridinyl, where substitution by $R^{27}$ can occur on any carbon containing substituent;

J, K, and L are independently selected at each occurrence from the group consisting of CH and CX';

M is $CR^5$;

$R^4$ is taken together with $R^{29}$ to form a five membered ring and is —CH=;

X is Br, I, $S(O)_nR^8$, $OR^8$, $NR^{14}R^{15}$, $R^{18}$ substituted alkyl, or amino-$(C_1$–$C_2)$ alkyl;

X' is hydrogen, Br, I, $S(O)_nR^8$, $OR^8$, $NR^{14}R^{15}$, $R^{18}$ substituted alkyl, or amino-$(C_1$–$C_2)$ alkyl;

$R^5$ is independently selected at each occurrence from the group consisting of halogen, –$C(=NOR^{16})$—$C_1$–$C_4$-alkyl, $C_1$–$C_6$ alkyl, $C_1$–$C_6$ alkoxy, $(CHR^{16})_kOR^8$, —$NR^{14}R^{15}$, $(CHR^{16})_pS(O)_nR^8$, $(CHR^{16})_pNR^{14}R^{15}$, $C_3$–$C_6$ cycloalkyl, $C(=O)R^8$, and $C(=O)NR^8R^{15}$; $R^6$ and $R^7$ are independently selected at each occurrence from the group consisting of hydrogen, $C_1$–$C_6$ alkyl, $C_3$–$C_6$ cycloalkyl, —$(CH_2)_kR^{13}$, $(C_3$–$C_6)$cycloalkyl-$(C_1$–$C_6)$alkyl, —$(C_1$–$C_6$ alkyl)-aryl, heteroaryl, —$(C_1$–$C_6$ alkyl)-heteroaryl or aryl, wherein the aryl or heteroaryl groups are optionally substituted with 1–3 groups selected from hydrogen, $C_1$–$C_2$ alkyl, $C_1$–$C_2$ alkoxy, amino, $NHC(=O)(C_1$–$C_2$ alkyl), $NH(C_1$–$C_2$alkyl), and $N(C_1$–$C_2$ alkyl)$_2$, or can be taken together to form —$(CH_2)_qA(CH_2)_r$—, optionally substituted with 0–2 $R^{17}$, or, when considered with the commonly attached nitrogen, can be taken together to form a heterocycle, said heterocycle being substituted on carbon with 1–2 groups consisting of hydrogen, $C_1$–$C_3$ alkyl, hydroxy, or $C_1$–$C_3$ alkoxy;

A is $CH_2$, O, $NR^{25}$, $C(=O)$, or $S(O)_n$;

$R^8$ is independently selected at each occurrence from the group consisting of hydrogen; $C_1$–$C_6$ alkyl; —$(C_4$–$C_{12})$ cycloalkylalkyl; $(CH_2)_kR^{22}$; $C_3$–$C_{10}$ cycloalkyl; —$NR^6R^7$; aryl; —$NR^{16}(CH_2)_nNR^6R^7$; —$(CH_2)_kR^{25}$; and $(CH_2)_t$heteroaryl or $(CH_2)_t$aryl, either of which can optionally be substituted with 1–3 groups selected from the group consisting of hydrogen, $C_1$–$C_2$ alkyl, $C_1$–$C_2$ alkoxy, amino, $NHC(=O)(C_1$–$C_2$alkyl), $NH(C_1$–$C_2$alkyl), $N(C_1$–$C_2$ alkyl)$_2$,, $R^9$ is hydroxy, $C_1$–$C_4$ alkyl, $C_1$–$C_4$ alkoxy, and $C_3$–$C_6$ cycloalkyl substituted with 0–2 $R^{18}$;

$R^{14}$ and $R^{15}$ are independently selected at each occurrence from the group consisting of hydrogen, $C_1$–$C_2$ alkyl, $(CH_2)_tR^{22}$, and aryl substituted with 0–2 $R^{18}$;

$R^{16}$ is independently selected at each occurrence from the group consisting of hydrogen and $C_1$–$C_2$ alkyl;

$R^{17}$ is independently selected at each occurrence from the group consisting of hydrogen, $C_1$–$C_2$ alkyl, $C_1$–$C_2$ alkoxy, halo, and $NR^{23}R^{24}$;

$R^{18}$ is independently selected at each occurrence from the group consisting of hydrogen, $C_1$–$C_2$ alkyl, $C_1$–$C_2$alkoxy, halo, and $NR^{23}R^{24}$;

$R^{22}$ is independently selected at each occurrence from the group consisting of $OR^{24}$, $SR^{24}$, $R^{23}R^{24}$, and —$C(=O)R^{25}$;

$R^{23}$ and $R^{24}$ are independently selected at each occurrence from hydrogen and $C_1$–$C_2$ alkyl;

$R^{25}$, which can be optionally substituted with 0–3 $R^{17}$, is independently selected at each occurrence from the group consisting of phenyl, pyrazolyl, imidazolyl, 2-methyl-3-pyridinyl, 4-methyl-3-pyridinyl, furanyl, 5-methyl-2-furanyl, 2,5-dimethyl-3-furanyl, 2-thienyl, 3-thienyl, 5-methyl-2-thienyl, 2-pheno-thiazinyl, 4-pyrazinyl, 1H-indazolyl, 2-pyrrolidonyl, 2H-pyrrolyl, 3H-indolyl, 4-piperidonyl, 4aH-carbazolyl, 4H-quinolizinyl, azocinyl, benzofuranyl, carbazolyl, chromanyl, chromenyl, cinnolinyl, decahydroquinolinyl, furazanyl, indolinyl, indolizinyl, indolyl, isobenzofuranyl, isochromanyl, isoindolinyl, isoindolyl, isoquinolinyl, benzimidazolyl, isothiazolyl, isoxazolyl, morpholinyl, naphthyridinyl, octahydroisoquinolinyl, oxazolidinyl, oxazolyl, piperazinyl, piperidinyl, pteridinyl, purinyl, pyranyl, pyrazolidinyl, pyridazinyl, pyridyl, pyrimidinyl, pyrrolidinyl, pyrrolinyl, pyrrolyl, quinazolinyl, quinolinyl, quinoxalinyl, quinuclidinyl, β-carbolinyl, tetrahydrofuranyl, tetrazolyl, thiazolyl, triazinyl; and 1-tetrahydroquinolinyl or 2-tetrahydroisoquinolinyl either of which can be substituted with 0–3 groups chosen from keto and $C_1$–$C_4$ alkyl;

$R^{25a}$ is independently selected at each occurrence from the group consisting of H and $C_1$–$C_4$ alkyl;

$R^{29}$ is taken together with $R^4$ to form a five membered ring and is —$C(R^{30})$=;

$R^{30}$ is hydrogen, cyano, $C_1$–$C_2$ alkyl, or halogen;

k is 1–3;

p is 0–2;

q and r are 2; and t and w are independently selected at each occurrence from 1–2.

More preferred compounds of this invention are those compounds of Formula I wherein, when Y is $CR^{3a}$ or N:

$R^1$ is independently selected at each occurrence from the group consisting of $C_1$–$C_2$ alkyl, $C_1$–$C_2$ haloalkyl, $NR^6R^7$, and $OR^8$;

$R^3$ is independently selected at each occurrence from the group consisting of $C_1$–$C_4$ alkyl, $C_1$–$C_2$ haloalkyl, $NR^6R^7$, $OR^8$, $C(=O)R^9$, $C(=O)NR^6R^7$, $(CH_2)_kNR^6R^7$, $(CH_2)_kOR^8$, —$C(CN)(R^{25})(R^{16})$ provided that $R^{25}$ is not an —NH— containing ring, —$C(OH)(R^{25})(R^{25a})$, —$(CH_2)_pS(O)_n$-alkyl, —$C(=O)R^{25}$, —CH$(CO_2R^{16})_2$, 2-pyridinyl, indolinyl, indolyl, pyrazoyl, imidazolyl, 3-pyridinyl, 4-pyridinyl, furanyl, 2,5-dimethyl-3-furanyl, 2-thienyl, 3-thienyl, 5-methyl-2-thienyl, 1H-indazolyl, 2H-pyrrolyl, 3H-indolyl, 4-piperidonyl, 4H-quinolizinyl, benzofuranyl, carbazolyl, chromenyl, cinnolinyl, decahydroquinolinyl, furazanyl, imidazolidinyl, indolinyl, indolizinyl, indolyl, isobenzofuranyl, isoindolinyl, isoindolyl, isoquinolinyl (benzimidazolyl), isothiazolyl, isoxazolyl, morpholinyl, naphthyridinyl, octahydroisoquinolinyl, oxazolidinyl, oxazolyl, piperazinyl, piperidinyl, pteridinyl, purinyl, pyranyl, pyrazolidinyl, pyrazolinyl, pyrazolyl, pyridazinyl, pyrimidinyl, pyrrolidinyl, pyrrolinyl pyrrolyl, quinazolinyl, quinolinyl, quinoxalinyl, quinuclidinyl, β-carbolinyl, tetrahydrofuranyl, tetrahydroisoquinolinyl, tetrahydroquinolinyl, tetrazolyl, thiazolyl, triazinyl; and 1-tetrahydroquinolinyl or 2-tetrahydroisoquinolinyl either of which can be substituted with 0–3 groups chosen from keto and $C_1$–$C_4$ alkyl;

$R^{1a}$, $R^2$, and $R^{3a}$ are independently selected at each occurrence from the group consisting of hydrogen, methyl, and cyano;

X is Cl, Br, I, $OR^8$, $NR^{14}R^{15}$, $(CH_2)_mOR^{16}$, or $(CHR^{16})NR^{14}R^{15}$;

X' is hydrogen, Cl, Br, I, $OR^8$, $NR^{14}R^{15}$, $(CH_2)_mOR^{16}$, or $(CHR^{16})NR^{14}R^{15}$;

$R^5$ is halo, $C_1$–$C_6$ alkyl, $C_1$–$C_3$ haloalkyl, $C_1$–$C_6$ alkoxy, $(CHR^{16})_pOR^8$, $(CHR^{16})_pNR^{14}R^{15}$, or $C_3$–$C_6$ cycloalkyl;

$R^6$ and $R^7$ are independently selected at each occurrence from the group consisting of
$C_1$–$C_6$ alkyl, $(CHR^{16})_pOR^8$, $C_1$–$C_6$ alkoxy, and
—$(CH_2)_kR^{13}$, or can be taken together to form
—$(CH_2)_qA(CH_2)_r$—, optionally substituted with —$CH_2OCH_3$;

A is $CH_2$, O, $S(O)_n$, $N(C(=O)R^{17})$, $N(R^{19})$, $C(H)(OR^{20})$, $NR^{25}$, or $C(=O)$;

$R^8$ is independently selected at each occurrence from the group consisting of hydrogen, $C_1$–$C_6$ alkyl, $C_3$–$C_6$ cycloalkyl, $(CH_2)_rR^{22}$, —$NR^6R^7$, —$NR^{16}(CH_2)_nNR^6R^7$, and —$(CH_2)_kR^{25}$, $R^9$ is $C_1$–$C_4$ alkyl;

$R^{14}$ and $R^{15}$ are independently selected at each occurrence from the group consisting of hydrogen, $C_1$–$C_2$ alkyl, $C_3$–$C_6$ cycloalkyl, and $C_4$–$C_6$ cycloalkyl-alkyl;

$R^{16}$ is hydrogen;

$R^{1a}$ is $C_1$–$C_3$ alkyl;

$R^{20}$ is independently selected at each occurrence from the group consisting of hydrogen, $C_1$–$C_2$ alkyl, and $C_2$–$C_3$ alkenyl;

$R^{22}$ is independently selected at each occurrence from the group consisting of $OR^{24}$, —$S(O)_nR^{19}$, and —$C(=O)R^{25}$;

$R^{23}$ and $R^{24}$ are independently selected at each occurrence from hydrogen and $C_1$–$C_2$ alkyl;

$R^{25}$, which can be optionally substituted with 0–3 $R^{17}$, is independently selected at each occurrence from the group consisting of phenyl, pyrazolyl, imidazolyl, 2-methyl-3-pyridinyl, 4-methyl-3-pyridinyl, furanyl, 5-methyl-2-furanyl, 2,5-dimethyl-3-furanyl, 2-thienyl, 3-thienyl, 5-methyl-2-thienyl, 2-pheno-thiazinyl, 4-pyrazinyl, 1H-indazolyl, 2-pyrrolidonyl, 2H-pyrrolyl, 3H-indolyl, 4-piperidonyl, 4aH-carbazolyl, 4H-quinolizinyl, azocinyl, cinnolinyl, decahydroquinolinyl, furazanyl, indolinyl, indolizinyl, indolyl, isoindolinyl, isoindolyl, isoquinolinyl (benzimidazolyl), isothiazolyl, isoxazolyl, morpholinyl, naphthyridinyl, octahydroisoquinolinyl, oxazolidinyl, oxazolyl, piperazinyl, piperidinyl, pteridinyl, purinyl, pyranyl, pyrazolidinyl, pyridazinyl, pyridyl, pyrimidinyl, pyrrolidinyl, pyrrolinyl, pyrrolyl, quinazolinyl, quinolinyl, quinoxalinyl, quinuclidinyl, tetrahydrofuranyl, tetrazolyl, thiazolyl, triazinyl; and 1-tetrahydroquinolinyl or 2-tetrahydroisoquinolinyl either of which can be substituted with 0–3 groups chosen from keto and $C_1$–$C_4$ alkyl;

$R^{25a}$, which can be optionally substituted with 0–3 $R^{17}$, is independently selected at each occurrence from the group consisting of H, phenyl, pyrazolyl, imidazolyl, 2-methyl-3-pyridinyl, 4-methyl-3-pyridinyl, furanyl, 5-methyl-2-furanyl, 2,5-dimethyl-3-furanyl, 2-thienyl, 3-thienyl, 5-methyl-2-thienyl, 2-pheno-thiazinyl, 4-pyrazinyl, 1H-indazolyl, 2-pyrrolidonyl, 2H-pyrrolyl, 3H-indolyl, 4H-quinolizinyl, azocinyl, cinnolinyl, decahydroquinolinyl, furazanyl, indolinyl, indolizinyl, indolyl, isobenzofuranyl, isoindolinyl, isoindolyl, isoquinolinyl, benzimidazolyl, isothiazolyl, isoxazolyl, morpholinyl, naphthyridinyl, octahydroisoquinolinyl, oxazolidinyl, oxazolyl, piperazinyl, piperidinyl, pyranyl, pyrazolidinyl, pyridazinyl, pyridyl, pyrimidinyl, pyrrolidinyl, pyrrolinyl, pyrrolyl, quinazolinyl, quinolinyl, quinoxalinyl, β-carbolinyl, tetrahydrofuranyl, tetrazolyl, thiazolyl, triazinyl; and 1-tetrahydroquinolinyl or 2-tetrahydroisoquinolinyl either of which can be substituted with 0–3 groups chosen from keto and $C_1$–$C_4$ alkyl;

k is 1–3;

p and q are 0–2; and r is 1–2.

Other more preferred compounds of this invention are those compounds of Formula I wherein, when Y is $CR^{29}$:

$R^1$ is methyl;

$R^3$ is $C_1$–$C_2$ alkyl, $NR^6R^7$, $OR^8$, $SR^8$, $C_1$–$C_2$ alkyl or aryl substituted with $R^{27}$, halogen, or is N-linked piperidinyl, piperazinyl, morpholino, thiomorpholino, imidazolyl, or is 2-pyridinyl, 3-pyridinyl, 4-pyridinyl, where substitution by $R^{27}$ can occur on any carbon containing substituent;

X is Br, I, $S(O)_nR^8$, $OR^8$, $NR^{14}R^{15}$, or alkyl substituted with $R^5$;

X' is hydrogen, Br, I, $S(O)_nR^8$, $OR^8$, $NR^{14}R^{15}$, or alkyl substituted with $R^5$;

$R^5$ is halogen, $C_1$–$C_2$ alkyl, $C_1$–$C_2$ alkoxy, or —$NR^{14}R^{15}$;

$R^6$ and $R^7$ are independently selected at each occurrence from the group consisting of hydrogen and $C_1$–$C_2$ alkyl, or, when considered with the commonly attached nitrogen, can be taken together to form piperidine, piperazine, morpholine or thiomorpholine;

$R^8$ is independently selected at each occurrence from the group consisting of hydrogen, $C_1$–$C_2$ alkyl, and aryl optionally substituted with 1–2 groups selected from hydrogen, $C_1$–$C_2$ alkyl, $C_1$–$C_2$ alkoxy, NHC(=O)($C_1$–$C_2$ alkyl), NH($C_1$–$C_2$alkyl), and N($C_1$–$C_2$ alkyl)$_2$;

$R^{14}$ and $R^{15}$ are independently selected at each occurrence from the group consisting of hydrogen and $C_1$–$C_2$ alkyl; and $R^{30}$ is hydrogen or cyano.

The following compounds are specifically preferred:

N-(2,4-dimethoxyphenyl)-N-methyl-4,6-dimethyl-2-pyrimidinamine;

N-(2-bromophenyl)-N-allyl-4,6-dimethyl-2-pyrimidinamine;

N-(2-bromo-4-(1-methylethyl)phenyl)-N-methyl-4,6-dimethyl-2-pyrimidinamine;

N-(2-bromophenyl)-N-ethyl-4,6-dimethyl-2-pyrimidinamine;

N-(2-bromo-4-methylphenyl)-N-methyl-4-morpholino-6-methyl-2-pyrimidinamine;

N-(2,4-dimethoxyphenyl)-N-ethyl-4,6-dimethyl-2-pyrimidinamine;

N-(2,4-dibromophenyl)-N-methyl-4,6-dimethyl-2-pyrimidinamine;

N-(2-bromo-4-ethylphenyl)-N-methyl-4,6-dimethyl-2-pyrimidinamine;
N-(2-bromo-4-tert-butylphenyl)-N-ethyl-4,6-dimethyl-2-pyrimidinamine;
N-(2-bromo-4-tert-butylphenyl)-N-methyl-4,6-dimethyl-2-pyrimidinamine;
N-(2-bromo-4-trifluoromethylphenyl)-N-methyl-4,6-dimethyl-2-pyrimidinamine;
N-(2-bromo-4-trifluoromethylphenyl)-N-ethyl-4,6-dimethyl-2-pyrimidinamine;
N-(2,4,6-trimethoxyphenyl)-N-methyl-4,6-dimethyl-2-pyrimidinamine;
N-(2,4,6-trimethoxyphenyl)-N-ethyl-4,6-dimethyl-2-pyrimidinamine;
N-(2-bromo-4-(1-methylethyl)phenyl)-N-ethyl-4-morpholino-6-methyl-2-pyrimidinamine;
N-(2-bromo-4-(1-methylethyl)phenyl)-N-allyl-4-morpholino-6-methyl-2-pyrimidinamine;
N-(2-bromo-4-n-butylphenyl)-N-allyl-4,6-dimethyl-2-pyrimidinamine;
N-(2-bromo-4-n-butylphenyl)-N-ethyl-4,6-dimethyl-2-pyrimidinamine;
N-(2-bromo-4-n-butylphenyl)-N-propyl-4,6-dimethyl-2-pyrimidinamine;
N-(2-bromo-4-(1-methylethyl)phenyl)-N-ethyl-4,6-dimethyl-2-pyrimidinamine;
N-(2-bromo-4-cyclohexylphenyl)-N-ethyl-4,6-dimethyl-2-pyrimidinamine;
N-(2-bromo-4-(1-methylethyl)phenyl)-N-ethyl-4,6-diethyl-2-pyrimidinamine;
N-(2-bromo-4-n-butylphenyl)-N-ethyl-4,6-diethyl-2-pyrimidinamine;
N-(2-bromo-4-(1-methylethyl)phenyl)-N-ethyl-4-(4-formyl-piperazino)-6-methyl-2-pyrimidinamine;
N-(2-bromo-4-(1-methylethyl)phenyl)-N-allyl-4,6-dimethyl-2-pyrimidinamine;
N-(2-iodo-4-(1-methylethyl)phenyl)-N-ethyl-4,6-dimethyl-2-pyrimidinamine;
N-(2-bromo-4-(1-methylethyl)phenyl)-N-ethyl-4-methyl-6-trifluoromethyl-2-pyrimidinamine;
N-(2-bromo-4-methoxyethyl)-N-ethyl-4,6-dimethyl-2-pyrimidinamine;
N-(2-iodo-4-(1-methylethyl)phenyl)-N-ethyl-4-morpholino-6-methyl-2-pyrimidinamine;
N-(2-bromo-4-(1-methylethyl)phenyl)-N-ethyl-4-methyl-6-(2-thiopheno)-2-pyrimidinamine;
N-(2-bromo-4-(1-methylethyl)phenyl)-N-cyanomethyl-4,6-dimethyl-2-pyrimidinamine;
N-(2-bromo-4-(1-methylethyl)phenyl)-N-cyclopropylmethyl-4,6-dimethyl-2-pyrimidinamine;
N-(2-bromo-4-(1-methylethyl)phenyl)-N-propargyl-4,6-dimethyl-2-pyrimidinamine;
N-(2-iodo-4-(1-methylethyl)phenyl)-N-ethyl-4-thiomorpholino-6-methyl-2-pyrimidinamine;
N-(2-iodo-4-methoxyethylphenyl)-N-ethyl-4,6-dimethyl-2-pyrimidinamine;
N-(2-iodo-4-methoxymethylphenyl)-N-ethyl-4,6-dimethyl-2-pyrimidinamine;
N-(2-iodo-4-methoxyethylphenyl)-N-ethyl-4-morpholino-6-methyl-2-pyrmidinamine;
N-(2-iodo-4-methoxymethylphenyl)-N-ethyl-4-morpholino-6-methyl-2-pyrimidinamine;
N-(2-methylthio-4-methoxymethylphenyl)-N-ethyl-4,6-dimethyl-2-pyrimidinamine;
N-(2-dimethylamino-4-methoxymethylphenyl)-N-ethyl-4,6-dimethyl -2-pyrimidinamine;
N-(2-methylthio-4-methoxymethylphenyl)-N-ethyl-4,6-dimethyl-2-pyrimidinamine;
N-(2-methylthio-4-(1-methylethyl)phenyl)-N-ethyl-4,6-dimethyl-2-pyrimidinamine;
N-(2-dimethylamino-4-(1-methylethyl)phenyl)-N-ethyl-4,6-dimethyl-2-pyrimidinamine;
N-(2,4-dimethylthiophenyl)-N-ethyl-4,6-dimethyl-2-pyrimidinamine;
N-(2-methylthio-4-methylthiomethylphenyl)-N-ethyl-4,6-dimethyl-2-pyrimidinamine;
N-(2,6-dibromo-4-(1-methylethyl)phenyl)-N-ethyl-4,6-dimethyl-2-pyrimidinamine;
N-(2,6-dibromo-4-(1-methylethyl)phenyl)-N-ethyl-4-methyl-6-thiomorpholino-2-pyrimidinamine;
N-(2,4-diiodophenyl)-N-ethyl-4,6-dimethyl-2-pyrimidinamine;
N-(2,4-diiodophenyl)-N-ethyl-4-morpholino-6-methyl-2-pyrimidinamine;
N-(2-bromo-4-(1-methylethyl)phenyl)-N-ethyl-4-methyl-2-pyrimidinamine;
N-(2-bromo-4-(1-methylethyl)phenyl)-N-ethyl-4-methyl-6-(N-methyl-2-hydroxyethylamino)-2-pyrimidinamine;
N-(2,6-dimethoxy-4-methylphenyl)-N-ethyl-4,6-dimethyl-2-pyrimidinamine;
N-(4-iodophenyl)-N-methyl-4,6-diethyl-2-pyrmidinamine;
N-(2-iodophenyl)-N-methyl-4,6-dimethyl-2-pyrimidinamine;
N-(2-trifluoromethylphenyl)-N-methyl-4,6-dimethyl-2-pyrimidinamine;
4,6-dimethyl-2-(N-(2-bromo-4-(1-methylethyl)phenyl)-N-methylamino)pyridine;
4,6-dimethyl-2-(N-(2-bromo-4-(1-methylethyl)phenyl)-N-ethylamino)pyridine;
N-(2-bromo-4-(1-methylethyl)phenyl)-N-ethyl-2,4-dimethoxy-6-pyrimidinamine;
2,6-dimethyl-4-(N-(2-bromo-4-(1-methylethyl)phenyl)amino)pyridine;
N-(2-bromo-4-(1-methylethyl)phenyl)-N-ethyl-6-methyl-4-(4-morpholinylcarbonyl)-2-pyrimidinamine;
N-(2-bromo-4-(1-methylethyl)phenyl)-N-ethyl-6-methyl-4-(morpholinylmethyl)-2-pyrimidinamine;
N-(2-bromo-4-(1-methylethyl)phenyl)-N-ethyl-6-methyl-4-(1-piperidinylcarbonyl)-2-pyrimidinamine;
Methyl-2-((2-bromo-4-(1-methylethyl)phenyl)ethylamino)-6-methyl-4-pyrimidinecarboxylate;
2-((2-bromo-4-(1-methylethyl)phenyl)ethylamino)-N-cyclohexyl-6-methyl-4-pyrimidinecarboxamide;
N-(2-bromo-4-(1-methylethyl)phenyl)-N-ethyl-6-methyl-4-(4-methyl-1-piperazinylcarbonyl)-2-pyrimidinamine;
N-{2-bromo-4-(1-methylethyl)phenyl}-N-ethyl-4,6-dimethyl-1,3,5-triazin-2-amine;
N-{2-bromo-4-(1-methylethyl)phenyl}-N-ethyl-4-methyl-6-(4-morpholinyl)-1,3,5-triazin-2-amine;
N-ethyl)-N-{2-iodo-4-(1-methylethyl)phenyl}-4-methyl-6-(4-thiomorpholinyl)-1,3,5-triazin-2-amine;
N-ethyl-N-{2-iodo-4-(1-methylethyl)phenyl}-4-methyl-6-(4-morpholinyl)-1,3,5-triazin-2-amine;
N-ethyl-N-{2 -iodo-4-(1-methylethyl)phenyl}-4-methyl-6-(1-piperidinyl)-1,3,5-triazin-2-amine;
1-(2-bromo-4-isopropylphenyl)-4,6-dimethyl-7-azaindole;
1-(2-bromo-4-isopropylphenyl)-3-cyano-4,6-dimethyl-7-azaindole;
1-(2-bromo-4-isopropylphenyl)-3-cyano-4-phenyl-6-methyl-7-azaindole;
1-(2-bromo-4-isopropylphenyl)-4-phenyl-6-methyl-7-azaindole;
1-(2-bromo-4,6-dimethoxyphenyl)-1)-3-cyano-4,6-dimethyl-7-azaindole:
1-(2-bromo-4,6-dimethoxyphenyl)-4,6-dimethyl-7-azaindole;

N-{2-bromo-4(1-methylethyl)phenyl}-N-ethyl-4-N,N-diethylamino-6-methyl-1,3,5 triazin-2-amine;
N-{2-bromo-4(1-methylethyl)phenyl}-N-ethyl-4,6-dichloro-1,3,5 triazin-2-amine;
N-{2-bromo-4(1-methylethyl)phenyl}-N-ethyl-4,6-dimethoxy-1,3,5 triazin-2-amine;
N-{2-bromo-4(1-methylethyl)phenyl}-N-ethyl-4-imidazolino-6-methyl-1,3,5 triazin-2-amine;
N-(2-bromo-4,6-dimethoxyphenyl)-N-ethyl-4-morpholino-6-methyl-1,3,5 triazin-2-amine;
N-(2-bromo-4,6-dimethoxyphenyl)-N-ethyl-4-N,N-dimethylamino-6-methyl-1,3,5 triazin-2-amine;
N-(2,4,6-trimethoxyphenyl)-N-ethyl-4-morpholino-6-methyl-1,3,5 triazin-2-amine,
N-{2-bromo-4(1-methylethyl)phenyl}-N-ethyl-4-N,N-dimethylamino-6-methyl-1,3,5 triazin-2-amine;
N-{2-bromo-4(1-methylethyl)phenyl}-N-ethyl-4-thiozolidino-6-methyl-1,3,5 triazin-2-amine;
N-{2-bromo-4(1-methylethyl)phenyl}-N-ethyl-4-benzyloxy-6-methyl-1,3,5 triazin-2-amine;
N-{2-bromo-4(1-methylethyl)phenyl}-N-ethyl-4-phenyloxy-6-methyl-1,3,5 triazin-2-amine;
N-(2-bromo-4,6-dimethoxyphenyl)-N-ethyl-4-{4-(ethylpiperizinoate)}-6-methyl-1,3,5 triazin-2-amine;
N-(2-bromo-4,6-dimethoxyphenyl)-N-ethyl-4-{4-(piperizinic acid)}-6-methyl-1,3,5 triazin-2-amine;
N-{2-bromo-4(1-methylethyl)phenyl}-N-ethyl-4-{3-(malon-2-yldiethyl ester)}-6-methyl-1,3,5-triazin-2-amine;
N-(2-bromo-4,6-dimethoxyphenyl)-N-ethyl-4-(1-cyano-1-phenylmethyl)-6-methyl-1,3,5 triazin-2-amine;
N-(2-bromo-4,6-dimethoxyphenyl)-N-1-methylethyl-4-morpholino-6-methyl-1,3,5 triazin-2-amine;
N-(2-iodo-4-dimethylhydroxymethylphenyl)-N-ethyl-4,6-dichloro-1,3,5 triazin-2-amine;
N-{2-bromo-4-(1-methylethyl)phenyl}-N-ethyl-4-methyl-6-(thiomethyl)-2-pyrimidinamine;
N-{2-bromo-4-(1-methylethyl)phenyl}-N-ethyl-4-methyl-6-(thiomethyl)-2-pyrimidinamine, S-dioxide;
N-{2-bromo-4-(1-methylethyl)phenyl}-N-ethyl-4-methyl-6-(thiomethyl)-2-pyrimidinamine, S-oxide;
N-{2-bromo-4(1-methylethyl)phenyl}-N-ethyl-4-methyl-6-benzyloxy-1,3,5 triazin-2-amine;
N-(2-iodo-4-dimethylhydroxymethyl)-N-ethyl-4,6-dichloro-1,3,5 triazin-2-amine;
N-{2-iodo-4-(1-methylethyl)phenyl}-N-allyl-4-morpholino-6-methyl-2-pyrimidinamine;
N-{2-iodo-4-(1-methylethyl)phenyl}-N-ethyl-4-chloro-6-methyl-2-pyrimidinamine;
N-{2-methylthio-4-(1-methylethyl)phenyl}-N-ethyl-4(S)-(N-methyl-2-pyrrolidinomethoxy)-6-methyl-2-pyrimidinamine;
N-{2,6-dibromo-4-(1-methylethyl)phenyl}-4-thiomorpholino-6-methyl-2-pyrimidinamine;
N-{2-methylthio-4-(1-methylethyl)phenyl}-N-ethyl-4,6-dimethyl-2-pyrimidinamine;
N-{2-methylthio-4-(1-methylethyl)phenyl}-N-ethyl-4,6-dimethyl-2-pyrimidinamine;
N-{2-methylsulfinyl-4-(1-methylethyl)phenyl}-N-ethyl-4,6-dimethyl-2-pyrimidinamine;
N-{2-iodo-4-(1-methylethyl)phenyl}-N-ethyl-4-thiazolidino-6-methyl-2-pyrimidinamine;
N-(2-iodo-4-methoxymethylphenyl)-N-ethyl-4,6-dimethyl-2-pyrimidinamine;
N-(4,6-dimethyl-2-pyrimidinamino)-2,3,4,5-tetrahydro-4-(1-methylethyl)-1,5-benzothiazepine;
N-{2-methylsulfonyl-4-(1-methylethyl)phenyl}-N-ethyl-4,6-dimethyl-2-pyrimidinamine;
N-{2-ethylthio-4-(1-methylethyl)phenyl}-N-ethyl-4,6-dimethyl-2-pyrimidinamine;
N-(2-ethylthio-4-methoxyiminoethylphenyl)-N-ethyl-4,6-dimethyl-2-pyrimidinamine;
N-(2-methylthio-4-methoxyiminoethylphenyl)-N-ethyl-4,6-dimethyl-2-pyrimidinamine;
N-(2-methylsulfonyl-4-methoxyiminoethylphenyl)-N-ethyl-4,6-dimethyl-2-pyrimidinamine;
N-(4-bromo-2-methylthiophenyl)-N-ethyl-4,6-dimethyl-2-pyrimidinamine;
N-(4-ethyl-2-methylthiophenyl)-N-(1-methylethyl)-4,6-dimethyl-2-pyrimidinamine;
N-(4-ethyl-2-methylthiophenyl)-N-ethyl-4,6-dimethyl-2-pyrimidinamine;
N-{2-methylthio-4-(N-acetyl-N-methylamino)phenyl}-N-ethyl-4,6-dimethyl-2-pyrimidinamine;
N-(4-carboethoxy-2-methylthiophenyl)-N-ethyl-4,6-dimethyl-2-pyirmidinamine;
N-(4-methoxy-2-methylthiophenyl)-N-ethyl-4,6-dimethyl-2-pyrimidinamine;
N-(4-cyano-2-methylthiophenyl)-N-ethyl-4,6-dimethyl-2-pyrimidinamine;
N-(4-acetyl-2-methylthiophenyl)-N-ethyl-4,6-dimethyl-2-pyrimidinamine;
N-(4-propionyl-2-methylthiophenyl)-N-ethyl-4,6-dimethyl-2-pyrimidinamine;
N-{4-(1-methoxyethyl)-2-methylthiophenyl}-N-ethyl-4,6-dimethyl-2-pyrimidinamine;
N-{4-(N-methylamino)-2-methylthiophenyl}-N-ethyl-4,6-dimethyl-2-pyrimidinamine;
N-{4-(N,N-dimethylamino)-2-methylthiophenyl}-N-ethyl-4,6-dimethyl-2-pyrimidinamine;
N-{2-bromo-4-(1-methylethyl)phenyl}-N-ethyl-4-formyl-6-methyl-2-pyrimidinamine;
N-{2-bromo-4-(1-methylethyl)phenyl}-N-ethyl-4-hydroxyethoxymethyl-6-methyl-2-pyrimidinamine;
N-(2-bromo-6-hydroxy-4-methoxyphenyl)-N-ethyl-4,6-dimethyl-2-pyrimidinamine;
N-(3-bromo-4,6-dimethoxyphenyl)-N-ethyl-4,6-dimethyl-2-pyrimidinamine;
N-(2,3-dibromo-4,6-dimethoxyphenyl)-N-ethyl-4,6-dimethyl-2-pyrimidinamine;
N-(2,6-dibromo-4-(ethoxy)phenyl)-N-ethyl-4,6-dimethyl-2-pyrimidinamine;
1-(2-bromo-4-isopropylphenyl)-3-cyano-4,6-dimethyl-7-azaindole;
1-(2-bromo-4-isopropylphenyl)-4,6-dimethyl-7-azaindole;
1-(2-bromo-4-isopropylphenyl)-3-cyano-6-methyl-4-phenyl-7-azaindole;
1-(2-bromo-4-isopropylphenyl)-6-methyl-4-phenyl-7-azaindole;
1-(2-bromo-4,6-dimethoxyphenyl)-3-cyano-4,6-dimethyl-7-azaindole;
1-(2-bromo-4,6-dimethoxyphenyl)-4,6-dimethyl-7-azaindole;
1-(2-bromo-4-isopropylphenyl)-6-chloro-3-cyano4-methyl-7-azaindole;
1-(2-bromo-4-isopropylphenyl)-6-chloro-4-methyl-7-azaindole;
1-(2-bromo-4-isopropylphenyl)-4-chloro-34yano-methyl-7-azaindole;
1-(2-bromo-4-isopropylphenyl)-4-chloro-6-methyl-7-azaindole;
N-(2-bromo-6-methoxy-pyridin-3-yl)-N-ethyl-4,6-dimethyl-2-pyrimidinamine;
N-(3-bromo-5-methyl-pyridin-2-yl)-N-ethyl-4,6-dimethyl-2-pyrimidinamine;

N-(6-methoxy-pyridin-3-yl)-N-ethyl-4,6-dimethyl-2-pyrimidinamine;
N-(2-bromo-6-methoxy-pyridin-3-yl)-N-ethyl-4-methyl-6-(4-morpholinyl)-1,3,5 triazin-2-amine;
N-{2-bromo-4-(1-methylethyl)phenyl}-N-ethyl-4-{N-(2-furylmethyl)-N-methylamino}carbonyl-6-methylpyrimidinamine;
N-{2-bromo-4-(1-methylethyl)phenyl}-N-ethyl-4-{(4,4-ethylenedioxypiperidino)carbonyl}-6-methylpyrimidinamine;
N-{2-bromo-4-(1-methylethyl)phenyl}-N-ethyl-4-(4-oxopiperidino)carbonyl-6-methylpyrimidinamine;
N-{2-bromo-4-(1-methylethyl)phenyl}-N-ethyl-4-(4-oxopiperidino)methyl-6-methylpyrimidinamine, hydrochloride salt;
N-{2-bromo-4-(1-methylethyl)phenyl}-N-ethyl-4-(imidazol-1-yl)methyl-6-methylpyrimidinamine;
N-{2-bromo-4-(1-methylethyl)phenyl}-N-ethyl-4-{3-(methoxyphenyl)methoxymethyl}-6-methylpyrimidinamine;
N-{2-bromo-4-(1-methylethyl)phenyl}-N-ethyl-4-(2-thiazolyl)carbonyl-6-methylpyrimidinamine;
N-{2-bromo-4-(1-methylethyl)phenyl}-N-ethyl-4-(2-imidazolyl)carbonyl-6-methylpyrimidinamine;
N-{2-bromo-4-(1-methylethyl)phenyl}-N-ethyl-4-(5-indolylcarbonyl)-6-methylpyrimidinamine;
N-{2-bromo-4-(1-methylethyl)phenyl}-N-ethyl-4-(4-fluorophenyl)carbonyl-6-methylpyrimidinamine;
N-{2-bromo-4-(1-methylethyl)phenyl}-N-ethyl-4-carboxy-6-methylpyrimidinamine;
N-{2-bromo-4-(1-methylethyl)phenyl}-N-ethyl-4-acetyl-6-methylpyrimidinamine;
N-{2-bromo-4-(1-methylethyl)phenyl}-N-ethyl-4-(hydroxy-3-pyridyl-methyl)-6-methylpyrimidinamine;
N-{2-bromo-4-(1-methylethyl)phenyl}-N-ethyl-4-{4-(methoxyphenyl)-3-pyridyl-hydroxymethyl}-6-methylpyrimidinamine;
N-{2-bromo-4-(1-methylethyl)phenyl}-N-ethyl-4-(3-pyrazolyl)-6-methylpyrimidinamine, hydrochloride salt;
N-{2-bromo-4-(1-methylethyl)phenyl}-N-ethyl-4-(1-aminoethyl)-6-methylpyrimidinamine;
N-{2-bromo-4-(1-methylethyl)phenyl}-N-ethyl-4-{2-(4-tetrazolyl)-1-methylethyl}-6-methylpyrimidinamine;
2-(N-{2-bromo-4-(2-propyl)phenyl}amino)-4-carbomethoxy-6-methylpyrimidine;
2-(N-{2-bromo-4-(2-propyl)phenyl}-N-ethylamino)-4-carbomethoxy-6-methylpyrimidine;
2-(N-{2-bromo-4-(2-propyl)phenyl}-N-ethylamino)-6-methylpyrimidine-4-morpholinocarbonyl;
9{2-bromo-4-(2-propyl)phenyl}-2-methyl-6-morpholino purine;
9{2-bromo-4-(2-propyl)phenyl}-2-methyl-6-morpholino-8-azapurine;
1{2-bromo-4-(2-propyl)phenyl}-2-methyl-6-morpholino-5,7-diaza-indazole; and
2-(N-{2-bromo-4-(2-propyl)phenyl}-N-ethylamino)-4-(morpholinomethyl)-6-methylpyrimidine.

The above-described compounds and their corresponding salts possess antagonistic activity for the corticotropin releasing factor receptor and can be used for treating affective disorders, anxiety, depression, irritable bowel syndrome, immune suppression, Alzheimer's disease, gastrointestinal diseases, anorexia nervosa, drug and alcohol withdrawal symptoms, drug addiction, inflammatory disorders, or fertility problems in mammals.

Further included in this invention is a method of treating affective disorders, anxiety, depression, irritable bowel syndrome, immune suppression, Alzheimer's disease, gastrointestinal diseases, anorexia nervosa, drug and alcohol withdrawal symptoms, drug addiction, inflammatory disorders, or fertility problems in mammals in need of such treatment comprising administering to the mammal a therapeutically effective amount of a compound of formula (I):

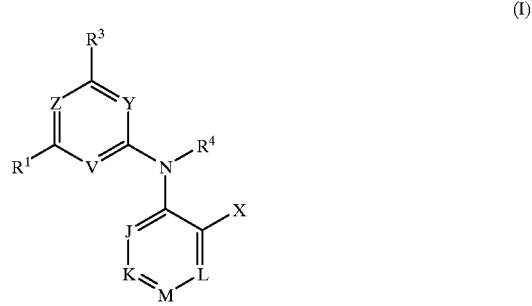

(I)

or a pharmaceutically acceptable salt or prodrug thereof, wherein Y is $CR^{3a}$, N, or $CR^{29}$;

when Y is $CR^{3a}$ or N:

$R^1$ is independently selected at each occurrence from the group consisting of $C_1$–$C_4$ alkyl, halogen, $C_1$–$C_2$ haloalkyl, $NR^6R^7$, $OR^8$, and $S(O)_nR^8$;

$R^3$ is $C_1$–$C_4$ alkyl, aryl, $C_3$–$C_6$ cycloalkyl, $C_1$–$C_2$ haloalkyl, halogen, nitro, $NR^6R^7$, $OR^8$, $S(O)_nR^8$, $C(=O)R^9$, $C(=O)NR^6R^7$, $C(=S)NR^6R^7$, —$(CHR^{16})_k$ $NR^6R^7$, $(CH_2)_kOR^8$, $C(=O)NR^{10}CH(R^{11})CO_2R^{12}$, —$C(OH)(R^{25})(R^{25a})$, —$(CH_2)_pS(O)_n$-alkyl, —$(CHR^{16})R^{25}$, —$C(CN)(R^{25})(R^{16})$ provided that $R^{25}$ is not —NH— containing rings, —$C(=O)R^{25}$, —CH$(CO_2R^{16})_2$, $NR^{10}C(=O)CH(R^{11})NR^{10}R^{12}$, $NR^{10}CH(R^{11})CO_2R^{12}$; substituted $C_1$–$C_4$ alkyl, substituted $C_2$–$C_4$ alkenyl, substituted $C_2$–$C_4$ alkynyl, substituted $C_1$–$C_4$ alkoxy, aryl-(substituted $C_1$–$C_4$) alkyl, aryl-(substituted $C_1$–$C_4$) alkoxy, substituted $C_3$–$C_6$ cycloalkyl, amino-(substituted $C_1$–$C_4$) alkyl, substituted $C_1$–$C_4$ alkylamino, where substitution by $R^{27}$ can occur on any carbon containing substituent; 2-pyridinyl, imidazolyl, 3-pyridinyl, 4-pyridinyl, 2-methyl-3-pyridinyl, 4-methyl-3-pyridinyl, furanyl, 5-methyl-2-furanyl, 2,5-dimethyl-3-furanyl, 2-thienyl, 3-thienyl, 5-methyl-2-thienyl, 2-pheno-thiazinyl, 4-pyrazinyl, azetidinyl, phenyl, 1H-indazolyl, 2-pyrrolidonyl, 2H,6H-1,5,2-dithiazinyl, 2H-pyrrolyl, 3H-indolyl, 4-piperidonyl, 4aH-carbazolyl, 4H-quinolizinyl, 6H-1,2,5-thiadiazinyl, acridinyl, azocinyl, azepinyl, benzofuranyl, benzothiophenyl, carbazolyl, chromanyl, chromenyl, cinnolinyl, decahydroquinolinyl, furazanyl, imidazolidinyl, indolinyl, indolizinyl, indolyl, isobenzofuranyl, isochromanyl, isoindolinyl, isoindolyl, isoquinolinyl benzimidazolyl, isothiazolyl, isoxazolyl, morpholinyl, naphthyridinyl, octahydroisoquinolinyl, oxazolidinyl, oxazolyl, phenanthridinyl, phenanthrolinyl, phenazinyl, phenoxathiinyl, phenoxazinyl, phthalazinyl, piperazinyl, piperidinyl, pteridinyl, purinyl, pyranyl, pyrazolidinyl, pyrazolinyl, pyrazolyl, pyridazinyl, pyrimidinyl, pyrrolidinyl, pyrrolinyl, pyrrolyl, quinazolinyl, quinolinyl, quinoxalinyl, quinuclidinyl, β-carbolinyl, tetrahydrofuranyl, tetrahydroisoquinolinyl, tetrahydroquinolinyl, tetrazolyl, thianthrenyl, thiazolyl, thiophenyl, triazinyl, xanthenyl; or 1-tetrahydroquinolinyl or 2-tetrahydroisoquinolinyl either of which can be substituted with 0–3 groups chosen from keto and $C_1$–$C_4$ alkyl;

J, K, and L are independently selected at each occurrence from the group of
N, CH, and CX';

M is $CR^5$ or N;

V is $CR^{1a}$ or N;

Z is $CR^2$ or N;

$R^{1a}$, $R^2$, and $R^{3a}$ are independently selected at each occurrence from the group consisting of hydrogen, halo, halomethyl, $C_1$–$C_3$ alkyl, and cyano;

$R^4$ is $(CH_2)_mOR^{16}$, $C_1$–$C_4$ alkyl, allyl, propargyl, $(CH_2)_m R^{13}$, or —$(CH_2)_mOC(O)R^{16}$;

X is halogen, $S(O)_2R^8$, $SR^8$, halomethyl, —$(CH_2)_pOR^8$, —$OR^8$, cyano, —$(CHR^{16})_pNR^{14}R^{15}$, —$C(=O)R^8$, $C_1$–$C_6$ alkyl, $C_4$–$C_{10}$ cycloalkylalkyl, $C_1$–$C_{10}$alkenyl, $C_2$–$C_{10}$alkynyl, $C_1$–$C_{10}$alkoxy, aryl-$(C_2$–$C_{10})$-alkyl, $C_3$–$C_6$ cycloalkyl, aryl-$(C_1$–$C_{10})$-alkoxy, nitro, thio-$(C_1$–$C_{10})$-alkyl, —$C(=NOR^{16})$—$C_1$–$C_4$-alkyl, —$C(=NOR^{16})H$, or —$C(=O)NR^{14}R^{15}$ where substitution by $R^{18}$ can occur on any carbon containing substituents;

X' is independently selected at each occurrence from the group consisting of hydrogen, halogen, $S(O)_nR^8$, halomethyl, —$(CHR^{16})_pOR^8$, cyano, —$(CHR^{16})_p NR^{14}R^{15}$, $C(=O)R^8$, $C_1$–$C_6$ alkyl, $C_2$–$C_{10}$ alkenyl, $C_2$–$C_{10}$ alkynyl, $C_1$–$C_{10}$ alkoxy, aryl-$(C_1$–$C_{10})$-alkyl, $C_3$–$C_6$ cycloalkyl, aryl-$(C_1$–$C_{10})$-alkoxy, nitro, thio-$(C_1$–$C_{10})$-alkyl, —$C(=NOR^{16})$—$C_1$–$C_4$-alkyl, —$C(=NOR^{16})H$, and —$C(=O)NR^{14}R^{15}$ where substitution by $R^{18}$ can occur on any carbon containing substituents;

$R^5$ is halo, —$C(=NOR^{16})$—$C_{1-4}$-alkyl, $C_1$–$C_6$ alkyl, $C_1$–$C_3$ haloalkyl, —$(CHR^{16})_pOR^8$, —$(CHR^{16})_pS(O)_n R^8$, —$(CHR^{16})_pNR^{14}R^{15}$, $C_3$–$C_6$cycloalkyl, $C_2$–$C_{10}$alkenyl, $C_1$–$C_{10}$ alkynyl, aryl-$(C_2$–$C_{10})$-akyl, aryl-$(C_1$–$C_{10})$-alkoxy, cyano, $C_3$–$C_6$ cycloalkoxy, nitro, amino-$(C_2$–$C_{10})$-alkyl, thio-$(C_2$–$C_{10})$-alkyl, $SO_n(R^8)$, $C(=O)R^8$, —$C(=NOR^{16})H$, or —$C(=O)NR^{14}R^{15}$, where substitution by $R^{18}$ can occur on any carbon containing substituents;

$R^6$ and $R^7$ are independently selected at each occurrence from the group consisting of hydrogen, $C_1$–$C_6$ alkyl, $C_3$–$C_{10}$ cycloalkyl, $C_1$–$C_6$ alkoxy, $(C_4$–$C_{12})$-cycloalkylalkyl, —$(CH_2)_kR^{13}$, $(CHR^{16})_pOR^8$, —$(C_1$–$C_6$ alkyl)-aryl, heteroaryl, aryl, —$S(O)_n$-aryl or —$(C_1$–$C_6$ alkyl)-heteroaryl or aryl wherein the aryl or heteroaryl groups are optionally substituted with 1–3 groups selected from the group consisting of hydrogen, halogen, $C_1$–$C_6$ alkyl, $C_1$–$C_6$ alkoxy, amino, NHC$(=O)(C_1$–$C_6$ alkyl), NH($C_1$–$C_6$ alkyl), N($C_1$–$C_6$ alkyl)$_2$, nitro, carboxy, $CO_2(C_1$–$C_6$ alkyl), cyano, and $S(O)_z$—($C_1$–$C_6$-alkyl); or can be taken together to form —$(CH_2)_qA(CH_2)_r$—, optionally substituted with 0–3 $R^{17}$; or, when considered with the commonly attached nitrogen, can be taken together to form a heterocycle, said heterocycle being substituted on carbon with 1–3 groups consisting of hydrogen, $C_1$–$C_6$ alkyl, hydroxy, or $C_1$–$C_6$ alkoxy;

A is $CH_2$, O, $NR^{25}$, $C(=O)$, $S(O)_n$, $N(C(=O)R^{17})$, $N(R^{19})$, $C(H)(NR^{14}R^{15})$, $C(H)(OR^{20})$, $C(H)(C(=O)R^{21})$, or $N(S(O)_nR^{21})$;

$R^8$ is independently selected at each occurrence from the group consisting of hydrogen; $C_1$–$C_6$ alkyl; —$(C_4$–$C_{12})$ cycloalkylalkyl; $(CH_2)_nR^{22}$; $C_3$–$C_{10}$ cycloalkyl; —$NR^6R^7$; aryl; —$NR^{16}(CH_2)_nNR^6R^7$; —$(CH_2)_kR^{25}$; and $(CH_2)_t$heteroaryl or $(CH_2)_t$aryl, either of which can optionally be substituted with 1–3 groups selected from the group consisting of hydrogen, halogen, $C_1$–$C_6$ alkyl, $C_1$–$C_6$ alkoxy, amino, NHC$(=O)(C_1$–$C_6$ alkyl), NH($C_1$–$C_6$ alkyl), N($C_1$–$C_6$ alkyl)$_2$, nitro, carboxy, $CO_2(C_1$–$C_6$ alkyl), cyano, and $S(O)_z(C_1$–$C_6$-alkyl);

$R^9$ is independently selected at each occurrence from $R^{10}$, hydroxy, $C_1$–$C_4$ alkoxy, $C_3$–$C_6$ cycloalkyl, $C_1$–$C_4$ alkenyl, aryl substituted with 0–3 $R^{18}$, and —$(C_1$–$C_6$ alkyl)-aryl substituted with 0–3 $R^{18}$;

$R^{10}$, $R^{16}$, $R^{23}$, and $R^{24}$ are independently selected at each occurrence from hydrogen or $C_1$–$C_4$ alkyl;

$R^{11}$ is $C_1$–$C_4$ alkyl substituted with 0–3 groups chosen from the following: keto, amino, sulfhydryl, hydroxyl, guanidinyl, p-hydroxyphenyl, imidazolyl, phenyl, indolyl, indolinyl, or, when taken together with an adjacent $R^{10}$, are $(CH_2)_t$;

$R_{12}$ is hydrogen or an appropriate amine protecting group for nitrogen or an appropriate carboxylic acid protecting group for carboxyl;

$R^{13}$ is independently selected at each occurrence from the group consisting of CN, $OR^{19}$, $SR^{19}$, and $C_3$–$C_6$ cycloalkyl;

$R^{14}$ and $R^{15}$ are independently selected at each occurrence from the group consisting of hydrogen, $C_4$–$C_{10}$ cycloalkyl-alkyl, and $R^{19}$;

$R^{17}$ is independently selected at each occurrence from the group consisting of $R^{10}$, $C_1$–$C_4$ alkoxy, halo, $OR^{23}$, $SR^{23}$, $NR^{23}R^{24}$, and $(C_1$–$C_6)$ alkyl $(C_1$–$C_4)$ alkoxy;

$R^{18}$ is independently selected at each occurrence from the group consisting of $R^{10}$, hydroxy, halogen, $C_1$–$C_2$ haloalkyl, $C_1$–$C_4$ alkoxy, $C(=O)R^{24}$, and cyano;

$R^{19}$ is independently selected at each occurrence from the group consisting of $C_1$–$C_6$ alkyl, $C_3$–$C_6$ cycloalkyl, $(CH_2)_wR^{22}$, and aryl substituted with 0–3 $R^{18}$;

$R^{20}$ is independently selected at each occurrence from the group consisting of $R^{10}$, $C(=O)R^{31}$, and $C_2$–$C_4$ alkenyl;

$R^{21}$ is independently selected at each occurrence from the group consisting of $R^{10}$, $C_1$–$C_4$¯ alkoxy, $NR^{23}R^{24}$, and hydroxyl;

$R^{22}$ is independently selected at each occurrence from the group consisting of cyano, $OR^{24}$, $SR^{24}$, $NR^{23}R^{24}$, $C_1$–$C_6$ alkyl, $C_3$–$C_6$ cycloalkyl, —$S(O)_nR^{31}$, and —$C(=O)R^{25}$;

$R^{25}$, which can be optionally substituted with 0–3 $R^{17}$, is independently selected at each occurrence from the group consisting of phenyl, pyrazolyl, imidazolyl, 2-methyl-3-pyridinyl, 4-methyl-3-pyridinyl, furanyl, 5-methyl-2-furanyl, 2,5-dimethyl-3-furanyl, 2-thienyl, 3-thienyl, 5-methyl-2-thienyl, 2-pheno-thiazinyl, 4-pyrazinyl, azetidinyl, 1H-indazolyl, 2-pyrrolidonyl, 2H,6H-1,5,2-dithiazinyl, 2H-pyrrolyl, 3H-indolyl, 4-piperidonyl, 4aH-carbazolyl, 4H-quinolizinyl, 6H-1,2,5-thiadiazinyl, acridinyl, azocinyl, azepinyl, benzofuranyl, benzothiophenyl, carbazolyl, chromanyl, chromenyl, cinnolinyl, decahydroquinolinyl, furazanyl, indolinyl, indolizinyl, indolyl, isobenzofuranyl, isochromanyl, isoindolinyl, isoindolyl, isoquinolinyl benzimidazolyl, isothiazolyl, isoxazolyl, morpholinyl, naphthyridinyl, octahydroisoquinolinyl, oxazolidinyl, oxazolyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazolidinyl, pyridazinyl, pyridyl, pyrimidinyl, pyrrolidinyl, pyrrolinyl, pyrrolyl, quinazolinyl, quinolinyl, quinoxalinyl, quinuclidinyl, β-carbolinyl, tetrahydrofuranyl, tetrazolyl, thianthrenyl, thiazolyl, thiophenyl, triazinyl, xanthenyl; and 1-tetrahydroquinolinyl or 2-tetrahydroisoquinolinyl either of which can be substituted with 0–3 groups chosen from keto and $C_1$–$C_4$ alkyl;

$R^{25a}$, which can be optionally substituted with 0–3 $R^{17}$, is independently selected at each occurrence from the group consisting of H and $R^{25}$;

$R^{27}$ is independently selected at each occurrence from the group consisting of $C_1$–$C_3$ alkyl, $C_2$–$C_4$ alkenyl, $C_2$–$C_4$ alkynyl, $C_2$–$C_4$ alkoxy, aryl, nitro, cyano, halogen, aryloxy, and heterocycle optionally linked through O;

$R^{31}$ is independently selected at each occurrence from the group consisting of $C_1$–$C_4$ alkyl, $C_3$–$C_7$ cycloalkyl, $C_4$–$C_{10}$ cycloalkyl-alkyl, and aryl-($C_1$–$C_4$) alkyl;

k, m, and r are independently selected at each occurrence from 1–4;

n is independently selected at each occurrence from 0–2;

p, q, and z are independently selected at each occurrence from 0–3;

t and w are independently selected at each occurrence from 1–6, provided that when J is CX' and K and L are both CH, and M is $CR^5$, then
  (A) when V and Y are N and Z is CH and $R^1$ and $R^3$ are methyl,
    (1) and $R^4$ is methyl, then
      (a) $R^5$ can not be methyl when X is OH and X' is H;
      (b) $R^5$ can not be —$NHCH_3$ or —$N(CH_3)_2$ when X and X' are —$OCH_3$; and
      (c) $R^5$ can not be –$N(CH_3)_2$ when X and X' are —$OCH_2CH_3$;
    (2) and $R^4$ is ethyl, then
      (a) then $R^5$ can not be methylamine when X and X' are —$OCH_3$;
      (b) $R^5$ can not be OH when X is Br and X' is OH; and
      (c) $R^5$ can not be —$CH_2OH$ or —$CH_2N(CH_3)_2$ when X is —$SCH3$ and X' is H;
  (B) when V and Y are N, Z is CH, $R^4$ is ethyl, $R^5$ is iso-propyl, X is Br, X' is H, and
    (1) $R^1$ is $CH_3$, then
      (a) $R^3$ can not be OH, piperazin-1-yl, —$CH_2$-piperidin-1-yl, —$CH_2$-(N-4-methylpiperazin-1-yl), —C(O)NH-phenyl, —$CO_2H$, —$CH_2O$-(4-pyridyl), —$C(O)NH_2$, 2-indolyl, —$CH_2O$-(4-carboxyphenyl), —$N(CH_2CH_3)$(2-bromo-4-isopropylphenyl);
    (2) $R^1$ is —$CH_2CH_2CH_3$ then $R^3$ can not be —$CH_2CH_2CH_3$;
  (C) when V, Y and Z are N, $R^4$ is ethyl, and
    (1) $R^5$ is iso-propyl, X is bromo, and X' is H, then
      (a) $R^3$ can not be OH or —$OCH_2CN$ when $R^1$ is $CH_3$; and
      (b) $R^3$ can not be —$N(CH_3)_2$ when $R^1$ is —$N(CH_3)_2$;
    (2) $R^5$ is —OCH—, X is —$OCH_3$, and X' is H, then $R^3$ and $R^1$ can not both be chloro;

further provided that when J, K, and L are all CH and M is $CR^5$, then (D) at least one of V, Y, and Z must be N;
  (E) when V is $CR^{1a}$, Z and Y can not both be N;
  (F) when Y is $CR^{3a}$, Z and V can not both be N;
  (G) when Z is $CR^2$, V and Y must both be N;
  (H) Z can be N only when both V and Y are N or when V is $CR^{1a}$ and Y is $CR^{3a}$;
  (I) when V and Y are N, Z is $CR^2$, and $R^2$ is H or $C_1$–$C_3$ alkyl, and $R^4$ is $C_1$–$C_3$ alkyl, $R^3$ can not be 2-pyridinyl, indolyl, indolinyl, imidazolyl, 3-pyridinyl, 4-pyridinyl, 2-methyl-3-pyridinyl, 4-methyl-3-pyridinyl, furanyl, 5-methyl-2-furanyl, 2,5-dimethyl-3-furanyl, 2-thienyl, 3-thienyl, 5-methyl-2-thienyl, 2-phenothiazinyl, or 4-pyrazinyl;
  (J) when V and Y are N; Z is $CR^2$; $R^2$ is H or $C_1$–$C_3$ alkyl; $R^4$ is $C_1$–$C_4$ alkyl; $R^5$, X, and/or X' are OH, halo, $CF_3$, $C_1$–$C_4$ alkyl, $C_1$–$C_4$ alkoxy, $C_1$–$C_4$ alkylthio, cyano, amino, carbamoyl, or $C_1$–$C_4$ alkanoyl; and $R^1$ is $C_1$–$C_4$ alkyl, then $R^3$ can not be —NH(substituted phenyl) or —N($C_1$–$C_4$ alkyl)(substituted phenyl);

and wherein, when Y is $CR^{29}$:

J, K, L, M, Z, A, k, m, n, p, q, r, t, w, $R^3$, $R^{10}$, $R^{11}$, $R^{12}$, $R^{13}$, $R^{16}$, $R^{18}$, $R^{19}$, $R^{21}$, $R^{23}$, $R^{24}$, $R^{25}$, and $R^{27}$ are as defined above and $R^{25a}$, in addition to being as defined above, can also be $C_1$–$C_4$ alkyl, but V is N;

$R^1$ is $C_1$–$C_2$ alkyl, $C_2$–$C_4$ alkenyl, $C_2$–$C_4$ alkynyl, $C_2$–$C_4$ alkoxy, halogen, amino, methylamino, dimethylamino, aminomethyl, or N-methylaminomethyl;

$R^2$ is independently selected at each occurrence from the group consisting of hydrogen, halo, $C_1$–$C_3$ alkyl, nitro, amino, and —$CO_2R^{10}$;

$R^4$ is taken together with $R^{29}$ to form a 5-membered ring and is —$C(R^{28})$= or —N= when $R^{29}$ is —$C(R^{30})$= or —N=, or —$CH(R^{28})$— when $R^{29}$ is X is Cl, Br, I, $S(O)_nR^8$, $OR^8$, halomethyl, —$(CHR^{16})_pOR^8$, cyano, —$(CHR^{16})_pNR^{14}R^{15}$, $C(=O)R^8$, $C_1$–$C_6$ alkyl, $C_2$–$C_{10}$ alkenyl, $C_2$–$C_{10}$ alkynyl, $C_1$–$C_{10}$ alkoxy, aryl-($C_1$–$C_{10}$)-alkyl, $C_3$–$C_6$ cycloalkyl, aryl-($C_1$–$C_{10}$)-alkoxy, nitro, thio-($C_1$–$C_{10}$)-alkyl, —$C(=NOR^{16})$—$C_1$–$C_4$-alkyl, –$C(=NOR^{16})$H, or $C(=O)NR^{14}R^{15}$ where substitution by $R^{18}$ can occur on any carbon containing substituents;

X' is hydrogen, Cl, Br, I, $S(O)_nR^8$, —$(CHR^{16})_pOR^8$, halomethyl, cyano, —$(CHR^{16})_pNR^{14}R^{15}$, $C(=O)R^8$, $C_1$–$C_6$ alkyl, $C_2$–$C_{10}$ alkenyl, $C_2$–$C_{10}$ alkynyl, $C_1$–$C_{10}$, alkoxy, aryl-($C_1$–$C_{10}$)-alkyl, $C_3$–$C_6$ cycloalkyl, aryl-($C_2$–$C_{10}$)-alkoxy, nitro, thio-($C_2$–$C_{10}$)-alkyl, —$C(=NOR^{16})$-$C_1$–$C_4$-alkyl, —$C(=NOR^{16})$H, or $C(=O)NR^8R^{15}$ where substitution by $R^{18}$ can occur on any carbon containing substituents;

$R^5$ is halo, —$C(=NOR^{16})$-$C_1$–$C_4$-alkyl, $C_1$–$C_6$ alkyl, C1–C3 haloalkyl, $C_1$–$C_6$ alkoxy, $(CHR^{16})_pOR^8$, $(CHR^{16})_pS(O)_nR^8$, $(CHR^{16})_pNR^{14}R^{15}$, $C_3$–$C_6$ cycloalkyl, $C_1$–$C_{10}$ alkenyl, $C_2$–$C_{10}$ alkynyl, aryl-($C_2$–$C_{10}$)-alkyl, aryl-($C_1$–$C_{10}$)-alkoxy, cyano, $C_3$–$C_6$ cycloalkoxy, nitro, amino-($C_1$–$C_{10}$)-alkyl, thio-($C_1$–$C_{10}$)-alkyl, $SO_n(R^8)$, $C(=O)R^8$, —$C(=NOR^{16})$H, or $C(=O)NR^8R^{15}$ where substitution by $R^{18}$ can occur on any carbon containing substituents;

$R^6$ and $R^7$ are independently selected at each occurrence from the group consisting of hydrogen, $C_1$–$C_6$ alkyl, $C_3$–$C_{10}$ cycloalkyl, —$(CH_2)_kR^{13}$, ($C_4$–$C_{12}$)-cycloalkylalkyl, $C_1$–$C_6$ alkoxy, —($C_1$–$C_6$ alkyl)-aryl, heteroaryl, aryl, —S(O)$_z$-aryl or —(C$_1$–C$_6$ alkyl)-heteroaryl or aryl wherein the aryl or heteroaryl groups are optionally substituted with 1–3 groups selected from hydrogen, halogen, C$_1$–C$_6$ alkyl, C$_1$–C$_6$ alkoxy, amino, NHC(=O)(C$_1$–C$_6$ alkyl), NH(C$_1$–C$_6$ alkyl), N(C$_1$–C$_6$ alkyl), nitro, carboxy, CO$_2$(C$_1$–C$_6$ alkyl), and cyano; or can be taken together to form —(CH$_2$)$_q$A(CH$_2$)$_r$—, optionally substituted with 0–3 R$^{17}$; or, when considered with the commonly attached nitrogen, can be taken together to form a heterocycle, said heterocycle being substituted on carbon with 1–3 groups consisting of hydrogen, C$_1$–C$_6$ alkyl, hydroxy, or C$_1$–C$_6$ alkoxy;

R$^8$ is independently selected at each occurrence from the group consisting of hydrogen, C$_1$–C$_6$ alkyl, —(C$_4$–C$_{12}$) cycloalkylalkyl, (CH$_2$)$_r$R$^{22}$, C$_3$–C$_{10}$ cycloalkyl, —(C$_1$–C$_6$ alkyl)-aryl, heteroaryl, —NR$^{16}$, —N(CH$_2$)$_n$NR$^6$R$^7$; —(CH$_2$)$_k$R$^{25}$, —(C$_1$–C$_6$ alkyl)-heteroaryl or aryl optionally substituted with 1–3 groups selected from hydrogen, halogen, C$_1$–C$_6$ alkyl, C$_1$–C$_6$ alkoxy, amino, NHC(=O)(C$_1$–C$_6$ alkyl), NH(C$_1$–C$_6$ alkyl), N(C$_1$–C$_6$ alkyl)$_2$, nitro, carboxy, CO$_2$(C$_1$–C$_6$ alkyl), and cyano;

R$^9$ is independently selected at each occurrence from R$_2$, hydroxy, C$_1$–C$_4$ alkoxy, C$_3$–C$_6$ cycloalkyl, C$_2$–C$_4$ alkenyl, and aryl substituted with 0–3 R$^{18}$;

R$^{14}$ and R$^{15}$ are independently selected at each occurrence from the group consisting of hydrogen, C$_1$–C$_6$ alkyl, C$_3$–C$_6$ cycloalkyl, (CH$_2$)$_r$R$^{22}$, and aryl substituted with 0–3 R$^{18}$;

R$^{17}$ is independently selected at each occurrence from the group consisting of R$^{10}$, C$_1$–C$_4$ alkoxy, halo, OR$^{23}$, SR$^{23}$, and NR$^{23}$R$^{24}$;

R$^{20}$ is independently selected at each occurrence from the group consisting of R$^{10}$ and C(=O)R$^{31}$;

R$^{22}$ is independently selected at each occurrence from the group consisting of cyano, R$^{24}$, SR$^{24}$, NR$^{23}$R$^{24}$, C$_3$–C$_6$ cycloalkyl, —S(O)$_n$R$^{31}$, and —C(=O)R$^{25}$;

R$^{26}$ is hydrogen or halogen:

R$^{28}$ is C$_1$–C$_2$ alkyl, C$_2$–C$_4$ alkenyl, C$_2$–C$_4$ alkynyl, hydrogen, C$_1$–C$_2$ alkoxy, halogen, or C$_2$–C$_4$ alkylamino; R$^{29}$ is taken together with R$^4$ to form a five membered ring and is: —CH(R$^{30}$)— when R$^4$ is —CH(R$^{28}$)—, —C(R$^{30}$)= or —N= when R$^4$ is —C(R$^{28}$)= or —N=;

R$^{30}$ is hydrogen, cyano, C$_1$–C$_2$ alkyl, C$_1$–C$_2$ alkoxy, halogen, C$_1$–C$_2$ alkenyl, nitro, amido, carboxy, or amino;

R$^{31}$ is C$_1$–C$_4$ alkyl, C$_3$–C$_7$ cycloalkyl, or aryl-(C$_1$–C$_4$) alkyl;

provided that when J, K, and L are all CH, M is CR$^5$, Z is CH, R$^3$ is CH$_3$, R$^{28}$ is H, R$^5$ is iso-propyl, X is Br, X' is H, and R$^1$ is CH$_3$, then R$^{30}$ can not be H, —CO$_2$H, or —CH$_2$NH$_2$;

and further provided that when J, K and L are all CH; M is CR$^5$; Z is N; and (A) R$^{29}$ is —C(R$^1$)=; then one of R$^{28}$ or R$^{30}$ is hydrogen;

(B) R$^{29}$ is N; then R$^3$ is not halo, NH$_2$, NO$_2$, CF$_3$, CO$_2$H, CO$_2$-alkyl, alkyl, acyl, alkoxy, OH, or —(CH$_2$)$_m$Oalkyl;

(C) R$^{29}$ is N; then R$^{28}$ is not methyl if X or X' are bromo or methyl and R$^5$ is nitro; or (D) R$^{29}$ is N, and R$^1$ is CH$_3$ and R$^3$ is amino; then R$^5$ is not halogen or methyl.

Further included in this invention are pharmaceutical compositions comprising a pharmaceutically acceptable carrier and therapeutically effective amount of any one of the above-described compounds.

The compounds provided by this invention (and especially labelled compounds of this invention) are also useful as standards and reagents in determining the ability of a potential pharmaceutical to bind to the CRF receptor. These would be provided in commercial kits comprising a compound provided by this invention.

DETAILED DESCRIPTION OF THE PREFERRED EMBODIMENTS

In the present invention it has been discovered that the provided compounds useful as antagonists of Cortocotropin Releasing Factor and for the treatment of effective disorders, anxiety, or depression.

The present invention also provides methods for the treatment of effective disorder, anxiety or depression by administering to a host a therapeutically effective amount of a compound of formula (I) as described above. By therapeutically effective amount is meant an amount of a compound of the present invention effective to antagonize abnormal levels of CRF or treat the symptoms of affective disorder, anxiety or depression in a host.

The compounds herein described may have asymmetric centers. All chiral, diastereomeric, and racemic forms are included in the present invention. Many geometric isomers of olefins, C=N double bonds, and the like can also be present in the compound described herein, and all such stable isomers are comtemplated in the present invention. It will be appreciated that certain compounds of the present invention contain an asymmetrically substituted carbon atom, and may be isolated in optically active or racemic forms. It is well known in the art how to prepare optically active forms, such as by resolution of racemic forms or by synthesis, from optically active starting materials. Also, it is realized that cis and trans geometric isomers of the compounds of the present invention are described and may be isolated as a mixture of isomers or as separated isomers forms. All chiral, diastereomeric, and racemic forms and all geometric isomers forms of a structure are intended, unless the specific stereochemistry or isomer form is specifically indicated.

When any variable (for example, R$^1$ through R$^{10}$, m, n, A, w, Z, etc.) occurs more than one time in any constituent or in formula (I) or any other formula herein, its definition on each occurrence is independent of its definition at every other occurrence. Thus, for example, in —NR$^8$R$^9$, each of the substituents may be independently selected from the list of possible R$^8$ and R$^9$ groups defined. Also, combinations of substituents and/or variables are permissible only if such combinations result in stable compounds.

As used herein, "alkyl" is intended to include both branched and straight-chain saturated aliphatic hydrocarbon groups having the specified number of carbon atoms. "Alkenyl" is intended to include hydrocarbon chains of either a straight or branched configuration and one or more unsaturated carbon-carbon bonds which may occur at any stable point along the chain, such as ethenyl, propenyl, and the like. "Alkynyl" is intended to include hydrocarbon chains of either a straight or branched configuration and one or more triple carbon-carbon bonds which may occur at any stable point along the chain, such as ethynyl, propynyl and the like. "Haloalkyl" is intended to include both branched and straight-chain saturated aliphatic hydrocarbon groups having the specified number of carbon atoms, substituted with 1 or more halogens; "alkoxy" represents an alkyl group of indicated number of carbon atoms attached through an oxygen bridge; "cycloalkyl" is intended to include saturated ring groups, including mono-, bi- or poly-cyclic ring systems, such as cyclopropyl, cyclobutyl, cyclopentyl, cyclohexyl, and so forth. "Halo" or "halogen" as used herein refers to fluoro, chloro, bromo, and iodo.

As used herein, "aryl" or "aromatic residue" is intended to mean phenyl, biphenyl or naphthyl.

The term "heteroaryl" is meant to include unsubstituted, monosubstituted or disubstituted 5-, 6- or 10-membered mono- or bicyclic aromatic rings, which can optionally contain from 1 to 3 heteroatoms selected from the group consisting of O, N, and S and are expected to be active. Included in the definition of the group heteroaryl, but not limited thereto, are the following: 2-, or 3-, or 4-pyridyl; 2- or 3-furyl; 2- or 3-benzofuranyl; 2-, or 3-thiophenyl; 2- or 3-benzo[b]thiophenyl; 2-, or 3-, or 4-quinolinyl; 1-, or 3-, or 4-isoquinolinyl; 2- or 3-pyrrolyl; 1- or 2- or 3-indolyl; 2-, or 4-, or 5-oxazolyl; 2-benzoxazolyl; 2- or 4- or 5-imidazolyl; 1- or 2- benzimidazolyl; 2- or 4- or 5-thiazolyl; 2-benzothiazolyl; 3- or 4- or 5-isoxazolyl; 3- or 4- or 5-pyrazolyl; 3- or 4- or 5-isothiazolyl; 3- or 4-pyridazinyl; 2- or 4- or 5-pyrimidinyl; 2-pyrazinyl; 2-triazinyl; 3- or 4-cinnolinyl; 1-phthalazinyl; 2- or 4-quinazolinyl; or 2-quinoxalinyl ring. Particularly preferred are 2-, 3-, or 4-pyridyl; 2-, or 3-furyl; 2-, or 3-thiophenyl; 2-, 3-, or 4-quinolinyl; or 1-, 3-, or 4-isoquinolinyl.

As used herein, "carbocycle" or "carbocyclic residue" is intended to mean any stable 3- to 7-membered monocyclic or bicyclic or 7- to 14-membered bicyclic or tricyclic or an up to 26-membered polycyclic carbon ring, any of which may be saturated, partially unsaturated, or aromatic. Examples of such carbocyles include, but are not limited to, cyclopropyl, cyclopentyl, cyclohexyl, phenyl, biphenyl, naphthyl, indanyl, adamantyl, or tetrahydronaphthyl (tetralin).

As used herein, the term "heterocycle" is intended to mean a stable 5- to 7-membered monocyclic or bicyclic or 7- to 10-membered bicyclic heterocyclic ring which is either saturated or unsaturated, and which consists of carbon atoms and from 1 to 4 heteroatoms independently selected from the group consisting of N, O and S and wherein the nitrogen and sulfur heteroatoms may optionally be oxidized, and the nitrogen may optionally be quaternized, and including any bicyclic group in which any of the above-defined heterocyclic rings is fused to a benzene ring. The heterocyclic ring may be attached to its pendant group at any heteroatom or carbon atom which results in a stable structure. The heterocyclic rings described herein may be substituted on carbon or on a nitrogen atom if the resulting compound is stable. Examples of such heterocycles include, but are not limited to, pyridyl, pyrimidinyl, furanyl, thienyl, pyrrolyl, pyrazolyl, imidazolyl, tetrazolyl, benzofuranyl, benzothiophenyl, indolyl, indolenyl, quinolinyl, isoquinolinyl or benzimidazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl or octahydroisoquinolinyl, azocinyl, triazinyl, 6H- 1,2,5-thiadiazinyl, 2H,6H-1,5,2-dithiazinyl, thiophenyl, thianthrenyl, furanyl, pyranyl, isobenzofuranyl, chromenyl, xanthenyl, phenoxathiinyl, 2H-pyrrolyl, pyrrole, imidazolyl, pyrazolyl, isothiazolyl, isoxazole, pyridinyl, pyrazinyl, pyrimidinyl, pyridazinyl, indolizinyl, isoindole, 3H-indolyl, indolyl, 1H-indazolyl, purinyl, 4H-quinolizinyl, isoquinolinyl, quinolinyl, phthalazinyl, naphthyridinyl, quinoxalinyl, quinazolinyl, cinnolinyl, pteridinyl, 4aH-carbazolyl, carbazolyl, β-carbolinyl, phenanthridinyl, acridinyl, perimidinyl, phenanthrolinyl, phenazinyl, phenothiazinyl, furazanyl, phenoxazinyl, isochromanyl, chromanyl, pyrrolidinyl, pyrrolinyl, imidazolidinyl, imidazolinyl, pyrazolidinyl, pyrazolinyl, piperidinyl, piperazinyl, indolinyl, isoindolinyl, quinuclidinyl, morpholinyl or oxazolidinyl. Also included are fused ring and spiro compounds containing, for example, the above heterocycles.

The term "substituted", as used herein, means that one or more hydrogens of the designated moiety is replaced with a selection from the indicated group, provided that no atom's normal valency is exceeded, and that the substitution results in a stable compound. When a substituent is keto (i.e., =O), then 2 hydrogens attached to an atom of the moiety are replaced.

By "stable compound" or "stable structure" is meant herein a compound that is sufficiently robust to survive isolation to a useful degree of purity from a reaction mixture and formulation into an efficacious therapeutic agent.

As used herein, the term "appropriate amino acid protecting group" means any group known in the art of organic synthesis for the protection of amine or carboxylic acid groups. Such amine protecting groups include those listed in Greene and Wuts, "Protective Groups in Organic Synthesis" John Wiley & Sons, New York (1991) and "The Peptides: Analysis, Synthesis, Biology, Vol. 3, Academic Press, New York (1981), the disclosure of which is hereby incorporated by reference. Any amine protecting group known in the art can be used. Examples of amine protecting groups include, but are not limited to, the following: 1) acyl types such as formyl, trifluoroacetyl, phthalyl, and p-toluenesulfonyl; 2) aromatic carbamate types such as benzyloxycarbonyl (Cbz) and substituted benzyloxycarbonyls, 1-(p-biphenyl)-1-methylethoxycarbonyl, and 9-fluorenylmethyloxycarbonyl (Fmoc); 3) aliphatic carbamate types such as tert-butyloxycarbonyl (Boc), ethoxycarbonyl, diisopropylmethoxycarbonyl, and allyloxycarbonyl; 4) cyclic alkyl carbamate types such as cyclopentyloxycarbonyl and adamantyloxycarbonyl; 5) alkyl types such as triphenylmethyl and benzyl; 6) trialkylsilane such as trimethylsilane; and 7) thiol containing types such as phenylthiocarbonyl and dithiasuccinoyl.

The term "amino acid" as used herein means an organic compound containing both a basic amino group and an acidic carboxyl group. Included within this term are natural amino acids, modified and unusual amino acids, as well as amino acids that are known to occur biologically in free or combined form but usually do not occur in proteins. Included within this term are modified and unusual amino acids, such as, those disclosed in, for example, Roberts and Vellaccio (1983) The Peptides, 5: 342–429, the teaching of which is hereby incorporated by reference. Modified or unusual amino acids that can be used in the practice of the invention include, but are not limited to, D-amino acids, hydroxylysine, 4-hydroxyproline, an N-Cbz-protected amino acid, ornithine, 2,4-diaminobutyric acid, homoarginine, norleucine, N-methylaminobutyric acid, naphthylalanine, phenylglycine, β-phenylproline, tert-leucine, 4-aminocyclohexylalanine, N-methyl-norleucine, 3,4-dehydroproline, N,N-dimethylaminoglycine, N-methylaminoglycine, 4-aminopiperidine-4-carboxylic acid, 6-aminocaproic acid, trans-4-(aminomethyl)-cyclohexanecarboxylic acid, 2-, 3-, and 4-(aminomethyl)-benzoic acid, 1-aminocyclopentanecarboxylic acid, 1-aminocyclopropanecarboxylic acid, and 2-benzyl-5-aminopentanoic acid.

The term "amino acid residue" as used herein means that portion of an amino acid (as defined herein) that is present in a peptide.

The term "peptide" as used herein means a compound that consists of two or more amino acids (as defined herein) that are linked by means of a peptide bond. The term "peptide" also includes compounds containing both peptide and non-peptide components, such as pseudopeptide or peptide mimetic residues or other non-amino acid components. Such a compound containing both peptide and non-peptide components may also be referred to as a "peptide analog".

The term "peptide bond" means a covalent amide linkage formed by loss of a molecule of water between the carboxyl group of one amino acid and the amino group of a second amino acid.

As used herein, "pharmaceutically acceptable salts" refer to derivatives of the disclosed compounds wherein the parent compound of formula (I) is modified by making acid or base salts of the compound of formula (I). Examples of pharmaceutically acceptable salts include, but are not limited to, mineral or organic acid salts of basic residues such as amines; alkali or organic salts of acidic residues such as carboxylic acids; and the like.

"Prodrugs" are considered to be any covalently bonded carriers that release the active parent drug according to formula (I) in vivo when such prodrug is administered to a mammalian subject. Prodrugs of the compounds of formula (I) are prepared by modifying functional groups present in the compounds in such a way that the modifications are cleaved, either in routine manipulation or in vivo, to the parent compounds. Prodrugs include compounds of formula (I) wherein hydroxy, amine, or sulfhydryl groups are bonded to any group that, when administered to a mammalian subject, cleaves to form a free hydroxyl, amino, or sulfhydryl group, respectively. Examples of prodrugs include, but are not limited to, acetate, formate and benzoate derivatives of alcohol and amine functional groups in the compounds of formula (I); and the like.

Pharmaceutically acceptable salts of the compounds of the invention can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa. (1985), p. 1418, the disclosure of which is hereby incorporated by reference.

SYNTHESIS

The novel substituted-2-pyridinamines, substituted triazines, substituted pyridines and substituted anilines of the present invention can be prepared by one of the general schemes outlined below (Scheme 1–23).

Compounds of the Formula (I), wherein Z is $CR^2$ and J is $CX'$ and K and L are both CH, can be prepared as shown in Scheme 1. 2-Hydroxy-4,6-dialkylpyrimidine (II) was converted to the corresponding derivative (III) with an appropriate leaving group in the 2-position such as, but not limited to, Cl, Br, $SO_2CH_3$, $OSO_2CH_3$, or $OSO_2C_6H_4$—$CH_3$, or $SCH_3$ by treatment with phosphorous oxychloride ($POCl_3$), phosphorous oxybromide ($POBr_3$), methanesulfonyl chloride (MsCl), p-toluenesulfonyl chloride (TsCl), or sodium thiomethoxide optionally followed by oxidation with hydrogen peroxide, chlorine gas, or an organic peracid, such as, m-chloroperbenzoic

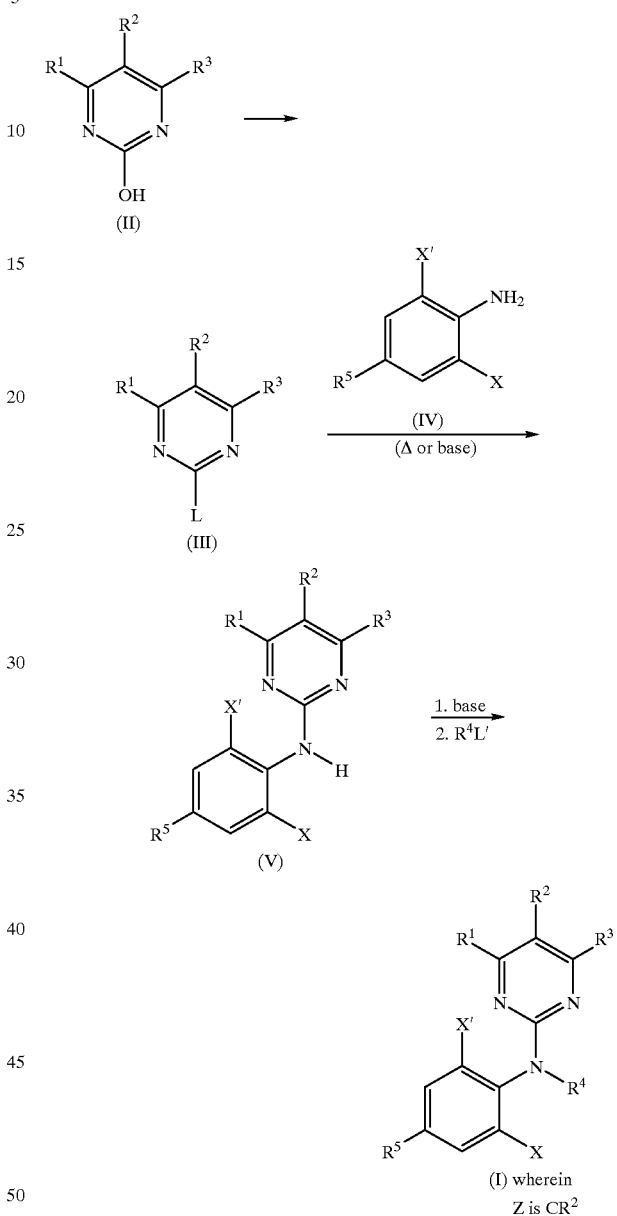

acid, respectively. This derivative was reacted with the appropriate 2,4-substituted aniline (IV) in a high boiling solvent, such as, but not limited to, ethylene glycol, methoxyethoxyethanol etc., or in an aprotic solvent such as tetrahydrofuran, dioxane, toluene, xylene, or N,N-dimethylformamide, facilitated by the optional use of a base such as sodium hydride (NaH), lithium diisopropylamide (LDA), which are preferred. The coupled product (V) was treated with a base such as NaH or LDA in an aprotic solvent such as tetrahydrofuran (THF) or N,N-dimethylformamide (DMF) or in a combination of potassium tert-butoxide in t-butanol (tBuOK/tBuOH) followed by an alkylating agent $R^4L'$, such as an alkyl iodide, mesylate or tosylate to afford the corresponding alkylated product of Formula (I).

The compounds of Formula (I), wherein V and Y are N and Z, J, K, and L are all CH, can be prepared as shown in Scheme 2. The substituted aniline (VI) was converted to the corresponding guanidinium salt (VII) by treatment with the appropriate reagent such as cyanamide.

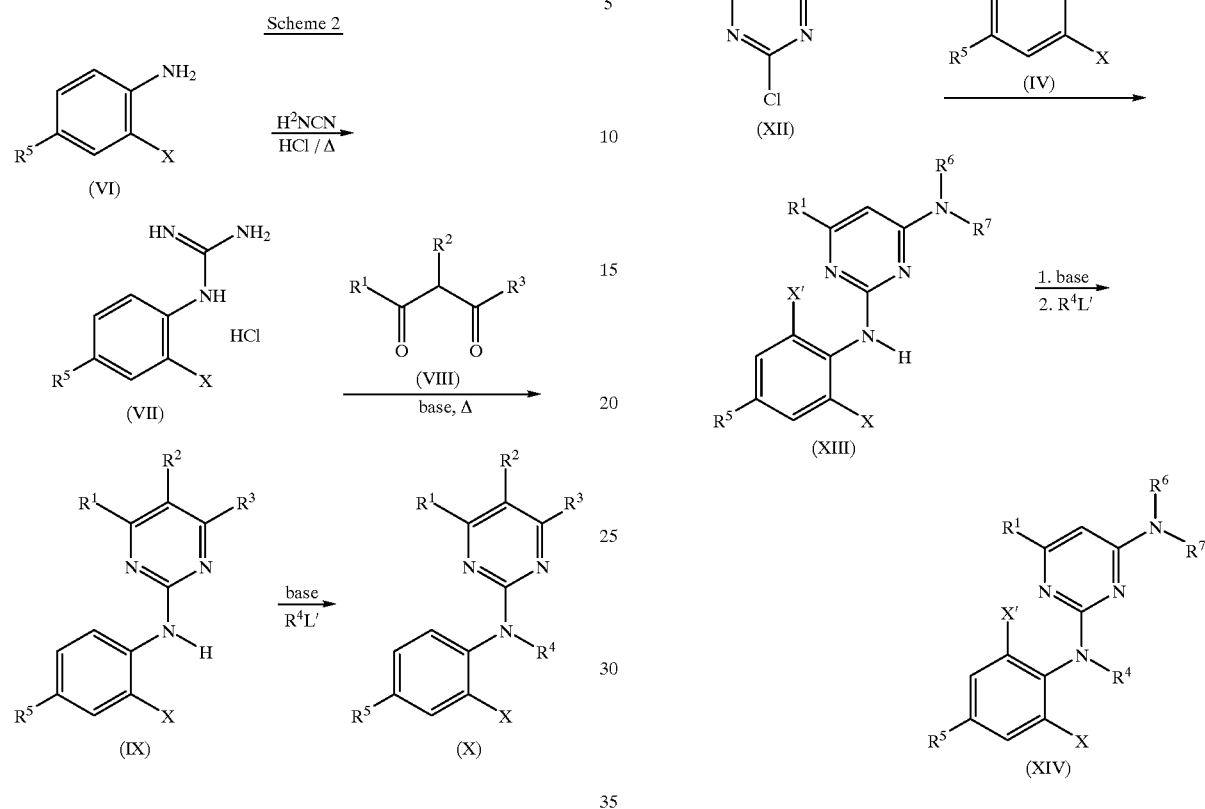

The guanidinium salt (VII) was reacted with a β-diketone (VIII) in the presence of a base such as potassium carbonate ($K_2CO_3$) in N,N-dimethylformamide (DMF) or in an alcoholic solvent in the presence of the corresponding alkoxide to afford the corresponding pyrimidine (IX). This was subsequently alkylated to provide (X), a compound of Formula (I) wherein X' is hydrogen, by conditions identical to those described in Scheme 1.

Compounds of the Formula (I), wherein V and Y are N and Z, J, K, and L are all CH and $R^3$ is $NR^6R^7$, can be prepared as shown in Scheme 3. Treatment of 2,4-dichloro-6-alkylpyrimidine (XI) with a primary or secondary amine in the presence of a non-nucleophilic base such as a trialkylamine afforded selectively the corresponding 4-substituted amino adduct (XII).

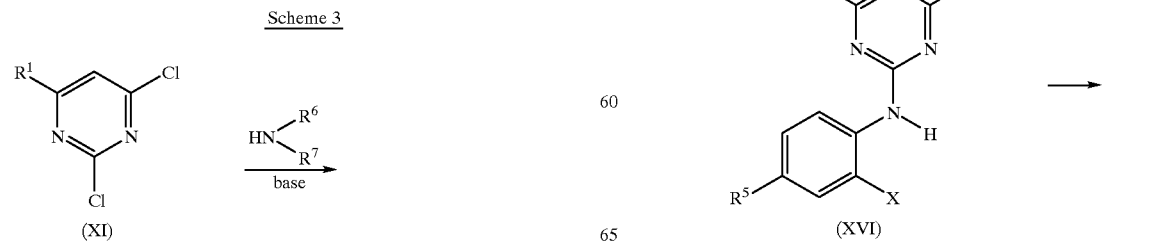

This in turn, was reacted with the substituted aniline (IV) under conditions identical to those described in Scheme 1 to afford the corresponding secondary pyrimidinamine (XIII). This was alkylated under conditions described in Schemes 1 and 2.

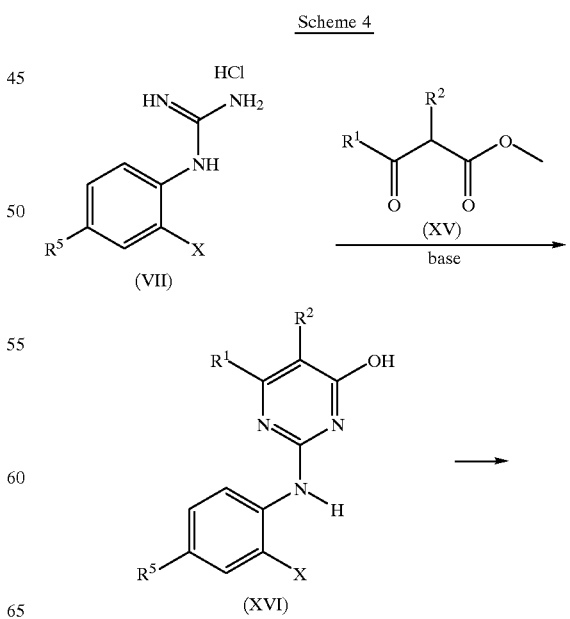

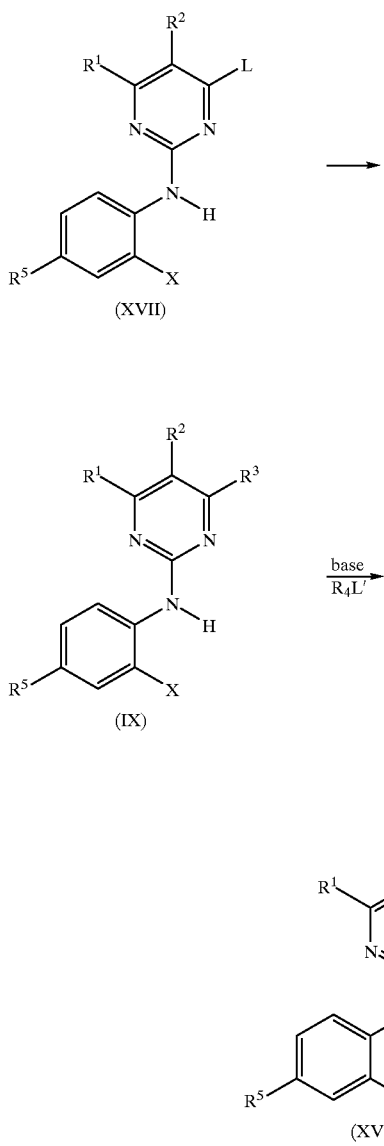

(XVII)

↓ base R₄L'

(IX)

↓

(XVIII)

Compounds of Formula (I) wherein J, K, and L are CH and Z is CR² and V and Y are N can also be prepared by the route outlined in Scheme 4. The guanidinium salt (XII) was reacted with a β-ketoester (XV) in the presence of a base such as an alkoxide in the corresponding alcoholic solvent to give the adduct (XVI). Treatment of the hydroxy group in (XVI) with either phosphorous oxychloride, phosphorous oxybromide, methanesulfonyl chloride, p-toluenesulfonyl chloride, or trifluoromethanesulfonic anhydride provided (XVII), wherein the L is a leaving group and is, respectively, Cl, Br, I, OMs, OTs, or OTf. The L group of (XVII) was displaced with a nucleophile such as NR⁶R⁷, OR⁶, SR⁶, CN, an organolithium, organomagnesium, organosodium, organopotassium, an alkyl cuprate, or in general an organometallic reagent to the corresponding adduct (IX), which was further alkylated under the standard conditions to produce (XVIII).

Compounds of the Formula (I) that are substituted at the 2-position of the phenyl ring could be prepared as outlined in Scheme 5.

Scheme 5

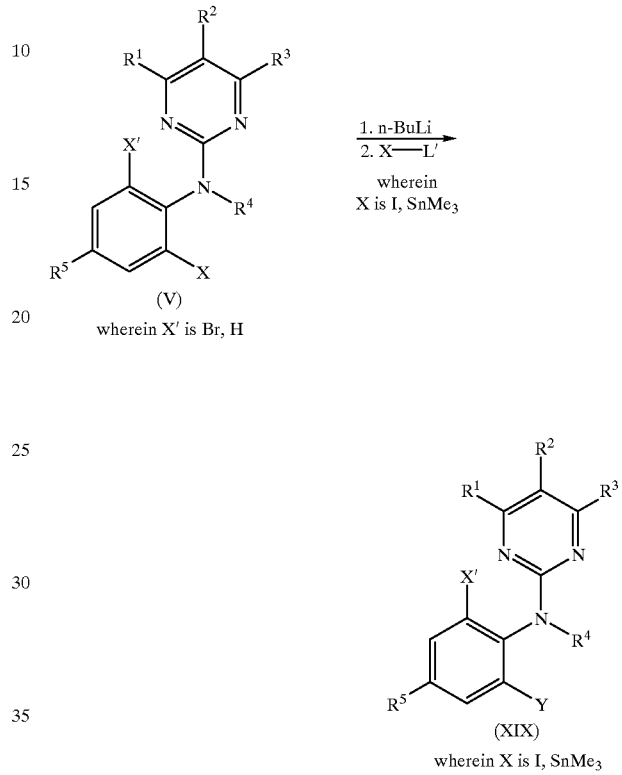

(V)
wherein X' is Br, H (XIX)
wherein X is I, SnMe₃

Compounds of the Formula (I) wherein X is other than bromine can be prepared by the intermediates shown in Scheme 5. Reaction of the 2-halo compound (V) wherein X is bromine or hydrogen with a metalating agent such as, but not limited to, n-BuLi or t-BuLi in an aprotic solvent, preferably ether or tetrahydrofuran, provided the corresponding 2-lithio intermediate (X=Li, not isolated) which was further reacted with an electrophile such as iodine or trimethyltin chloride ((CH₃)₃SnCl) to give the corresponding 2-substituted product (XIX). These intermediates can also be further reacted using palladium-catalyzed coupling reactions well known to one of skill in the art to prepare the compounds of the invention.

Compounds of the Formula (I) wherein Z, K and L are all CH, J is N or CH, and R' is ethyl can be prepared as illustrated in Scheme 6. Sequential addition/re-oxidation of an alkyllithium to 2-chloropyrimidine can provide intermediate (XXII) wherein the R¹ and R³ can be independent of one another. Displacement of the chlorine by a suitable nitrogen nucleophile such as an aniline under similar conditions of Scheme 1, followed by attachment of the R⁴ group by alkylation in an analogous method of Schemes 1 or 2 can provide the compounds of the invention.

Scheme 6

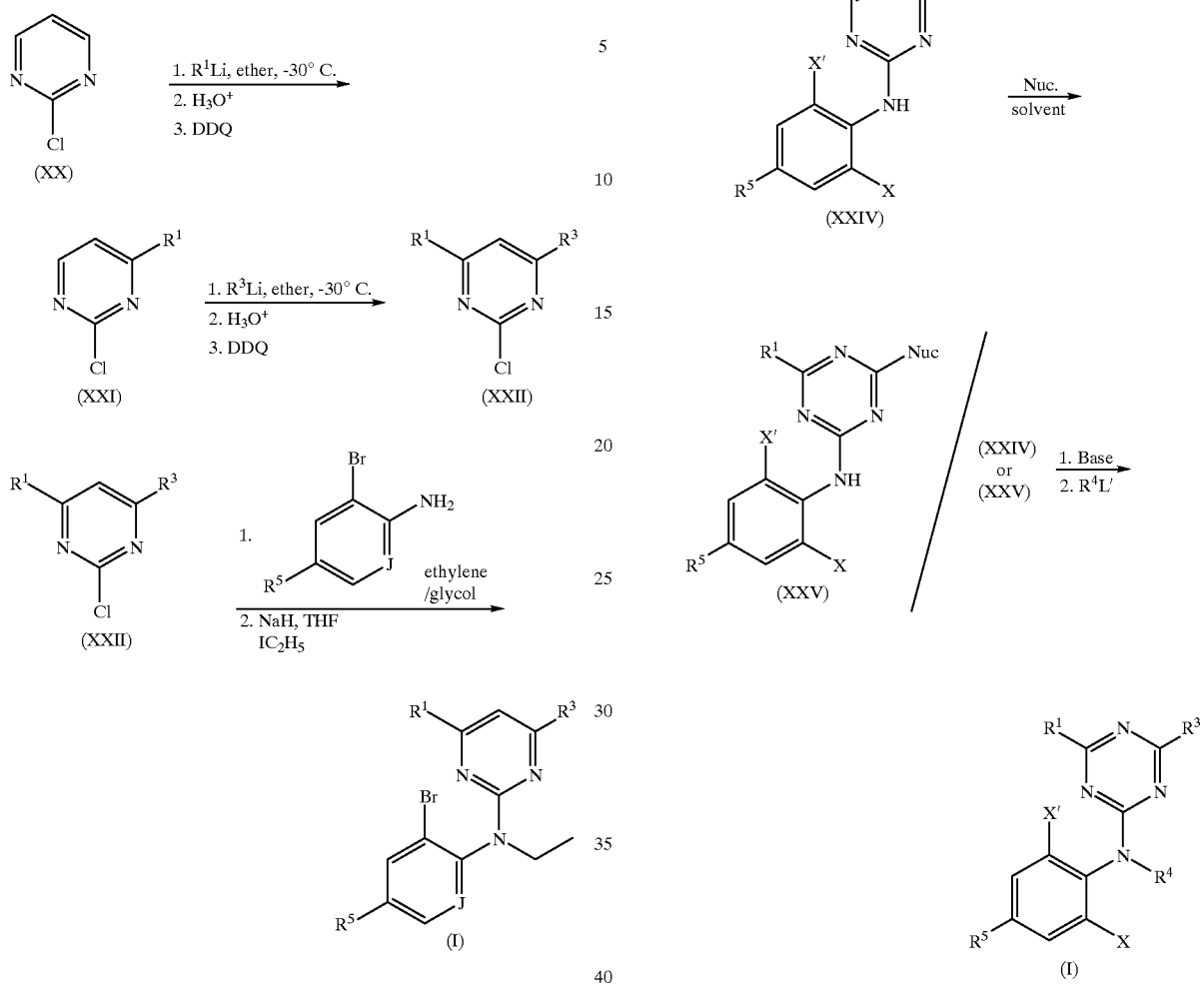

Compounds of the Formula (I) wherein Z is N can be prepared according to the method outlined in Scheme 7. Known triazine (XXIII), synthesis of which is reported in *J. Amer. Chem. Soc.* 77:2447 (1956), can be reacted with a substituted aniline (IV) in a analogous manner to Scheme 1. Similarly, the 2,4 dichloro 6-methyltriazine, which can be prepared via the method reported in U.S. Pat. No. 3,947,374 can be coupled to the substituted aniline (IV) to provide (XXIV) where $R^3$ is chlorine. Nucleophilic addition in protic or aprotic solvents allows for a variety of substituents at this position (XXV). Alkylation of the secondary amine as previously described provide triazine compounds of formula (I).

Scheme 7

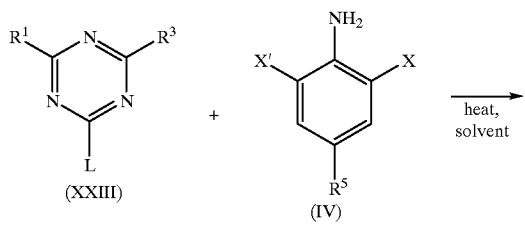

Compounds wherein $R^3$ is carboxy-derived are synthesized according to Scheme 8. A pyrimidine ester of formula (XXVI), which is prepared by the literature method reported in Budesinsky and Roubinek, *Collection. Czech. Chem. Comm.* 26:2871–2885 (1961) is reacted with an amine of formula (IV) in the presence of an inert solvent to afford an intermediate of formula (XXVII). Inert solvents include lower alkyl alcohols of 1 to 6 carbons, dialkyl ethers of 4 to 10 carbons, cyclic ethers of 4 to 10 carbons (preferably dioxane), dialkylformamides (preferably N,N-dimethylformamide), dialkylacetamides, (preferably N,N-dimethylacetamide), cyclic amides, (preferably N-methylpyrrolidinone), dialkyl sulfoxides (preferably dimethyl sulfoxide), hydrocarbons of 5 to 10 carbons or aromatic hydrocarbons of 6 to carbons. Compounds of formula (XXVII) are treated with a base and a compound of Formula $R^4X$, where X is halogen (preferably Cl, Br or I) in an inert solvent. Such bases include a tertiary amine, an alkali metal hydride Scheme 8

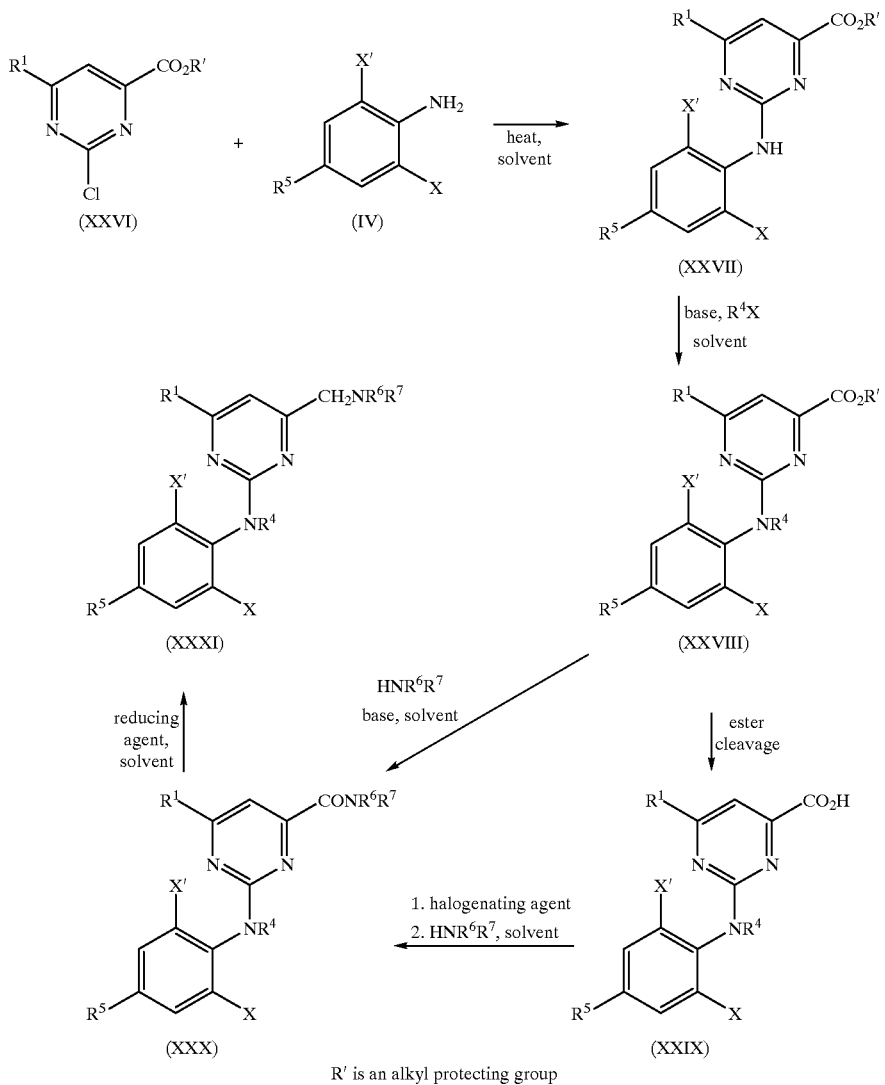

R' is an alkyl protecting group (preferably sodium hydride), an aromatic amine (preferably pyridine), or an alkali metal carbonate or alkoxide. The choice of inert solvent must be compatible with the choice of base (see J. March, Advanced Organic Chemistry (New York: J. Wiley and Sons, 1985) pp. 364–366, 412; H. O. House, Modern Synthetic Reactions (New York: W. A. Benjamin Inc., 1972, pp. 510–536)). Solvents include lower alkyl alcohols of 1 to 6 carbons, lower alkanenitriles (preferably acetonitrile), dialkyl ethers of 4 to 10 carbons, cyclic ethers of 4 to 10 carbons (preferably tetrahydrofuran or dioxane), dialkylformamides (preferably N,N-dimethylformamide), cyclic amides, (preferably N-methylpyrrolidinone), dialkyl sulfoxides (preferably dimethyl sulfoxide), hydrocarbons of 5 to 10 carbons or aromatic hydrocarbons to 6 to 10 carbons. Esters of formula (XXVIII) may be converted to acids of formula (XXIX) by acidic or basic hydrolysis (cf. J. March, Advanced Organic Chemistry (New York: J. Wiley and Sons, 1985) pp. 334–338) or by treatment with an alkali metal salt (preferably LiI or NaCN) in the presence of an inert solvent at temperatures ranging from 50 to 200° C. (preferably 100 to 180° C.) (cf. McMurray, J. E. Organic Reactions, Dauben, W. G. et al., eds., J. Wiley and Sons, New York (1976), Vol. 24, pp. 187–224). Inert solvents include dialkylformamides (preferably N,N-dimethylformamide), dialkylacetamides, (preferably N,N-dimethylacetamide), cyclic amides, (preferably N-methylpyrrolidinone), and dialkyl sulfoxides (preferably dimethyl sulfoxide), or aromatic amines (preferably pyridine). Acids of formula (XXIX) may be treated with a halogenating agent to give an acid halide, which may or may not be isolated, then reacted with an amine of formula $HNR^6R^7$, with or without an inert solvent, with or without a base, as taught by the literature (J. March, Advanced Organic Chemistry, J. Wiley and Sons, New York (1985), pp. 370–373, 389), to provide amides of formula (XXX). Halogenating agents include thionyl chloride ($SOCl_2$), oxalyl chloride (($COCl)_2$), phosphorous trichloride ($PCl_3$), phosphorous pentachloride ($PCl_5$), or phosphorous oxychloride ($POCl_3$). Inert solvents include lower halocarbons of 1 to 6 carbons and 2 to 6 halogens (preferably dichloromethane or dichloroethane), dialkyl ethers of 4 to 10 carbons, cyclic ethers of 4 to 10 carbons (preferably dioxane) or aromatic hydrocarbons to 6 to 10 carbons. Bases include trialkyl amines or aromatic amines (preferably pyridine). Alternatively, esters of formula (XXVIII) may be reacted with an amine of formula $HNR^6R^7$, with or without an inert solvent, with or without a base, as taught by the literature (cf. J. March, Advanced Organic Chemistry (New York: J. Wiley and Sons, 1985) pp. 370–373, 389) to generate amides of formula (XXX). Solvents include lower alkyl alcohols of 1 to 6 carbons, lower alkanenitriles (preferably acetonitrile), dialkyl ethers of 4 to 10 carbons, cyclic ethers of 4 to 10 carbons (preferably tetrahydrofuran or dioxane), dialkylformamides (preferably N,N-dimethylformamide), dialkylacetamides, (preferably N,N-dimethylacetamide), cyclic amides, (preferably N-methylpyrrolidinone), dialkyl sulfoxides (preferably dimethyl sulfoxide), hydrocarbons of 5 to 10 carbons or aromatic hydrocarbons to 6 to 10 carbons. Such bases include a tertiary amine, an alkali metal hydride (preferably sodium hydride), an aromatic amine (preferably pyridine), or an alkali metal carbonate or alkoxide. Amides of formula (XXX) may be treated with a reducing agent in an inert solvent to provide amines of formula (XXXI). Such reducing agents include, but are not limited to, alkali metal aluminum hydrides, preferably lithium aluminum hydride, alkali metal borohydrides (preferably lithium borohydride), alkali metal trialkoxyaluminum hydrides (such as lithium tri-t-butoxyaluminum hydride), dialkylaluminum hydrides (such as di-isobutylaluminum hydride), borane, dialkylboranes (such as di-isoamyl borane), alkali metal trialkylboron hydrides (such as lithium triethylboron hydride). Inert solvents include lower alkyl alcohols of 1 to 6 carbons, ethereal solvents (such as diethyl ether or tetrahydrofuran), aromatic or non-aromatic hydrocarbons of 6 to 10 carbons. Reaction temperatures for the reduction range from about −78° to 200° C., preferably about 50° to 120° C. The choice of reducing agent and solvent is known to those skilled in the art as taught in the above cited March reference (pp. 1093–1110).

Scheme 9 depicts the synthesis and chemical modifications to form compounds of formula (XXXIII). Esters of formula (XXVIII) or acids of formula (XXIX) may be treated with a reducing agent in an inert solvent to provide alcohols of formula (XXXII). Such reducing agents include, but are not limited to, alkali metal aluminum hydrides, preferably lithium aluminum hydride, alkali metal borohydrides (preferably lithium borohydride), alkali metal trialkoxyaluminum hydrides (such as lithium tri-t-butoxyaluminum hydride), dialkylaluminum hydrides (such as di-isobutylaluminum hydride), borane, dialkylboranes (such as di-isoamyl borane), alkali metal trialkylboron hydrides (such as lithium triethylboron hydride). Inert solvents include lower alkyl alcohols of 1 to 6 carbons, ethereal solvents (such as diethyl ether or tetrahydrofuran), aromatic or non-aromatic hydrocarbons of 6 to 10 carbons. Reaction temperatures for the reduction range from about −78° to 200° C., preferably about 50° to 120° C. The choice of reducing agent and solvent is known to those skilled in the art as taught in the above cited March reference (pp. 1093–1110). Alcohols of Formula (XXXII) may be converted to ethers of formula (XXXIII) by treatment with a base and a compound of Formula $R^8X$, where X is halogen. Bases which may be used for this reaction include, but are not limited to, alkali metal hydrides, preferably sodium hydride, alkali metal carbonates, preferably potassium carbonate, alkali metal dialkylamides, preferably lithium di-isopropylamide, alkali metal bis-(trialkylsilyl)amides, preferably sodium bis-(trimethylsilyl)amide, alkyl alkali metal compounds (such as butyl lithium), alkali metal alkoxides (such as sodium ethoxide), alkyl alkaline earth metal halides (such as methyl magnesium bromide), trialkylamines (such as triethylamine or di-isopropylethylamine), polycyclic di-amines (such as 1,4 diazabicyclo[2.2.2]octane or 1,8-diazabicyclo-[5.4.0]undecene) or quaternary ammonium salts (such as Triton B). The choice of inert solvent must be compatible with the choice of base (J. March, Advanced Organic Chemistry (New York: J. Wiley and Sons, 1985) pp. 255–446; H. O. House, Modern Synthetic Reactions (New York:

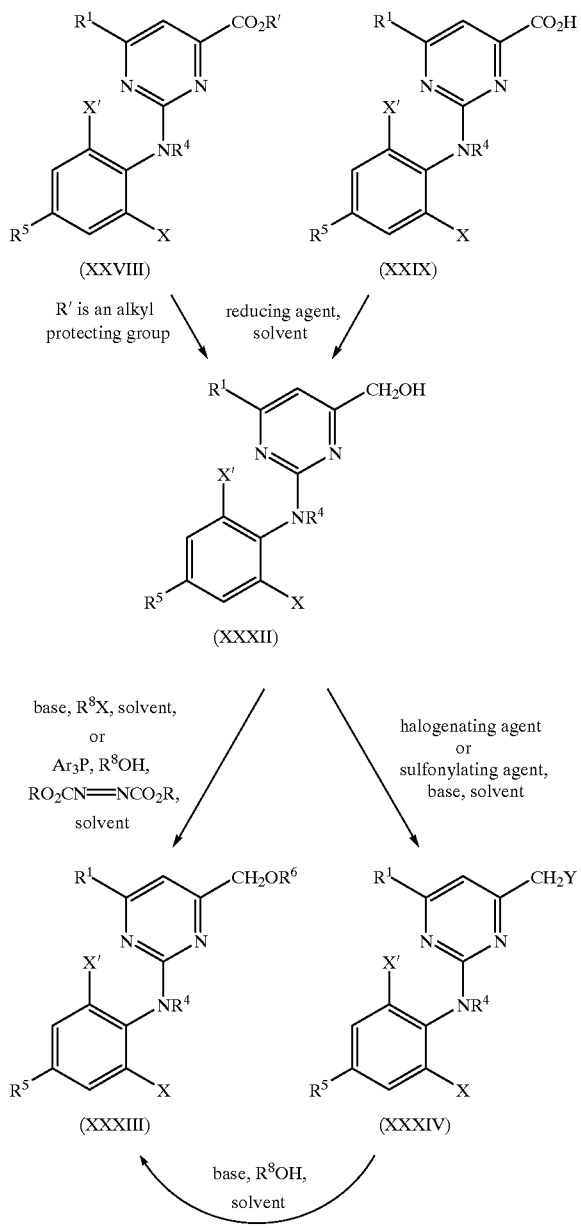

Scheme 9

W. A. Benjamin Inc., 1972, pp. 546–553)). Solvents include lower alkyl alcohols of 1 to 6 carbons, dialkyl ethers of 4 to 10 carbons, cyclic ethers of 4 to 10 carbons, preferably tetrahydrofuran or dioxane, dialkylformamides, preferably N,N-dimethylformamide, dialkylacetamides, preferably N,N-dimethylacetamide, cyclic amides, preferably N-methylpyrrolidinone, hydrocarbons of 5 to 10 carbons or aromatic hydrocarbons to 6 to 10 carbons.

Alternatively, compounds of formula (XXXII) may be converted to compounds of formula (XXXIV), where Y is halide, arylsulfonyloxy (preferably p-toluenesulfonyloxy), alkylsulfonyloxy (such as methanesulfonyloxy), haloalkylsulfonyloxy (preferably trifluoromethyl-sulfonyloxy), by reaction with a halogenating agent or a sulfonylating agent. Examples of halogenating agents include, but are not limited to, $SOCl_2$, $PCl_3$, $PCl_5$, $POCl_3$, $Ph_3P$—$CCl_4$, $Ph_3P$—$CBr_4$, $Ph_3P$—$Br_2$, $Ph_3P$—$I_2$, $PBr_3$, $PBr_5$. The choice of halogenating agents and reaction conditions are known to those skilled in the prior art (March reference, pp. 382–384). Sulfonylating agents include, but are not limited to, (lower alkyl) sulfonyl chlorides (preferably methanesulfonyl chloride), (lower haloalkyl) sulfonic anhydrides (preferably trifluoromethylsulfonic anhydride, phenyl or alkyl substituted-phenyl sulfonyl chlorides (preferably p-toluenesulfonyl chloride). The sulfonylation or halogenations may require a base as taught by the literature (March reference, pp. 1172, 382–384). Such bases include a tertiary amine, an alkali metal hydride (preferably sodium hydride), an aromatic amine (preferably pyridine), or an alkali metal carbonate or alkoxide. Solvents for the halogenation or sulfonylation should be inert under the reaction conditions as taught by the literature. Such solvents include lower halocarbons (preferably dichloromethane or dichloroethane), or ethereal solvents (preferably tetrahydrofuran or dioxane). Intermediates of formula (XXXIV) may then be converted to compounds of formula (XXXIII) by treatment with a compound of formula $R^8OH$ with or without a base, in an inert solvent (March reference, pp. 342–343). Such bases include alkali metal hydrides, preferably sodium hydride, alkali metal carbonates, preferably potassium carbonate, alkali metal dialkylamides, preferably lithium diiisopropylamide, alkali metal bis-(trialkylsilyl)amides, preferably sodium bis-(trimethylsilyl)amide, alkyl alkali metal compounds (such as n-butyllithium), alkali metal alkoxides (such as sodium ethoxide), alkyl alkaline earth metal halides (such as methyl magnesium bromide), trialkylamines (such as triethylamine or di-isopropylethylamine), polycyclic diamines (such as 1,4 diazabicyclo[2.2.2]octane or 1,8-diazabicyclo[5.4.0] undecene) or quaternary ammonium salts (such as Triton B). Solvents include lower alkyl alcohols of 1 to 6 carbons, dialkyl ethers of 4 to 10 carbons, cyclic ethers of 4 to 10 carbons, preferably tetrahydrofuran or dioxane, dialkylformamides, preferably N,N-dimethylformamide, dialkylacetamides, preferably N,N-dimethylacetamide, cyclic amides, preferably N-methylpyrrolidinone, hydrocarbons of 5 to 10 carbons or aromatic hydrocarbons to 6 to 10 carbons.

Intermediates of formula (XXXIII) may be prepared from intermediates of formula (XXXII) by reaction with a tri-arylphosphine (preferably triphenylphosphine), a di-(lower alkyl) azodicarboxylate) and a compound of formula $R^8OH$ in the presence of an inert solvent as described in the general literature (Mitsunobu, O., *Synthesis* 1:1–28 (1981)).

Compounds of formula (XXXI) may be prepared by treatment of a compound of formula (XXXIV) with a compound of Formula $HNR^6R^7$, with or without a base, in an inert solvent (Scheme 9). Such bases and inert solvents may be the same ones used for the transformation of compounds (XXVIII) to compounds (XXX) in Scheme 8.

Compounds of Formula (I) which are substituted at the 4-position of the pyrimidine ring can be prepared as outlined in Scheme 10.

Scheme 10

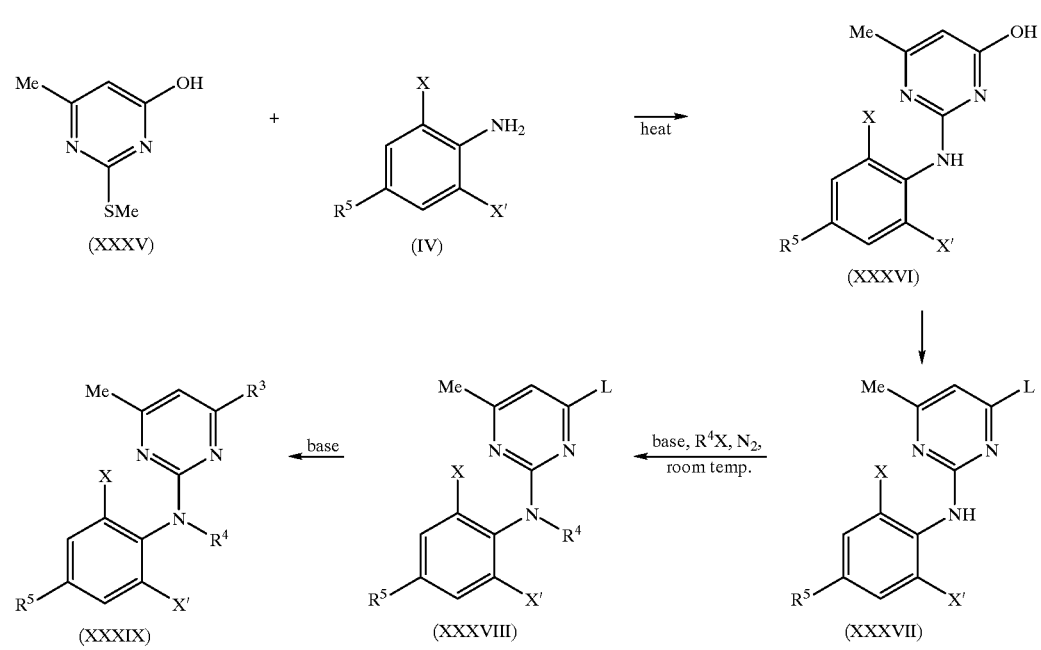

Known pyrimidine (XXXV), synthesis of which is reported in *Eur. J. Med. Chem.* 23:60 (1988), can be reacted with a substituted aniline (IV) in an analogous manner to Scheme 1. Treatment of the hydroxy group in (XXXVI) with either phosphorous oxychloride, phosphorous oxybromide, p-toluenesulfonyl chloride, or trifluoromethanesulfonic anhydride provided (XXXVII), wherein the L is a leaving group. Alkylation under the standard conditions gives (XXXVIII). The L group of (XXXVIII) was displaced with a nucleophile such as $NR^6R^7$, $OR^6$, $SR^6$, CN, or an organometallic reagent to the corresponding adduct (XXXIX).

Compounds of the Formula (I), wherein X or X' is alkylmercapto, or functionalized alkylmercapto can be synthesized under the conditions described in Scheme 11.

the sulfide XLIV with a reducing agent such as sodium borohydride and alkylated on the sulfur with the appropriate alkylating agent such as an alkyl halide, tosylate or mesylate. The rearrangement of XLI may be carried out with a strong base such as lithium, sodium, or potassium hydride; lithium, sodium, or potassium dialkylamide; or lithium

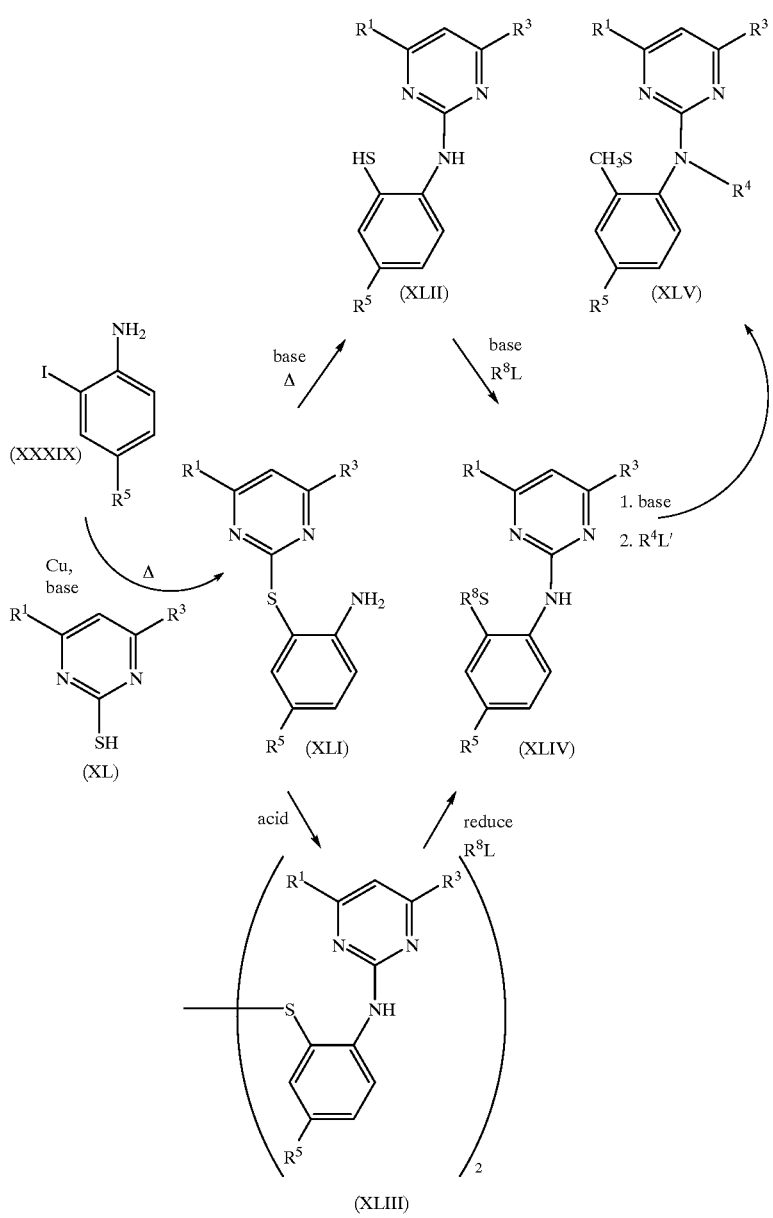

Scheme 11

Treatment of the appropriately ortho-functionalized aniline XXXIX with a substituted 2-mercaptopyrimidine XL in the presence of a base such as potassium carbonate, sodium carbonate, alkali metal alkoxide, potassium sodium or lithium hydride, a lithium, sodium or potassium dialkylamide, or an alkali metal in the presence of copper powder or copper salts gives the corresponding aryl sulfide XLI which is subjected to a Smiles rearrangement by treatment with an strong acid such as hydrochloric, hydrobromic, hydriodic, sulfuric, phosphoric or perchloric, to give the corresponding disulfide XLIII. This is reduced to sodium or potassium metal, in an appropriate solvent such as decahydronaphthalene, xylenes, high boiling alcohols, dimethylformamide, dimethylsulfoxide, dimethylacetamide, and N-methylpyrrolidinone. The rearrangement product can be selectively alkylated on the sulfur with the use of a base such as potassium, sodium or lithium carbonate, potassium, sodium or lithium alkoxide, or trialkylamine and the appropriate alkylating agent as described above. The alkylsulfide can be further alkylated on the nitrogen by using identical conditions as described above to yield compound XLV.

Compounds of formula (I), wherein $R^3$ is $(CH_2)_kOR^8$ and $R^8$ is $(CH_2)_tC(=O)OR^{24}$, $(CH_2)_tC(=O)NR^6R^7$, or $(CH_2)_tNR^6R^7$ can be made according to Scheme 12.

Scheme 12

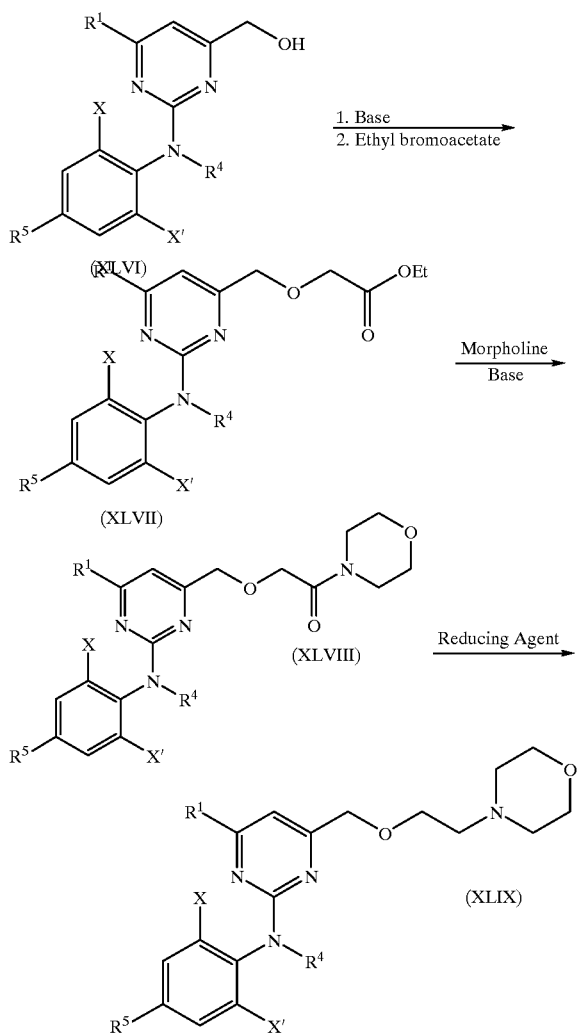

Compounds XLVII, XLVIII, and XLIX are made using the product of Example 24 as starting material by procedures analogous to those used to make the products of Examples 25, 16, and 17 respectively.

The novel 7-azaindoles of the present invention are prepared by Scheme 13 outlined below. The potassium salt of formylsuccinonitrile is treated with the appropriate substituted aniline L to give LI. This undergoes base catalyzed cyclization to a 1-aryl-2-amino-4-cyanopyrrole LII. Reaction with an appropriate 1,3-dicarbonyl compound gives the desired 7-azaindole LIII.

Scheme 13

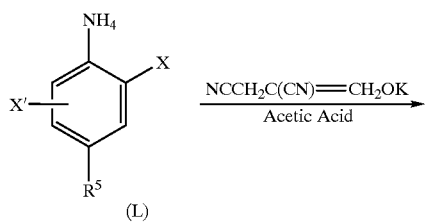

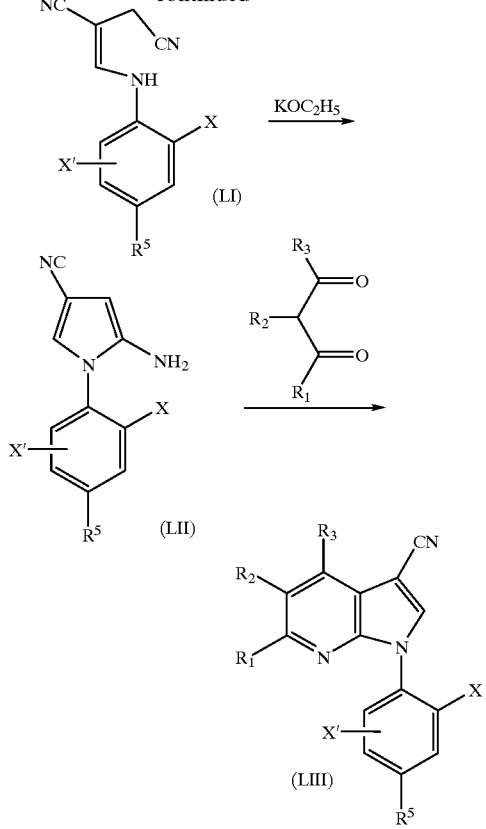

The nitrile substituent at position 3 of structure LIII is readily removed by refluxing the 3-cyano compound with 65% sulfuric acid. Position 3 then can be resubstituted by halogenation or nitration. Reduction of the nitro group can provide the 3-amino substituent.

Alternatively, the nitrile group can be converted to desired L groups by methods described in "Comprehensive Organic Transformations", by Richard C. Larock, VCH Publishers, Inc., New York, N.Y., 1989. For instance, the nitrile group can be reduced with diisobutylaluminum hydride to give the 3-aldehyde. The 3-aldehyde can be reduced via the hydrazone under Wolff-Kishner conditions (KOH in hot diethylene glycol) to give L=methyl. Furthermore, the aldehyde can be converted to $L=CH=CH_2$ by adding it to a mixture of methyltriphenylphosphonium bromide and potassium tertiary-butoxide in tetrahydrofuran (Wittig reaction). Reduction of the ethenyl group to give $L=CH_2CH_3$ can be effected by hydroboration-protonolysis (*J. Am. Chem. Soc.* 81:4108(1959)).

Scheme 13 generally provides a mixture isomeric in substituents $R^1$ and $R^3$, which then can be separated, Sometimes the preferred isomer is the one obtained in lower yield. In that event Scheme 14 can be used to prepare the preferred isomer. Intermediate LII is treated with the appropriate acyl- or aroyl-acetic ester under either thermal or acid-catalyzed conditions to give the 6-hydroxy compound LV. Compound LV is converted to the 6-chloro compound LVI and de-cyanylated to compound LVII. When $R^1$ substituents other than chloro are desired, the chloro group can be converted to other substituents. For instance, treatment of compound LVII with an alkyl Grignard reagent can provide compound LVIII where $R^1$=alkyl. Heating with a primary or secondary amine can provide compound LVIII where $R^1$=amino.

Scheme 14

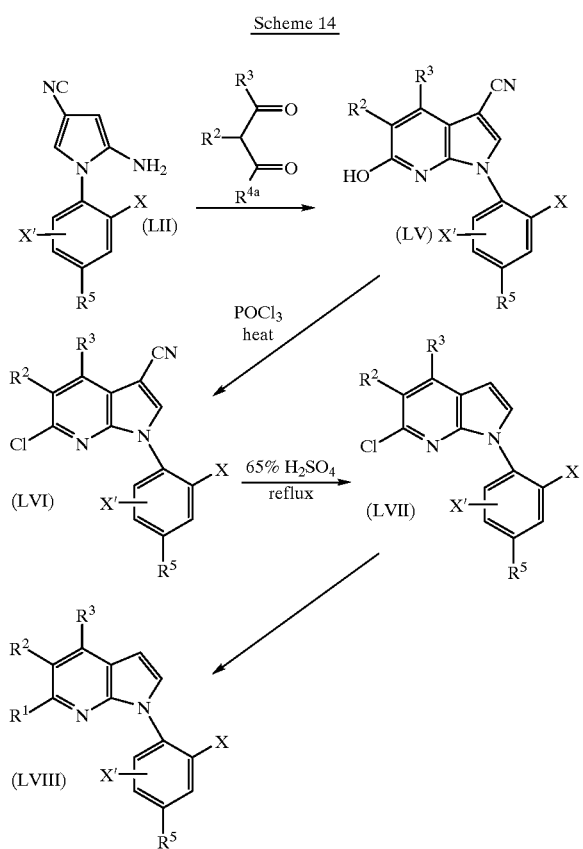

Scheme 15 affords another route to compounds of this invention. Intermediate LII can be treated with the appropriate acylacetaldehyde dialkyl acetal under acid catalyzed conditions to give compounds LXa and LXb, 7-azaindoles unsubstituted at positions 4 and 6 respectively. Compound LXa can be oxidized with m-chloroperoxybenzoic acid to give the N-oxide compound LXI. Heating compound LXI with phosphorus oxychloride can give compound XIIa, which can be decyanylated to compound LXIII.

Compound LXIV where $R^3$ is an amino substituent can be prepared by heating LXIII with the appropriate amine; where $R^3$=alkoxide, the metal alkoxide can be heated with LXIII; where $R^3$=aryl, compound LXIII can treated with the arylboronic acid in the presence of tetrakis (triphenylphosphine)palladium (TTPP) and sodium carbonate; and where $R^3$=alkyl, alkenyl, aralkyl, and cycloalkyl, compound LXIII can be coupled with the appropriate organotin reagent, also in the presence of 7TPP.

Compound LXIV where $R^3$ is a nitro group can be prepared by nitration of LXI, decyanylation, and reduction of the N-oxide with a trivalent phosphorus compound such as triethyl phosphite.

Compound LXb can be substituted in the 6 position using methods described for the substitution of LXa.

Scheme 15

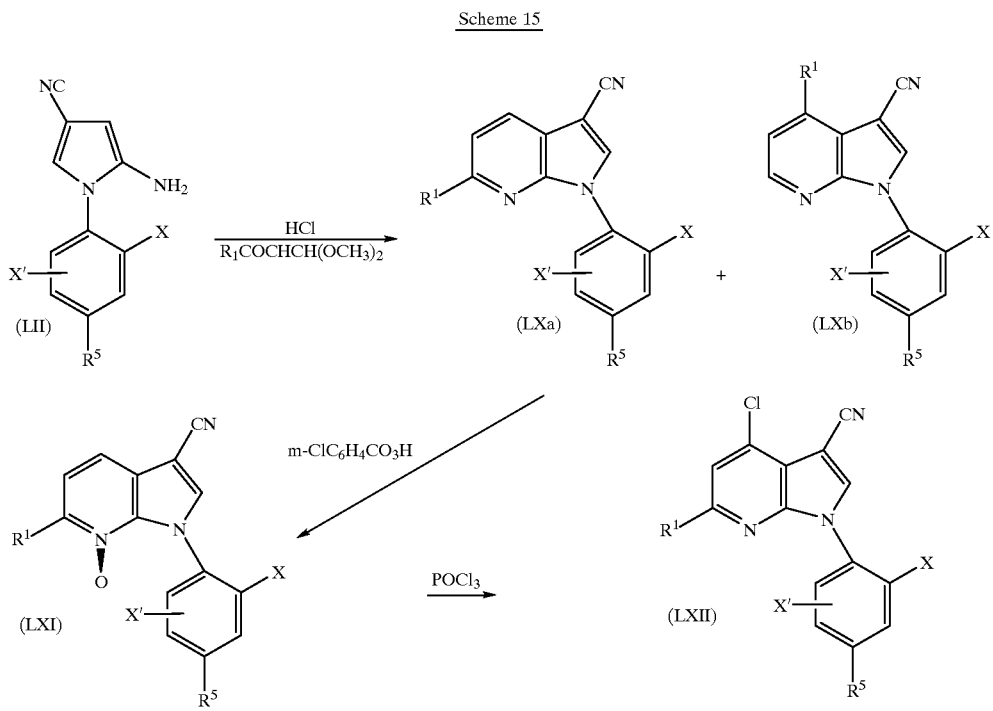

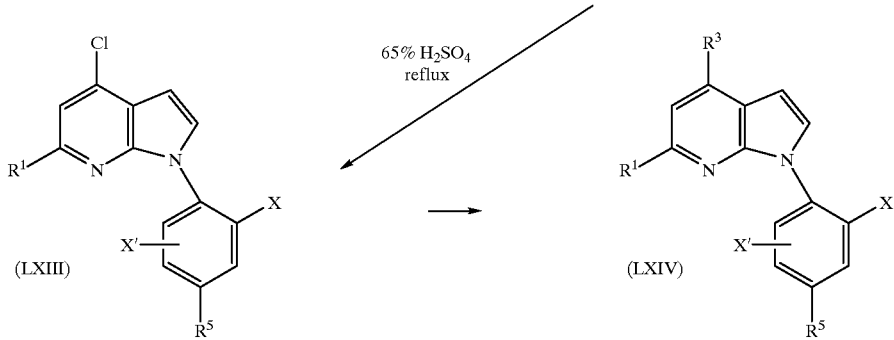

The novel 7-azabenzimidazoles of this invention can be prepared as outlined in Scheme 16 where $R^{29}$ is nitrogen. Compounds L and LXV can react upon heating in the presence of a base, e.g. sodium hydride, to give the diarylamine LXVI. Reduction of the nitro group with stannous chloride can give LXVII, which can be closed to the 7-azabenzimidazole LXVIII.

The purines of this invention can be prepared as shown in Schemes 17 and 18.

Compounds L and LXIX (*J. Heterocyclic Chem.* 28:465 (1991)) can be heated in the presence of a base, e.g. sodium hydride, to give compound LXX. Heating LXX with the appropriate carboxylic acid in the presence of a mineral acid catalyst can give LXXI where $R^{28}$ is hydrogen, alkyl, alkenyl, or alkynyl. The chloro substituent can then be Scheme 16

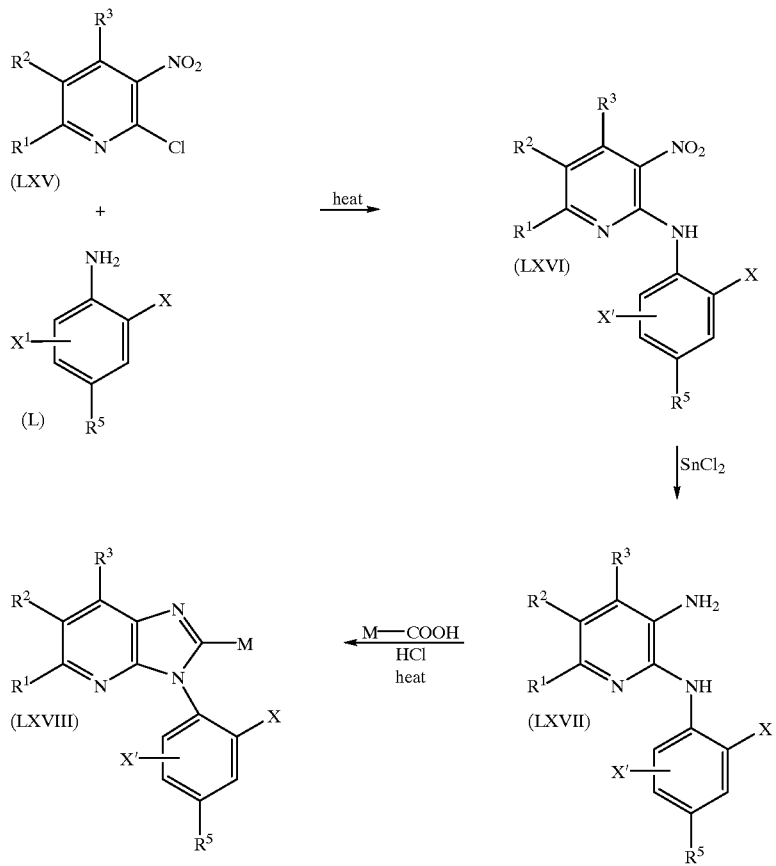

converted to $R^3$ to give compounds LXXII by using one of the methods described above for the introduction of $R^3$ to obtain compounds LXIV.

Scheme 17

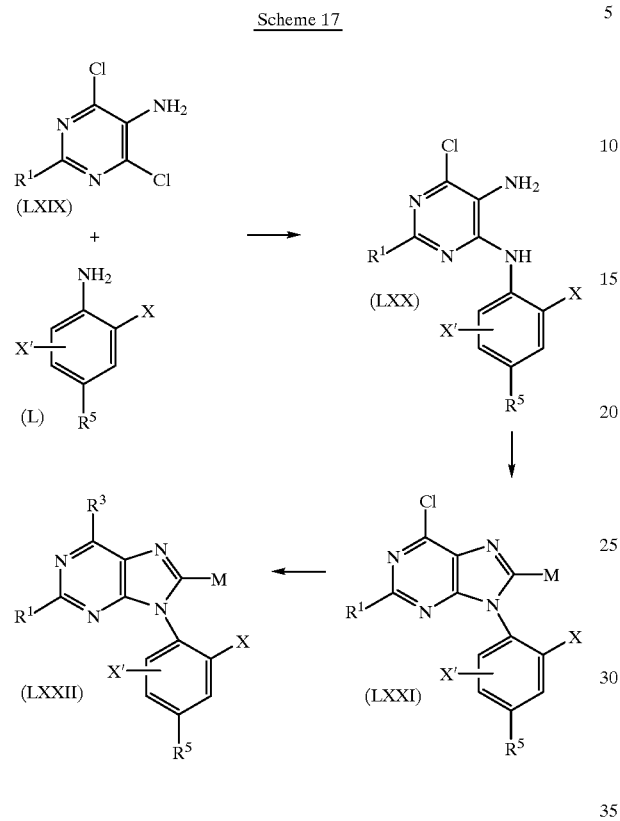

Scheme 18 can be used to prepare purines where $R^{28}$ is halogen or alkoxide. Compounds LXX can be heated with a dialkyl carbonate, such as diethyl carbonate, to give the carbonyl compound LXXIII; if the conversion is undesirably slow, more reactive species such as trichloromethyl chlorocarbonate or carbonyl diumidazole can be used in place of diethyl carbonate. The chloro substituent can then be converted to $R^3$ to give LXXIV by using one of the methods described above for the introduction of $R^3$ to obtain LXIV. Heating LXXIV with phosphorus oxychloride can give the 2-chloropurine, LXXV. To prepare the 2-alkoxypurines, LXXVI, LXXV can be heated with a metal salt of the alcohol $R^{31}OH$, e.g. the sodium or potassium salt, wherein in $R^{31}$ is $C_1$–$C_4$ alkyl.

Scheme 18

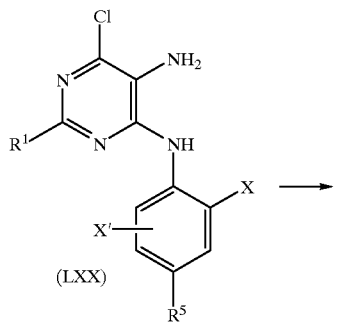

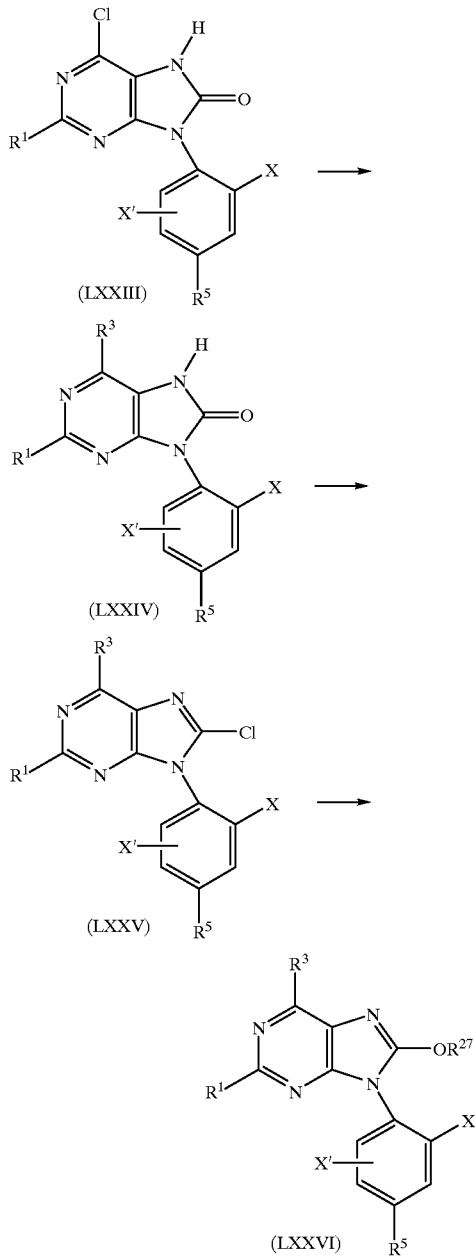

The method of synthesis of the 7-azaindolines of this invention is shown in Scheme 19.

A number of compounds of the general structure LXXVIII with desired $R^1$ and $R^2$ groups have been described by W. Paudler and T.-K. Chen, *J. Heterocyclic Chem.* 7:767 (1970). These can be oxidized with a peracid, e.g. m-chloroperoxybenzoic acid, to the sulfone LXXIX. Sulfone LXXIX can be heated in the presence of the desired aniline and a base, e.g. sodium hydride to give the diaryl amine LXXX. Alkylation of LXXX with the desired unsubstituted or 4-substituted 3-butynyl iodide (or 3-butynol mesylate) can give LXXXI. LXXXI can undergo an intramolecular Diels-Alder reaction to give LXXXII.

In a number of cases, the desired 4-substituted 3-butynyl iodide is not readily available or is unstable. In that event unsubstituted 3-butynyl iodide is used to give compound LXXXII where $R^3$=H.

Scheme 19

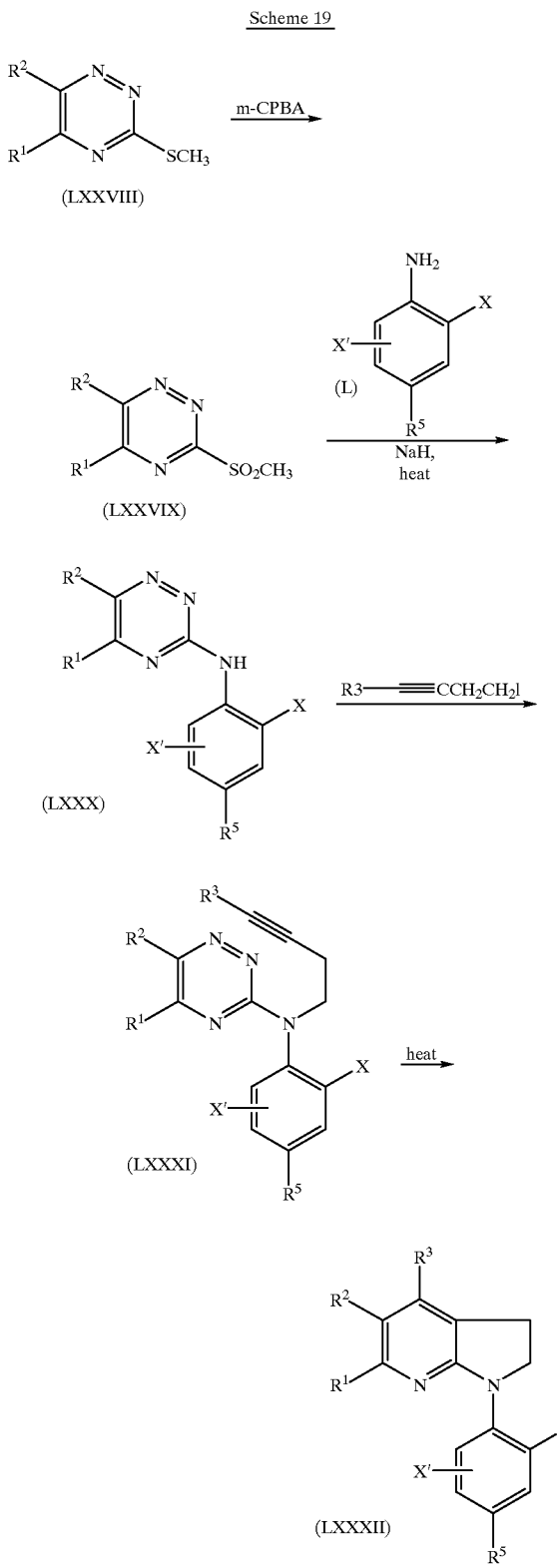

The synthesis of the 5,7-diazaindoles of this invention is outlined in Scheme 20.

The desired formamidine LXXXIII can be treated with LXXXIV in the presence of sodium ethoxide in ethanol to give the pyrimidine LXXXV. Refluxing LXXXV in phosphorus oxychloride gives the dichloropyrimidine LXXXVI. Compound LXXXVI can be converted to the carbonyl compound LXXXVII by treatment with one equivalent of ozone at −78° to give an ozonide, which on treatment with sodium iodide and acetic acid gives the desired carbonyl compound. The preparation of LXXXVII ($R^1$=H, $R^{28}$=$CH_3$ and $R^1$=$R^{28}$=$CH_3$) by a different route has been described by E. Basagni et al., *Bull. Soc. Chim. Fr.,* 4338 (1969).

Before the coupling reaction, the carbonyl of compound LXXXVII is protected by treatment with 2,2-dimethoxypropane in the presence of a catalytic amount of acid to give compound LXXXVIII. Compound LXXXVIII is then coupled with the appropriate aniline L by heating in the presence of a base, e.g. sodium hydride, to give compound LXXXIX. Compound LXXXIX can be cyclized to give the 5,7-diazaindole XC, the target compound wherein $R^3$=Cl. Compound XC is also a useful intermediate for the preparation of Compounds XCI with other $R^3$ groups. For example, heating the chloro compound with the appropriate amine gives the desired amino compound. Heating with a metal alkoxide gives the desired alkoxy compound. Treating compound XC ($R^3$=Cl) with $R^3$MgBr ($R^3$=alkyl, aryl, or aralkyl) converts the chloro compound to the desired alkyl, aryl, or aralkyl compound XCI.

Scheme 20

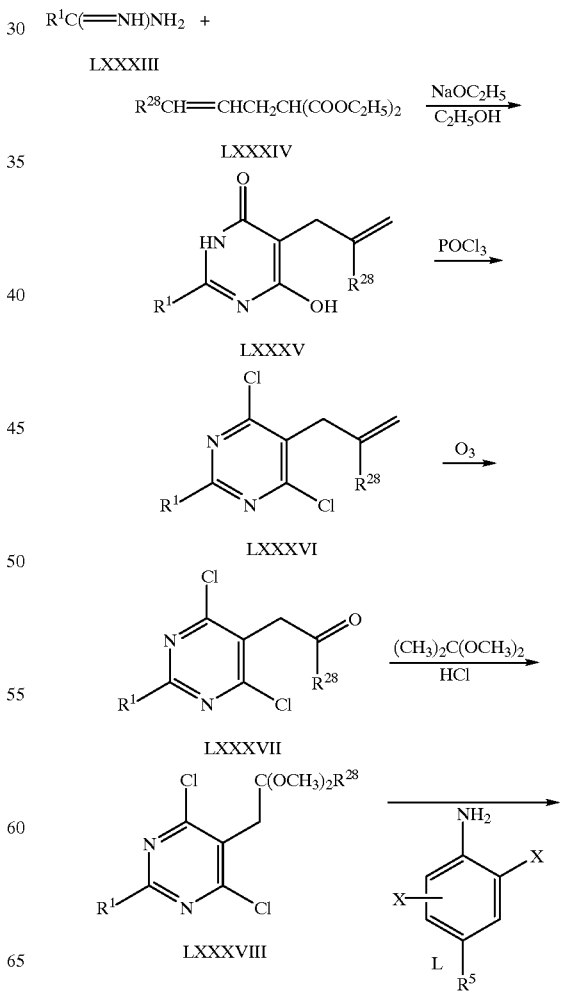

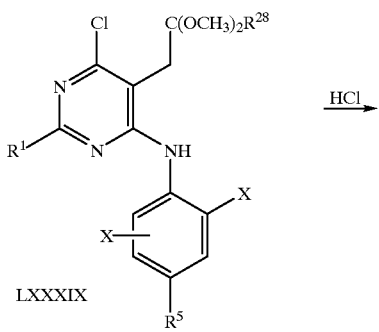

LXXXIX

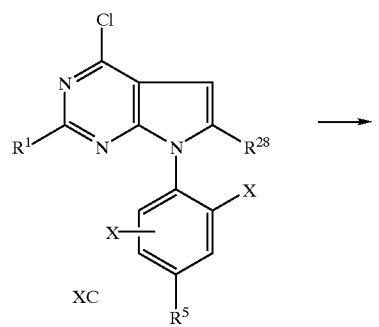

XC

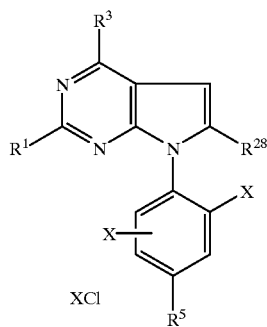

XCI

Compounds wherein $R^5$ is dimethylhydroxymethyl, $X'$ is iodine and $R^1$ and $R^3$ are chlorine can be prepared according to scheme 21. Ethyl 4-aminobenzoate is iodinated in a methylene chloride/water (50:50) mixture in the presence of sodium bicarbonate to provide compound (XCII). This material is coupled to cyanuric chloride, then the secondary amine is alkylated in an analogous manner to that in Scheme 1 to yield XCIII. Compound XCIII is treated with 5 equivalents of MeMgBr to provide the desired material of formula (XCIV).

Scheme 21

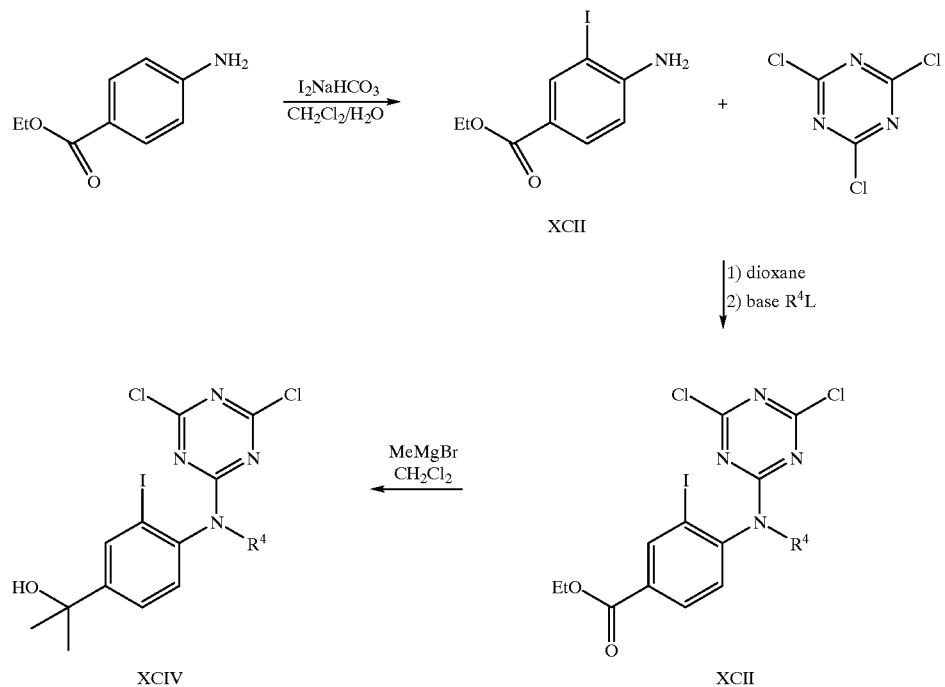

Scheme 22 depicts the synthesis of compounds of Formula (I), where Y=N, Z=CR$^2$ and R$^3$ is COR$^{25}$, CH(OH)R$^{25}$ or C(OH)R$^{25}$R$^{25a}$. An ester of Formula (XCVI) may be converted to an amide of Formula (C) by treatment with an amine of Formula HN(OR$^a$)R$^b$, where R$^a$ and R$^b$ are lower alkyl (preferably Me), in the presence of a trialkylaluminum reagent (preferably Me$_3$Al) in an inert solvent preferably an aromatic hydrocarbon (e.g., benzene) or an ethereal solvent (e.g., tetrahydrofuran) as taught by the prior art (cf. J. I. Levin, E. Turos, S. M. Weinreb, *Synthetic Communications* 12:989–993 (1982)). Amides of Formula (C) may be converted to ketones of Formula (CI) by treatment with an organolithium reagent R$^{25}$Li or an organomagnesium halide R$^{25}$MgX, where X=Cl, Br or I, in an inert solvent, preferably an ethereal solvent (e.g., diethyl ether or tetrahydrofuran), as taught by the prior art (cf. S. Nahm and S. M. Weinreb, *Tetrahedron Letters* 22:3815–3818 (1981)). Alternatively, ketones of Formula (CI) can be prepared from acids of Formula (XCV) by treatment with an organolithium reagent R$^{25}$Li in the presence of an inorganic salt (preferably a transition metal halide (e.g., CeCl$_3$)) in an inert solvent (preferably an ethereal solvent (e.g., tetrahydrofuran)) as taught by the prior art (cf. Y. Ahn and T. Cohen, *Tetrahedron Letters* 35:203–206 (1994)). Alternatively, esters of Formula (XCVI) can be converted directly to ketones of Formula (XCVIII) by reaction with an organolithium reagent R$^{25}$Li or an organomagnesium halide R$^{25}$MgX, where X=Cl, Br or I, in an inert solvent (preferably an ethereal solvent e.g., diethyl ether or tetrahydrofuran) at temperatures ranging from –100 to 150° C. (preferably –78 to 80° C.) (cf. J. March, Advanced Organic Chemistry (New York: J. Wiley and Sons, 1985, pp.433–434). Ketones of Formula (XCVIII) can be converted to alcohols of Formula (XCIX) by reaction with an organolithium reagent R$^{25}$Li or an organomagnesium halide R$^{25}$MgX, where X=Cl, Br or I, in an inert solvent (preferably an ethereal solvent (e.g. diethyl ether or tetrahydrofuran) at temperatures ranging from –100 to 150° C. (preferably –78 to 80° C.) (cf. the above March reference, pp. 434–435). Alternatively, esters of Formula (XCVI) can be converted to alcohols of Formula (XCIX) by reaction with an organolithium reagent R$^{25a}$Li or an organomagnesium halide R$^{25a}$MgX, where X=Cl, Br or I, in an inert solvent (preferably an ethereal solvent e.g., diethyl ether or tetrahydrofuran) at temperatures ranging from –100 to 150° C. (preferably –78 to 100° C.), preferably using an excess amount of organometallic reagent (cf. the above March reference, pp. 434–435). In this last instance, R$^{25}$=R$^{25}$. Ketones of Formula (XCVIII) can be converted to alcohols of Formula (C) by treatment with a reducing agent in an inert solvent. Such reducing agents include, but are not limited to, alkali metal aluminum hydrides, preferably lithium aluminum hydride, alkali metal borohydrides (preferably sodium borohydride), alkali metal trialkoxyaluminum hydrides (such as lithium tri-t-butoxyaluminum hydride), dialkylaluminum hydrides (such as di-isobutylaluminum hydride), borane, dialkylboranes (such as di-isoamyl borane), alkali metal trialkylboron hydrides (such as lithium triethylboron hydride). Inert solvents include lower alkyl alcohols of 1 to 6 carbons, ethereal solvents (such as diethyl ether or tetrahydrofuran), aromatic or non-aromatic hydrocarbons of 6 to 10 carbons. Reaction temperatures for the reduction range from about –78° to about 200° C., preferably about 0° to about 120° C. The choice of reducing agent and solvent is known to those skilled in the art as taught in the above cited March reference (Advanced Organic Chemistry, pp. 1093–1110).

Scheme 22

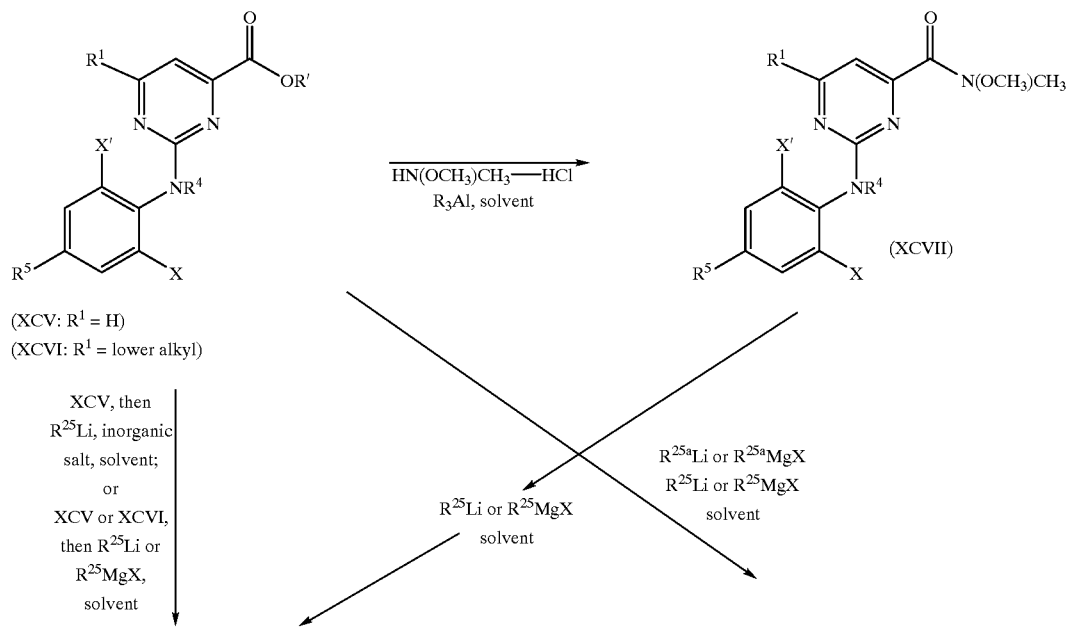

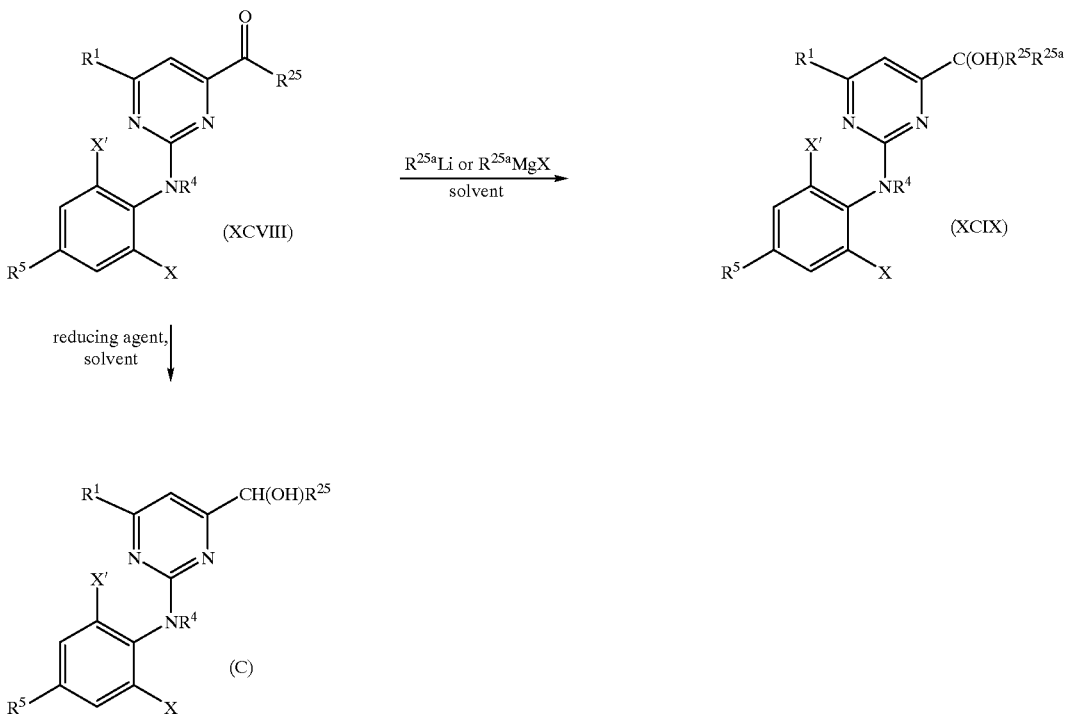

Compounds of Formula (I) can also be prepared by the procedures outlined in Scheme 23. A compound of Formula (CI) (Formula I, where Z=CR², Y=N, R³=(CHR¹¹)$_p$CN) can be reacted with sodium azide and ammonium chloride in a polar solvent at high temperatures (preferably 70 to 150° C.) to give a tetrazole of Formula (CII) as taught by the prior art (cf. R. N. Butler, Tetrazoles, in Comprehensive Heterocyclic Chemistry; A. R. Katritzky, C. W. Rees, Eds.; (New York: Pergamon Press, 1984), pp. 828–832). Such polar solvents may be dialkylformamides (preferably N,N-dimethylformamide), dialkylacetamides, (preferably N,N-dimethylacetamide), cyclic amides, (preferably N-methylpyrrolidinone), dialkyl sulfoxides (preferably dimethyl sulfoxide) or dioxane. A compound of Formula (CIII) (Formula I, where Y=N, Z=CR² and R³=COCH₃) may be treated with a halogenating agent in an inert solvent to give a haloketone of Formula (CIV). Such halogenating agents include bromine, chlorine, iodine, N-halosuccinimides (e.g. N-bromosuccinimide), N-halophthalimides (e.g., N-bromophthalimide) or N-tetrasubstituted ammonium perbromides (e.g., tetraethylammonium perbromide) (cf. the above March reference, Advanced Organic Chemistry, pp. 539–531; S. Kajigaeshi, T. Kakinami, T. Okamoto, S. Fujisaki, *Bull. Chem. Soc. Japan* 60:1159–1160 (1987) and references cited therein). Inert solvents include lower halocarbons of 1 to 6 carbons and 2 to 6 halogens (preferably dichloromethane or dichloroethane), dialkyl ethers of 4 to 10 carbons, cyclic ethers of 4 to 10 carbons (preferably dioxane) or aromatic hydrocarbons to 6 to 10 carbons. Haloketones of Formula (CIV) may be converted to imidazoles of Formula (CVII) by treatment with formamide with or without an inert solvent as taught by the prior art (H. Brederick and G. Theilig, *Chem. Ber.* 86:88–108 (1953)). Alternatively, ketones of Formula (CIII) may be converted to vinylogous amides (CV) by reaction with N,N-di(lower alkyl)formamide di(lower alkyl)acetals (e.g., N,N-dimethylformamide dimethyl acetal) or Gold's reagent ((dimethylaminomethyleneaminomethylene)-dimethylammonium chloride) in an inert solvent with or without base as taught by the prior art (cf. J. T. Gupton, S. S. Andrew, C. Colon, *Synthetic Communications* 12:35–41 (1982); R. F. Abdulla, K. H. Fuhr, *J. Organic Chem.* 43:4248–4250 (1978)). Such inert solvents include aromatic hydrocarbons of 6 to 10 carbons, lower alkyl alcohols of 1 to 6 carbons, dialkyl ethers of 4 to 10 carbons, or cyclic ethers of 4 to 10 carbons (preferably dioxane). Such bases may include a tertiary amine, an alkali metal hydride (preferably sodium hydride), an aromatic amine (preferably pyridine), or an alkali metal carbonate or alkoxide. Vinylogous amides (CV) can be condensed with hydrazine in an inert solvent to form pyrazoles of Formula (CVI) as taught by the prior art (cf. G. Sarodnick, *Chemische Zeitung* 115:217–218 (1991); Y. Lin, S. A. Lang, *J. Heterocyclic Chem.* 14:345 (1977); E. Stark et al., *Chemische Zeitung* 101:161 (1977); J. V. Greenhill, *Chem. Soc. Reviews* 6:277 (1977)). Such inert solvents include aromatic hydrocarbons of 6 to 10 carbons, lower alkyl alcohols of 1 to 6 carbons, dialkyl ethers of 4 to 10 carbons, or cyclic ethers of 4 to 10 carbons (preferably dioxane).

Scheme 23

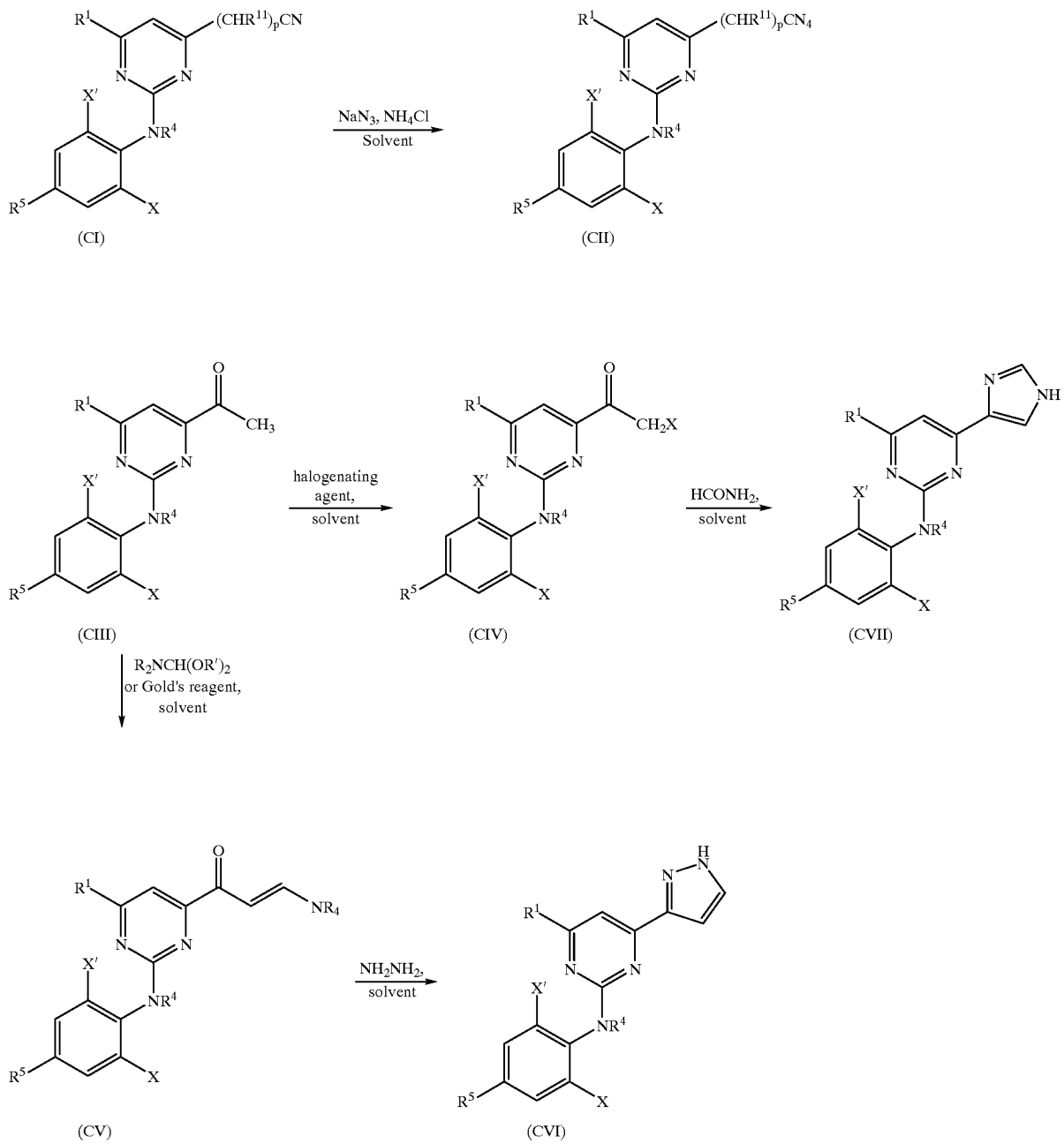

The purines and 8-aza-purines of the present invention are readily synthesized following the methods shown in Schemes 24 and 25. The purine (CXI) is derived from an appropriately substituted pyrimidine (CVIII). The trisubstituted hydroxypyrimidine is nitrated under standard conditions with fuming nitric acid. Following conversion of the hydroxy compound to the chloro derivative via treatment with phosphorus oxychloride, reduction of the nitro group with iron powder in acetic acid and methanol yielded the aminopyrimidine (CIIX). Compound CIIX is reacted with the appropriately substituted aniline in the presence of base catalyst to yield an anilinopyrimidine (CX), which was then converted to the desired purine (CXI) via reaction with triethylorthoformate in acetic anhydride. Starting from compound CX, the desired 8-aza-purine can be prepared via reaction with sodium nitrite in acetic acid.

Scheme 24

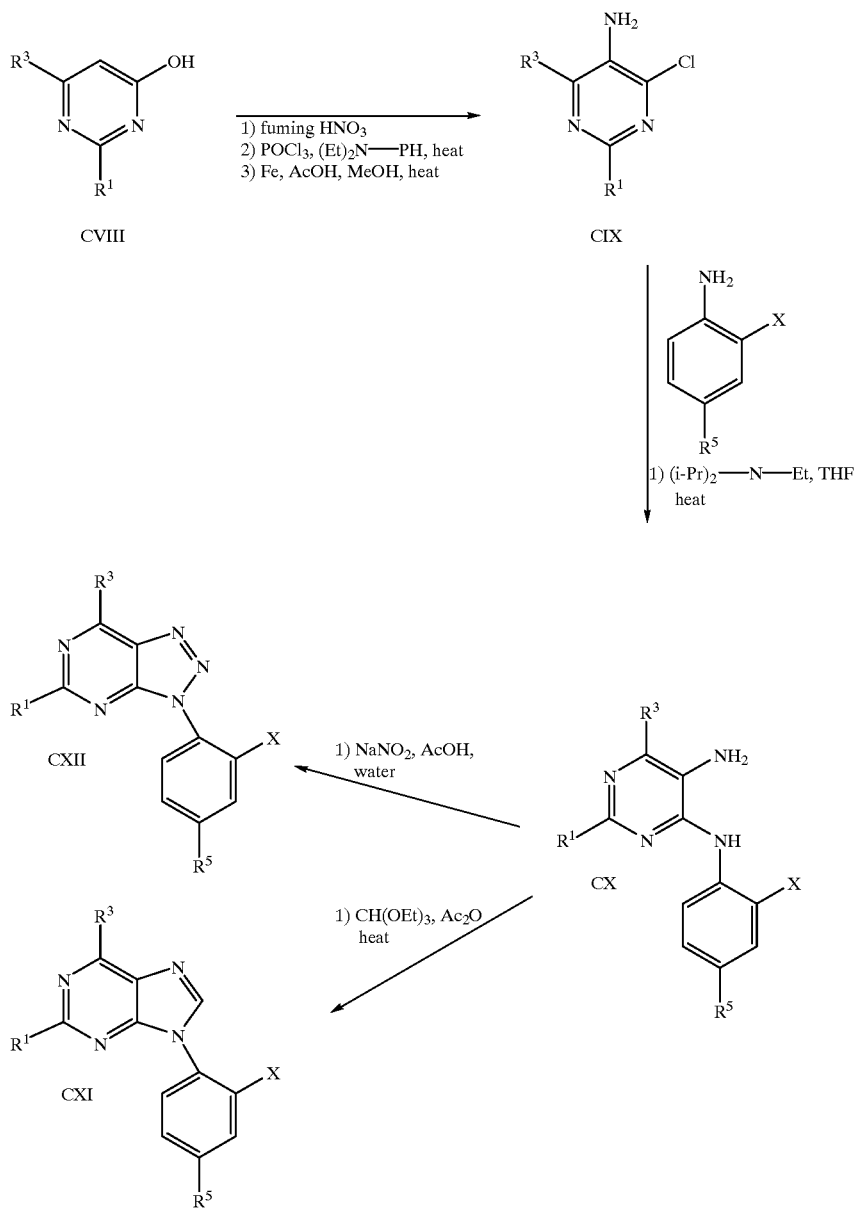

If R³ of the purine is a chloro group, that substituent can be further elaborated to other R³ substituents as shown in Scheme 25. Compound (CXII), wherein R³ is chlorine, is reacted with a nucleophile with or without an inert solvent at temperatures ranging from 20° C. to 200° C., to effect the formation of the 8-azapurine (CXIII). In a similar fashion, the R³ of an appropriately substituted purine (CXI) may be converted to other functional groups to yield the purine (CXIV) having the desired substitution pattern. Similarly, if R¹ is a chloro group, it may be converted to another functional group via reaction with an appropriate nucleophile. Nucleophiles include amine, hydroxy, or mercapto compounds or their salts.

Scheme 25

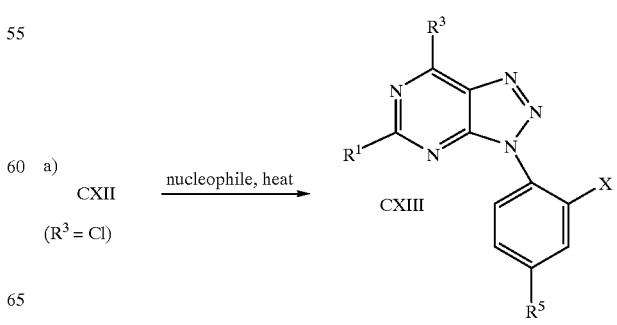

b) CXI (R³ = Cl) —nucleophile, heat→ CXIV

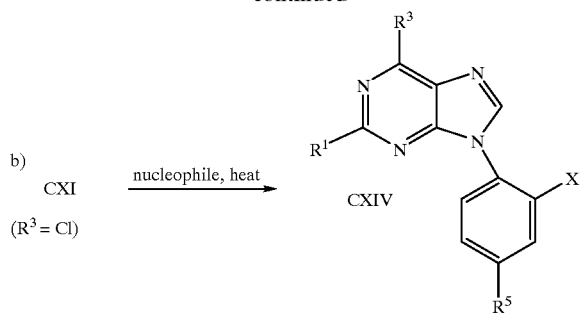

Compounds of the Formula (I) wherein J, K, and/or L are N, such as (CXXVII), (CXXVIII), (CXXIX), or (CXXX), were prepared according to Schemes 26 and 27. The preparation of the lower ring heterocycle of the compound of the Formula (I) is shown in Scheme 26. 2,4-Dihydroxy-5-nitropyrimidine (CXV) was first converted to the dichloro compound (CXVI) via treatment with phosphorus oxychloride. Compound (CXVI) was then converted to the symmetrically bis-substituted pyrimidines, (CXVII) and (CXVIII), via reaction with the appropriate $R^5$ or X group radicals, $MR^5$ and MX, respectively, where M is a metal atom. It is understood that compounds of the Formula (I) wherein $R^5$ and X have the same definition fall within the scope of this invention. A method of forming the unsymmetrically bis-substituted compounds (CXIX) and (CXX) is treatment of (CXVI) with equimolar amounts of $MR^5$ and X to form a statistical distribution of products, (CXVII), (CXVIII), (CXIX) and (CXX), which can be purified by standard techniques, such as, recrystallization or chromatography, The desired (N-pyrimidino-N-alkyl)aminopyrimidines of the present invention were prepared according to Scheme 27. An appropriately substituted 2-hydroxypyrimidine (CXXI) was converted to the 2-chloropyrimidine (CXXII) via treatment with phosphorus oxychloride. The intermediate (N-pyrimidino)aminopyrimidines, (CXXIII), (CXXIV), (CXXV), and (CXXVI), were prepared via treatment of (CXXII) with the appropriate 5-aminopyrimidine, (CXVII), (CXVIII), (CXIX) and (CXX) respectively, in the presence of a base, such as, NaH. Simple alkylation of the amino groups in (CXXIII), (CXXIV), (CXXV), and (CXXVI) via treatment with $R^4I$ and sodium hydride gave the desired (N-pyrimidino-N-alkyl)aminopyrimidines, (CXXVII), (CXXVIII), (CXXIX), and (CXXX).

Scheme 26

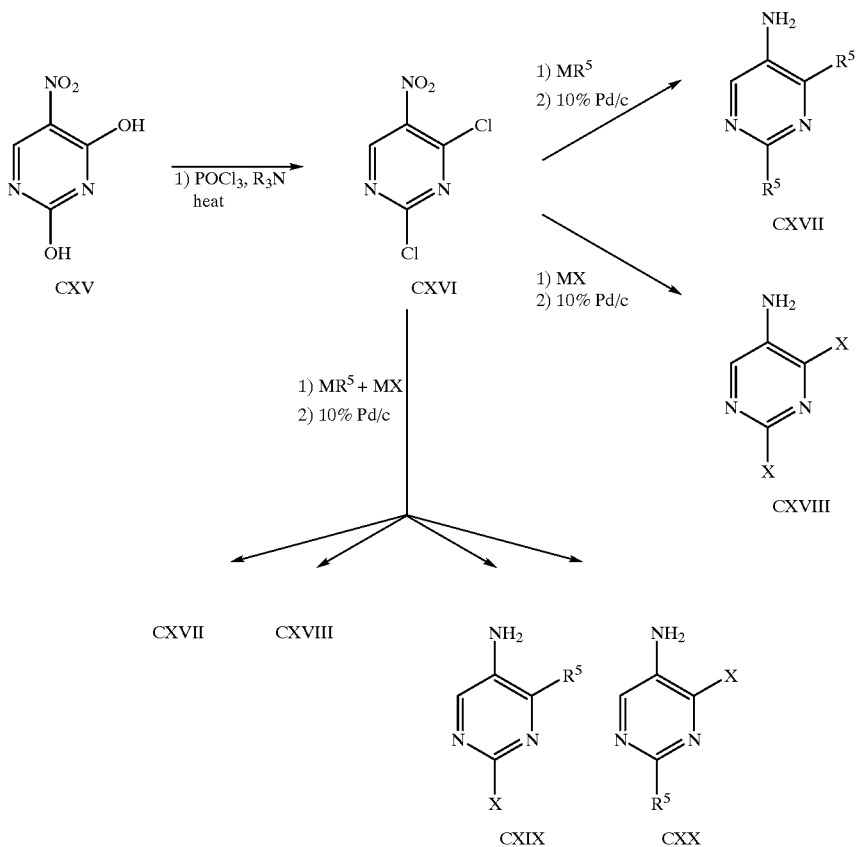

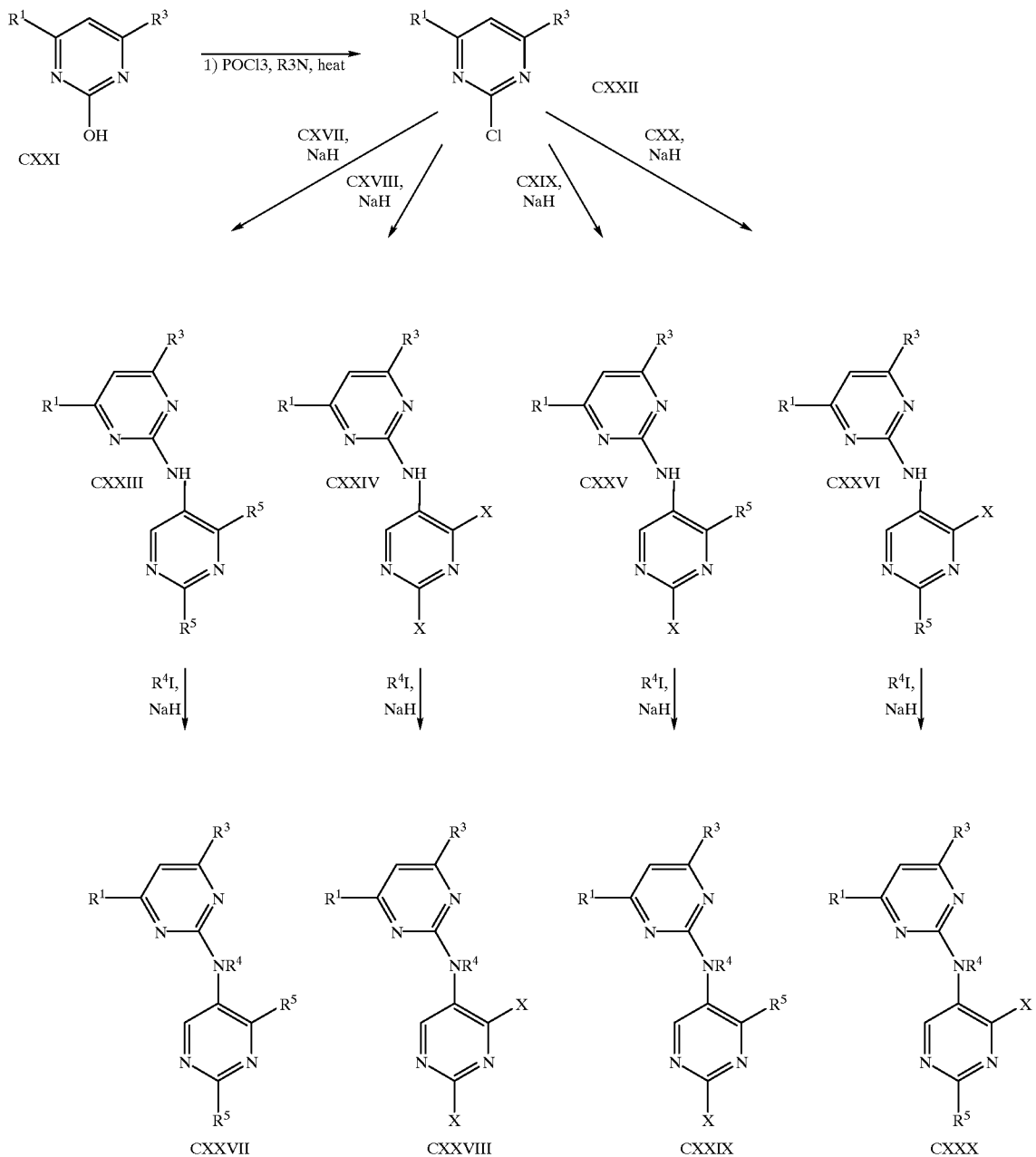

Scheme 27

The (N-heterocycle-N-alkyl)aminopyrimidines or N-heterocycle-N-alkyl)aminotriazines of the present invention may also be prepared according to Scheme 28. Commercially available amino substituted heterocycles (CXXXI) may be brominated using a tetrasubstituted ammonium tribromide, preferably benzyltrimethylammonium tribromide (BTMA Br$_3$) to yield the appropriately substituted o-bromo-aminoheterocycle (CXXXII). Such reactions are carried out in an inert solvent, such as, lower alcohols or halocarbons of 1 to 4 carbons and 1 to 4 halogens in the presence of a base, such as, alkali metal or alkaline earth metal carbonates. Compound (CXXXII) is then coupled to a substituted pyrimidine or triazine (CXXXIII) to form an (N-heterocycle)aminopyrimidine (CXXXIVa) or (N-heterocycle)aminotriazine (CXXXIVb). (CXXXIVa or b) is then further alkylated in the presence of a base to the target (N-heterocycle-N-alkyl)aminopyrimidine (CXXXVa) or (N-heterocycle-N-alkyl)aminotriazine (CXXXVb), respectively.

Scheme 28

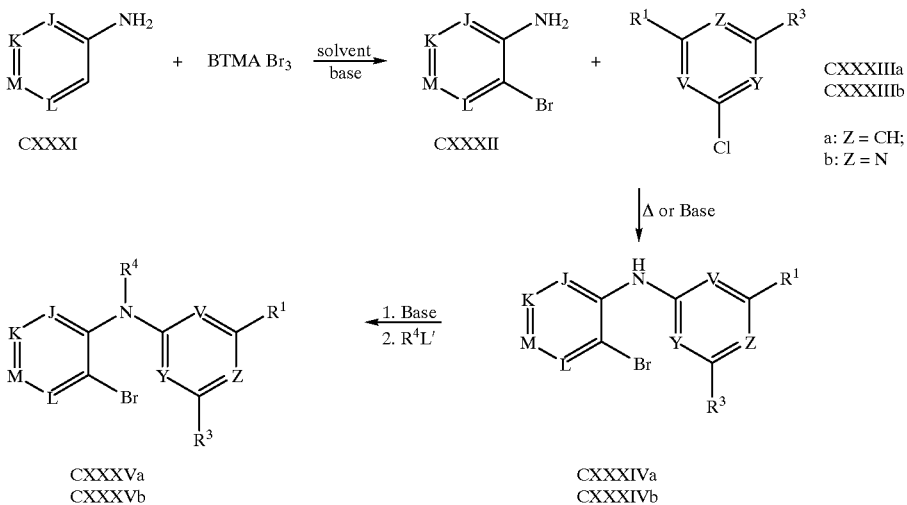

a: Z = CH;
b: Z = N

The compounds of the invention and their syntheses are further illustrated by the following examples and preparations. All temperatures are in degrees Celsius.

EXAMPLE 1

N-(2-bromo-4-methylphenyl)-N-methyl-4,6-dimethyl-2-pymidinamine

Part A: To 4,6-dimethyl-2-hydroxypyrimidine (37.1 g), cooled in an ice bath was slowly added phosphorous oxychloride (60 mL) and the mixture was stirred at 0° C. for 15 minutes and heated to reflux for 23 hours. The mixture was allowed to cool to room temperature, poured slowly over ice and extracted with diethyl ether (20×100 mL). The combined ether layers were dried over magnesium sulfate and concentrated in vacuo to yield an off-white crystalline solid (19.77 g). The remaining material was subjected to lighter-than-water liquid/liquid extraction using diethyl ether for 19.5 hours to yield additional off-white crystalline solid (3.53 g) after concentration. A total of 23.31 g of 2-chloro-4,6-dimethylpyrimidine was obtained (55% yield).

Part B: To a solution of the product from Part A (2.0 g) in ethylene glycol (80 mL) was added 2-bromo-4-methylaniline (2.6 g, 1 eq) and the mixture was heated to reflux for 4.5 hours. After cooling to room temperature, the mixture was partitioned between water (200 mL) with ethyl acetate (3×100 mL). The ethyl acetate layers were combined, washed with brine, dried over magnesium sulfate, and concentrated under vacuum to yield a brown solid (4.92 g). This product was purified on a silica gel-60 column using 25% ethyl acetate in hexanes as eluent. The intermediate, N-(2-bromo-4-methylphenyl)-4,6-dimethyl-2-pyrimidinamine (3.29 g) was obtained as light tan fine crystals (80% yield).

Part C: To the product from Part B (1.0 g) in dry tetrahydrofuran (40 mL) was added potassium tert-butoxide in 2-methyl-2-propanol (1.0 M, 6.8 mL) and iodomethane (1.0 mL, 5 eq). The mixture was stirred for 72 hours at room temperature. After partitioning between water (50 ml) using ethyl acetate (2×100 ml), the ethyl acetate layers were combined, washed with brine, dried over magnesium sulfate, and concentrated in vacuo to yield a yellow liquid (1.06 g). The crude product was purified on a silica gel-60 column using 15% ethyl acetate in hexanes as eluent. The title compound, as the free base, was obtained as a thick yellow liquid (0.89 g; 85% yield). Anal. Calcd $C_{14}H_{16}BrN_3$: % C, 54.92; % H, 5.27; % N, 13.72; ; % Br: 26.09. Found: % C, 54.61; % H, 5.25; % N, 13.55; % Br; 26.32.

The hydrochloride salt was made using anhydrous hydrogen chloride in diethyl ether; mp 120–121° C.

EXAMPLE 2

N-(2-bromo-4-(1-methylethyl)phenyl)-N-methyl-4,6-dimethyl-2-pymidinamine

Part A: A mixture of the product from Example 1, Part A (2.01 g, 14.01 mmoles), 2-bromo-4-(1-methylethyl)aniline (3 g, 14.10 mmoles) in ethylene glycol (20 mL) was heated to reflux for 1.5 hours. Following cooling to room temperature and partitioning between ethyl acetate (200 mL) and aqueous sodium hydroxide (1 M, 50 mL), the organic layer was washed with brine, dried, and concentrated in vacuo. The residue was chromatographed on silica gel using 5% ethyl acetate in hexanes to give 2-N-(2-bromo-4-(1-methylethyl)phenyl)-4,6-dimethylpyrimidinamine(3.28 g).

Part B: The product from Part A (1.64 g, 5.12 mmoles) was treated with sodium hydride (60% in oil, 0.41 g, 10.25 mmoles) in tetrahydrofuran (10 mL) at 25° C. for 15 minutes and iodomethane (0.82 mL, 13 mmoles) was added. The mixture was stirred at 25° C. for 90 hours and partitioned between ethyl acetate (100 mL) and water (30 mL). The water was extracted with additional ethyl acetate (60 mL) and the combined organic extracts were washed with brine, dried, and concentrated in vacuo. The residue was chromatographed on silica gel using 8% ethyl acetate in hexanes to give the title compound (1.4 g) as the free-base.

The free-base was dissolved in ether (10 mL) and treated with a solution of anhydrous hydrogen chloride in ether (1 M, 6 mL). The precipitated solid was collected and dried under vacuum (mp 163–164° C.).

EXAMPLE 3

N-(2-bromo-4-ethylphenyl)-N-methyl-4,6-dimethyl-2-pypimidinamine

Part A: 2-Bromo-4-acetylacetanilide (2 g, 7.81 mmoles) was dissolved in trifluoroacetic acid (20 mL) and triethylsilane (2.8 mL, 17.5 mmoles) was added. The mixture became warm and was stirred without cooling for 4 h. Then it was basified with conc. NH$_4$OH and NaHCO$_3$ and extracted with EtOAc (2×100 mL). The organic extracts were combined, washed with brine, dried and stripped in vacuo. The residue was >90% clean and directly used in the next step.

Part B: Using the product from Part A and the procedure outlined for Example 1, the desired compound was obtained in good yield.

EXAMPLE 4

N-(2-bromo-4-(1-methylethyl)phenyl)-N-ethyl-4-morpholino-6-methyl-2-pymidinamine Part A: A mixture of 2,4-dichloro-6-methylpyrimidine (4 g, 24.54 mmoles), morpholine (2.14 mL, 24.54 mmoles) and N,N-diisopropylethylamine (4.52 mL) in ethanol (60 mL) was stirred at 0° C. for 3 hours, 25° C. for 24 hours, followed by reflux for 1 hour. The solvent was removed under vacuum and the residue was partitioned between ethyl acetate (200 mL) and aq. sodium hydroxide (1 M, 50 mL). The organic layer was washed with water and brine and dried and concentrated in vacuo. The residue was recrystallized from ethyl acetate/hexanes to give 2-chloro-4-morpholino-6-methylpyrimidine (3.8 g).

Part B: The product from Part A (1 g, 4.67 mmoles) and 2-bromo-4-(1-methylethyl)aniline (1 g, 4.67 mmoles) were heated to reflux in ethylene glycol (6 mL) for 1.5 hours. After cooling, the mixture was partitioned between ethyl acetate (100 mL) and aq. sodium hydroxide (1 M, 20 mL). The organic layer was washed with water and brine, dried and concentrated on a rotary evaporator. The residue was chromatographed on silica gel using 25% ethyl acetate in hexanes to give 2-N-(2-bromo-4-(1-methylethyl)phenyl)-4-morpholino-6-methylpyrimidinamine (1.5 g).

Part C: The product from Part B (1.0 g, 2.56 mmoles) was treated with sodium hydride (60% in oil, 0.15 g, 3.75 mmoles) in tetrahydrofuran (10 mL) at 25° C. for 20 minutes, followed by addition of iodoethane (0.32 mL, 4 mmoles). The mixture was stirred at 25° C. for 24 hours and heated to reflux for 5 hours. After partitioning between ethyl acetate (100 mL) and water (20 mL), the organic extract was washed with brine, dried, and concentrated in vacuo. The residue was chromatographed on silica gel using 12% ethyl acetate in hexanes to give the title compound (0.94 g) as the free-base.

The hydrochloride salt of the above title compound was prepared by dissolving the isolate in ether (10 mL) and treating with anhydrous hydrogen chloride in ether (1 M, 4 mL). The precipitated solid was collected and dried under vacuum (mp 219–222° C.).

EXAMPLE 5

N-(2-bromo-4-(1-methylethyl)phenyl)-N-ethyl-4,6dimethyl-2-pyrimidinamine

Part A: To a solution of 2-bromo-4-(1-methylethyl)aniline (6 g, 28.2 mmoles) and cyanamide (4.7 g, 112.08 mmoles) dissolved in ethyl acetate (100 mL) and ethanol (13 mL) was added hydrogen chloride in ether (1 M, 38 mL, 38 mmoles) and the mixture was stirred at 25° C. for 1 hour. The volume of the reaction was reduced by 75 mL by distillation. The residue was heated to reflux for 3 hours and after cooling, ether (120 mL) was added. The precipitated solid, 2-bromo-4-(1-methylethyl)phenylguanidinium hydrochloride, was collected and dried (10.4 g), and was used in the next reaction without purification.

Part B: A mixture of the product from Part A (5.0 g, 13.47 mmoles), potassium carbonate (1.86 g, 13.47 mmoles) and 2,4-pentanedione (2.8 mL, 27.28 mmoles) in N,N-dimethylformamide (35 mL) was heated to reflux for 24 hours. After cooling, the reaction was partitioned between ethyl acetate (120 mL) and aq. sodium hydroxide (0.5 M, 100 mL). The aqueous layer was extracted with additional ethyl acetate (120 mL) and the combined organic extracts were washed with water, brine, dried and concentrated in vacuo. The residue was chromatographed on silica gel eluting with 8% ethyl acetate in hexanes to give 2-N-(2-bromo-4-(1-methylethyl)phenyl)-4,6-dimethylpyrimidinamine (3.37 g).

Part C: The product isolated from Part B (3.0 g, 9.37 mmoles) was alkylated with sodium hydride and iodoethane in tetrahydrofuran in an analogous manner to that described for Example 4, Part C. The title compound was isolated as the free-base (2.88 g).

The hydrochloride salt was prepared in a manner analogous to that of Example 4 using hydrogen chloride in ether, to give a solid, mp 151–153° C.

EXAMPLE 6

N-ethyl-N-(2-bromo-4-(2-methoxyethyl)phenyl)4-morpholino-6-methyl-2-pyrimidinamine Part A: To 4-Hydroxyethylaniline, 16.55 g (0.12 moles) in a mixture of pyridine (23 mL, 0.29 moles) and CH$_2$Cl$_2$ (100 mL) cooled to 0° C. was added acetyl chloride (18.8 mL, 0.26 moles) dropwise. The mixture was stirred at 0° C. for 2 h and at 25° C. for 48 h and then added to saturated NaHCO$_3$ solution (100 mL). The CH$_2$Cl$_2$ was separated, washed with brine, dried and stripped in vacuo. The residue was chromatographed on silica gel using 25% and 1:1 EtOAc/hexanes to give the product (24 g, 90% yield).

Part B: 4-Acetoxyethylacetanilide was brominated according to the method described in *Org. Synth. Coll.* Vol I, 111, wherein the anilide (14 g, 63 mmoles) was dissolved in glacial acetic acid (70 mL) and bromine (4 mL, 77.4 mmoles) was added dropwise. The resulting solution was stirred at 25° C. for 60 hours. A solution of sodium sulfite (20 mL) was then added, followed by H$_2$O (200 mL) and the precipitated bromide was isolated by filtration. The filtrate was further diluted with H$_2$O (300 mL) and cooled to give an additional amount of bromide. The isolated bromide was heated to reflux in HCl solution (6M, 100 mL) for 2 h and the resulting mixture was neutralized with solid NaHCO$_3$ and extracted with EtOAc (2×160 mL each). The combined EtOAc extracts were washed with brine, dried and stripped in vacuo. The residue was chromatographed on silica gel using 1:1 EtOAc/hexanes to give the product (2.8 g) in 20% yield for the two steps.

Part C: 2-Bromo-4-hydroxyethylaniline (1.6 g, 7.3 mmoles) and 2-chloro-4,6-dimethylpyrimidine (1.1 g, 7.3 mmoles) were reacted in ethylene glycol (6 mL) at reflux for 1.5 h. After cooling the mixture was partitioned between EtOAc (100 mL) and NaOH solution (0.5M, 25 mL). The aqueous layer was extracted with additional EtOAc (50 mL) and the combined organic extracts were washed with brine, dried and stripped in vacuo. The residue was chromatographed on silica gel using 1:1 EtOAc/hexanes to give the product (1.3 g) in 64% yield.

Part D: The product from Part C (1.39 g, 4.77 mmoles) was dissolved in dry CH$_2$Cl$_2$ (30 mL) and 3,4-dihydro-2H- pyran (1.65 mL, 11.98 mmoles) was added, followed by conc. sulfuric acid (Conc. $H_2SO_4$, 0.2 mL). The mixture was stirred at 25° C. for 60 h and solid KpCp, (1 g) was added, followed by saturated NaHCO (50 mL), The mixture was partitioned between EtOAc (120 mL) and $NaHCO_3$ solution (20 mL). The EtOAc was washed with brine, dried, and stripped in vacuo. The dried crude product, dissolved in dry THF (15 mL) was treated with sodium hydride (60% in oil, 380 mg) at 25° C. for 15 min and then iodoethane (1 mL, 9.45 mmoles) was added.

The mixture was stirred at 25° C. for 12 h and heated to reflux for 4 h. Then it was partitioned between EtOAc (120 mL) and $H_2O$ (20 mL). The EtOAc was washed with brine, dried and stripped in vacuo. The residue was chromatographed on silica gel using 15% EtOAc/hexanes to give the product (1.6 g) in 78% yield for the two steps.

Part E: The product from Part D was dissolved in MeOH (20 mL) and conc. $H_2SO_4$ (0.4 mL) was added, followed by HCl in ether (1M, 1.5 mL). The mixture was stirred at 25° C. for 2 h, quenched with solid $K_2CO_3$ (1 g), and partitioned between EtOAc (100 mL) and $NaHCO_3$ solution (30 mL) and NaOH solution (2 mL, 2 M). The $H_2O$ layer was extracted with additional EtOAc (60 mL) and the combined EtOAc extracts were washed with brine, dried, and stripped in vacuo. The residue was chromatographed on silica gel using 40% EtOAc/hexanes to give the product (1.23 g) in 95% yield.

Part F.: The product from Part E (720 mg, 2.06 mmoles) was treated with NaH (60% in oil, 120 mg, 3 mmoles) in THF (10 mL) at 0° C. for 5 min and at 25° C. for 15 min. Iodomethane (0.25 mL, 4 mmoles) was added and the resulting mixture was stirred at 25° C. for 20 h. The reaction was partitioned between EtOAc (100 mL) and $H_2O$ (25 mL). The EtOAc was washed with brine, dried, and stripped in vacuo. The residue was chromatographed on silica gel using 20% EtOAc/hexanes to give the product (680 mg) (91% yield), which was converted into the hydrochloride salt by treatment with 1 M HCl/ether, mp 117–118.5° C.

EXAMPLE 7

N-Ethyl-N-(2-iodo4-(1-methylethyl)phenyl)4-morpholinyl-6-methyl-2-pyrimidinamine A solution of the free-based Example 4 (1.4 g, 3.34 mmoles) dissolved in tetrahydrofuran (15 mL) at –78° C. was treated with n-butyllithium (1.6 M in hexanes, 3.3 mL, 3.7 mmoles). After stirring 15 minutes, a solution of iodine (1.0 g, 4 mmoles) in tetrahydrofuran (5 mL) was added dropwise and the mixture was stirred at –78° C. for an additional 30 minutes before warming to 25° C. The reaction was partitioned between ethyl acetate (100 mL) and sodium bisulfite solution (satd., 20 mL). The ethyl acetate layer was washed with water, brine, dried and concentrated in vacuo. The residue was chromatographed on silica gel using 15% ethyl acetate in hexanes as eluent to give the title compound (0.9 g) as a solid, mp 96–98° C.

EXAMPLE 8

N-(2-Bromo-4-(1-methylethyl)phenyl)-N-ethyl-6-methyl-4-(2-thienyl)-2-pyrimidinamine Part A: 2-Chloropyrimidine (2.0 g) was dissolved in diethyl ether (50 mL) and chilled to –30° C. A solution of methyllithium in ether (1.4 molar, 15 mL) was slowly added and the reaction was stirred at –30° C. for 30 minutes, then at 0° C. for an additional 30 minutes. A mixture of acetic acid (glacial, 1.2 mL), water (0.5 mL) and tetrahydrofuran (5 mL) was added to quench the reaction. 2,3-Dichloro-5,6-dicyano-1,4-benzoquinone (4.79 g) in tetrahydrofuran (20 mL) was then added and the reaction was allowed to stir for 5 minutes at room temperature. The mixture was chilled to 0° C. and aqueous sodium hydroxide solution (3 M, 50 mL) was added and the reaction mixture allowed to stir for 10 minutes. The organic layer was separated and washed with water and dried with magnesium sulfate. The solvent was removed in vacuo and the resulting residue chromatographed on silica gel (solvent 30% ethyl acetate in hexanes; $R_f$ 0.4) to yield 2-chloro-4-methylpyrimidine (1.4 g), m.p. 48–50° C.

Part B: To thiophene (0.66 g) in dry ether (25 mL) at 0° C. was added n-butyl lithium in hexanes (1.6 M, 2.7 mL) and the reaction was stirred at 0° C. for 15 minutes. After cooling to –30° C., a solution of 2-chloro-4-methylpyrimidine (1.0 g) in ether (10 mL) was slowly added and the reaction was stirred at –30° C. for 30 minutes and at 0° C. an additional 30 minutes before quenching with a mixture of acetic acid (glacial, 0.45 mL), water (0.5 mL) and tetrahydrofuran (1.0 mL). 2,3-Dichloro-5,6-dicyano-1,4 -benzoquinone (1.77 g) in tetrahydrofuran (5 mL) was added and the reaction mixture was stirred at room temperature for 5 minutes, then cooled to 0° C. before aq. sodium hydroxide solution (3 M, 50 mL) was added. The organic layer was separated, washed with water, and dried with magnesium sulfate. The solvent was evaporated and the resultant crude oil was chromatographed on silica gel (30% ethyl acetate in hexanes; $R_f$ 0.55) to yield 2-chloro-4-methyl-6-(2-thienyl)pyrimidine (0.21 g). Anal. Calcd: % C, 51.46; % H, 3.33; % N, 13.33. Found: % C, 51.77; % H, 3.35; % N, 12.97.

Part C; 2-Bromo-4-(1-methylethyl)aniline (0.26 g) and 2-chloro-4-methyl-6-(2-thienyl)pyrimidine (0.21 g) in ethylene glycol were heated at reflux for 24 hours. The reaction mixture was diluted with ethyl acetate, washed with aq. sodium hydroxide solution (10% , 3×100 mL) and the organic phase was dried. Solvent removal gave a crude brown oil, which was purified on silica gel using 20% ethyl acetate in hexanes ($R_f$ 0.5) as eluent to provide N-(2-bromo-4-isopropylphenyl)-4-methyl-6-(2-thienyl)-2-pyrimidinamine (0.1 g) as a solid, mp 98–101° C. Mass spec ($NH_3$-CI/DDIP): 390 $(M+H)^{30}$.

Part D: The product from Part C (0.1 g) was slowly added to a solution of sodium hydride (50 mg) in dry tetrahydrofuran, after which iodoethane (0.1 g) was added and the mixture was refluxed for 24 hours. The reaction mixture was cooled and water (0.5 mL) was added. The solvent was evaporated and the crude material was taken up in ethyl acetate, washed with water (3×50 mL) and dried. The solvent was evaporated and the crude product chromatographed on silica gel using 10% ethyl acetate in hexanes ($R_f$ 0.5) to give the title compound (70 mg) as the free-base.

The HCl salt of this material was prepared using the procedure reported above; mp 95–97° C.; Mass spec. ($NH_3$-CI/DDIP): 417 $(M+H)^+$. Anal. Calcd for $C_{20}$, $H_{22}N_3BrS·HCl$: % C, 53.10; % H, 5.09; % N, 9.51. Found: % C, 53.78; % H, 5.22; % N, 9.10.

EXAMPLE 9

N-(2-Bromo-4-(1-methylethyl)phenyl)-N-cyclopropylmethyl-4,6-dimethyl-2-pyrimidinamine)

By analogy to Example 2 the title compound was prepared by substituting 2-bromo-4-(1-methylethyl)aniline (4.0 g) and 2-chloro-4,6-dimethylpyrimidine in Part A, to give the desired pyrimidinamine intermediate, Mass spec. (NH$_3$-CI/DDIP): 321 (M+H)$^+$. By substituting (bromomethyl) cyclopropane in Part B of this same Example, the desired material was obtained, Mass spec. (NH$_3$-CI/DDIP): 374 (M+H)$^+$.

The hydrochloride salt of this free base was prepared, mp 146–148° C.

EXAMPLE 10

N-(2-Bromo-4-(1-methylethyl)phenyl)-N-propargyl4,6-dimethyl-2-pyrimidinamine

By using 2-(2-bromo-4-(1-methylethyl)anilino)-4,6-dimethylpyrimidine and substituting propargyl chloride in Example 9, the title compound was isolated as the free-base, Mass spec. (NH$_3$-CI/DDIP): 358 (M+H)$^+$.

The hydrochloride salt of the free base was prepared.

EXAMPLE 11

N-Ethyl-N-(2-iodo4-(2-methoxyethyl)phenyl)4,6-dimethyl-2-pyrimidinamine, hydrochloride Part A: 4-Hydroxyethylaniline was iodinated in a manner analogous to that described in Example 6 in conjunction with that reported in *Tet. Lett.* 33:373–376 (1992). The aniline (2 g, 14.58 mmoles) was dissolved in CH$_3$CN (25 mL) and H$_2$O (15 mL) containing NaHCO$_3$ (1.68 g, 20 mmoles) was added. The mixture was cooled to 12–15° C. by addition of ice and iodine (3.9 g, 15.35 mmoles) was added. The mixture was stirred at 25° C. for 16 h and then it was partitioned between EtOAc (100 mL) and NaOH solution (20 mL, 1M). The EtOAc was washed with brine, dried and stripped in vacuo. The residue was chromatographed on silica gel using 1:1 EtOAc/hexanes to give 1.8 g product, a 47% yield.

Part B: The product from Part A (6.3 g, 23.94 mmoles) was dissolved in a mixture of EtOAc (100 mL) and EtOH (10 mL) and cyanamide (4.7 g, 112.5 mmoles) was added, followed by HCl in ether (31 mL, 1 M). The flask was fitted with a distillation head and 50 mL solvent was distilled off. The residual mixture was diluted with EtOH (15 mL) and heated to reflux for 5 h. After cooling, Et$_2$O (100 mL) was added and the precipitated salt was washed with EtOAc and dried to give the product (4.5 g) in 55% yield.

Part C: The guanidinium salt from Part B (8.53 g, 24.95 mmoles), potassium carbonate (3.84 g, 27.72 mmoles) and 2,4-pentanedione (9 mL, 42.65 mmoles) were heated to reflux in DMF (70 mL) for 16 h. The reaction mixture was partitioned between EtOAc (150 mL) and H$_2$O (50 mL) and the organic layer was washed with H$_2$O (2×80 mL), brine, dried and stripped in vacuo. The residue was chromatographed on silica gel using 1:1 EtOAc/hexanes to give the product (2.8 g) in 30% yield.

Part D: To the product from Part C (3.3 g (8.93 mmoles) in CH$_2$Cl$_2$ (60 mL) and 3,4-dihydro-2H-pyran (3.1 mL, 22.7 mmoles) was added Conc. H$_2$SO$_4$ (0.5 mL) and the mixture was stirred at 25° C. for 16 h. An additional portion of H$_2$SO$_4$ (0.2 mL) was added and stirring was continued for 3 h. EtOAc (100 mL) and saturated NaHCO$_3$ (100 mL) was added and the layers separated. The aqueous layer was extracted with additional EtOAc (100 mL) and the combined organic extracts were washed with NaHCO$_3$, brine, dried and stripped in vacuo. The residue was chromatographed on silica gel using 20% EtOAc/hexanes to give the product (1.2 g) in 31% yield.

Part E: The product from Part D was dissolved in dry THF (15 mL) and NaH (60% in oil, 220 mg, 5.5 mmoles) was added. The mixture was stirred at 25° C. for 15 min and iodoethane (0.5 mL, 5.7 mmoles) was added. The mixture was stirred at 25° C. for 16 h and then heated to reflux for 2 h. The reaction product was then partitioned between EtOAc (100 mL) and H$_2$O (30 mL). The organic layer was washed with brine, dried and stripped in vacuo. The residue was chromatographed on silica gel using 10% EtOAc/hexanes to give the product (1.1 g). This material was dissolved in MeOH (20 mL). HCl in ether (3 mL, 1M) was added and the mixture was stirred at 25° C. for 2 h. Then it was partitioned between EtOAc (100 mL) and NaOH (30 mL, 1 M). The EtOAc was washed with brine, dried and stripped in vacuo. The residue was used in the next step without purification.

Part F: The product from Part E (950 mg, 2.4 mmoles) in dry THF (10 mL) was treated with NaH (60% in oil, 140 mg, 3.5 mmoles), stirred at 25° C. for 15 min and 0.25 mL Iodoethane (4 mmoles) was added. The resulting mixture was stirred at 25° C. for 16 h and then partitioned between EtOAc (100 mL) and H$_2$O (20 mL). The organic layer was washed with brine, dried and stripped in vacuo. The residue was chromatographed on silica gel using 20% EtOAc/hexanes to give the product (500 mg), which was converted into the hydrochloride salt in the usual manner, mp 129–131° C.

EXAMPLE 12

N-(2-Bromo-4-(1-methylethyl)phenyl)-N-ethyl-4-methyl-2-pymidinamine

Part A: The product from Example 8, Part A (0.2 g) and 2-bromo-4-(1-methylethyl)aniline were coupled using the same method described in Example 8, Part C to provide N-(2-bromo-4-(1-methylethyl)phenyl)-4-methyl-2-pyrimidinamine (0.7 g) as a viscous oil; Mass spec. (NH$_3$-CI/DDIP): 307 (M+H).

Part B: The product from Part A was alkylated with iodoethane using the same method described in Example 8, Part D to give the desired N-(2-bromo-4-(1-methylethyl)phenyl)-N-ethyl-4-methyl-2-pyrimidinamine (0.3 g) as the free base.

The hydrochloride salt of this material was prepared in the usual manner; mp 145–147° C. Mass spec. (NH$_3$-CI/DDIP). 334 (M+H)$^+$.

EXAMPLE 13

N-(2-Bromo-4-(1-methylethyl)phenyl)-N-ethyl-4-methyl-6-(N-methyl-2-hydroxyethlamino)-2-pyrimidinamine Part A: A solution of 2,4-dichloro-6-methylpyrimidine (1.0 g) and 2-(methylamino)ethanol (0.4 g) in ethanol (50 mL) was refluxed for 24 hours. The solvent was evaporated to give a crude residue, which was chromatographed on silica gel using 5% methanol in chloroform to yield 2-chloro-4-methyl-6-(N-methyl-2-hydroxyethylamino) pyrimidine (370 mg).

Mass spec. (NH$_3$-CII/DDIP): 202 (M+H)$^+$.

Part B: The hydroxyl group in the product from Part A was protected as the methoxymethyl ether (MOM-ether) using N,N-di(1 -methylethyl)ethylamine and bromomethyl methyl ether (0.35 g) in dry tetrahydrofuran to provide the protected adduct (310 mg, Mass spec. 246 (M+H)$^+$), which was carried on without purification.

Part C: The protected MOM-ether was coupled with 2-bromo-4-(1-methylethyl)aniline using the procedure of Example 8, Part C. Under these conditions, the methoxymethyl protecting group was also removed providing N-(2-bromo-4-(1-methylethyl)phenyl)-4-methyl-6-(N-methyl-2-hydroxyethylamine)-2-pyrimidinamine (mass spec. $NH_3$-CI/DDIP 379 $(M+H)^+$). This hydroxyl group was reprotected for subsequent reactions as described in Part B, (Mass spec. for MOM-ether ($NH_3$-CI/DDIP): 453 $(M+H)^+$). Alkylation with iodoethane was carried out using the method of Example 8, Part D. The MOM-ether was deprotected by stirring at room temperature in a solution of methanol (5 mL) and hydrochloric acid (1 M, 5 mL) for 24 hours. Upon workup and isolation, the title compound was obtained as the free-base.

The hydrochloride salt was prepared using the described procedure. High Res. Mass Spec; 407.144640 $(M+H)^+$; Expected 407.144648 $(M+H)^+$.

EXAMPLE 14

N-ethyl-N-(2-iodo4-(1-methylethyl)phenyl)4-thiomorpholino-6-methyl-2-pyrimidinamine, S-oxide The desired product was obtained by sodium periodate oxidation of the product of Example 22, according to the method of J. H. Bushweller et. al. *J. Org. Chem.* 54:2404, (1989).

EXAMPLE 15

N-(2-Bromo-4-(isopropoxy)phenyl)-N-ethyl-4,6dimethyl-2-pymidinamine

Part A: The synthesis of 2-bromo-4-isopropoxy-aniline was accomplished using the bromination procedure for 4-isopropoxy-aniline reported by Kajigaeshi et al. in *Bull. Chem. Soc. Jpn.* 61:597–599 (1988). The aniline, 1 eq. benzyltrimethylammonium tribromide, and 2 eq. calcium carbonate were stirred at room temperature in a solution of MeOH:$CH_2Cl_2$ (2:5) for one hour. The solids were removed by filtration and the filtrate was evaporated under vacuum. The residue was taken up in $H_2O$ and this mixture was then extracted three times with $CH_2Cl_2$. The combined extracts were dried over $MgSO_4$, filtered, and evaporated under vacuum to give a brown oil, which was purified on silica gel using 15% EtOAc in hexanes. ($R_f$=0.43)

Part B: Using the procedure for Example 1, Parts B–C and substituting the aniline from Part A, the title compound was obtained.

EXAMPLE 16

N-(2-bromo-4-(1-methylethyl)phenyl)-N-ethyl-4-methyl-6-(4-morpholinylcarbonyl)-2-pyrimidinamine To sodium hydride (60% in oil, 0.24 g, 6.0 mmol) suspended in anhydrous THF (10 mL) was added morpholine (0.52 g, 6.0 mmol) with stirring; the reaction mixture was warmed to reflux temperature and stirred for 1 hour. The reaction mixture was then cooled to ambient temperature and 2-(N-(2-bromo-4-(2-propyl)phenyl)-N-ethylamino)-4-carbomethoxy-6-methyl-pyrimidine (2.0 g, 5.1 mmol) was added. Stirring was continued for 26 hours. The reaction mixture was then poured onto a 1N NaOH solution, stirred and extracted three time with EtOAc. The combined organic layers were dried over $MgSO_4$, filtered and concentrated in vacuo. Column chromatography ($Et_2O$) afforded the title compound as a solid (900 mg, 39% yield): mp 145° C.; NMR ($CDCl_3$, 300 MHz):d 7.5 (d, 1H, J=1), 7.2 (dd, 1H, J=7,1), 7.1 (d, 1H, J=7), 6.8 (br s, 1H), 4.3–4.15 (m, 1H), 3.9–3.3 (m, 11H), 3.1–3.0 ( m, 1H), 2.9 (septet, 1H, J=7), 1.3 (d, 6H, J=7), 1.15 (t, 3H, J=7); Anal. ($C_{21}H_{27}BrN_4O_2$) Calcd: C, 56.38; H, 6.08; N, 12.52; Br, 17.86; Found: C, 56.07; H, 6.05; N, 12.29; Br, 18.08.

EXAMPLE 17

N-(2-bromo-4-(1-methylethyl)phenyl)-N-ethyl-6-methyl-4-(4-morpholinylmethyl)-2-pyrimidinamine A solution of N-(2-bromo-4-(1-methylethyl)phenyl)-N-ethyl-4-methyl-6-(4-morpholinylcarbonyl)-2-pyrimidinamine (750 mg, 1.72 mmol) in anhydrous THF (1.4 mL) was stirred at ambient temperature under a nitrogen atmosphere. A solution of borane in THF (1 M, 3.6 mL, 3.6 mmol) was added dropaise. The reaction mixture was then warmed to reflux temperature and stirred for 20 hours. After cooling to room temperature, acetic acid (3.5 mL) was added slowly and the mixture was heated to reflux temperature and stirred for 30 min. After being cooled to ambient temperature, the reaction mixture was poured onto a 3N NaOH solution, mixed and extracted three times with EtOAc. The combined organic layers were dried over $MgSO_4$, filtered and concentrated in vacuo. Column chromatography (EtOAc) of the residue afforded the title compound as an oil (300 mg, 39% yield, $R_f$ 0.3): NMR ($CDCl_3$, 300 MHz): d 7.5 (s, 1H), 7.2 (d, 1H, J=7), 7.15 (d, 1H, J=7), 6.5 ( s, 1H), 4.3–4.1 (m, 1H), 3.8–3.6 (m, 7H), 3.5–3.3 (m, 2H),2.9 (septet, 1H, J=7), 2.55–2.35 (br m, 3H), 2.35–2.25 ( m, 2H), 1.3 (d, 6H, J=7), 1.2 (t, 3H, J=7); CI-HRMS: calcd: 433.1603 (M+H), found: 433.1586.

EXAMPLE 18

Methyl 2-((2-bromo-4-(1-methylethyl)phenyl) ethylamino)-6-methyl-4-pyrimidinecarboxylate To sodium hydride (60% in oil, 4.8 g, 120 mmol) in THF (150 mL) at ambient temperature under a nitrogen atmosphere was added methyl-2-((2-bromo-4-(1-methylethyl) phenyl)amino)-6-methyl-4-pyrimidinecarboxylate (42.8 g, 118 mmol) portionwise over 30 min. After the gas evolution subsided, iodoethane (31.2 g, 16 mL, 200 mmol) was added in one portion and the reaction mixture was heated to a gentle reflux for 24 h. After cooling to room temperature, the reaction mixture was quenched carefully with water and extracted three times with ethyl acetate. The combined organic extracts were washed with water twice, dried over magnesium sulfate and filtered. Solvent was removed in vacuo to afford a brown oil. Column chromatography of the oil ($Et_2O$:hexanes::1:1) provided two fractions: (1) methyl-2-((2-bromo-4-(1-methylethyl)phenyl)amino)-6-methyl-4-pyrimidinecarboxylate (4.6 g, 11% yield, $R_f$=0.8) and (2) the title product (20 g, $R_f$=0.7) as a crude oil. The title product was recrystallized from hexanes and dried in vacuo to give a solid (18.0 g, 39% yield): mp 81–82° C.: NMR($CDCl_3$, 300 MHz):d 7.5 (br s, 1H), 7.25 (d, 1H, J=7), 7.15 (d, 1H, J=7), 7.1 (s, 1H), 4.3–4.1 (m, 1H), 4.05–3.75 (m, 4H), 2.95 (septet, 1H, J=7), 2.3 (br s, 3H), 1.3 (d, 6H, J=7), 1.25 (t, 3H, J=7); CI-HRMS: calcd: 392.0974 (M+H), found: 392.0960.

EXAMPLE 19

N-(2-bromo-4-(1-methylethyl)phenyl)-N-ethyl-4-methyl-6-(4-methylpiperazinylcarbonyl)-2-pyrimidinamine Using a method analogous to that used for Example 16, but substituting 4-methylpiperazine, the desired product was obtained; mp 81–82° C.

EXAMPLE 20

N-(2-Bromo-4-(2-hydroxyethyl)phenyl)-N-ethyl-4, 6-dimethyl-2-pyrimidinamine

The THP-hydroxyl protecting group was removed using HCl in ether product as described earlier to arrive at the title compound; mp 58–60° C.

EXAMPLE 21

N-ethyl-N-(2-methoxy4-(1-methylethyl)phenyl)4,6-dimethyl-2-pyimidinamine

Part A: Using the method of Example 1 and substituting 2-amino-5-methylphenol, the intermediate secondary amine was obtained.

Part B: By double methylating the amino and the phenol groups using excess sodium hydride and iodomethane in THF, the desired product was obtained.

EXAMPLE 22

N-ethyl-N-(2-iodo4-(1-methylethyl)phenyl)4-thiomorpholino-6-methyl-2-pyrimidinamine Using the iodination method of Example 11 and the general synthesis described in Example 4 the desired compound was obtained; mp 51–53° C.

EXAMPLE 23

N-[2-bromo-4-(1-methylethyl)phenyl]-N-ethyl-4-methyl-6-(4-morpholinyl)-1,3,5-triazin-2-amine Part A: Methyl magnesium bromide (300 mmole, 3M in ether, Aldrich) was added dropwise over a 10 min period to a solution of cyanuric chloride (12.9 g, 69.9 mmole) in $CH_2Cl_2$ (300 mL) under $N_2$ at −20° C. and stirring was continued at −20° C. for 4.5 hours. Water (36 mL) was added dropwise while keeping the reaction temperature below −15° C. The reaction mixture was allowed to reach room temperature and magnesium sulfate (40 g) was added. It was let stand for one hour. The reaction mixture was filtered and the solvent removed leaving a yellow solid (11.06 g). This material was purified using flash chromatography ($CH_2Cl_2$, silica) and gave 2,4-dichloro-6-methyl-s-triazine as a white solid (7.44 g) in 65% yield.

Part B: 2,4-dichloro-6-methyl-s-triazine (3 g, 18.29 mmol), 2-bromo-N-ethyl-4-isopropylaniline (6.07 g, 25.07 mmol) and diisopropylethylamine (3.2 g, 25.07 mmol) in dioxane (60 mL) under $N_2$ were heated at reflux for three hours. The solvent was removed and the residue was purified using flash chromatography ($CH_2Cl_2$, silica) to provide the product (4.58 g) as a clear oil in 68% yield.

Part C: The product from Part B (500 mg, 1.35 mmol) was dissolved in dioxane (20 mL) under $N_2$ at room temperature and morpholine (247 mg, 2.84 mmol) was added in one portion. Stirring was continued at room temperature for 17 hours. The reaction solvent was stripped away and the residue was triturated with ethyl acetate/hexane (1:3). The triturated material was purified using flash chromatography (EtOAc/hexane, 1:3 Silica). The product was collected as a clear oil (550 mg) in 97% yield. $C_{19}H_{26}N_3OBr$

EXAMPLE 24

N-(2-bromo-4-(1-methylethyl)phenyl)-N-ethyl-4-m ethyl-6-(hydroxymethyl)-2-pyrimidinamine The product of Example 18 and lithium borohydride (1.5 eq.) were stirred in dry THF under nitrogen for fifty hours. The reaction was then poured into water and extracted three times with $CHCl_3$. The combined extracts were dried over $MgSO_4$, filtered, and evaporated under vacuum to give a nearly quantitative yield of the product as a light yellow oil.

EXAMPLE 25

N-(2-bromo-4-(1-methylethyl)phenyl)-N-ethyl-4-methyl-6-(methoxymethyl)-2-pyrimidinamine To the product of Example 24 and sodium hydride (1.1 eq.) in dry THF under nitrogen was added iodomethane (1.1 eq.) and after four hours the reaction was poured into $H_2O$ and extracted three times with $CHCl_3$. The combined extracts were dried over $MgSO_4$, filtered, and evaporated under vacuum. The material was purified by chromatography on silica gel using 10% EtOAc in hexanes to give a light yellow oil. ($R_f$=0.37)

Example 26

N-(2-bromo-4-(1-methylethyl)phenyl)-N-ethyl-4-methyl-6-(thiomethyl)-2-pyrimidinamine Part A: 2-Bromo-4-isopropylaniline (8.9 g, 42 mmol) and 6-hydroxy-4-methyl-2-thiomethylpyrimidine (5 g, 32 mmol) were combined under $N_2$ and heated at 190° C. for 8 hours. The reaction mixture was cooled to room temperature. The residue was purified using flash chromatography ($CH_2Cl_2$/MeOH, 25:1, silica) to provide 9.16 g (89% yield) white solid.

Part B: The product from Part A (6 g, 18.6 mmol) and phosphorus oxychloride (20 mL, 214 mmol) were refluxed under $N_2$ for 15 minutes. The reaction mixture was cooled to room temperature, slowly poured onto ice (200 g), stirred about 30 minutes until the ice had melted, and the aqueous mixture was extracted with ethyl acetate (3×100 mL). The combined organic extracts were treated with water (100 mL) and brine (100 mL), dried over anhydrous sodium sulfate, filtered and stripped leaving 6.1 g tan oil. This material was purified using flash chromatography ($CH_2Cl_2$/hexane, 1:1, silica) to give 4.48 g (70% yield) of clear oil.

Part C: To the product of Part B (4.3 g, 12.65 mmol) in dimethylformamide (30 mL) under $N_2$ was added sodium hydride (658 mg, 16.45 mmol, 60% dispersion in oil) was added in small portions. After addition was complete, stirring was continued 4 hours at room temperature. Water (100 mL) was added to the reaction mixture and it was extracted with ethyl acetate (3×100 mL). The combined organic extracts were treated with water (100 mL) and brine (100 mL). The organic layer was dried over anhydrous sodium sulfate, filtered and stripped leaving 4.8 g tan oil. This material was purified using flash chromatography (EtOAc/hexane, 1:6, silica gel) to afford 4.4 g (95% yield) of oil.

Part D: The product of Part C (2 g, 5.4 mmol) and sodium thiomethoxide (558 mg, 7.6 mmol) in dioxane (50 mL) under $N_2$ were heated to reflux (20 hrs.). The solvent was stripped and the residue was purified using flash chromatography ($CH_2Cl_2$/hexane, 1:1, silica) to give 1.86 g (91% yield) of clear oil. Analysis: MS ($NH_3$—CI/DDIP) : 380 $(M+H)^+$.

EXAMPLE 27

N-(2-bromo-4-(1-methylethyl)phenyl)-N-ethyl-4-methyl-6-(thiomethyl)-2-pyrimidinamine, dioxide To the product of example 26 (1.8 g=4.8 mmol) in $CH_2Cl_2$ (100 mL) under $N_2$ was added 3-chloroperbenzoic acid (3.16 g, 14.67 mmol, 80–85% purity) in small portions and after addition, stirring was continued for 30 minutes. Unreacted peroxide was consumed using 10% sodium sulfite (5 mL), and the reaction mixture was diluted with $CH_2Cl_2$ (150 mL) followed by washing with 5% sodium bicarbonate (100 mL) and brine (100 mL). The organic layer was dried over anhydrous sodium sulfate, filtered and stripped leaving 2.19 g yellow oil. This material was purified using flash chromatography ($CH_2Cl_2$, silica) to provide 1.6 g of oil (79% yield). MS (NH3-CI/DDIP): 412 (M+H)$^+$.

EXAMPLE 28

N-(2-bromo-4-(1-methylethyl)phenyl)-N-ethyl-4-methyl-6-(thiomethyl)-2-pyrimidinamine, S-oxide To Example 26 product (770 mg, 2 mmol) in methanol (200 mL) was added sodium periodate (648 mg, 3 mmol) in water (10 mL) in one portion and the reaction mixture was refluxed 28 hours. The reaction solvent was stripped away and the residue was partitioned between ethyl acetate (200 mL) and water (50 mL). The organic layer was separated and treated with brine (50 mL). The organic layer was dried over anhydrous sodium sulfate, filtered and stripped leaving 820 mg tan residue. This material was purified using flash chromatography (EtOAc/hexane, 1:1, silica) to afford 570 mg (71% yield) of oil. MS (NH3-CI/DDIP) : 396 (M+H)$^+$.

EXAMPLE 29

N-[2-bromo-4(1-methylethyl)phenyl]-N-ethyl-4-methyl-6-benzyloxy-1,3,5 triazin-2-amine Benzyl alcohol (197 mg, 1.82 mmol, 1.2 eq) was added slowly to a solution of NaH (73 mg 60% dispersion, 1.82 mmol) in dry DMF and stirred at room temperature for 15 minutes. The product from Part B (560 mg, 1.52 mmol) was then added and the resulting mixture stirred at room temperature for 2 hours, The reaction mixture was then poured into water and extracted three times with ethyl acetate. The organic layer was dried over magnesium sulfate, filtered and concentrated in vacuo. The crude oil was chromatographed on silica using 20% ethyl acetate in hexanes as solvent to afford the title compound. $C_{22}H_{25}N_4OBr$ Calcd: C, 55.46; H, 5.46; N, 11.76; Found: C, 55.30; H, 5.41; N, 12.02.

EXAMPLE 30

N-[2-iodo-4-dimethylhydroxymethylphenyl]-N-ethyl-4-6-dichloro-1,3,5 triazin-2-amine Part A: Ethyl 4-aminobenzoate (5.0 gr, 30.27 mmol) and sodium bicarbonate (3.81 g, 45.40 mmol, 1.5 eq.) were added to a 50:50 mixture of methylene chloride and water. The mixture was chilled to 0 degrees and $I_2$, (11.53 g, 45.40 mmol, 1.5 eq.) was added slowly. The reaction mixture was allowed to come to room temperature and was stirred for 72 hours. The layers were then separated and the aqueous layer washed with methylene chloride. All organics were combined and dried over magnesium sulfate, filtered and concentrated in vacuo. The resulting oil was chromatographed on silica using 30% ethyl acetate in hexanes as solvent to afford ethyl 3-iodo-4-aminobenzoate. $C_9H_{10}NO_2I$ MS 292 (M+H)$^+$ 309 (M+NH$_4$)$^+$.

Part B: The product from part A (1.0 g, 3.4 mmol) was added to a stirring solution of NaH (0.21 gr, 5.2 mmol) in 25 mL of dry DMF and allowed to stir at room temperature for 10 minutes. Ethyl iodide (0.8 g, 5.2 mmol) was then added and the mixture was allow to stir for 24 hours. The reaction was then poured into water and extracted with ethyl acetate. The organic layer was dried with magnesium sulfate, filtered, and concentrated in vacuo. The crude material was chromatographed on silica using 30% ethyl vacuo. The crude material was chromatographed on silica using 30% ethyl acetate in hexanes as solvent to afford ethyl 3-iodo-4-(N-ethyl)aminobenzoate. $C_{11}H_{14}NO_2I$ MS 320(M+H)$^+$.

Part C: The product from part B (0.32 g, 1.0 mmol) was dissolved in dioxane and cyanuric chloride (0.18 g, 1.0 mmol) was added slowly. The reaction was heated to reflux for 4 hours, stirred at room temperature for 24 hours, then poured into water and extracted with ethyl acetate. The organic layer was dried with magnesium sulfate, filtered, and concentrated in vacuo. The crude material was chromatographed on silica using 10% ethyl vacuo. The crude material was chromatographed on silica using 10% ethyl acetate in hexanes as solvent to afford N-[2-iodo-4-ethylcarboylate]-N-ethyl-4-6-dichloro-1,3,5triazin-2-amine. $C_{14}H_{13}N_4O_2C_2I$ MS 467 (M+H)$^+$.

Part D: The product of part C (0.26 g, 0.6 mmol) was dissolved in 20 mL methylene chloride and chilled to -20 degrees. Methyl magnesium slowly. The reaction was allowed to come to room temperature and stirred for 4 hours, then poured into water and the layers were separated. The aqueous layer was extracted with methylene chloride and the organic layers combined, dried with magnesium sulfate, filtered, and concentrated in vacuo. The crude material was chromatographed on silica gel using 30% ethyl acetate in hexanes as solvent to afford the title compound. $C_{15}H_{18}N_4OICl$ MS 453 (M +H)$^+$.

EXAMPLE 31

N-(2-iodo4-(1-methylethyl)phenyl)-N-allyl4-morpholino-6-methyl-2-pyrimidinamine mp 109–112° C. Elemental analysis for $C_{21}H_{27}N_4IO$ HCl: Theory C, 48.99; H, 5.48; N, 10.88; I, 24.65; Cl, 6.89. Found C, 48.81; H, 5.43; N, 10.59, I, 24.67; Cl, 6.86.

EXAMPLE 32

N-(2-iodo4-(1-methylethyl)phenyl)-N-ethyl-4-chloro-6-methyl-2-pyrimidinamine

Guanidine 39.5 mmoles crude, obtained by treatment of the corresponding guanidinium salt with $K_2CO_3$, 15 mL (118 mmoles) ethyl acetoacetate and 2.0 g (14.47 mmoles) $K_2CO_3$ were heated to reflux in 120 mL absolute ethanol for 100 hr. Then the solvent was stripped in vacuo and the residue was chromatographed on silica gel using 40% EtOAc/hexanes as eluent to give 4 g product, a 27% yield for the three steps.

The 4-hydroxypyrimidine obtained from the above reaction (2.47 g, 6.69 mmoles) was dissolved into 20 mL POCl$_3$ and stirred at 25° C. for 4 hr. The reaction mixture was poured into ice, stirred for 30 min, and extracted with 100 mL EtOAc. The EtOAc extract was washed with brine, dried and stripped in vacuo. The residue was chromatographed on silica gel using 20% EtOAc/hexanes to give 1.64 g of the corresponding 4-chloropyrimidine (63% yield).

1.6 g (4.13 mmoles) 4-chloropyrimidine obtained above, and 0.33 g (8.25 mmoles) of NaH (60% in oil) in 10 mL dry DMF at 25° C. were stirred together for 15 min. Then 0.7 mL (8.75 mmoles) of EtI was added and the reaction was stirred at 0° C. for 2 h and at 25° C. for 16 h. It was then partitioned between 100 mL EtOAc and 25 mL water and the EtOAc was washed with water (2×30 mL), brine, dried and stripped in vacuo. The residue was chromatographed on silica gel using 8% EtOAc/hexanes to give 1.2 g product as a viscous liquid (70% yield); elemental analysis for $C_{16}H_{19}N_3ClI$: Theory: C, 46.23; H, 4.61; N, 10.11; Cl, 8.53; I, 30.53. Found: C, 46.36; H, 4.57; N, 9.89; Cl, 8.79; I, 30.38.

EXAMPLE 33

N-(2-methylthio4-(1-methylethyl)phenyl)-N-ethyl-4 (S)-(N-methyl-2'-pyrrolidinomethoxy)-6-methyl-2-pyrimidinamine The chloropyrimidine described above, 0.66 g (1.59 mmoles), 70 mg (1.76 mmoles) of NaH (60% in oil) and 0.19 mL (1.6 mmoles) (S)-N-methylprolinol in 10 mL of dry THF under nitrogen were stirred at 25° C. for 36 h and then refluxed for 2h. The mixture was partitioned between 10 mL EtOAc and 20 mL water and the EtOAc was washed with water, brine, dried and stripped in vacuo. The residue was chromatographed on silica gel using 0.5% $NH_4OH$/5% $CH_3OH$/$CH_2Cl_2$ as eluent to give 340 mg product, which was converted into the dihydrochloride salt by treatment with 1 M HCl in ether, mp 101–103° C. (dec). Elemental analysis for $C_{22}H_{31}N_4IO$. 2HCl: Theory C, 46.57; H, 5.86; N, 9.88; Cl, 12.50. Found C, 46.69; H, 6.02; N, 9.45; Cl, 12.69.

EXAMPLE 34

N-(2,6-dibromo-4-(1-methylethyl)phenyl)4-thiomorpholino-6-methyl-2-pyrimidinamine 580 mg (2.46 mmoles) of 2-chloro-4-thiomorpholino-6-methylpyrimidine, 793 mg (2.7 mmoles) of2,6-dibromo-4-isopropylaniline and 216 mg (5.4 mmoles) of NaH (60% in oil) were refluxed in toluene for 6 hr and purified by silica gel chromatography using 25% EtOAc/hexanes (79% yield); mp 194–195° C. Elemental analysis for $C_{18}H_{22}N_4Br_2S$: Theory C, 44.46; H, 4.56; N, 11.52; Br: 32.87; S,6.59. Found: C, 44.67; H, 4.54; N, 11.24; Br: 32.8; S, 6.62.

EXAMPLE 35

N-(2-methylthio-4-(1-methylethyl)phenyl)-N-ethyl-4,6-dimethyl-2-pyrimidinamine

The product was synthesized by lithium-bromine exchange of the appropriately substituted 2-bromo-4-isopropylanilinopyrimidine with nBuLi in THF at 0° C. followed by reaction with dimethyldisulfide. It was purified by silica gel chromatography using 8% EtOAc/hexanes as eluent, (37% yield); mp 64–66° C. Elemental analysis for $C_{18}H25N_3S$: C, 68.53; H, 7.99; N, 13.32; S, 10.16. Found: C, 68.43; H, 7.94; N, 13.16; S, 10.02.

EXAMPLE 36

N-(2-methylthio-4-(1-methylethyl)phenyl)-N-ethyl-4,6dimethyl-2-pyrimidinamine

The hydrochloride salt of Example 35, was formed in the usual manner; mp 141–142° C. Elemental analysis for $C_{18}H_{25}N_3S$ HCl: Theory C, 61.43; H, 7.45; N, 11.94; S, 9.11; Cl, 10.07. Found: C, 61.07; H, 7.40; N, 11.80; S, 9.37; Cl, 9.77.

EXAMPLE 37

N-(2-methylsulfinyl-4-(1-methylethyl)phenyl)-N-ethyl-4,6-dimethyl-2-pyrimidinamine The sulfide of Example 35, (300 mg, 0.95 mmoles), was reacted with 300 mg (1.41 mmoles) $NaIO_4$ in 6 mL MeOH and 3 mL water at 25° C. for 24 h. The reaction mixture was partitioned between 100 mL EtOAc and 25 mL water and the EtOAc extract was washed with water, brine, dried and stripped in vacuo. The residue was purified by silica gel chromatography using 1:1 EtOAc/hexanes as eluent to give 220 mg product, (70% yield); mp 144–146° C. Elemental analysis for $C_{18}H_{25}N_3O_5$: Theory C, 65.22; H, 7.60; N, 12.68; S, 9.67. Found: C, 65.12; H, 7.63; N, 12.48; S, 9.71.

EXAMPLE 38

N-(2-iodo-4-(1-methylethyl)phenyl)-N-ethyl-4-thiazolidino-6-methyl-2-pyrimidinamine The title compound was obtained as a viscous liquid. Elemental analysis for $C_{19}H_{25}N_4IS$: Theory C, 48.72; H, 5.38; N, 11.96; S, 6.84; I, 27.09. Found: C, 48.80; H, 5.36; N, 11.84; S, 6.95; I, 27.05.

EXAMPLE 39

N-(2-iodo-4-methoxymethylphenyl)-N-ethyl-4,6-dimethyl-2-pyrimidinamine

The title compound was obtained as a viscous liquid. Elemental analysis for $C_{16}H_{20}N_3IO$: Theory C, 48.37; H, 5.08; N, 10,58. Found C, 48.27; H, 5.00; N, 10.07.

EXAMPLE 40

N-(4,6-dimethyl-2-pyrimidinamino)-2,3,4,5-tetrahydro-4-(1-methylethyl)-1,5-benzothiazepine To 4 grams, (15.32 mmoles) of 2-iodo-4-isopropylaniline, and 2.53 g (18.4 mmoles) of 4,6-dimethyl-2-mercaptopyrimidine in 30 mL DMF, were added 4.8 g (34.4 mmoles) of $K_2CO_3$ and 600 mg (9.2 mmoles) of Cu powder and the resulting mixture was heated to reflux for 2 h. After cooling, 30 mL EtOAc was added and the solids were filtered off. The filtrate was partitioned between 200 mL EtOAc and 50 mL water and the EtOAc layer was washed with water (3×60 mL), brine, dried and stripped in vacuo to provide an oily residue that was used without further purification; MS(m/e) 275 (M+2, 20%); 274 (M+1, 100%).

To 0.6 g (2.2 mmoles) of the above crude product in 8 mL dry xylenes was added 132 mg (3.3 mmoles) NaH (60% in oil) and the mixture was heated to reflux for 5 h. Then 0.22 mL (2.2 mmoles) of 1,3-dibromopropane was added and the reaction was heated for another 2 h. Another 60 mg (1.2 mmoles) NaH (60% in oil) was added and heating was continued for another 3 h. After cooling the solids were filtered off, the solvent removed in vacuo, and the filtrate chromatographed on silica gel using 8% EtOAc/hexanes to give 220 mg product (32% yield for the two steps); High res MS: calc 314.169095; measured: 314.168333. This was converted into the hydrochloride salt by treatment with 1M HCl in ether, mp 157–159° C.

EXAMPLE 41

N-(2-methylsulfonyl-4-(1-methylethyl)phenyl)-N-ethyl-4,6-dimethyl-2-pyrimidinamine The sulfoxide of Example 37, (100 mg, 0.3 mmoles) was stirred in 4 mL of $CH_2Cl_2$ and 8 mL water with 20 mg (0.09 mmole) of benzyltriethylammonium chloride and 94.5 mg (0.6 mmole) $KMnO_4$ at 25° C. for 16 h. The mixture was partitioned between 60 mL EtOAc and 40 mL water and the EtOAc was washed with water, brine, dried and stripped in vacuo. The residue was purified by silica gel chromatography using 25% EtOAc/hexanes to give 85 mg product (81% yield); mp 174–175.3° C. Elemental analysis for $C_{18}H_{25}N_3O_2S$: Theory C, 62.22; H, 7.25; N, 12.09; S, 9.23. Found: C, 62.13; H, 7.28; N, 11.93; S, 9.12.

EXAMPLE 42

N-(2-ethylthio-4-(1-methylethyl)phenyl)-N-ethyl-4, 6dimethyl-2-pyrimidinamine

The title compound was prepared in the same manner as the product of Example 36; mp 128–130° C. Elemental analysis for $C_{19}H_{27}N_3S$ HCl: Theory C, 62.36; H, 7.71; N, 11.48; S, 8.76; Cl, 9.69. Found: C, 62.64; H, 7.75; N, 11.43; S, 8.59; Cl, 9.58.

EXAMPLE 43

N-(2-ethylthio-4-methoxyiminoethylphenyl)-N-ethyl-4,6-dimethyl-2-pyrimidinamine

The title compound was prepared in the same manner as the product of Example 44; mp 77–78° C. Elemental analysis for $C_{19}H_{26}N_4OS$: Theory C, 63.66; H, 7.31; N, 15.63; S, 8.95. Found C, 63.70; H, 7.32; N, 15.64; S, 8.94.

EXAMPLE 44

N-(2-methylthio-4-methoxyiminoethylphenyl)-N-ethyl-4,6-dimethyl-2-pyrimidinamine To 4 g (29.6 mmoles) of 4'-aminoacetophenone in 20 mL $CH_2Cl_2$ and 50 mL water containing 3.6 g (42 mmoles) $NaHCO_3$ was added 9.0 g (35.4 mmoles) of $I_2$. The mixture was stirred at 25° C. for 20 h. Then 20 mL of saturated aqueous $Na_2SO_3$ was added and the mixture was stirred for 10 min and partitioned between 120 mL EtOAc and 10 mL water. The EtOAc extract was washed with brine, dried and stripped in vacuo and the residue chromatographed on silica gel using 25% EtOAc/hexanes as eluent to give 6.1 g product (79% yield).

To 3.05 g (11.69 mmoles) of 4'-amino-3'-iodoacetophenone in a mixture of 40 mL ethanol and 10 mL 3M NaOH was added 2.10 g (25.20 mmoles) methoxyamine hydrochloride and the mixture was heated to reflux for 2 h. The ethanol was stripped off in vacuo, the residue was partitioned between 100 mL EtOAc and 30 mL water and the EtOAc was washed with water, brine, dried and stripped in vacuo. The residue was chromatographed on silica gel using 20% EtOAc/hexanes to give 2.8 g product (83% yield).

The above product 1.5 g (5.18 mmoles) was coupled with 4,6-dimethyl-2-mercaptopyrimidine as described above, to give the corresponding adduct in 70% yield, after chromatographic purification.

The above product, 1.1 g (3.64 mmoles) was treated with 190 mg (4.73 mmoles) NaH (60% in oil) in 7 mL dry xylenes at reflux for 5.5 hours. The reaction mixture was then partitioned between 100 mL EtOAc and 20 mL water and the EtOAc was washed with water, brine, dried and stripped in vacuo. The residue was purified by silica gel chromatography using 25% EtOAc/hexanes to give 900 mg product (82% yield).

The above product, 900 mg (2.98 mmoles) was treated with 470 mg (3.4 mmoles) $K_2CO_3$ and 0.22 mL (3.54 mmoles) $CH_3I$ at 25° C. for 4 h. Then it was partitioned between 100 mL EtOAc and 20 mL water, the EtOAc was washed with brine, dried and stripped in vacuo. The residue was used for the next reaction without further purification.

The above product, 940 mg (2.97 mmoles) was treated with 160 mg (4.0 mmoles) NaH (60% in oil) in 7 mL dry DMF for 20 min at 25° C. and then 0.32 mL (4.0 mmoles) EtI was added. The mixture was stirred at 25° C. for 16 h and partitioned between 100 mL EtOAc and 20 mL water, the EtOAc was washed with brine, dried, stripped in vacuo and the residue was chromatographed on silica gel using 20% EtOAc/hexanes to give 600 mg product (58% yield); mp 106–108° C. Elemental analysis for $C_{18}H_{24}N_4OS$: Theory C, 62.76; H, 7.02; N, 16.27; S, 9.31. Found C, 62.75; H, 7.03; N, 16.12; S, 9.45.

EXAMPLE 45

N-(2-methylsulfonyl-4-methoxyiminoethylphenyl)-N-ethyl-4,6-dimethyl-2-pyrimidinamine The sulfide obtained from the sequence described above (0.3 g, 0.87 mmoles) was dissolved in 10 mL $CH_2Cl_2$ and 0.53 g (2.61 mmoles) of m-chloroperbenzoic acid (mCPBA 85%) was added and the mixture was stirred at 25° C. for 16 min. The reaction mixture was quenched with $Na_2SO_3$ and partitioned between 40 mL $CH_2Cl_2$ and 30 mL 5% $NaHCO_3$. The organic layer was dried, stripped in vacuo and the residue was chromatographed on silica gel using 40% EtOAc/hexanes to give 430 mg product, a 40% yield, mp 151–154° C. Elemental analysis for $C_{18}H_{24}N_4O_3S$: Theory C, 57.43; H, 6.43; N, 14.88; S, 8.52. Found: C, 57.24; H, 6.40; N, 14.18; S, 8.60.

EXAMPLE 46

N-(4-bromo-2-methylthiophenyl)-N-ethyl-4,6-dimethyl-2-pyrimidinamine

2-Iodo-4-bromoaniline was coupled with 4,6-dimethyl-2-mercaptopyrimidine in 93% yield. One gram of the adduct (3.22 mmoles) was dissolved in 10 mL methanol and 4 mL (4 mmoles) 1 M HCl in ether was added. The mixture was stirred at 25° C. for 2 h, the solvent was stripped in vacuo and the residue was partitioned between 150 mL of an 1:1 mixture EtOAc and $CH_2Cl_2$ and 80 mL satd. $NaHCO_3$. The organic layer was dried and stripped in vacuo to give 900 mg of the disulfide product, which was dissolved in 10 mL absolute ethanol and cooled to 0° C. To that solution 110 mg (2.92 mmoles) of $NaBH_4$ was added and the mixture was allowed to warm to 25° C. and stirred for 20 min before 0.36 mL (5.76 mmoles) $CH_3I$ was added and the mixture was stirred at 25° C. for 2 h. The solvent was stripped in vacuo and the residue was partitioned between 100 mL EtOAc and 30 mL satd. $NaHCO_3$. The EtOAc was washed with brine, dried and stripped in vacuo. The residue was chromatographed on silica gel using 20% EtOAc/hexanes to give 840 mg product, 80% yield for the two steps. MS(m/e): 326 (M+3, 100%); 324 (M+1, 93%).

This was ethylated under the conditions described above in 90% yield, mp91–93° C. Elemental analysis for $C_{15}H_{18}BrN_3S$: Theory C,51.15; H, 5.15; N, 11.93; Br, 22.68; S, 9.10. Found C, 51.25; H, 5.15; N, 11.89; Br, 22.42; S, 9.22.

EXAMPLE 47

N-(4-ethyl-2-methylthiophenyl)-N-(1-methylethyl)4, 6-dimethyl-2-pyrimidinamine

The title compound was prepared in a manner similar to the product of Example 46; mp 85–87° C. Elemental analysis for $C_{18}H_{25}N_3S$: Theory C, 68.53; H, 7.99; N, 13.32; S, 10.16. Found: C, 68.56; H, 8.08; N, 13.24; S, 10.27.

EXAMPLE 48

N-(4-ethyl-2-methylthiophenyl)-N-ethyl-4,6-dimethyl-2-pyrimidinamine

The title compound was prepared in a manner similar to the product of Example 46; mp 140–141° C. Elemental analysis for $C_{17}H_{23}N_3S \cdot HCl$: Theory C, 60.43; H, 7.16; N, 12.44; S, 9.49; Cl, 10.49. Found C, 60.42; H, 6.89; N, 12.36; S, 9.61; Cl, 10.63.

EXAMPLE 49

N-(2-methylthio-4-(N-acetyl-N-methylamino)phenyl)-N-ethyl-4,6-dimethyl-2-pyrimidinamine The title compound was prepared in a manner similar to the product of Example 46; mp 158–160° C. Elemental analysis for $C_{18}H_{24}N_4OS$: Theory C, 62.76; H, 7.02; N, 16.26; S, 9.31. Found C, 62.67; H, 7.07; N, 16.24; S, 9.56.

EXAMPLE 50

N-(4-carboethoxy-2-methylthiophenyl)-N-ethyl-4,6-dimethyl-2-pyrimidinamine

The title compound was prepared in a manner similar to the product of Example 46; mp 99–100° C. Elemental analysis for $C_{18}H_{23}N_3O_2S$: Theory C, 62.58; H, 6.71; N, 12.16; S, 9.28. Found C, 62.83; H, 6.78; N, 12.08; S, 9.44.

EXAMPLE 51

N-(4-methoxy-2-methylthiophenyl)-N-ethyl-4,6-dimethyl-2-pyrimidinamine

A mixture of 352 mg (1 mmole) 4-bromo-2-methylmercaptoanilinopyrimidine, 14.3 mg (0.1 mmole) CuBr and 0.5 mL (2.5 mmoles) 25% w/w MeONa in MeOH was heated to reflux in 5 mL dry DMF for 1.5 h. The reaction mixture was partitioned between 100 mL EtOAc and 30 mL water and the EtOAc layer was washed with water (2×30 mL), brine, dried and stripped in vacuo. The residue was chromatographed on silica gel using 20% EtOAc/hexanes to give 210 mg product (69% yield); mp 128–130° C. Elemental analysis for $C_{16}H_{21}N_3OS \cdot \frac{1}{4}H_2O$: Theory C, 62.41; H, 7.07; N, 13.64; S, 10.41. Found C, 62.06; H, 6.97; N, 13.26; S, 10.47.

EXAMPLE 52

N-(4-cyano-2-methylthiophenyl)-N-ethyl-4,6-dimethyl-2-pyrimidinamine

The title compound was prepared in a manner similar to the product of Example 51; mp 112–113° C. Elemental analysis for $C_{16}H_{18}N_4S$: Theory C, 64.40; H, 6.08; N, 18.78; S, 10.74. Found: C, 64.28; H, 6.16 N, 18.58; S, 11.08.

EXAMPLE 53

N-(4-acetyl-2-methylthiophenyl)-N-ethyl-4,6-dimethyl-2-pyrimidinamine

To 0.5 g (1.68 mmoles) of the nitrile of Example 52 in 10 mL dry $C_6H_6$ was added 1.1 mL (3.3 mmoles) of a 3 M solution $CH_3MgI$ in ether and the mixture was stirred at 25° C. for 2 h and at reflux for 1 h. The reaction was quenched with water and 10% HCl and stirred for 20 min before 1 M NaOH was added until the solution was alkaline and the mixture was extracted with 100 mL EtOAc. The organic layer was washed with water, brine, dried and stripped in vacuo. The residue was chromatographed on silica gel using 20% EtOAc/hexanes to give 370 mg product (70% yield); mp 125–126° C. Elemental analysis for $C_{17}H_{21}N_3OS$: Theory C, 64.73; H, 6.71; N, 13.32; S, 10.16. Found C, 64.53; H, 6.73; N, 13.08; S, 10.19.

EXAMPLE 54

N-(4-propionyl-2-methylthiophenyl)-N-ethyl-4,6-dimethyl-2-pyrimidinamine

The title compound was prepared in a manner similar to the product of Example 53; mp 139–141° C. Elemental analysis for $C_{18}H_{23}N_3OS$: Theory C, 65.62; H, 7.04; N, 12.75; S, 9.73. Found C, 65.33; H, 7.19; N, 12.51; S, 9.62.

EXAMPLE 55

N-(4-(1-methoxyethyl)-2-methylthiophenyl)-N-ethyl-4,6-dimethyl-2-pyrimidinamine To 1.05 g (3.33 mmoles) of the ketone of Example 53 in 20 mL absolute ethanol cooled to 0° C. was added 127 mg (3.32 mmoles) $NaBH_4$ and the mixture was allowed to warm to 25° C. and stirred for 16 h. Then the solvent was stripped in vacuo and the residue was partitioned between 100 mL EtOAc and 30 mL 0.3 M NaOH. The EtOAc was washed with water, brine, dried and stripped in vacuo. The residue was chromatographed on silica gel using 2:1 EtOAc/hexanes to give 1 g product; mp 46–49° C. The above alcohol, 0.72 g (2.27 mmoles), was reacted with 108.09 mg (2.7 mmoles) of NaH (60% in oil) in 5 mL dry DMF at 25° C. for 20 min and then 0.3 mL (4.8 mmoles) of $CH_3I$ was added. The mixture was stirred for 20 h and an additional 60 mg (1.5 mmoles) of NaH (60%) was added, as well as 0.1 mL $CH_3I$ and the mixture was stirred for an additional 16 h. It was then partitioned between 100 mL EtOAc and 30 mL water and the EtOAc was washed with water (2×30 mL), brine, dried and stripped in vacuo. The residue was chromatographed on silica gel using 20% EtOAc/hexanes to give 600 mg product as a viscous liquid. This was converted into the hydrochloride salt by treatment with 1 M HCl in ether, mp 120–122° C.

EXAMPLE 56

N-(4-(N-methylamino)-2-methylthiophenyl)-N-ethyl-4,6-dimethyl-2-pyrimidinamine A solution of 0.2 g (0.58 mmole) 4-N-acetyl-N-methyl-2-methylmercaptoanilinopyrimidine, in 10 mL ethanol and 2 mL water containing 272 mg (5 mmoles) KOH was refluxed for 4 h. An additional 200 mg of KOH was added and the heating was continued for 3 h. The ethanol was stripped in vacuo and the residue was partitioned between 100 mL EtOAc and 30 mL water. The EtOAc extract was washed with brine, dried and stripped in vacuo. The residue was chromatographed on silica gel using 1:1 EtOAc/hexanes to give 140 mg product, an 80% yield, mp 141–142° C. Elemental analysis for $C_{16}H_{22}N_4S$: Theory C, 63.54; H, 7.33; N, 18.52; S, 10.60. Found C, 63.63; H, 7.41; N, 18.55; S, 10.80.

EXAMPLE 57

N-(4-(N,N-dimethylamino)-2-methylthiophenyl)-N-ethyl-4,6-dimethyl-2-pyrimidinamine To 0.36 g (1.2 mmoles) 4-N-methyl-2-methylmercaptoanilinopyrimidine in 4 mL dry DMF was added 60 mg (1.5 mmoles) NaH (60% in oil) and the mixture was stirred for 20 min before 0.1 mL (1.67 mmoles) $CH_3I$ was added and the reaction was continued at 25° C. for 16 h. It was then partitioned between 100 mL EtOAc and 20 mL water. The EtOAc extract was washed with water, brine, dried and stripped in vacuo. The residue was chromatographed on silica gel using 20% EtOAc/hexanes to give 150 mg product (40% yield); mp 119–120° C. Elemental analysis for $C_{17}H_{24}N_4S$: Theory C, 64.52; H, 7.64; N, 17.70; S, 10.13. Found C, 64.55; H, 7.65; N, 17.50; S, 10.31.

EXAMPLE 58

N-(2-Bromo-4-(1-methylethyl)phenyl)-N-ethyl-4-formyl-6-methyl-2-pyrimidinamine

Example 23 product (453 mg, 1.2 mmol) and manganese dioxide (1.7g, 20 mmol) were heated to reflux in 25 mL dichloromethane for three days. The reaction was filtered through a pad of Celite, and the filtrate was concentrated in vacuo to give a light yellow oil. The oil was purified by silica gel chromatography using 10% ethyl acetate in hexanes to yield 112 mg of a white solid. CI-HRMS: calcd: 362.0868 (M+H), found: 362.0864.

EXAMPLE 59

N-(2-Bromo-4-(1-methylethyl)phenyl)-N-ethyl-4-hydroxyethoxymethyl-6-methyl-2-pyrimidinamine Compound XLVII from Scheme 12 above (0.41 g, 0.92 mmol) and sodium borohydride (76 mg, 2 mmol) in 10 mL ethanol were stirred for 21 hours at room temperature. The reaction was acidified with 1.0 N hydrochloric acid, stirred for ten minutes, basified with 1.0 N sodium hydroxide and extracted with dichloromethane. The combined extracts were dried with magnesium sulfate and stripped in vacuo to yield a clear oil which was chromatographed on silica gel using 30% ethyl acetate in hexanes to give 345 mg product (92% yield). CI-HRMS: calcd: 408.1287 (M+H), found: 408.1284.

EXAMPLE 60

N-(2-Bromo-6-hydroxy-4-methoxyphenyl)-N-ethyl-4,6-dimethyl-2-pyrimidinamine

N-(2-Bromo-4,6-dimethoxyphenyl)-N-ethyl-4,6-dimethyl-2-pyrimidinamine (214 mg, 0.58 mmol) in 15 mL dichloromethane under nitrogen was cooled in a dry ice/acetone bath, and boron tribromide (1.0 M in dichloromethane, 0.58 mL) was slowly added. The reaction was allowed gradually to warm to room temperature whereupon it was stirred overnight. After quenching with water, the aqueous portion was basified with saturated sodium bicarbonate and extracted with dichloromethane. The combined extracts were dried with magnesium sulfate and concentrated in vacuo to give a tan solid. The solid was recrystallized from ethyl acetate/hexanes to yield 58 mg product; mp 157–160° C. Anal. Calcd: %C, 51.15; %H, 5.15; %N, 11.93; %Br, 22.69. Found: %C, 51.02; %H, 5.10; %N, 11.83; %Br, 22.52.

EXAMPLE 61

N-(3-Bromo-4,6-dimethoxyphenyl)-N-ethyl-4,6-dimethyl-2-pyrimidinamine

Part A (Synthesis of 3-bromo-4,6-dimethoxy aniline): To a mixture of 2,4-dimethoxy aniline (5.0 g, 33 mmol) and potassium carbonate (10.4 g, 75 mmol) in 30 mL chloroform was slowly added bromine (5.27 g, 33 mmol) in 20 mL chloroform. After stirring two hours the reaction was washed three times with water, dried with magnesium sulfate, and concentrated in vacuo to give a dark solid. The material was purified by chromatography on silica gel using 20% ethyl acetate in hexanes to yield 1.77 g product as a tan solid (23% yield).

Part B: Using the procedure for Example 1; Parts B–C and substituting the aniline from Part A above, the title compound was obtained.

EXAMPLE 62

N-(2,3-Dibromo-4,6-dimethoxyphenyl)-N-ethyl-4,6-dimethyl-2-pyrimidinamine

Part A (Synthesis of 2,3dibromo-4,6-dimethoxy aniline): 2,4-dimethoxy aniline, 1 eq. benzyltrimethylammonium tribromide, and 2 eq. calcium carbonate were stirred at room temperature in a solution of methanol:dichloromethane (2:5) for one hour. The solution was filtered, the filtrate was evaporated under vacuum, and the residue taken up in water and extracted three times with dichloromethane. The combined extracts were dried over magnesium sulfate, filtered, and evaporated under vacuum to give a brown oil, which was purified on silica gel using 20% ethyl acetate in hexanes. (Rf=0.2)

Part B: Using the procedure for Example 1; Parts B–C and substituting the aniline from Part A above, the title compound was obtained.

EXAMPLE 63

N-(2,6-Dibromo-4-(ethoxy)phenyl)-N-ethyl-4,6-dimethyl-2-pyrimidinamine

Part A: The synthesis of 2,6-dibromo-4-ethoxy-aniline was accomplished using the bromination procedure for 4-ethoxy-aniline reported by Kajigaeshi et. al. in *Bull. Chem. Soc. Jpn.* 61:597–599 (1988). The aniline, 1 eq. benzyltrimethylammonium tribromide, and 2 eq. calcium carbonate were stirred at room temperature in a solution of $MeOH:CH_2Cl_2$ (2:5) for one hour. The solids were collected, the filtrate was evaporated under vacuum, and the residue taken up in $H_2O$ and extracted three times with $CH_2Cl_2$. The combined extracts were dried over $MgSO_4$, filtered, and evaporated under vacuum to give a brown oil, which was purified on silica gel using 10% EtOAc in hexanes.

Part B: Using the procedure for Example 1; Parts B–C and substituting the aniline from Part A above, the title compound was obtained.

EXAMPLE 64

1-(2-Bromo-4-isopropylphenyl)-3-cyano-4,6-dimethyl-7-azaindole

Part A: A solution of 42.80 g (0.200 mole) of the potassium salt of formyl-succinonitrile (K. Gewald, Z. *Chem.*, 1:349 (1961)) and 29.20 g (0.200 mole) of 2-bromo-4-isopropylaniline in a mixture of 50 mL of glacial acetic acid and 120 mL of ethanol was refluxed (nitrogen atmosphere) for two hours. The mixture was stripped of most of the acetic acid and ethanol and the residue was taken up in ethyl acetate. This solution was washed with 10% sodium bicarbonate solution, dried with anhydrous sodium sulfate, and evaporated to give a dark, oily residue, which was chromatographed on silica gel with 80:20 hexane-ethyl acetate to give 24.23 g (40%) of N-(2-bromo-4-isopropylphenyl)-aminomethylene-succinonitrile. Mass spec: $(m+NH_4)^+$=321.0; calculated, 321.0.

Part B: To a solution of 10 mL of 1M potassium tert-butoxide in tetrahydrofuran and 10 mL of ethanol was added 1.11 g (3.65 mmole) of N-(2-bromo-4-isopropyl-phenyl)-aminomethylene-succinonitrile (Part A). The mixture was stirred for 16 hrs under a nitrogen atmosphere. The solvents were removed by evaporation. The residue was taken up in ethyl acetate and washed successively with 1 N hydrochloric acid, 10% sodium bicarbonate solution, and brine. The solution was dried with anhydrous sodium sulfate and evaporated to give a dark residue. The residue was dissolved in dichloromethane, 20 g of silica gel was added, and the mixture was evaporated to dryness. This mixture was placed on top of a chromatographic column of 150 g of silica gel in hexane. The column was eluted successively with 10, 15, 20, 25; and 30% ethyl acetate in hexane to give 0.65 g (59% yield) of 1-(2-bromo-4-isopropylphenyl)-2-amino-4-cyano-pyrrole. Mass spec: $(m+H)^+$=304.0; calculated, 304.0. The $R_f$=0.22 on silica gel thin layer chromatography by elution with 70:30 hexane-ethyl acetate. The preparation was scaled up for Part C.

Part C: A mixture of 18.51 g (0.0609 mole) of 1-(2-bromo-4-isopropylphenyl)-2-amino-4-cyano-pyrrole, 300 mL of ethanol, 0.6 mL of conc. hydrochloric acid, and 10 mL (9.75 g, 0.0974 mole) of 2,4-pentanedione was refluxed with stirring under a nitrogen atmosphere for 4 hrs. The mixture was allowed to cool and the solvent was removed under reduced pressure. The residue was dissolved in ethyl acetate. The solution was washed with 10% sodium bicarbonate solution, then with brine. The solution was dried with anhydrous sodium sulfate and evaporated to give 21.76 g of dark, tarry residue. The residue was chromatographed on silica gel by eluting in step gradients of 0, 10, 15, 20, 25; and 30% ethyl acetate in hexane. The initial fraction is 17.6 g (78%) 1-(2-bromo-4-isopropylphenyl)-3-cyano-4,6-dimethyl-7-azaindole; m.p. 105.8°. Mass spec: $(m+H)^+$= 368.0749; calculated, 368.0762 ($^{79}$Br). $R_f$=0.45 on silica gel thin layer chromatography with 70:30 hexane-ethyl acetate.

EXAMPLE 65

1-(2-Bromo-4-isopropylphenyl)-4,6-dimethyl-7-azaindole

A mixture of 4.00 g of 1-(2-bromo-4-isopropylphenyl)-3-cyano-4,6-dimethyl-7-azaindole and 40 mL of 65% sulfuric acid was refluxed for one hour. The solution was cooled and poured onto ice. Conc. ammonium hydroxide was added until the mixture was alkaline to pH paper. The mixture was extracted with ethyl acetate. The solution was dissolved in 60:40 hexane-ethyl acetate and passed through a short column of silica gel. The eluate was evaporated, and the residue was crystallized from 20 mL of hexane to give 2.45 g (66% yield) of 1-(2-bromo-4-isopropylphenyl)-4,6-dimethyl-7-azaindole. Mass spec: $(m+H)^+$=343.0818; calculated, 343.0810. $R_f$=0.57 on silica gel with 70:30 hexane-ethyl acetate.

EXAMPLE 66

1-(2-Bromo-4-isopropylphenyl)-3-cyano-6-methyl-4-phenyl-7-azaindole

A mixture of 737 mg (2.00 mmole) of the product from Example 64 (Part B), 324 mg (2.00 mmole) of benzoylac-etone and 25 mL of xylene was heated in a flask equipped with a water separator for 2 hours. The solvent was removed by evaporation, and the residue chromatographed on silica gel, eluting in step gradients with 0, 5, 10; and 15% ethyl acetate in hexane. Both 1-(2-bromo-4-isopropylphenyl)-3-cyano-4-methyl-6-phenyl-7-azaindole and 1-(2-bromo-4-isopropylphenyl)-3-cyano-6-methyl-4-methyl-7-azaindole were obtained. The $R_f$ values were respectively 0.38 and 0.28 (silica gel with 80:20 hexane-ethyl acetate). The assignment of the structures was based on the nmr data of the de-cyanylated compounds in Example 67.

EXAMPLE 67

1-(2-Bromo-4-isopropylphenyl)-6-methyl-4-phenyl-7-azaindole

A mixture 130 mg (0.302 mmole) of 1-(2-bromo-4-isopropylphenyl)-3-cyano-6-methyl-4-phenyl-7-azaindole (Example 66) and 10 mL of 65% sulfuric acid were refluxed for one hour. The mixture was poured onto ice, Conc. ammonium hydroxide was added until the mixture was basic to pH paper. The mixture was extracted with ethyl acetate. The extract was evaporated and chromatographed on silica gel with 70:30 hexane-ethyl acetate. There was obtained 112 mg (92% yield) of 1-(2-bromo-4-isopropylphenyl)-6-methyl-4-phenyl-7-azaindole. Mass spec: $(m+H)^+$=405.10; calculated, 405.10.

In the same way, 1-(2-bromo-4-isopropylphenyl)-4-methyl-6-phenyl-7-azaindole was obtained, mp 95.8°.

EXAMPLE 68

1-(2-Bromo-4,6-dimethoxyphenyl)-3-cyano-4,6-dimethyl-7-azaindole

Part A: N-(2-bromo-4,6-dimethoxyphenyl)-aminomethylene-succinonitrile was prepared from 2-bromo-4,6-dimethoxyaniline by the method described in Example 64, Part A. Mass spec: $(m+H)^+$=322.0; calculated, 322.16. $R_f$=0.19 (silica gel with 60:40 hexane-ethyl acetate).

Part B: The product from Part A was cyclized by the method described in Example 64, Part B to give 1-(2-bromo-4,6-dimethoxy-phenyl)-2-amino-4-cyano-pyrrole (79% yield). $R_f$=0.19 (silica gel with 60:40 hexane-ethyl acetate).

Part C: The product from Part B was treated with 2,4-pentanedione as described in Example 64, Part C to give 1-(2-bromo-4,6-dimethoxyphenyl)-3-cyano-4,6-dimethyl-7-azaindole (92% yield). Mass spec: $(m+H)^+$=388.0; calculated, 388.0. $R_f$=0.44 (silica gel with 60:40 hexane-ethyl acetate).

EXAMPLE 69

1-(2-bromo-4,6-dimethoxyphenyl,)-4,6-dimethyl-7-azaindole

A mixture of 200 mg of 1-(2-bromo-4,6-dimethoxyphenyl)-3-cyano-4,6-dimethyl-7-azaindole and 10 ml of 65% sulfuric acid was refluxed for one hour. The mixture was worked up as described in Example 65 to give 185 mg of crude product. A 40 mg portion was purified by preparative liquid chromatography on a nitrile column using 95:5 1-chlorobutane-acetonitrile to give 11 mg of 1-(2-bromo-4,6-dimethoxyphenyl)-4,6-dimethyl-7-azaindole. Mass spec: $(m+H)^+$=360.9; calculated, 361.1.

EXAMPLE 70

1-(2-Bromo-4-isopropylphenyl)-6-chloro-3-cyano-4-methyl-7-azaindole

Part A: A solution of 3.04 g of the product of Example 64 (Part B), 1.9 mL (1.94 g; 14.9 mmole) of ethyl acetoacetate, and 0.1 mL of conc. hydrochloric acid in 30 mL of ethanol was refluxed for 16 hours. A precipitate formed upon cooling. The precipitate was removed by filtration to give 1.68 g of crystals; mp 202.4° C., of 1-(2-bromo-4-isopropylphenyl)-4-methyl-7-azaindole-6-one. TLC on silica gel with 70:30 hexane-ethyl acetate showed a single spot, $R_f$=0.29. Mass spec. (m+H)$^+$=370.5; calcd., 370.05 ($^{79}$Br).

Part B: A mixture of 185 mg of the 7-azaindole-6-one (Part A) and 50 ml of phosphorus oxychloride was heated in an autoclave at 180° C. for 10 hrs. The excess phosphorus oxychloride was removed by distillation at reduced pressure. The residue was distributed between ethyl acetate and water. The ethyl acetate layer was separated and washed with 10% sodium bicarbonate solution, then with brine. The solution was dried (Na$_2$SO$_4$) and evaporated. TLC of the residue on silica gel with 70:30 hexane-ethyl acetate showed a major new product, $R_f$=0.52 with minor spots at $R_f$ 0.45 and 0.29. Chromatography on silica gel with step gradients of 5, 10, 15, and 20% ethyl acetate in hexane gave 109 mg of the $R_f$ 0.52 product; mp 123.8° C. This is 1-(2-bromo-4-isopropylphenyl)-6-chloro-3-cyano-4-methyl-7-azaindole.

EXAMPLE 71

1-(2-Bromo-4-isopropylphenyl)-6-chloro-4-methyl-7-aziandole

A mixture of 52 mg of 1-(2-bromo-4-isopropyphenyl)-6-chloro-3-cyano-4-methyl-7-azaindole and 10 mL of 65% sulfuric acid was refluxed for one hour. The cooled solution was poured onto ice, and 17 mL of conc. ammonium hydroxide was added. The alkaline mixture was extracted with ethyl acetate. The extract was washed (brine), dried (Na$_2$SO$_4$), and evaporated. TLC of the residue on silica gel with 70:30 hexane-ethyl acetate showed a major new spot, $R_f$=0.58; with a trace of unchanged starting material ($R_f$ 0.52). The crude product was purified by preparative TLC to give 39 mg of non-crystaline product, which slowly crystallized on standing. Mass spec. (m+H)$^+$=363.0247; calcd., 363.0264 ($^{79}$Br, $^{35}$Cl).

EXAMPLE 72

1-(2-Bromo-4-isopropylphenyl)-3-cyano-6-methyl-7-azaindole

To a solution of 1.085 g (5.07 mmole) of the product from Example 64 (part B) and 0.80 mL (0.797 g; 6.03 mmole) of acetoacetaldehyde dimethyl acetal in 20 mL of ethanol was added 0.10 mL of conc. hydrochloric acid. The mixture was refluxed for 16 hours, then cooled and evaporated to give a dark, thick oil. TLC on silica gel with 70:30 hexane-ethyl acetate showed two major spots at $R_f$ 0.47 and 0.41. The oil was dissolved in ethyl acetate, 20 mL silica gel powder was added, and the mixture was evaporated to dryness. The powdery residue was loaded on top of a column of 60 mL of silica gel in hexane. The column was eluted in step gradients of 0, 5, 10, 15, 20, and 25% ethyl acetate in hexane. The first fraction to elute was 0.32 g of the desired 1-(2-bromo-4-isopropyl-phenyl)-3-cyano-6-methyl-7-azaindole, Rf 0.47. The material can be crystallized from hexane to give 176 mg of crystals; mp 176.0° C. Mass spec. (m+H)$^+$=354.0595; calcd., 354.0606.

EXAMPLE 73

1-(2-Bromo-4-isopropylphenyl)-6-methyl-7-azaindole

Material from Example 72 was treated with 65% sulfuric acid as described in Example 65 to give the desired product as a viscous oil. TLC on silica gel with 70:30 hexane-ethyl acetate showed Rf =0.57. Mass spec. (m+H)$^+$=329.0641; calcd., 329.0653 ($^{79}$Br).

EXAMPLE 74

1-(2-Bromo-4-isopropylphenyl)-4-chloro-3-cyano-6-methyl-7-azaindole

Part A: A solution of 1.24 g of 1-(2-bromo-4-isopropyl-phenyl)-3-cyano-6-methyl-7-azaindole (Example 72) and 1.42 g of 85% 3-chloro-peroxybenzoic acid in 20 mL of chloroform was refluxed for 6 hrs. The mixture was cooled and washed first with 10% sodium bicarbonate solution, then with brine. The solution was dried (Na$_2$SO$_4$) and evaporated to give a residue. TLC on silica gel with 95:5 dichloromethane-methanol showed a trace spot at $R_f$ 0.88 and a major spot at $R_f$ 0.34. The material was purified by chromatography on silica gel with dichoromethane, followed by 1% methanol in dichloromethane, to give a trace of unchanged 1-(2-bromo-4-isopropylphenyl)-3-cyano-6-methyl-7-azaindole ($R_f$ 0.88) and 0.92 g of 1-(2 -bromo-4-isopropylphenyl)-3-cyano-6-methyl-7-azaindole 7-oxide ($R_f$ 0.34); mp 179.2°. Mass spec. (m+H)$^+$=370.0559; calcd., 370.0555 ($^{79}$Br).

Part B: A mixture of 370 mg of the 7-oxide (Part A) and 5 mL of phosphorus oxychloride was refluxed for two hours. The solution was cooled, poured on ice, and stirred until most of the phosphorus oxychloride was hydrolysed. The mixture was made alkaline with conc. ammonium hydroxide and extracted with ethyl acetate. The extract was dried (Na$_2$SO$_4$) and evaporated to give a viscous residue. TLC on silica gel with 95:5 dichloromethane-methanol showed a major spot at $R_f$=0.79. The material was purified by preparative TLC on silica gel with 70:30 hexane-ethyl acetate to give crystals. Recrystallization from hexane gave 158 mg of 1-(2-bromo-4-isopropylphenyl)-4-chloro-3-cyano-6-methyl-7-azaindole; mp 123.3° C. Mass spec. (m+H)$^+$= 388.0197; calcd., 388.0216 ($^{79}$Br, $^{35}$Cl).

EXAMPLE 75

1-(2-Bromo-4-isopropylphenyl)-4-chloro-6-methyl-7-azaindole

A mixture of 190 mg of the 3-cyano-7-azaindole (Example 71) and 5 mL of 65% sulfuric acid was refluxed for 30 minutes. The solution was poured onto ice and extracted with ethyl acetate. The extract was washed with brine, dried (Na$_2$SO$_4$), and evaporated to give a residue. TLC of the residue on silica gel with 60:40 hexane-ethyl acetate showed a major spot at $R_f$=0.67. The residue was purified by preparative TLC to give 130 mg of a viscous oil, which is 1-(2-Bromo-4-isopropylphenyl)-4-chloro-6-methyl-7-azaindole. Mass spec. (m+H)$^+$=363.0246; calcd., 363.0264 ($^{79}$Br, $^{35}$Cl).

EXAMPLE 76

N-[2-bromo-6-methoxy-pyridin-3-yl]-N-ethyl-4-6-dimethyl-2-pyrimidinamine

Part A: To 3.18 grams (25.6 mmol) of commercially available 5-amino-2-methoxypyridine in a solution of methylene chloride (50 ml) and methanol (20 ml) was added benzyltrimethylammonium tribromide (10 g, 25.6 mmol) and the mixture was stirred at room temperature for 24 hours. The solvent was then stripped and the resulting residue was taken up in water and extracted (3×100 mL)

with ethyl acetate. The organic extracts were dried with magnesium sulfate, filtered, and concentrated in vacuo. The crude material was chromatographed on silica using 30% ethyl acetate in hexanes as solvent to afford 5-amino-2-bromo-6-methoxypyridine. $C_6H_7N_2OBr$ MS 203 (M+H)$^+$.

Part B: The product of part A above was coupled to 2-chloro-4,6-dimethylpyrimidine (Example 1; part A) using NaH (1.2 eq) in DMF to give N-[2-bromo-6-methoxy-pyridin-3-yl]-4,6-dimethyl-2-pyrimidinamine. $C_{12}H_{13}N_4OBr$ MS 309 (M+H)$^+$.

Part C: The product of part B above was alkylated in the same manner as used in Example 4; part C to provide the title compound. $C_{14}H_{17}N_4OBr$ MS 337 (M+H)$^+$.

EXAMPLE 77

N-[3-bromo-5-methyl-pyridin-2-yl]-N-ethyl-4-6-dimethyl-2-pyrimidinamine

Part A: A 1.0 gram (5.35 mmol) portion of commercially available 2-amino-3-bromo-5-methylpyridine was coupled to 2-chloro-4,6 -dimethylpyrimidine (Example 1; part A) using NaH (1.2 eq) in DMF to give N-[3-bromo-5-methyl-pyridin-2-yl]-4,6-dimethyl-2-pyrimidinamine. $C_{12}H_{13}N_4Br$ MS 293 (M+H)$^+$.

Part B: The product of part A was alkylated in the same manner as used in Example 4; part C to provide the title compound. $C_{14}H_{17}N_4Br$ MS 321 (M+H)$^+$.

EXAMPLE 78

N-[6-methoxy-pyridin-3-yl]-N-ethyl-4-6-dimethyl-2-pyrimidinamine

To 200 mg of N-[2-bromo-6-methoxy-pyridin-3-yl]-N-ethyl-4-6-dimethyl-2-pyrimidinamine in 25 ml dry DMF was added 500 mg $K_2CO_3$, 100 mg of CuI, and 0.4 mL of morpholine and the reaction was heated to reflux for 6 hour. The reaction mixture was then filtered and poured into water and then extracted with ethyl acetate (3×50 mL). The extracts were dried and the solvent removed and the resulting residue was chromatographed on silica gel with 20% ethyl acetate in hexane as the solvent (rf 0.4) to provide the title compound. $C_{14}H_{18}N_4O$ MS 259 (M+H)$^+$.

EXAMPLE 79

N-[2-bromo-6-methoxy-pyridin-3-yl]-N-ethyl-4-methyl-6-(4-morpholinyl)-1,3,5 triazin-2-amine Part A: To 2,4-dichloro-6-methyl-s-triazine (Part A, Example 23, 2.0 grams, 12.3 mmol) in 50 mL of $CH_2Cl_2$ chilled to 0 degrees was added morpholine (1.1 mL, 12.3 mmol) and the reaction was allowed to come to room temperature and stirred for 2 hours. The reaction was then poured into water and the layers separated. The aqueous layer was washed with $CH_2Cl_2$, (3×50 mL) and the organic layers were combined and dried. The solvent was stripped and the crude material was chromatographed on silica with 30% ethyl acetate in hexane as the solvent to give 2-chloro-4-(N-morpholino)-6-methyl-s-triazine. $C_8H_{11}N_4OCl$ (M+H)$^+$.

Part B: The product of Example 76; Part A (0.6 gram, 3.0 mmol) and the product of Example 79; Part A (0.63 gram, 3.0 mmol) in dioxane were stirred at room temperature for 24 hours. The reaction mixture poured into water then extracted with ethyl acetate (3×50 mL). The extracts were dried with magnesium sulfate, filtered, and concentrated in vacuo. The crude material was chromatographed on silica using 30% ethyl acetate in hexanes as solvent to afford the coupled material $C_{14}H_{17}N_6O_2Br$ MS 381 (M+H)$^+$.

Part C: The product of part B above was alkylated in the same manner as used in Example 5; part C to provide the title compound. $C_{16}H_{21}N_6O_2Br$ MS 409 (M+H)$^+$.

EXAMPLE 80

N-(2-bromo-4-(1-methylethyl)phenyl)-N-ethyl-4-(N-(2-furylmethyl)-N-methylamino)carbonyl-6-methylpyrimidinamine Sodium hydride (60% in oil, 0.1 g, 2.4 mmol), washed with hexanes and decanted twice, was suspended in anhydrous N,N-dimethylformamide (DMF) (5 mL) and a solution of N-(2-bromo-$^4$-(1-methylethyl)phenyl)-N-ethyl-4-((2-furylmethyl)-amino)carbonyl-6-methylpyrimidinamine (1.0 g, 2.2. mmol) in anhydrous DMF (5 mL) was added dropwise with stirring. After 30 min, iodomethane (0.37 g, 2.6 mmol) was added and the reaction mixture was stirred for 18 h. Water (50 mL) was added carefully and the aqueous mix was extracted three times with chloroform. The combined organic layers were dried over $MgSO_4$, filtered and concentrated in vacuo to give a brown oil. Column chromatography (ethyl acetate:hexanes::1:2) afforded the title product as a brown oil (850 mg, 82% yield, $R_f$ 0.35): NMR ($CDCl_3$ 300 MHz): 7.5 (d, 1H, J=9), 7.3 (d, 1H, J=12), 7.25–7.2 (m, 1H), 7.12 (dd, 1H, J=8, 1), 6.8 (s, 1H), 6.3 (d, 1H, J=12), 6.0 (br s, 0.5H), 5.9 (br s, 0.5H), 4.65 (br s, 2H), 4.2 (br s, 1H), 3.75–3.6 (m, 1H), 3.0–2.8 (m, 4H), 2.4 (br s, 3H), 1.40 (d, 6H, J=7), 1.2 (t, 3H, J=8);

CI-HRMS: Calcd ($C_{23}H_{27}BrN_4O_2$): 471.1396 (M+H); Found: 471.1387.

EXAMPLE 81

N-(2-bromo-4-(1-methylethyl)phenyl)-N-ethyl-4-((4,4-ethylenedioxypiperidino)carbonyl)-6-methylpyrimidinamine Sodium hydride (60% in oil, 0.12 g, 3 mmol), washed with hexanes and decanted twice, was suspended in anhydrous THF (5 mL) and a solution of 4-piperidone ethylene glycol ketal (0.43 g, 3 mmol) in anhydrous THF (5 mL) was added dropwise with stirring. The reaction mixture was heated to reflux temperature, stirred for 30 min and then cooled to ambient temperature. A solution of methyl 2-((2-bromo-4-(1-methylethyl)-phenyl)ethylamino)-6-methyl-4-pyrimidinecarboxylate (Example 18) (1.0 g, 2.54 mmol) in anhydrous THF (10 mL) was added and the reaction mixture was stirred at room temperature for 98 h. The reaction mixture was poured onto a 1N NaOH solution (100 mL), mixed and extracted three times with ethyl acetate and the combined organic layers were dried over $MgSO_4$, filtered and concentrated in vacuo to give a brown oil. Column chromatography (chloroform:methanol::9:1) afforded N-(2-bromo-4-(1-methylethyl)phenyl)-N-ethyl-4-(4,4-ethylenedioxy-piperidino)carbonyl-6-methylpyrimidinamine as an orange-yellow oil (260 mg, 52% yield, $R_f$ 0.75):CI-HRMS: Calcd ($C_{24}H_{31}BrN_4O_3$): 503.16578 (M+H); Found: 503.16571.

EXAMPLE 82

N-(2-bromo-4-(1-methylethyl)phenyl)-N-ethyl-4-(4-oxopiperidino)carbonyl-6-methylpyrimidinamine A solution-of N-(2-bromo-4-(1-methylethyl)phenyl)-N-ethyl-4-((4,4-ethylenedioxypiperidino)carbonyl)-6- methylpyrimidinamine (260 mg) in a mixture of a 1N HCl solution (2.5 mL) and THF (2.5 mL) was stirred at reflux temperature for 20 h. The reaction mixture was poured into a 1N NaOH solution, and extracted three times with ethyl acetate. The combined organic layers were dried over MgSO$_4$, filtered and concentrated in vacuo to give the title product as a yellow oil (240 mg, 100% yield, R$_f$ 0.75): NMR (CDCl$_3$, 300 MHz): 7.5 (s, 1H), 7.2 (d, 1H, J=8), 7.1 (d, 1H, J=8), 6.8 (br s, 1H), 4.3–4.1 (m, 1H), 3.95–3.85 (m, 1H), 3.75–3.6 (m, 1H), 3.55–3.4 (m, 1H), 2.95–2.85 (m, 1H), 2.6–2.3 (m, 4H), 2.0–1.6 (m, 2H), 1.4–1.15 (m, 12H); CI-HRMS: Calcd (C$_{22}$H$_{27}$BrN$_4$O$_2$): 459.1396 (M+H); Found: 459.1386.

EXAMPLE 83

N-(2-bromo-4-(1-methylethyl)phenyl)-N-ethyl-4-(4-oxopiperidino)methyl-6-methylpyriimidinamine, hydrochloride salt A solution of borane in tetrahydrofuran (1M, 29 mL, 29 mmol) was added dropwise to a solution of N-(2-bromo-4-(1-methylethyl)phenyl)-N-ethyl-4-(4,4-ethylenedioxy-piperidino)carbonyl-6-methylpyrimidinamine (1.67 g, 3.3 mmol) in anhydrous THF (7 mL) with stirring under a nitrogen atmosphere. The reaction mixture was heated to reflux temperature and stirred for 20 h, then cooled to ambient temperature. A solution of glacial acetic acid was added dropwise; then the reaction mixture was heated to reflux temperature and stirred for 4 h, then cooled to ambient temperature. The reaction mixture was concentrated in vacuo; the residue was treated with excess 1N NaOH solution, and extracted three times with ethyl acetate. The combined organic layers were dried over MgSO$_4$, filtered and concentrated in vacuo to give an oil. Column chromatography (ethyl acetate) afforded N-(2-bromo-4-(1-methylethyl)phenyl)-N-ethyl-4-(4,4-ethylenedioxy-piperidino)methyl-6-methylpyrimidinamine as a pale brown oil (860 mg): CI-MS, 489, 491 (M+H).

The ketal was dissolved in a mixture of a 33% HCl solution (10 mL) and THF (5 mL). The resulting solution was stirred at reflux for 65 h, then cooled to ambient temperature and basified with a 1N NaOH solution. The aqueous mix was extracted three times with ethyl acetate. The combined organic layers were dried over MgSO$_4$, filtered and concentrated in vacuo to give an oil. Column chromatography (ethyl acetate:hexanes::4:1) afforded the title product as its free base and as an oil (600 mg, 41% overall yield): CI-HRMS: Calcd (C$_{22}$H$_{29}$BrN$_4$O): 444.1603 (M+H); Found: 444.1594.

The above oil (0.55 g, 1.24 mmol) was dissolved in ether (5 mL) and treated with a 1N HCl solution in ether. The resulting precipitate was collected and washed with copious amounts of ether. Drying in vacuo afforded a white powder (500 mg, 84% yield): mp 186–188° C.; Anal. (C$_{22}$H$_{29}$BrN$_4$O-HCl): C, 54.92; H, 6.24; N, 11.65; Br, 16.64; Cl, 7.39; Found: C, 54.62; H, 6.37; N, 11.41; Br, 16.57; Cl, 7.35.

EXAMPLE 84

N-(2-bromo-4-(1-methylethyl)phenyl)-N-ethyl-4-(imidazol-1-yl)methyl-6-methylpyrimidinamine To a mixture of N-(2-bromo-4-(1-methylethyl)phenyl)-N-ethyl-4-hydroxymethyl-6-methylpyrimidinamine (1.57 g, 4.3 mmol), triethylamine(2.5 mL, 17 mmol) and dichloromethane (15 mL) at 0° C. under a nitrogen atmosphere was added methanesulfonyl chloride (0.54 g, 4.7 mmol) dropwise and the reaction mixture was stirred at 0° C. for 1.5 h. It was then washed successively with an ice-cold 1N HCl solution, a saturated NaHCO$_3$ solution and a saturated NaCl solution. Drying the methylene chloride solution over MgSO$_4$, filtration and removal of solvent in vacuo gave N-(2-bromo-4-(1-methylethyl)phenyl)-N-ethyl-4-methanesulfonyloxymethyl-6-methylpyrimidinamine as a clear colorless oil (1.6 g): NMR (CDCl$_3$, 300 MHz): 7.5 (d, 1H, J=1), 7.25–7.1 (m, 2H), 6.5 (s, 1H), 5.05–4.9 (br s, 2H), 4.3–4.1 (m, 1H), 3.8–3.6 (m, 1H), 3.0–2.85 (m, 1H), 2.8–2.6 (br s, 3H), 2.5–2.25 (br m, 3H), 1.3 (d, 6H, J=8), 1.2 (t, 3H, J=8); CI-MS, 442, 444 (M+H).

To sodium hydride (60% in oil, 0.1 g, 2.4 mmol), washed with hexanes and decanted twice, suspended in anhydrous THF (10 mL) was added imidazole (146 mg, 2.14 mmol) in one portion and the reaction mixture was warmed to reflux temperature and stirred for 2 h. A solution of the crude mesylate in anhydrous THF (10 mL) was added dropwise to the reaction mixture, which had been cooled to ambient temperature. The reaction mixture was stirred for 68 h, then it was poured onto water and extracted three times with ethyl acetate. The combined organic layers were dried over MgSO$_4$, filtered and concentrated in vacuo to give an oil. Column chromatography (ethyl acetate) afforded (1) N-(2-bromo-4-(1-methylethyl)phenyl)-N-ethyl-4-hydroxymethyl-6-methylpyrimidinamine (130 mg, 8% overall yield, R$_f$ 0.7) and (2) the title product (600 mg, 59% overall yield, R$_f$ 0.07): NMR (CDCl$_3$, 300 MHz): 7.6–7.4 (m, 2H), 7.2 (dd, 1H, J=7, 1), 7.15 (d, 1H, J=8), 7.05 (s, 1H), 7.0–6.8 (m, 1H), 6.05 (s, 1H), 4.95–4.8 (m , 2H), 4.25–4.1 (m, 1H), 3.8–3.6 (m, 1H), 3.0–2.85 (m, 1H), 2.4–2.1 (br m, 3H), 1.3 (d, 6H, J=8), 1.2 (t, 3H, J=8); CI-HRMS: Calcd (C$_{20}$H$_{24}$BrN5): 413.1293 (M+H), Found: 413.1275.

EXAMPLE 85

N-(2-bromo-4-(1-methylethyl)phenyl)-N-ethyl-4-(3-(methoxyphenyl)methoxymethyl)-6-methylpyrimidinamine To a mixture of N-(2-bromo-4-(1-methylethyl)phenyl)-N-ethyl-4-hydroxymethyl-6-methylpyrimidinamine (1.0 g, 2.7 mmol), triethylamine (1.4 mL, 10 mmol) and dichloromethane (20 mL) at 0° C. under a nitrogen atmosphere was added methanesulfonyl chloride (0.34 g, 3.0 mmol) dropwise. The reaction was performed as for Example 84, except the reaction time was 15 min.

Sodium hydride (0.12 g, 3 mmol) and 3-methoxybenzyl alcohol (0.41 g, 3 mmol) were reacted in anhydrous THF (10 mL) as for Example 84. A solution of the crude mesylate in anhydrous THF (10 mL) was added dropwise. The reaction mixture was stirred at reflux temperature for 18 h, cooled to room temperature, poured into a 1N NaOH solution and extracted three times with ethyl acetate. The combined organic layers were dried over MgSO$_4$, filtered and concentrated in vacuo to give an oil. Column chromatography (ethyl acetate:hexanes::1:1) afforded the title product as a viscous yellow liquid (800 mg, 60% overall yield, R$_f$ 0.7): NMR (CDCl$_3$, 300 MHz): 7.5 (s, 1H), 7.3–7.1 (m, 4H), 6.95–6.9 (m, 2H), 6.85 (br d, 1H, J=8), 6.75 (s, 1H), 5.6 (br s, 2H), 4.45–4.3 (m, 2H), 4.25–4.05 (m, 1H), 3.8 (s, 3H), 3.8–3.6 (m, 1H), 2.9 (septet, 1H, J=7), 2.3 (br s, 3H), 1.3 (d, 6H, J=7), 1.2 (t, 3H, J=7); CI-HRMS: Calcd (C$_{25}$H$_{30}$BrN$_3$O$_2$): 484.1599; Found: 484.1592.

EXAMPLE 86

N-(2-bromo-4-(1-methylethyl)phenyl)-N-ethyl-4-(2-thiazolyl)carbonyl-6-methylpyrimidinamine To a solution of n-butyl lithium in hexanes (2.4 M, 1.34 mL, 3.24 mmol) in anhydrous THF (5 mL) at −78° C. under a nitrogen atmosphere was added 2-bromothiazole (0.49 g, 0.27 mL, 3.0 mmol) dropwise. After the addition was complete, the reaction mixture was stirred at −78° C. for 30 min. A solution of methyl 2-(N-(2-bromo-4-(1-methylethyl)-phenyl)-N-ethylamino)-6-methyl-4-pyrimidinecarboxylate (Example 18) (1.0 g, 2.5 mmol) in anhydrous THF (10 mL) was added dropwise. The reaction mixture was then warmed to −60° C. and stirred for 4 h. A saturated aqueous solution of NaHCO$_3$ was added and the reaction mixture was warmed to ambient temperature. Three extractions with ethyl acetate, followed by two washings of the combined organic layers with water, drying over MgSO$_4$, filtration and concentration in vacuo gave a dark brown oil. Column chromatography (ethyl acetate: hexanes::1:1) afforded the title product, a brown solid (950 mg, 85% yield, R$_f$ 0.43): mp 97–98.5° C.; NMR (CDCl$_3$, 300 MHz):8.0 (s, 1H), 7.60 (s, 1H), 7.4–7.2 (m, 4H, J=6), 3.05–2.9 (m, 1H), 2.8–2.7 (m, 1H), 2.6 (br s, 3H), 1.4–1.2 (m, 9H); CI-HRMS Calcd: 445.0698 (M+H), Found: 445.0699; Anal.(C$_{20}$H$_{21}$BrN$_4$S): C, 54.05; H, 4.73; N, 12.61; Br, 18.02; S, 7.21; Found: C, 53.86; H, 4.66; N, 12.53; Br, 18.20; S, 7.46.

EXAMPLE 87

N-(2-bromo-4-(1-methylethyl)phenyl)-N-ethyl-4-(2-imidazolyl)carbonyl-6-methylpyrimidinamine To a solution of 1-(dimethylaminomethyl)imidazole (0.63 g, 5 mmol) in anhydrous diethyl ether (50 mL) at −78° C. under a nitrogen atmosphere was added a solution of n-butyl lithium in hexanes (2.4 M, 2.1 mL, 5 mmol) dropwise and the pale yellow suspension was stirred at −78° C. for 1 h. Methyl 2-(N-(2-bromo-4-(1-methylethyl)-phenyl)-N-ethylamino)-6-methyl-4-pyrimidinecarboxylate (Example 18) (1.47 g, 5 mmol) was added in one portion and the reaction mixture was warmed to room temperature over 23 h. A 1N HCl solution was added until pH=1 (test paper) and the reaction mixture was stirred for 4 h. A 3N NaOH solution was added until the solution became basic (pH=10; test paper). Three extractions with ethyl acetate, drying the combined organic layers over MgSO$_4$, filtration and concentration in vacuo gave a brown oily solid. Column chromatography (chloroform:methanol::9:1) afforded the title product, a yellow glass (900 mg, 42% yield, R$_f$ 0.43): mp 75–76° C.; NMR (CDCl$_3$, 300 MHz): 12.2–12.1 (m, 1H), 7.7 (d, 1H, J=1), 7.45–7.35 (m, 2H), 7.3–7.2 (m, 2H), 6.55 (br s, 1H), 4.3 (sextet, 1H, J=7), 3.8 (sextet, 1H, J=7), 3.05 (septet, 1H, J=7), 2.65 (br s, 3H), 1.4 (d, 6H, J=7), 1.3 (t, 3H, J=7); CI-HRMS: Calcd: 428.1086 (M+H), Found: 428.1089; Anal (C$_{20}$H$_{24}$BrN$_5$O) C, 56.08; H, 5.18; N, 16.35; Br, 18.66; Found: C, 56.20; H, 5.10; N, 15.88; Br, 18.73.

EXAMPLE 88

N-(2-bromo-4-(1-methylethyl)phenyl)-N-ethyl-4-(5-indolylcarbonyl)-6-methylpyrimidinamine To a suspension of potassium hydride (35% in oil, 0.16 g, 1.4 mmol), washed with hexanes and decanted twice, in anhydrous ether (5 mL), cooled to 0° C. under a nitrogen atmosphere was added a solution of 5-bromoindole (0.27 g, 1.4 mmol) in anhydrous ether. After being stirred for 30 min., the reaction mixture was cooled to −78° C. and transferred via cannula to a pre-cooled (−78° C.) mixture of t-butyl lithium (1.7 M in pentane, 1.6 mL, 2.7 mmol) in dry ether (5 mL). The resulting white suspension was stirred at −78° C. for 30 min and a solution of methyl 2-(N-(2-bromo-4-(1 -methylethyl)-phenyl)-N-ethylamino)-6-methyl-4-pyrimidinecarboxylate (Example 18) (0.5 g, 1.25 mmol) in anhydrous ether (5 mL) was added dropwise. After quenching the reaction mixture as in Example 87; it was extracted three times with ethyl acetate, followed by two washings of the combined organic layers with a saturated NaHCO$_3$ solution, drying over MgSO$_4$, filtration and concentration in vacuo to give a dark brown oil. Column chromatography (ethyl acetate: hexanes::1:4) afforded the title product, a light brown solid (140 mg, 24% yield, R$_f$ 0.2): mp 77–79° C.; NMR (DMSO-d$_6$, 400 MHz, 90° C.): 11.6–11.35 (br s, 1H), 8.30 (s, 1H), 7.75 (dd, 1H, J=8, 1), 7.55 (d, 1H, J=1), 7.4–7.35 (m, 2H), 7.35–7.25 (m, 2H), 6.9 (s, 1H), 6.60–6.55 (m, 1H), 4.1–3.7 (m, 2H), 2.95–2.8 (m, 1H), 2.4 (br s, 3H), 1.25–1.1 (m, 9H); Anal (C$_{25}$H$_{25}$BrN$_4$O): C, 62.90; H, 5.28; N, 11.74; Br, 16.74; Found: C, 63.13; H, 5.60; N, 11.37; Br, 16.80.

EXAMPLE 89

N-(2-bromo-4-(1-methylethyl)phenyl)-N-ethyl-4-(4-fluorophenyl)carbonyl-6-methylpyrimidinamine To a suspension of N,O-dimethylhydroxylamine hydrochloride (1.46 g, 15 mmol) in benzene (20 mL) at 5–10° C. under a nitrogen atmosphere was added a solution of trimethyl aluminum in toluene (2 M, 7.5 mL, 15 mmol) dropwise and the reaction mixture was then warmed to ambient temperature over 1 h. The reaction mixture was transferred to an addition funnel and added dropwise to a solution of methyl 2-(N-(2-bromo-4-(1-methylethyl)phenyl)-N-ethylamino)-6-methyl-4-pyrimidinecarboxylate (Example 18) (2.25 g, 5.73 mmol) in benzene (40 mL). The reaction mixture was heated at reflux and stirred for 16 h. After being cooled to room temperature, the mixture was poured into a 5% HCl solution (100 mL), mixed and extracted three times with ethyl acetate. The combined organic layers were dried over MgSO$_4$, filtered and concentrated in vacuo to give a brown oil. Column chromatography (ethyl acetate: hexanes::1:1) afforded N-(2-bromo-4-(1-methylethyl)phenyl)-N-ethyl-4-(N-methyl-N-methoxycarboxamido)-6-methylpyrimidinamine (1.0 g, 41% yield, R$_f$ 0.4): CI-MS, 421, 423 (M+H).

The crude amide was dissolved in anhydrous THF (10 mL). A solution of 4-fluorophenylmagnesium bromide in ether (2 M, 1.25 mL, 2.5 mmol) was added dropwise and the reaction mixture was stirred for 22 h. The reaction was quenched by pouring onto a 1 N NaOH solution (50 mL). The aqueous solution was extracted three times with ethyl acetate. The combined organic layers were dried over MgSO$_4$, filtered and concentrated in vacuo to give an orange yellow oil. Column chromatography (ethyl acetate:hexanes::1:9) afforded the title product as a yellow solid (700 mg, 65% yield, R$_f$ 0.5): mp 70° C.; NMR (CDCl$_3$, 300 MHz): 8.3–8.05 (m, 2H), 7.55 (d, 1H, J=1), 7.2–6.75 (m, 5H), 4.85–4.7 (m, 1H), 4.3–4.15 (m, 1H), 2.95 (septet, 1H, J=7), 2.5 (br s, 3H), 1.4–1.15 (m, 9H); CI-HRMS: Calcd(C$_{23}$H$_{23}$BrFN$_3$O): 456.1087 (M+H), Found: 456.1084.

EXAMPLE 90

N-(2-bromo-4-(1-methylethyl)phenyl)-N-ethyl-4-carboxy-6-methylpyriimidinamine

A mixture of methyl 2-(N-(2-bromo-4-(1-methylethyl)-phenyl)-N-ethylamino)-6-methyl-4-pyrimidinecarboxylate (Example 18) (10 g, 25 mmol), ethanol (100 mL) and a 1N NaOH solution (250 mL) was stirred at reflux temperature for 18 h. After being cooled to ambient temperature, the reaction mixture was concentrated twofold in vacuo and acidified with a concentrated HCl solution. Three extractions with chloroform, drying the combined organic layers over MgSO$_4$, filtration and removal of solvent in vacuo gave a pale brown solid (9.0 g, 95% yield): mp 102–104° C.; NMR (CDCl$_3$, 300 MHz): 7.55 (d, 1H, J=1), 7.25–7.20 (m, 2H), 7.15 (d, 1H, J=7), 4.30–4.10 (m, 1H), 3.88–3.7 (m, 1H), 3.00–2.85 (m, 1H), 2.55 (br s, 3H), 2.30 (br s, 1H), 1.30 (d, 6H, J=7), 1.20 (t, 3H, J=7); CI-HRMS: Calcd (C$_{17}$H$_{20}$BrN$_3$O): 378.0817(M+H); Found: 378.0813.

EXAMPLE 91

N-(2-bromo-4-(1-methylethyl)phenyl)-N-ethyl-4-acetyl-6-methylpyrimidinamine

Cerium trichloride (4.9 g, 19.6 mmol) was dried, with magnetic stirring, at 180° C. in vacuo for 4 h. After being cooled to room temperature and placed under a nitrogen atmosphere, the solid was stirred for 16 h in anhydrous THF (50 mL).

A solution of N-(2-bromo-4-(1-methylethyl)phenyl)-N-ethyl-4-carboxy-6-methylpyrimidinamine (3.7 g, 9.8 mmol) in anhydrous THF (25 mL) was cooled with stirring to −78° C. under a nitrogen atmosphere. A solution of methyl lithium in ether (1.4 M, 7 mL, 9.8 mmol) was added dropwise and the reaction mixture was stirred at −78° C. for 1 h. The CeCl$_3$ suspension was transferred via cannula into the reaction mixture and stirring at −78° C. was continued for 5 h. A solution of methyl lithium in ether (1.4 M, 7 mL, 9.8 mmol) was added dropwise and the reaction mixture was then warmed gradually to room temperature over 16 h. After cooling the reaction mixture to −78° C., the reaction was quenched with a 1 N HCl solution and warmed to room temperature. The resulting mixture was extracted three times with ethyl acetate. The combined organic layers were dried over MgSO$_4$, filtered and concentrated in vacuo to give an orange yellow oil. Column chromatography (ethyl acetate:hexanes::1:4) afforded the title product as an oil (2.5 g, 68% yield, R$_f$ 0.5): NMR (CDCl$_3$, 300 MHz): 7.55 (d, 1H, J=1), 7.25–7.15 (m, 2H), 6.95 (s, 1H), 4.30–4.10 (m, 1H), 3.90–3.70 (m, 1H), 3.00–2.85 (m, 1H), 2.80–2.05 (m, 6H), 1.35–1.20 (m, 9H); CI-HRMS: Calcd (C$_{18}$H$_{22}$BrN3O): 376.1024 (M+H), Found: 376.1042.

EXAMPLE 92

N-(2-bromo-4-(1-methylethyl)phenyl)-N-ethyl-4-(hydroxy-3-pyridyl-methyl)-6-methylpyrimidinamine (XU472)

Sodium borohydride (0.11 g, 2.8 mmol) was added to a solution of N-(2-bromo-4-(1-methylethyl)phenyl)-N-ethyl-4-(3-pyridylcarbonyl)-6-methylpyrimidinamine (0.6 g, 1.4 mmol) in ethanol (5 mL). After being stirred for 71 h, the reaction mixture was concentrated in vacuo, treated with a 1 N NaOH solution and extracted three times with ethyl acetate. The combined organic layers were washed with brine, dried over MgSO$_4$, filtered and concentrated in vacuo to give a colorless oil. Column chromatography (chloroform:methanol::9:1) afforded the title product as an oil (600 mg, 96% yield, R$_f$ 0.4): NMR (CDCl$_3$, 300 MHz): 8.65–8.45 (m, 2H), 7.55 (br s, 2H), 7.3–7.1 (m, 2H), 6.25–6.15 (m, 1H), 5.7–5.5 (m, 0.5H), 5.45–5.3 (m, 0.5H), 5.15–4.95 (m, 1H), 4.3–4.1 (m, 1H), 3.9–3.7 (m, 1H), 3.0–2.85 (m, 1H), 2.45–2.2 (m, 3H), 2.3–2.2 (m, 1H), 1.35–1.2 (m, 9H); CI-HRMS: Calcd (C$_{22}$H$_{25}$BrN4O): 441.1290 (M+H), Found: 441.1274.

EXAMPLE 93

N-(2-bromo-4-(1-methylethyl)phenyl)-N-ethyl-4-(4-(methoxyphenyl)-3-pyridyl-hydroxymethyl)-6-methylpyrimidinamine A solution of 4-bromoanisole (0.2 g, 1.1 mmol) in anhydrous THF (10 mL) was cooled with stirring to −78° C. under a nitrogen atmosphere. A solution of t-butyl lithium in pentane (1.7 M, 1.4 mL, 2.4 mmol) was added dropwise and the reaction mixture was stirred for 0.5 h. A solution of N-(2-bromo-4-(1-methylethyl)phenyl)-N-ethyl-4-(3-pyridyl-carbonyl)-6-methylpyrimidinamine (0.45 g, 1 mmol) in anhydrous THF (10 mL) was added dropwise and the reaction mixture was warmed gradually to ambient temperature over 18 h. The reaction mixture was poured onto a saturated NH$_4$Cl solution and extracted three times with ethyl acetate. The combined organic layers were dried over MgSO$_4$, filtered and concentrated in vacuo to give an oil. Column chromatography (ethyl acetate:hexanes::4:1) afforded the title product as a pale brown glass (170 mg, 31% yield, R$_f$ 0.2): mp 68–70° C.; NMR (CDCl$_3$, 300 MHz): 8.6–8.4 (m, 2H), 7.7–7.5 (m, 1H), 7.5 (s, 1H), 7.25–7.05 (m, 6H), 6.95–6.75 (m, 2H), 6.25–6.2 (m, 1H), 5.85–5.7 (m, 1H), 4.25–4.05 (m, 1H), 3.8 (br s, 3H), 3.95–3.75 (m, 1H), 3.00–2.8. (m, 1H), 2.45–2.1 (br s, 3H), 1.35–1.15 (m, 9H); CI-HRMS: Calcd(C$_{29}$H31BrN$_4$O$_2$): 547.1709 (M+H), Found: 547.1709.

EXAMPLE 94

N-(2-bromo-4-(1-methylethyl)phenyl)-N-ethyl-4-(3-pyrazolyl)-6-methylpyriimidinamine, Hydrochloride Salt Sodium (0.08 g, 3.5 mmol) was added to methanol (20 mL) with stirring. After the sodium reacted, a solution of N-(2-bromo-4-(1-methylethyl)phenyl)-N-ethyl-4-acetyl-6-methyl-pyrimidinamine (1.0 g, 2.67 mmol) in methanol (5 mL) was added and the reaction mixture was stirred for 5 min. Gold's reagent ((dimethylaminomethyleneaminomethylene))dimethyl-ammonium chloride (0.66 g, 4 mmol) was added and stirring was continued for 19 h. The reaction mixture was concentrated in vacuo; the residue was dissolved in chloroform and the solution was washed with a saturated NaHCO$_3$ solution, dried over MgSO$_4$ and filtered solvent removal in vacuo gave a brown solid, which upon trituration with hexanes afforded N-(2-bromo-4-(1-methylethyl)phenyl)-N-ethyl-4-(3-dimethylaminopropenoyl)-6-methylpyrimidinamine as a yellow solid (700 mg): NMR (CDCl$_3$, 300 MHz): 7.9–7.65 (br s, 1H), 7.5 (s, 1H), 7.25–7.2 (m, 2H), 7.15 (s, 1H), 6.1–5.8 (br s, 1H), 4.3–4.15 (m, 1H), 3.9–3.75 (m, 1H), 3.2–3.0 (br s, 3H), 3.0–2.85 (m, 1H), 2.8–2.6 (br s, 3H), 2.5–2.3 (br s, 3H), 1.35–1.2 (m, 9H): CI-MS, 431, 433 (M+H).

A solution of the above vinylogous amide and anhydrous hydrazine (0.15 g, 4.7 mmol) in toluene (15 mL) was stirred at reflux temperature under a nitrogen atmosphere for 16 h. The reaction mixture was poured onto water and extracted three times with ethyl acetate. The combined organic layers were dried over MgSO$_4$, filtered and concentrated in vacuo to give an oil. Column chromatography (ether) afforded the free base of the title product as a pale yellow glass (600 mg, 59% overall yield, R$_f$ 0.4): NMR (CDCl$_3$, 300 MHz): 7.6 (s, 1H), 7.55 (s, 1H), 7.3–7.2 (m, 2H), 6.8 (s, 1H), 6.75–6.6 (br s, 1H), 4.3–4.15 (m, 1H), 3.9–3.7 (m, 1H), 3.00–2.85 (m, 1H), 2.5–2.2 (br s, 3H), 1.3 (d, 6H, J=8), 1.25 (t, 3H, J=8); CI-HRMS: Calcd (C$_{19}$H$_{22}$BrN$_5$): 399.1137 (M+H), Found: 399.1140.

The free base was dissolved in ether and treated with an excess amount of a 1 N HCl solution in ether. The resulting precipitate was collected and washed with copious amounts of ether. Drying in vacuo at 60° C. afforded the title product as a powder (500 mg, 72% yield) mp 235–237° C.; NMR (DMSO-$d_6$, 300 MHz): 7.9–7.7 (m, 1H), 7.6 (s, 1H), 7.4–7.3 (m, 2H), 7.2 (s, 1H), 7.05–6.85 (m, 1H), 4.3–4.1 (m, 1H), 3.85–3.65 (m, 1H), 3.05–2.9 (m, 1H), 2.45–2.1 (br m, 3H), 1.25 (d, 6H, J=8), 1.2 (t, 3H, J=8); Anal. ($C_{19}H_{22}BrN_5$-HCl): C, 52.75; H, 5.31; N, 16.03; Br, 18.29; Cl, 8.12; Found: C, 52.53; H, 5.28; N, 15.93; Br, 18.44; Cl, 8.17.

EXAMPLE 95

N-(2-bromo-4-(1-methylethyl)phenyl)-N-ethyl-4-(1-aminoethyl)-6-methylpyrimidinamine A mixture of N-(2-bromo-4-(1-methylethyl)phenyl)-N-ethyl-4-acetyl-6-methyl-pyrimidinamine (0.5 g, 1.33 mmol), ammonium acetate (1.1 g, 14 mmol), sodium cyanoborohydride (59 mg, 0.9 mmol) and methanol (5 mL) was stirred at ambient temperature for 90 h. A concentrated HCl solution was added until the solution became acidic (pH=2), then the reaction mixture was concentrated in vacuo. The residue was taken up in water, basified with a concentrated NaOH solution and extracted three times with ether. The combined organic layers were dried over $MgSO_4$, filtered and concentrated in vacuo to give an oil. Column chromatography (ethyl acetate:hexanes:: 1: then chloroform:methanol:$NH_4OH$::95:5:0.5) gave (1) N-(2-bromo-4-(1-methylethyl)phenyl)-N-ethyl-4-(1-aminothyl)-6-methyl-pyrimidinamine (80 mg, 16% yield, $R_f$ 0.34 (ethyl acetate:hexanes::1;1)) and (2) the title product as a brown oil (180 mg, 36% yield, $R_f$ 0.34 (chloroform:methanol:$NH_4OH$::95:5:0.5)): NMR ($CDCl_3$, 300 MHz): 7.5 (d, 1H, J=1), 7.2–7.1 (m, 2H), 6.4 (s, 1H), 4.25–4.05 (m, 1H), 3.9–3.65 (m, 2H), 3.0–2.85 (m, 1H), 2.4–2.2 (br m, 3H), 1.9–1.6 (br m, 3H), 1.3 (d, 6H, J=8), 1.2 (t, 3H, J=8); CI-HRMS ($C_{18}H_{25}BrN_4$): 377.1341 (M+H), Found: 377.1330.

EXAMPLE 96

N-(2-bromo-4-(1-methylethyl)phenyl)-N-ethyl-4-(2-(4-tetrazolyl)-1-methylethyl)-6-methylpyrimidinamine A mixture of N-(2-bromo-4-(1-methylethyl)phenyl)-N-ethyl-4-(1-hydroxyethyl)-6-methylpyrimidinamine (1.1 g, 2.7 mmol), triethylamine (1.5 mL, 11 mmol) and dichloromethane (15 mL) was stirred at 0° C. under a nitrogen atmosphere. Methanesulfonylchloride (364 mg, 3.2 mmol) was added dropwise and the reaction mixture was then stirred for 1.5 h. The resulting turbid solution was washed successively with an ice-cold 1 N HCl solution, a saturated $NaHCO_3$ solution and a saturated NaCl solution. Drying over $MgSO_4$, filtration and removal of solvent in vacuo gave N-(2-bromo-4-(1-methylethyl)phenyl)-N-ethyl-4-(1-methanesulfonyloxyethyl)-6-methylpyrimidinamine as a clear colorless oil (1.0 g): NMR ($CDCl_3$, 300 MHz): 7.5 (d, 1H, J=1), 7.25–7.1 (m, 2H), 6.55 (s, 1H), 4.3–4.05 (m, 1H), 3.85–3.6 (m, 1H), 3.0–2.5 (m, 4H), 2.5–2.05 (br m, 3H), 1.3 (d, 6H, J=8), 1.2 (t, 3H, J=8); CI-MS, 456, 458 (M+H).

The crude mesylate was mixed with sodium cyanide (0.54 g, 11 mmol) in N,N-dimethylformamide (DMF) (20 mL) and stirred at reflux temperature for 67 h. After being cooled to room temperature, the reaction mix was poured onto water (200 mL), mixed and extracted with ethyl acetate three times. The combined organic layers were dried over $MgSO_4$, filtered and concentrated in vacuo to give an oil. Column chromatography (ethyl acetate:hexanes::1:9) afforded N-(2-bromo-4-(1-methylethyl)phenyl)-N-ethyl-4-(1-cyanoethyl)-6-methylpyrimidinamine as an oil (440 mg, $R_f$ 0.24): NMR ($CDCl_3$, 300 MHz): 7.5 (d, 1H, J=1), 7.25–7.1 (m, 2H), 6.65–6.55 (m, 1H), 4.3–4.05 (m, 1H), 3.9–3.5 (m, 2H), 3.0–2.85 (m, 1H), 2.55–2.0 (br m, 3H), 1.8–1.4 (br m, 3H), 1.4–1.1 (m, 9H); CI-MS: 387, 389 (M+H).

A mixture of the crude cyanide, sodium azide (600 mg, 9 mmol), ammonium chloride (492 mg, 9 mmol) and DMF (20 mL) was stirred at 100–105° C. for 112 h. After being cooled to room temperature, the reaction mixture was poured onto water (200 mL), basified with a 1 N NaOH solution (pH>10) and extracted three times with chloroform. The combined organic layers were dried over $MgSO_4$, filtered and concentrated in vacuo to give an oil. Column chromatography (chloroform:methanol::9:1) afforded a brown solid ($R_f$ 0.22). Recrystallization from ether gave the title product as a white solid (35 mg, 3% overall yield): mp 127–129° C.; NMR ($CDCl_3$, 400 MHz): 7.75 (s, 0.4H), 7.7(s, 0.6H), 7.45 (d, 0.6H, J=8), 7.4 (d, 0.4H, J=8), 7.3–7.2 (m, 2H), 6.5 (s, 0.4H), 6.48 (s, 0.6H), 4.28–4.0 (m, 1.4H), 4.28–4.18 (m, 0.6H), 3.94–3.82 (m, 0.6H), 3.8–3.7 (m, 0.4H), 3.1–3.0 (m, 1H), 2.45 (s, 3H), 1.5 (d, 3H, J=8), 1.4–1.3 (m. 5H), 1.3–1.2 (m, 4H); CI-HRMS: 430.1355 (M+H); 430.1347.

EXAMPLE 97

2-(N-(2-bromo-4-(2-propyl)phenyl)amino)-4-carbomethoxy-6-methylpyrimidine

A mixture of 2-chloro-4-carbomethoxy-6-methylpyrimidine (47.0 g, 252 mmol) and 2-bromo-4-(2-propyl)aniline (54.0 g, 252 mmol) in dioxane (400 mL) was stirred at reflux temperature for 20 h under a nitrogen atmosphere. The reaction mixture was cooled to ambient temperature and concentrated on a rotary evaporator. The residue was treated with a saturated sodium bicarbonate solution and extracted three times with ethyl acetate. The combined organic layers were dried over magnesium sulfate and filtered. Solvent was removed in vacuo to provide a red oil. Column chromatography (ethyl acetate:hexanes::1:1) gave the title product as a crude oil. Recrystallization from ether-hexanes, collection by filtration and drying in vacuo afforded the title compound as a solid (42.8 g, 17% yield): mp 75–76° C.; NMR ($CDCl_3$, 300 MHz): 8.4 (d, 1H, J=8); 7.65 (br s, 1H), 7.4 (d, 1H, J=1), 7.3 (s, 1H), 7.2 (dd, 1H, J=8,1), 4.0 (s, 3H), 2.85 (septet, 1H, J=7), 2.5 (br s, 3H), 1.25 (d, 6H, J=7); Anal. ($C_{16}H_{18}BrN_3O_2$): C, 52.76, H, 4.98; N, 11.54; Br, 21.94; Found: C, 52.71; H, 4.99; N, 11.38; Br, 21.83.

EXAMPLE 98

2-(N-(2-bromo-4-(2-propyl)phenyl)-N-ethylamino) 4-carbomethoxy-6-methylpyrimidine To sodium hydride (60% in oil, 4.8 g, 120 mmol), washed with hexanes (50 mL) twice and decanted in anhydrous tetrahydrofuran (150 mL) at ambient temperature under a nitrogen atmosphere was stirred 2-(N-(2-bromo-4-(2-propyl)phenylamino)-4-carbomethoxy-6-methylpyrimidine (42.8 g, 118 mmol) portionwise over 30 min. After gas evolution subsided, iodoethane (31.2 g, 16 mL, 200 mmol) was added in one portion and the reaction mixture was heated to a gentle reflux and stirred for 24 h. After being cooled to room temperature, the reaction mixture was quenched carefully with water and extracted three times with ethyl acetate. The combined organic layers were washed with water twice, dried over magnesium sulfate and filtered. Solvent was removed in vacuo to afford a brown oil. Column chromatography (ether:hexanes::1:1) provided two fractions: (1) 2-(N-(2-bromo-4-(2-propyl)phenylamino)-4-carbomethoxy-6-methylpyrimidine (4.6 g, 11% yield, $R_f$=0.8) and (2) the title product (20 g, $R_f$ =0.7) as a crude oil.

The title product was recrystallized from hexanes and dried in vacuo to give a solid (18.0 g, 39% yield): mp 81–82° C., NMR(CDCl$_3$, 300 MHz): 7.5 (br s, 1H), 7.25 (d, 1H, J=7), 7.15 (d, 1H, J=7), 7.1 (s, 1H), 4.3–4.1 (m, 1H), 4.05–3.75 (m, 4H), 2.95 (septet, 1H, J=7), 2.3 (br s, 3H), 1.3 (d, 6H, J=7), 1.25 (t, 3H, J=7); CI-HRMS: calcd: 392.0974 (M+H), found: 392.0960.

EXAMPLE 99

2-(N-(2-bromo-4-(2-propyl)phenyl)-N-ethylamino)-6-methylpyrimidine-4-carboxylic acid, morpholine amide To sodium hydride (60% in oil, 0.24 g, 6.0 mmol), washed with hexanes twice and decanted, and suspended in anhydrous tetrahydrofuran (10 mL) was added morpholine (0.52 g, 6.0 mmol) and the reaction mixture was warmed to reflux temperature and stirred for 1 h. The reaction mixture was then cooled to ambient temperature and 2-(N-(2-bromo-4-(2-propyl)phenyl)-N-ethylamino)-4-carbomethoxy-6-methyl-pyrimidine (2.0 g, 5.1 mmol) was added and stirring was continued for 26 h. The reaction mixture was then poured onto a 1 N NaOH solution, stirred and extracted three times with ethyl acetate. The combined organic layers were dried over magnesium sulfate, filtered and concentrated in vacuo. Column chromatography (ether) afforded the title compound as a solid (900 mg, 39% yield): mp 145° C.; NMR (CDCl$_3$, 300 MHz): 7.5 (d, 1H, J=1), 7.2 (dd, 1H, J=7,1), 7.1 (d, 1H, J=7), 6.8 (br s, 1H), 4.3–4.15 (m, 1H), 3.9–3.3 (m, 11H), 3.1–3.0 (m, 1H), 2.9 (septet, 1H, J=7), 1.3 (d, 6H, J=7), 1.15 (t, 3H, J=7); Anal. (C$_{21}$H$_{27}$BrN$_4$O$_2$) Calcd: C, 56.38; H, 6.08; N, 12.52; Br, 17.86; Found: C, 56.07; H, 6.05; N, 12.29; Br, 18.08.

EXAMPLE 100

2-(N-(2-bromo-4-(2-propyl)phenyl)-N-ethylamino)-4-(morpholinomethyl)-6-methylpyrimidine To a solution of 2-(N-(2-bromo-4-(2-propyl)phenyl)-N-ethylamino)-6-methylpyrimidine-4-carboxylic acid, morpholine amide (750 mg, 1.72 mmol) in anhydrous tetrahydrofuran (1.4 mL) at ambient temperature under a nitrogen atmosphere was added a solution of borane in tetrahydrofuran (1 M, 3.6 mL, 3.6 mmol) dropwise and the reaction mixture was heated at reflux temperature for 20 h. After cooling to room, acetic acid (3.5 mL) was slowly added and the mixture was heated at reflux for 30 min. After being cooled to ambient temperature, the reaction mixture was poured into a 3 N NaOH solution and extracted three times with ethyl acetate. The combined organic layers were dried over magnesium sulfate, filtered and concentrated in vacuo. Column chromatography (ethyl acetate) afforded the title compound as an oil (300 mg, 39% yield, $R_f$ 0.3): NMR (CDCl$_3$, 300 MHz) 7.5 (s, 1H), 7.2 (d, 1H, J=7), 7.15 (d, 1H, J=7), 6.5 (s, 1H), 4.3–4.1 (m, 1H), 3.8–3.6 (m, 7H), 3.5–3.3 (m, 2H), 2.9 (septet, 1H, J=7), 2.55–2.35 (br m, 3H), 2.35–2.25 (m, 2H), 1.3 (d, 6H, J=7), 1.2 (t, 3H, J=7); CI-HRMS: calcd: 433.1603 (M+H), found: 433.1586.

EXAMPLE 101

9[2-bromo-4(2-propyl)phenyl]-2-methyl-6-chloropurine

Part A: Fuming nitric acid (40 mL) was added in portions to 4,6-dihydroxy-2-methylpyrimidine while cooling the reaction flask on ice. After completion of addition, the reaction was stirred an additional 60 min over ice followed by another 60 min at room temperature. The reaction mixture was then poured over ice (60 g) and the ice allowed to melt. A light pink solid was isolated by filtration and washed with cold water (50 mL). The solid was dried in a vacuum oven overnight to yield 22.6 g of product.

Part B: The product of Part A was added portionwise to phosphorus oxychloride (125 mL) under a nitrogen atmosphere. N,N-diethylaniline (25 mL) was added portionwise and the reaction mixture was refluxed for 150 min. then cooled to room temperature. The reaction mixture was poured over ice (750 g) and stirred for 1 hr. The aqueous layer was extracted with diethyl ether (4×400 mL) and the extracts combined. The extracts were washed with brine (300 mL) and the organic layer dried over Na$_2$SO$_4$. The dried organic layer was filtered and stripped down to a tan solid (21.51 g).

Part C: The product of Part B (3.0 g) was added to acetic acid (5.5 mL) and methanol (25 mL). This solution was added to iron powder (3.0 g) and the reaction was stirred for two hrs at 60–65° C. The reaction was cooled to room temperature and the product was filtered. The filtrate was stripped to a brown solid, which was extracted with ethyl acetate (3×100 mL). The combined organic extracts were washed with NaOH (1 N, 2×100 mL), water (100 mL), and brine (100 mL). The organic layer was dried over Na$_2$SO$_4$, filtered, and stripped to yield (2.13 g) an amber liquid that solidified upon cooling. MS (M+H)$^+$178.

Part D: The product of Part C (2.0 g), 2-bromo-4-isopropylaniline (2.4 g), and diisopropylethylamine (1.52 g) were mixed and the reaction mass was heated to 160° C. for 25 min. Purification of the reaction mass by flash chromatography (CH$_2$Cl$_2$:MeOH, 50:1; silica) followed by stripping of the product-containing fractions yielded (1.45 g) an off white solid. MS (M+H)$^+$356.

Part E: The product of Part D (1.32 g), triethylorthoformate (10 mL), and acetic anhydride (10 mL) were mixed under nitrogen and refluxed for 4.5 hrs. The reaction mixture was reduced to an oil and water (50 mL) was added. The aqueous mixture was basified (pH 8) with solid Na$_2$CO$_3$ and extracted with CHCl$_3$ (3×80 mL). The combined organic extracts were dried over Na$_2$SO$_4$, filtered and stripped to yield an amber oil (1.63 g). Purification by flash chromatography (CH$_2$Cl$_2$:MeOH, 50:1; silica) yielded a light amber glass 9[2-bromo-4(2-propyl)phenyl]-2-methyl-6-chloropurine (0.94 g). Mp 49–52° C. MS (M+H)$^+$367.

EXAMPLE 102

9[2-bromo-4(2-propyl)phenyl]-2-methyl-6-morpholinopurine

9[2-bromo-4(2-propyl)phenyl]-2-methyl-6-chloropurine (1.3 g) and morpholine (10 mL) were combined under nitrogen and refluxed for 6 hrs. The reaction mixture was concentrated by rotovap and the residue was purified by flash chromatography (CH$_2$C$_2$:MeOH, 50:1; silica) to yield a yellow solid (0.54 g). MS (M+H)$^+$416, 418.

EXAMPLE 103

9[2-bromo-4(2-propyl)phenyl]-8-aza-2-methyl-6-chloropurine

Part A: Fuming nitric acid (40 mL) was added in portions to 4,6-dihydroxy-2-methylpyrimidine while cooling the reaction flask on ice. After completion of addition, the reaction was stirred an additional 60 min over ice followed by another 60 min at room temperature. The reaction mass was then poured over ice (60 g) and the ice allowed to melt. A light pink solid was isolated by filtration and washed with cold water (50 mL). The solid was dried in a vacuum oven overnight to yield 22.6 g of product.

Part B: The product of Part A was added portionwise to phosphorus oxychloride (125 mL) under a nitrogen atmosphere and N,N-diethylaniline (25 mL) was added portionwise. The reaction mixture was refluxed for 150 min, cooled to room temperature, poured over ice (750 g) and stirred for 1 hr. The aqueous layer was extracted with diethyl ether (4×400 mL) and the extracts combined. The extracts were washed with brine (300 mL), dried over $Na_2SO_4$, filtered, and stripped down to a tan solid (21.51 g).

Part C: The product of Part B (6.5 g) was added to acetic acid (11 mL) and methanol (50 mL). This solution was added to iron powder (6.0 g), stirred for two hrs at 60–65° C., cooled to room temperature, and filtered. The filtrate was stripped to a brown solid, which was extracted with ethyl acetate (3×100 mL). The combined organic extracts were washed with NaOH (1 N, 2×100 mL), water (100 mL), and brine (100 mL). The organic layer was dried over $Na_2SO_4$, filtered, and stripped to yield (4.75 g) an amber liquid that solidified upon cooling. MS $(M+H)^+178$.

Part D: The product of Part C (4.75 g) and 2-bromo-4-isopropylaniline (5.71 g) were mixed and the reaction mass heated to 140° C. for 60 min. The reaction mass was suspended in $CH_2Cl_2$ (300 mL) and the organic solution was washed with NaOH (1 N, 3×250 mL) and brine (250 mL). The organic phase was dried over $Na_2SO_4$, and stripped to a dark liquid (9.28 g). The liquid was purified by flash chromatography ($CH_2Cl_2$:MeOH, 50:1; silica) to yield (6.27 g) a light red solid. MS $(M+H)^+356$.

Part E: The product of Part D (2.0 g) was added to acetic acid (50%, 20 mL) and sodium nitrite (0.407 g) in water (2.0 mL) was added dropwise at room temperature. After 4.25 hrs, the reaction mixture was filtered and the collected solid was purified by flash chromatography ($CH_2Cl_2$:MeOH, 50:1; silica) to yield an orange oil 9 [2-bromo-4(2-propyl)phenyl]-8-aza-2-methyl-6-chloropurine (0.75 g). MS $(M+H)^+368$.

EXAMPLE 104

9[2-bromo-4(2-propyl)phenyl]-8-aza-2-methyl-6-morpholinopurine

9 [2-bromo-4(2-propyl)phenyl]-8-aza-2-methyl-6-chloropurine (1.34g) and morpholine (10 mL) were combined under nitrogen and refluxed for 2.5 hrs. $CH_2Cl_2$ (200 mL) was added to the reaction mixture and the resulting solution washed with water (2×100 mL) and brine (100 mL). The organic phase was dried over $Na_2SO_4$, concentrated by rotovap and the residue purified by flash chromatography ($CH_2Cl_2$, silica) to yield a yellow solid (0.62 g). MP 145–148° C. MS $(M+H)^+417, 419$.

EXAMPLE 105

2-(N-(2,4-dimethyoxypyrimidin-5-yl)-N-ethylamino)-4,6dimethylpyrimidine

Part A: 5-Nitrouracil (25 g) was added to phosphorus oxychloride (130 mL) and N,N-diethylamine (32 mL) and the reaction was heated to reflux for 70 min. under nitrogen. After cooling to room temperature, the reaction mixture was poured over ice (600 g) and the mixture stirred until it reached room temperature (60 min). The aqueous layer was extracted with diethyl ether (4×300 mL). The extracts were combined, washed with brine (200 mL), and dried over $Na_2SO_4$. The organic layer was then stripped to yield an orange red liquid (17.69 g).

Part B: The product of Part A (17.69 g) in 60 mL methanol was added dropwise to a solution of sodium methoxide (30% wt, 38 mL) while cooling the flask in an ice bath. After addition was complete, the reaction mixture was stirred overnight at room temperature and then refluxed for 4 hrs. After cooling to room temperature, the reaction mixture was poured over ice (500 g) and the white precipitate that formed (10.38 g) was collected by filtration.

Part C: The product of Part B (4.1 g) and Pd/C (10% wt, 0.15 g) were added to ethanol (70 mL), methanol (10 mL) and water (1 mL) in a Parr reactor. The reaction mass was treated with hydrogen until TLC analysis showed no starting material. The reaction mass was filtered through celite and the filtrate stripped yielding a tan solid (3.32 g).

Part D: The product of Part C (1.086 g) and 2-chloro-4,6-dimethyl-pyrimidine (1.0 g) were dissolved in THF (50 mL) under nitrogen. Sodium hydride (0.336 g, 60% wt dispersion in oil) was added portionwise. After addition, the reaction was refluxed for 5.5 hrs, cooled to room temperature and the solid removed by filtration. The filtrate was concentrated and purified by flash chromatography ($CH_2C_2$:MeOH, 90:10, silica) to give a solid (0.52 g). MS $(M+H)^+262$.

Part E: The product of Part D (2.0 g) and iodoethane (1.49 g) were dissolved in dimethylformamide (20 mL) under nitrogen. Sodium hydride (0.383 g, 60% wt dispersion in oil) was added portionwise. After addition, stirring was continued at room temperature for 22 hrs. Water (200 mL) was added and the mixture was extracted with ethyl acetate (3×200 mL). The combined extracts were washed with water (100 mL) and brine (100 mL), dried over $Na_2SO_4$, filtered, and stripped to give an amber liquid 2-(N-(2,4-dimethyoxypyrimidin-5-yl)-N-ethylamino)-4,6-dimethylpyrimidine (2.68 g). MS (M+H)+290.

Many of the compounds described above may be converted to their salts by addition of the corresponding acid in a solution of the compound in an organic solvent. The choice of addition salt described above is not intended to limit the invention, and is intended to be illustrative of the generality of the described syntheses. Physical properties of representative compounds that can be synthesized utilizing the methods described above are provided in the tables below (Table 1 through Table 17). The column in the tables headed "Synth. Ex." refers to the synthesis examples 1–105; supra. The designations "MS" and "HRMS" refer to low and high resolution mass spectral data, respectively.

TABLE 1

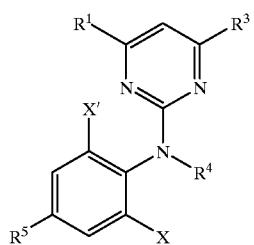

| Ex. | Synth. Ex. | R¹ | R³ | R⁴ | X, X' | R⁵ | mp, °C. |
|---|---|---|---|---|---|---|---|
| 1* | 1 | CH₃ | CH₃ | CH₃ | Br, H | CH₃ | 120–121 |
| 2* |  | CH₃ | CH₃ | CH₃ | CH₃O, H | CH₃O | 112–113 |
| 3* |  | CH₃ | CH₃ | allyl | Br, H | H | 127–129 |
| 4* | 2 | CH₃ | CH₃ | CH₃ | Br, H | iC₃H₇ | 163–164 |
| 5 |  | CH₃ | CH₃ | C₂H₅ | Br, H | H | 94–95 |
| 6 |  | CH₃ | morpholino | CH₃ | Br, H | CH₃ | 40–42 |
| 7 |  | CH₃ | CH₃ | C₂H₅ | CH₃O, H | CH₃O | 120–121 |
| 8 |  | CH₃ | CH₃ | CH₃ | Br, H | Br | 101–103 |
| 9* | 3 | CH₃ | CH₃ | CH₃ | Br, H | C₂H₅ | 126–127 |
| 10* |  | CH₃ | CH₃ | C₂H₅ | Br, H | tC₄H₉ | 191–193 |
| 11* |  | CH₃ | CH₃ | CH₃ | Br, H | tC₄H₉ | 193–195 |
| 12 |  | CH₃ | CH₃ | CH₃ | Br, H | CF₃ | 106–107 |
| 13* |  | CH₃ | CH₃ | C₂H₅ | Br, H | CF₃ | 125–130 |
| 14 |  | CH₃ | CH₃ | CH₃ | CH₃O, CH₃O | CH₃O | 145–146 |
| 15 |  | CH₃ | CH₃ | C₂H₅ | CH₃O, CH₃O | CH₃O | 115–116 |
| 16* | 4 | CH₃ | morpholino | C₂H₅ | Br, H | iC₃H₇ | 219–222 |
| 17* |  | CH₃ | morpholino | allyl | Br, H | iC₃H₇ | 208–211 |
| 18* |  | CH₃ | CH₃ | allyl | Br, H | nC₄H₉ | 116–118 |
| 19* |  | CH₃ | CH₃ | C₂H₅ | Br, H | nC₄H₉ | 124–126 |
| 20 |  | CH₃ | CH₃ | nC₃H₇ | Br, H | nC₄H₉ | 49–50 |
| 21* | 5 | CH₃ | CH₃ | C₂H₅ | Br, H | iC₃H₇ | 151–153 |
| 22* |  | CH₃ | CH₃ | C₂H₅ | Br, H | cC₆H₁₁ | 170–172 |
| 23* |  | C₂H₅ | C₂H₅ | C₂H₅ | Br, H | iC₃H₇ | 120–121 |
| 24* |  | C₂H₅ | C₂H₅ | C₂H₅ | Br, H | nC₄H₉ | 116–118 |
| 25 |  | CH₃ | 4-CHO-piperazino | C₂H₅ | Br, H | iC₃H₇ | 61–63 |
| 26* |  | CH₃ | CH₃ | allyl | Br, H | iC₃H₇ | 141–142 |
| 27* |  | CH₃ | CH₃ | C₂H₅ | I, H | iC₃H₇ | 149–150 |
| 28 |  | CH₃ | CF₃ | C₂H₅ | Br, H | iC₃H₇ | liquid |
| 29* | 6 | CH₃ | CH₃ | C₂H₅ | Br, H | C₂H₄—OCH₃ | 117–119 |
| 30 | 7 | CH₃ | 4-morpholino | C₂H₅ | I, H | iC₃H₇ | 96–98 |
| 31* | 8 | CH₃ | 2-thiopheno | C₂H₅ | Br, H | iC₃H₇ | 95–97 |
| 32 |  | CH₃ | CH₃ | CH₂CN | Br, H | iC₃H₇ |  |
| 33* | 9 | CH₃ | CH₃ | CH₂cyclopropyl | Br, H | iC₃H₇ | 146–148 |
| 34 | 10 | CH₃ | CH₃ | propargyl | Br, H | iC₃H₇ | MS |
| 35 | 11 | CH₃ | CH₃ | C₂H₅ | I, H | C₂H₄—OCH₃ |  |
| 36 |  | CH₃ | CH₃ | C₂H₅ | I, H | CH₂—OCH₃ |  |
| 37* |  | CH₃ | 4-allyloxy-piperidin-1-yl | C₂H₅ | Br, H | iC₃H₇ |  |
| 38 |  | CH₃ | morpholino | C₂H₅ | I, H | CH₂—OCH₃ |  |
| 39 |  | CH₃ | CH₃ | C₂H₅ | CH₃S, H | CH₂—OCH₃ |  |
| 40 |  | CH₃ | CH₃ | C₂H₅ | (CH₃)₂N, H | CH₂—OCH₃ |  |
| 41 |  | CH₃ | CH₃ | C₂H₅ | CH₃S, H | iC₃H₇ |  |
| 42 |  | CH₃ | CH₃ | C₂H₅ | (CH₃)₂N, H | iC₃H₇ |  |
| 43 |  | CH₃ | CH₃ | C₂H₅ | CH₃S, H | CH₃S |  |
| 44 |  | CH₃ | CH₃ | C₂H₅ | CH₃S, H | CH₂—SCH₃ |  |
| 45 |  | CH₃ | CH₃ | C₂H₅ | Br, Br | iC₃H₇ |  |
| 46 |  | CH₃ | thiomorpholino | C₂H₅ | Br, Br | iC₃H₇ |  |
| 47 |  | CH₃ | CH₃ | C₂H₅ | I, H | I |  |
| 48 |  | CH₃ | morpholino | C₂H₅ | I, H | I |  |
| 49* | 12 | H | CH₃ | C₂H₅ | Br, H | iC₃H₇ | 145–147 |
| 50 | 13 | CH₃ | N(CH₃)CH₂—CH₂OH | C₂H₅ | Br, H | iC₃H₇ | HRMS |
| 51* |  | CH₃ | CH₃ | CH₂CH₃ | CH₃O, CH₃O | CH₃ |  |
| 52* |  | CH₃ | CH₃ | CH₃ | H, H | I | 175–177 |
| 53* |  | CH₃ | CH₃ | CH₃ | I, H | H | 164–166 |
| 54* |  | CH₃ | CH₃ | CH₃ | CF₃, H | H |  |
| 55* |  | CH₃ | CH₃ | CH₂CH₃ | Br, H | C₂H₄—OCH₂CH₃ | 127–129 |
| 56 | 14 | CH₃ | thiomorpholino-S-oxide | C₂H₅ | I, H | iC₃H₇ | 52–55 |
| 57* | 15 | CH₃ | CH₃ | C₂H₅ | Br, H | O—iC₃H₇ | MS |
| 58 | 16 | CH₃ | C(═O)-4-morpholino | C₂H₅ | Br, H | iC₃H₇ | 145 |

TABLE 1-continued

[Structure: pyrimidine with R¹ and R³ at 4,6-positions, connected via N(R⁴) to a phenyl ring bearing X' (ortho), X (ortho), and R⁵ (para)]

| Ex. | Synth. Ex. | R¹ | R³ | R⁴ | X, X' | R⁵ | mp, °C |
|---|---|---|---|---|---|---|---|
| 59 | 17 | $CH_3$ | $CH_2$-4-morpholino | $C_2H_5$ | Br, H | $iC_3H_7$ | liquid |
| 60 | | $CH_3$ | C(=O)-1-piperidinyl | $C_2H_5$ | Br, H | $iC_3H_7$ | 107–108 |
| 61 | 18 | $CH_3$ | C(=O)$OCH_3$ | $C_2H_5$ | Br, H | $iC_3H_7$ | 81–82 |
| 62 | | $CH_3$ | C(=O)NH-cyclohexyl | $C_2H_5$ | Br, H | $iC_3H_7$ | 115 |
| 63 | 19 | $CH_3$ | C(=O)-4-methyl)-1-piperazinyl | $C_2H_5$ | Br, H | $iC_3H_7$ | 81–82 |
| 64 | 20 | $CH_3$ | $CH_3$ | $C_2H_5$ | Br, H | $CH_2$—$CH_2OH$ | 58–60 |
| 65* | 21 | $CH_3$ | $CH_3$ | $CH_3$ | $OCH_3$, H | $CH_3$ | |
| 66* | | $CH_3$ | $CH_3$ | $CH_3$ | H, H | $iC_3H_7$ | |
| 67 | | $CF_3$ | $CH_3$ | $C_2H_5$ | Br, H | $iC_3H_7$ | |
| 68* | | $CH_3$ | $CH_3$ | $CH_3$ | H, H | I | 175–177 |
| 69* | | $CH_3$ | $CH_3$ | $CH_3$ | $CF_3$, H | H | |
| 70* | | $CH_3$ | $CH_3$ | $CH_2CN$ | Br, H | $iC_3H_7$ | |
| 71* | | $CH_3$ | $CH_3$ | $CH_3$ | Br, H | H | |
| 72* | | $CH_3$ | (2-methoxymethyl)-1-pyrrolyl | $CH_3$ | Br, H | H | |
| 73 | 22 | $CH_3$ | 4-thiomorpholino | $C_2H_5$ | I, H | $iC_3H_7$ | 51–53 |
| 73* | 22 | $CH_3$ | 4-thiomorpholino | $C_2H_5$ | I, H | $iC_3H_7$ | 234–236 |
| 74 | | $CH_3$ | 4-hydroxy-1-piperidinyl | $C_2H_5$ | Br, H | $iC_3H_7$ | 61–63 |
| 138 | 24 | $CH_3$ | $CH_2OH$ | $CH_3$ | Br, H | $iC_3H_7$ | oil, MS |
| 139 | 25 | $CH_3$ | $CH_2OCH_3$ | $CH_3$ | Br, H | $iC_3H_7$ | oil, MS |
| 140 | 26 | $CH_3$ | $SCH_3$ | $C_2H_5$ | Br, H | $iC_3H_7$ | oil, MS |
| 141 | | $CH_3$ | $CH_3$ | $C_2H_5$ | $CH_3O$, Cl | $CH_3O$ | 99–102 |
| 142 | | $CH_3$ | [CH₃NH-(CH₂)₄-NH- group] | $C_2H_5$ | Br, H | $iC_3H_7$ | 78–81 |
| 143* | | $CH_3$ | [imidazol-4-yl-ethyl-NH- group] | $C_2H_5$ | Br, H | $iC_3H_7$ | 131–135 |
| 144* | | $CH_3$ | [morpholinoethyl-NH- group] | $C_2H_5$ | Br, H | $iC_3H_7$ | 98–102 |
| 145 | | $CH_3$ | $CH_3$ | H | $CH_3O$, Cl | $CH_3O$ | 170–173 |
| 146* | | $CH_3$ | $NHNH_2$ | $C_2H_5$ | Br, H | $iC_3H_7$ | 117–121 |
| 147 | | $CH_3$ | [—O—CH₂-(tetrahydrofuran-2-yl)] | $C_2H_5$ | Br, H | $iC_3H_7$ | oil, MS |
| 148 | | $CH_3$ | [—O—CH₂-(tetrahydrothiophen-2-yl)] | $C_2H_5$ | Br, H | $iC_3H_7$ | oil, MS |

TABLE 1-continued

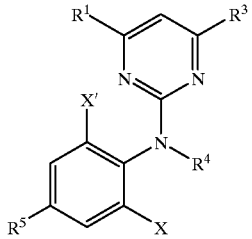

| Ex. | Synth. Ex. | R¹ | R³ | R⁴ | X, X' | R⁵ | mp, ° C. |
|---|---|---|---|---|---|---|---|
| 149 | | CH₃ | OCH₂Ph | C₂H₅ | Br, H | iC₃H₇ | oil, MS |
| 150 | | CH₃ | O(CH₂)₃SCH₃ | C₂H₅ | Br, H | iC₃H₇ | oil, MS |
| 152 | | CH₃ | 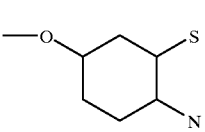 | C₂H₅ | Br, H | iC₃H₇ | oil, MS |
| 153 | | CH₃ | 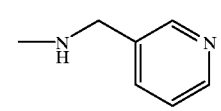 | C₂H₅ | Br, H | iC₃H₇ | oil, MS |
| 154 | | CH₃ | Cl | C₂H₅ | Br, H | iC₃H₇ | oil, MS |
| 155 | | CH₃ | NH₂ | C₂H₅ | Br, H | iC₃H₇ | oil, MS |
| 156 | | CH₃ | O(CH₂)₃SO₂CH₃ | C₂H₅ | Br, H | iC₃H₇ | oil, MS |
| 157 | | CH₃ | 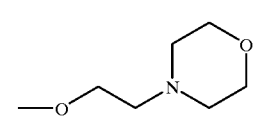 | C₂H₅ | Br, H | iC₃H₇ | oil, MS |
| 158 | | CH₃ | 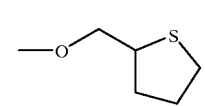 | C₂H₅ | Br, H | iC₃H₇ | oil, MS |
| 159 | 27 | CH₃ | SO₂CH₃ | C₂H₅ | Br, H | iC₃H₇ | oil, MS |
| 160 | 28 | CH₃ | SOCH₃ | C₂H₅ | Br, H | iC₃H₇ | oil, MS |
| 161* | | CH₃ | O(CH₂)₂N(CH₃)₂ | C₂H₅ | Br, H | iC₃H₇ | 143–146 |
| 162 | | CH₃ | O(CH₂)₃SOCH₃ | C₂H₅ | Br, H | iC₃H₇ | oil, MS |
| 163 | | CH₃ | NH(CH₂)₂N(CH₃)₂ | C₂H₅ | Br, H | iC₃H₇ | oil, MS |
| 164 | | CH₃ | NH(CH₂)₄NH₂ | C₂H₅ | Br, H | iC₃H₇ | oil, MS |
| 165 | 31 | CH₃ | morpholino | allyl | I, H | iC₃H₇ | 109–112 |
| 166 | 34 | CH₃ | thiomorpholino | H | Br, Br | iC₃H₇ | 194–195 |
| 167 | 32 | CH₃ | Cl | C₂H₅ | I, H | iC₃H₇ | liquid |
| 168 | 35 | CH₃ | CH₃ | C₂H₅ | SCH₃, H | iC₃H₇ | 64–66 |
| 169 | 37 | CH₃ | CH₃ | C₂H₅ | S(O)CH₃, H | iC₃H₇ | 144–146 |
| 170* | 36 | CH₃ | CH₃ | C₂H₅ | SCH₃, H | iC₃H₇ | 141–142 |
| 171 | 38 | CH₃ | thiazolidino | C₂H₅ | I, H | iC₃H₇ | liquid |
| 172 | 39 | CH₃ | CH₃ | C₂H₅ | I, H | CH₃OCH₂ | liquid |
| 173* | 40 | CH₃ | CH₃ | C₃H₆ | S—, H | iC₃H₇ | 157–159 |
| 174 | 41 | CH₃ | CH₃ | C₂H₅ | S(O)₂CH₃, H | iC₃H₇ | 174–176 |
| 175* | 42 | CH₃ | CH₃ | C₂H₅ | SC₂H₅, H | iC₃H₇ | 128–130 |
| 176 | 43 | CH₃ | CH₃ | C₂H₅ | SC₂H₅, H | CH₃CNO—CH₃ | 77–78 |
| 177 | 33 | CH₃ | N-methyl prolinol | C₂H₅ | SCH₃, H | iC₃H₇ | 101–103 |
| 178 | 44 | CH₃ | CH₃ | C₂H₅ | SCH₃, H | CH₃CNO—CH₃ | 106–108 |
| 179 | 45 | CH₃ | CH₃ | C₂H₅ | S(O)₂CH₃, H | CH₃CNO—CH₃ | 151–154 |
| 180 | 46 | CH₃ | CH₃ | C₂H₅ | SCH₃, H | Br | 91–93 |
| 181 | 47 | CH₃ | CH₃ | iC₃H₇ | SCH₃, H | C₂H₅ | 85–87 |
| 182* | 48 | CH₃ | CH₃ | C₂H₅ | SCH₃, H | C₂H₅ | 140–141 |
| 183 | 49 | CH₃ | CH₃ | C₂H₅ | SCH₃, H | CH₃NCO—CH₃ | 158–160 |
| 184 | 50 | CH₃ | CH₃ | C₂H₅ | SCH₃, H | CO₂C₂H₅ | 99–100 |
| 185 | 51 | CH₃ | CH₃ | C₂H₅ | SCH₃, H | OCH₃ | 128–130 |
| 186 | 52 | CH₃ | CH₃ | C₂H₅ | SCH₃, H | CN | 99–100 |

TABLE 1-continued

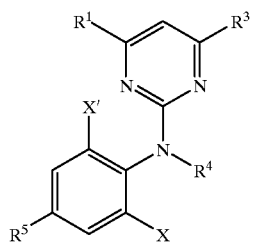

| Ex. | Synth. Ex. | R¹ | R³ | R⁴ | X, X' | R⁵ | mp, °C. |
|---|---|---|---|---|---|---|---|
| 187 | 53 | CH₃ | CH₃ | C₂H₅ | SCH₃, H | COCH₃ | 125–126 |
| 188 | 54 | CH₃ | CH₃ | C₂H₅ | SCH₃, H | COC₂H₅ | 139–141 |
| 189 | 55 | CH₃ | CH₃ | C₂H₅ | SCH₃, H | CH(OCH₃)CH₃ | liquid |
| 190 | 56 | CH₃ | CH₃ | C₂H₅ | SCH₃, H | NHCH₃ | 141–142 |
| 191 | 57 | CH₃ | CH₃ | C₂H₅ | SCH₃, H | N(CH₃)₂ | 119–120 |
| 192 | | CH₃ | pyrrolidino | C₂H₅ | Br, H | iC₃H₇ | 106–107 |
| 193 | | CH₃ | pyrrolidino | CH₃ | Br, H | iC₃H₇ | 119–120 |
| 194 | | C₂H₅ | piperidino | CH₃ | Br, H | iC₃H₇ | 211–212 |
| 195 | | CH₃ | piperidino | CH₃ | Br, H | iC₃H₇ | 186–187 |
| 196 | | CH₃ | CH₃ | C₃H₇ | Br, H | iC₃H₇ | 150–151 |
| 197 | | CH₃ | CH₃ | C₄H₉ | Br, H | iC₃H₇ | 159–160 |
| 198 | | CH₃ | CH₃ | N,N-diethylacetamidino | Br, H | iC₃H₇ | 101–102 |
| 199 | | CH₃ | CH₃ | N,N-diethylaminoethyl | Br, H | iC₃H₇ | 65–66 |
| 200 | | CH₃ | CH₃ | N,N-dimethylaminoethyl | Br, H | iC₃H₇ | 118–120 |
| 201 | | CH₃ | CH₃ | Et | Br, H | OEt | HRMS |
| 202 | | CH₃ | CH₃ | Et | Br, OMe | OMe | 113–115 |
| 203 | | CH₃ | CH₃ | H | Br, OMe | OMe | 177–179 |
| 204 | | CH₃ | CH₃ | H | Br, H | OMe | 118–119 |
| 205 | | CH₃ | CH₃ | Allyl | Br, OMe | OMe | 88–90 |
| 206 | | CH₃ | CH₃ | Et | Br, H | OMe | HRMS |
| 207 | | CH₃ | CH₂OCH₃ | Et | I, H | iC₃H₇ | HRMS |
| 208 | | CH₃ | CH₂O(4-methoxyphenyl) | Et | Br, H | iC₃H₇ | HRMS |
| 209 | | CH₃ | CH₂OPh | Et | Br, H | iC₃H₇ | HRMS |
| 210 | | CH₃ | CH₂O(2-pyridyl) | Et | Br, H | iC₃H₇ | HRMS |
| 211 | | CH₃ | CH₂OCH₂(4-methyl benzoate) | Et | Br, H | iC₃H₇ | HRMS |
| 212 | | CH₃ | CH₂OCH₂(3,4,5-trimethoxyphenyl) | Et | Br, H | iC₃H₇ | HRMS |
| 213 | | CH₃ | CH₂O(2-pyrimidinyl) | Et | Br, H | iC₃H₇ | HRMS |
| 214 | | CH₃ | CH₂O(3,4,5-trimethoxyphenyl) | Et | Br, H | iC₃H₇ | HRMS |
| 215 | | CH₃ | CH₂O(3-(N,N-dimethyl)anilino) | Et | Br, H | iC₃H₇ | HRMS |
| 216 | | CH₃ | CH₂OCH₂(3-pyridyl) | Et | Br, H | iC₃H₇ | HRMS |
| 217 | | CH₃ | CH₂O(4-methyl benzoate) | Et | Br, H | iC₃H₇ | 136–139 |
| 218 | | CH₃ | CH₂O(4-(1-imidazole)phenyl) | Et | Br, H | iC₃H₇ | HRMS |
| 219 | | CH₃ | CH₂OCH₂(4-pyridyl) | Et | Br, H | iC₃H₇ | HRMS |
| 220 | | CH₃ | CH₂OCH₃ | Et | Br, H | iC₃H₇ | |
| 221 | | CH₃ | CH₂OCH₂(2-furyl) | Et | Br, H | iC₃H₇ | HRMS |
| 222 | 58 | CH₃ | CHO | Et | Br, H | iC₃H₇ | HRMS |
| 223 | | CH₃ | CH₃ | H | Br, Br | OMe | 175–177 |
| 224 | 63 | CH₃ | CH₃ | Et | Br, Br | OEt | 107–108 |
| 225 | 59 | CH₃ | CH₂OCH₂CH₂OH | Et | Br, H | iC₃H₇ | HRMS |
| 226 | | CH₃ | CH₃ | Et | Br, Br | OMe | 101–103 |
| 227 | | CH₃ | CH₂OCH₂CH₂OCH₃ | Et | Br, H | iC₃H₇ | HRMS |
| 228 | | CH₃ | CH₃ | H | Br, Br | OEt | 165–167 |
| 229 | | CH₃ | CH₂OCH₂CO(4-morpholino) | Et | Br, H | iC₃H₇ | HRMS |
| 230 | 60 | CH₃ | CH₃ | Et | Br, OH | OMe | 157–160 |
| 231 | | CH₃ | CH₂OCH₂CH₂(4-morpholino) | Et | Br, H | iC₃H₇ | HRMS |
| 268 | | CH₃ | (4-(2-methoxyphenyl)piperazinyl)carbonyl | Et | Br, H | iC₃H₇ | 57–60 |
| 269 | | CH₃ | (1,2,3,4-tetrahydroquinolinyl)carbonyl | Et | Br, H | iC₃H₇ | 143–145 |
| 270 | | CH₃ | (2-furylmethyl)aminocarbonyl | Et | Br, H | iC₃H₇ | 87–88 |
| 271 | | CH₃ | MeNHCO | Et | Br, H | iC₃H₇ | oil, MS |
| 272 | | CH₃ | (4-(pyrazinyl)piperazino)carbonyl | Et | Br, H | iC₃H₇ | 51–53 |
| 273 | | CH₃ | (4-(2-pyrimidyl)piperazino)carbonyl | Et | Br, H | iC₃H₇ | 114–116 |
| 274 | | CH₃ | (4-(2-pyridyl)piperazino)carbonyl | Et | Br, H | iC₃H₇ | oil, MS |
| 275 | | CH₃ | (4-(2-methoxyphenyl)piperazinyl)methyl, HCl salt | Et | Br, H | iC₃H₇ | 102–104 |
| 276 | | CH₃ | N-(2-furylmethyl)-N-methylaminomethyl | Et | Br, H | iC₃H₇ | oil, MS |
| 277 | | CH₃ | (1,2,3,4-tetrahydroquinolinyl)methyl, HCl salt | Et | Br, H | iC₃H₇ | 88–90 |
| 278 | | CH₃ | (4-pyrazinylpiperazino)methyl | Et | Br, H | iC₃H₇ | oil, MS |
| 279 | | CH₃ | dimethylaminomethyl | Et | Br, H | iC₃H₇ | oil, MS |
| 280 | | CH₃ | (4-(2-pyridyl)piperazino)methyl, HCl salt | Et | Br, H | iC₃H₇ | 117–119 |
| 281 | | CH₃ | (4-(2-pyrimidyl)piperazino)methyl, HCl salt | Et | Br, H | iC₃H₇ | 125–127 |
| 282 | | CH₃ | Me₂NCO | Et | Br, H | iC₃H₇ | 80–82 |
| 283 | | CH₃ | 3-indoylcarbonyl, HCL salt | Et | Br, H | iC₃H₇ | 105–107 |
| 284 | | CH₃ | 3-pyridylcarbonyl | Et | Br, H | iC₃H₇ | 165–167 |
| 285 | | CH₃ | 3-phenylcarbonyl | Et | Br, H | iC₃H₇ | oil, MS |

TABLE 1-continued

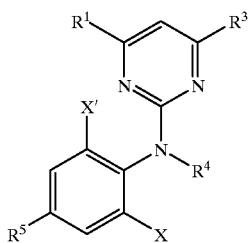

| Ex. | Synth. Ex. | R¹ | R³ | R⁴ | X, X' | R⁵ | mp, ° C. |
|---|---|---|---|---|---|---|---|
| 286 | | CH₃ | 3-pyrazolylcarbonyl | Et | Br, H | iC₃H₇ | 171–173 |
| 287 | | CH₃ | 4-methoxyphenylcarbonyl | Et | Br, H | iC₃H₇ | 104–106 |
| 288 | | CH₃ | 2-furylcarbonyl | Et | Br, H | iC₃H₇ | 136–138 |
| 289 | | CH₃ | bis(4-methoxyphenyl)hydroxymethyl | Et | Br, H | iC₃H₇ | 63–65 |
| 290 | | CH₃ | bis(2-furyl)hydroxymethyl | Et | Br, H | iC₃H₇ | 97–99 |
| 291 | | CH₃ | (2-furyl)hydroxymethyl | Et | Br, H | iC₃H₇ | oil, MS |
| 292 | | CH₃ | (4-methoxyphenyl)hydroxymethyl | Et | Br, H | iC₃H₇ | oil, MS |
| 293 | | CH₃ | diphenylhydroxymethyl | Et | Br, H | iC₃H₇ | 56–58 |
| 294 | | CH₃ | bis(4-pyridyl)hydroxymethyl | Et | Br, H | iC₃H₇ | 68–70 |
| 295 | | CH₃ | (1-hydroxy-1-methyl)ethyl | Et | Br, H | iC₃H₇ | oil, MS |
| 296 | | CH₃ | 1-hydroxyethyl | Et | Br, H | iC₃H₇ | oil, MS |

*Hydrochloride salt

TABLE 2

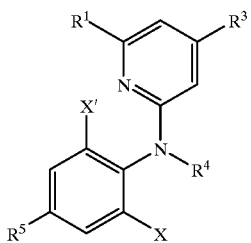

| Ex. | R¹ | R³ | R⁴ | X, X' | R⁵ | mp, ° C. |
|---|---|---|---|---|---|---|
| 75 | CH₃ | CH₃ | CH₃ | Br, H | CH₃ | |
| 76 | CH₃ | CH₃ | CH₃ | CH₃O, H | CH₃O | |
| 77 | CH₃ | CH₃ | allyl | Br, H | H | |
| 78* | CH₃ | CH₃ | CH₃ | Br, H | iC₃H₇ | 178–179 |
| 79 | CH₃ | CH₃ | C₂H₅ | Br, H | H | |
| 80 | CH₃ | morpholino | CH₃ | Br, H | CH₃ | |
| 81 | CH₃ | CH₃ | CH₂H₅ | CH₃O, H | CH₃O | |
| 82 | CH₃ | CH₃ | CH₃ | Br, H | Br | |
| 83 | CH₃ | CH₃ | CH₃ | Br, H | CH₂H₅ | |
| 84 | CH₃ | CH₃ | C₂H₅ | Br, H | tC₄H₉ | |
| 85 | CH₃ | CH₃ | CH₃ | Br, H | tC₄H₉ | |
| 86 | CH₃ | CH₃ | CH₃ | Br, H | CF₃ | |
| 87 | CH₃ | CH₃ | CH₂H₅ | Br, H | CF₃ | |
| 88 | CH₃ | CH₃ | CH₃ | CH₃O, CH₃O | CH₃O | |
| 89 | CH₃ | CH₃ | C₂H₅ | CH₃O, CH₃O | CH₃O | |
| 90 | CH₃ | morpholino | C₂H₅ | Br, H | iC₃H₇ | |
| 91 | CH₃ | morpholino | allyl | Br, H | iC₃H₇ | |
| 92 | CH₃ | CH₃ | allyl | Br, H | nC₄H₉ | |
| 93 | CH₃ | CH₃ | C₂H₅ | Br, H | nC₄H₉ | |
| 94 | CH₃ | CH₃ | nC₃H₇ | Br, H | nC₄H₉ | |
| 95* | CH₃ | CH₃ | C₂H₅ | Br, H | iC₃H₇ | 194–196 |
| 96 | CH₃ | CH₃ | C₂H₅ | Br, H | cC₆H₁₁ | |
| 97 | C₂H₅ | CH₃ | C₂H₅ | Br, H | iC₃H₇ | |
| 98 | C₂H₅ | C₂H₅ | C₂H₅ | Br, H | nC₄H₉ | |
| 99 | CH₃ | 4-CHO-piperazino | C₂H₅ | Br, H | iC₃H₇ | |
| 100 | CH₃ | CH₃ | allyl | Br, H | iC₃H₇ | |
| 101 | CH₃ | CH₃ | C₂H₅ | I, H | iC₃H₇ | |
| 102 | CH₃ | CF₃ | C₂H₅ | Br, H | iC₃H₇ | |

TABLE 2-continued

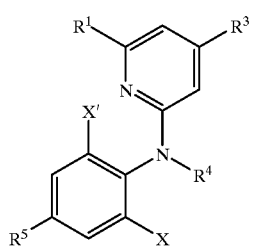

| Ex. | R¹ | R³ | R⁴ | X, X' | R⁵ | mp, °C. |
|---|---|---|---|---|---|---|
| 103 | $CH_3$ | $CH_3$ | $C_2H_5$ | Br, H | $C_2H_4$—$OCH_3$ | |
| 104 | $CH_3$ | morpholino | $C_2H_5$ | I, H | $iC_3H_7$ | |
| 105 | $CH_3$ | 2-thiopheno | $C_2H_5$ | Br, H | $iC_3H_7$ | |
| 106 | $CH_3$ | $CH_3$ | $CH_2CN$ | Br, H | $iC_3H_7$ | |
| 107 | $CH_3$ | $CH_3$ | $CH_2$cyclopropyl | Br, H | $iC_3H_7$ | |
| 108 | $CH_3$ | $CH_3$ | propargyl | Br, H | $iC_3H_7$ | |
| 109 | $CH_3$ | $CH_3$ | $C_2H_5$ | I, H | $C_2H_4$—$OCH_3$ | |
| 110 | $CH_3$ | $CH_3$ | $C_2H_5$ | I, H | $CH_2$—$OCH_3$ | |
| 111 | $CH_3$ | morpholino | $C_2H_5$ | I, H | $C_2H_4$—$OCH_3$ | |
| 112 | $CH_3$ | morpholino | $C_2H_5$ | I, H | $CH_2$—$OCH_3$ | |
| 113 | $CH_3$ | $CH_3$ | $C_2H_5$ | $CH_3S$, H | $CH_2$—$OCH_3$ | |
| 114 | $CH_3$ | $CH_3$ | $C_2H_5$ | $(CH_3)_2N$, H | $CH_2$—$OCH_3$ | |
| 115 | $CH_3$ | $CH_3$ | $C_2H_5$ | $CH_3S$, H | $iC_3H_7$ | |
| 116 | $CH_3$ | $CH_3$ | $C_2H_5$ | $(CH_3)_2N$, H | $iC_3H_7$ | |
| 117 | $CH_3$ | $CH_3$ | $C_2H_5$ | $CH_3S$, H | $CH_3S$ | |
| 118 | $CH_3$ | $CH_3$ | $C_2H_5$ | $CH_3S$, H | $CH_2$—$SCH_3$ | |
| 119 | $CH_3$ | $CH_3$ | $C_2H_5$ | Br, Br | $iC_3H_7$ | |
| 120 | $CH_3$ | thiomorpholino | $C_2H_5$ | Br, Br | $iC_3H_7$ | |
| 121 | $CH_3$ | $CH_3$ | $C_2H_5$ | I, H | I | |
| 122 | $CH_3$ | morpholino | $C_2H_5$ | I, H | I | |
| 123 | H | $CH_3$ | $C_2H_5$ | Br, H | $iC_3H_7$ | |
| 124 | $CH_3$ | $N(CH_3)CH_2$—$CH_2OH$ | $C_2H_5$ | Br, H | $iC_3H_7$ | |
| 125 | $CH_3$ | $CH_3$ | $CH_2CH_3$ | $CH_3O$, $CH_3O$ | $CH_3$ | |
| 126 | $CH_3$ | $CH_3$ | $CH_3$ | H, H | I | |
| 127 | $CH_3$ | $CH_3$ | $CH_3$ | I, H | H | |
| 128 | $CH_3$ | $CH_3$ | $CH_3$ | $CF_3$, H | H | |
| 129* | H | H | $CH_2CH_3$ | Br, H | $iC_3H_7$ | |

*Hydrochloride salt

TABLE 3

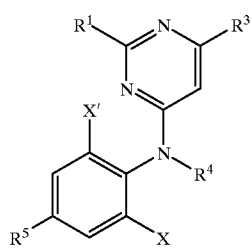

| Ex. | R¹ | R³ | R⁴ | X, X' | R⁵ | mp, °C. |
|---|---|---|---|---|---|---|
| 130* | $CH_3O$ | $CH_3O$ | $CH_2CH_3$ | Br, H | $iC_3H_7$ | 104–106 |

*Hydrochloride salt

TABLE 4

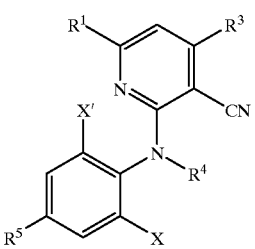

| Ex. | R¹ | R³ | R⁴ | X, X' | R⁵ | mp, °C. |
|---|---|---|---|---|---|---|
| 131* | $CH_3$ | $CH_3$ | H | Br, H | $iC_3H_7$ | 124–125 |

*Hydrochloride salt

TABLE 5

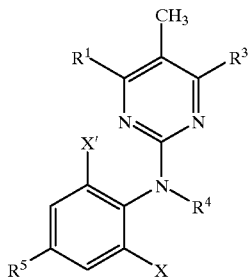

| Ex. | R¹ | R³ | R⁴ | X, X' | R⁵ | mp, °C. |
|---|---|---|---|---|---|---|
| 132* | CH₃ | CH₃ | CH₂CH₃ | Br, H | iC₃H₇ | 144–145 |

*Hydrochloride salt

TABLE 7

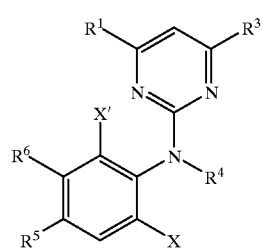

| Synth. Ex. | Ex. | R¹ | R² | R⁴ | X', X | R⁵ | R⁶ | mp, °C. |
|---|---|---|---|---|---|---|---|---|
| 251 | 62 | CH₃ | CH₃ | Et | Br, OMe | OMe | Br | 133–138 |

TABLE 6

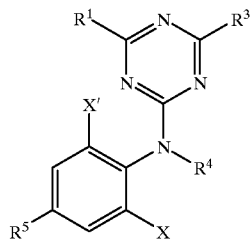

| Ex. | Synth. Ex. | R¹ | R³ | R⁴ | X, X' | R⁵ | mp, °C. |
|---|---|---|---|---|---|---|---|
| 133 | | CH₃ | CH₃ | Et | Br, H | iC₃H₇ | oil, MS |
| 134 | 23 | CH₃ | morpholino | Et | Br, H | iC₃H₇ | oil, MS |
| 134* | | CH₃ | morpholino | Et | Br, H | iC₃H₇ | 59–63 |
| 135 | | CH₃ | thiomorpholino | Et | I, H | iC₃H₇ | oil, MS |
| 136 | | CH₃ | morpholino | Et | I, H | iC₃H₇ | oil, MS |
| 137 | | CH₃ | piperidinyl | Et | I, H | iC₃H₇ | oil, MS |
| 232 | | CH₃ | N'N-diethyl | Et | Br, H | iC₃H₇ | oil, MS |
| 233 | | Cl | Cl | Et | Br, H | iC₃H₇ | oil, MS |
| 234 | | OCH₃ | OCH₃ | Et | Br, H | iC₃H₇ | oil, MS |
| 235 | | Cl | Cl | Et | I, H | iC₃H₇ | oil, MS |
| 236 | | CH₃ | imidazolino | Et | Br, H | iC₃H₇ | >200 |
| 237 | | CH₃ | morpholino | Et | Br, CH₃O | CH₃O | 90–95 |
| 238 | | CH₃ | N(CH₃)₂ | Et | Br, CH₃O | CH₃O | 65–58 |
| 239 | | CH₃ | morpholino | Et | CH₃O, CH₃O | CH₃O | oil, MS |
| 240 | | CH₃ | N(CH₃)₂ | Et | Br, H | iC₃H₇ | 72–75 |
| 241 | | CH₃ | thiazolidino | Et | Br, H | iC₃H₇ | 70–72 |
| 242* | 29 | CH₃ | benzyloxy | Et | Br, H | iC₃H₇ | 89–90 |
| 243 | | CH₃ | phenyloxy | Et | Br, H | iC₃H₇ | 140–142 |
| 244 | | CH₃ | 4-ethylcarboxypiperizine | Et | Br, CH₃O | CH₃O | 65–70 |
| 245 | | CH₃ | 4-carboxypiperizine | Et | Br, CH₃O | CH₃O | 95–100 |
| 246 | | CH₃ | HC(CO₂Et)₂ | Et | Br, H | iC₃H₇ | oil, MS |
| 247 | | CH₃ | PhCHCN | Et | Br, CH₃O | CH₃O | 50–52 |
| 248 | | CH₃ | morpholino | iC₃H₇O | Br, CH₃, O | CH₃O | oil, MS |
| 249* | 30 | Cl | Cl | Et | I, H | CH(CH₃)₂OH | oil, MS |
| 250 | | CH₃ | Cl | C₂H₅ | Br, H | iC₃H₇ | oil, MS |

*Hydrochloride salt

TABLE 7-continued

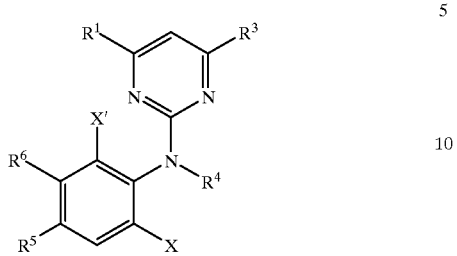

| Ex. | Synth. Ex. | R¹ | R² | R⁴ | X', X | R⁵ | R⁶ | mp, °C. |
|---|---|---|---|---|---|---|---|---|
| 252 |  | CH₃ | CH₃ | H | H, OMe | OMe | Br | 179–181 |
| 253 | 61 | CH₃ | CH₃ | Et | H, OMe | OMe | Br | 143–145 |

TABLE 8

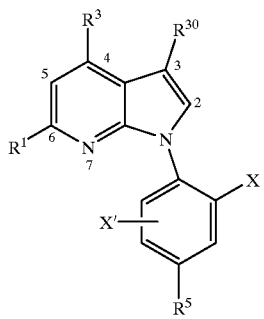

| Ex. | Synth. Ex. | R¹ | R³ | R³⁰ | X | X' | R⁵ | mp, °C. |
|---|---|---|---|---|---|---|---|---|
| 254 | 64 | CH₃ | CH₃ | CN | Br | H | i-Pr | 105.8 |
| 313 |  | CH₃ | CH₃ | CN | I | H | i-Pr |  |
| 314 |  | CH₃ | CH₃ | CN | Br | 6-CH₃ | i-Pr |  |
| 315 |  | CH₃ | —morpholino | CN | I | 6-CH₃ | i-Pr |  |
| 316 |  | CH₃ | Cl | CN | I | H | 1-methoxy ethyl |  |
| 317 |  | CH₃ | Ph | CN | I | H | 1-methoxy ethyl |  |
| 318 |  | CH₃ | CH₃ | CN | Cl | H | 1-methoxy ethyl |  |
| 319 |  | CH₃ | CH₃ | CN | I | H | 1-methoxy ethyl |  |
| 320 |  | CH₃ | CH₃ | CN | Br | H | 1-methoxy ethyl |  |
| 321 |  | CH₃ | —morpholino | CN | I | CH₃ | OCH₃ |  |
| 255 | 74 | CH₃ | Cl | CN | Br | H | i-Pr | 179.2 |
| 256 | 66 | CH₃ | Ph | CN | Br | H | i-Pr | oil |
| 322 |  | CH₃ | Ph | CN | —SCH₃ | H | i-Pr |  |
| 323 |  | CH₃ | CH₃ | H | Cl | OCH₃ | i-Pr |  |
| 257 | 65 | CH₃ | CH₃ | H | Br | H | i-Pr | MS 343.08 |
| 324 |  | CH₃ | CH₃ | H | —SCH₃ | H | i-Pr |  |
| 258 | 68 | CH₃ | CH₃ | CN | Br | OCH₃ | OCH₃ | MS 388.0 |
| 325 |  | CH₃ | —morpholino | H | I | 6-OCH₃ | i-Pr |  |
| 259 | 75 | CH₃ | Cl | H | Br | H | i-Pr | MS 363.0 |
| 326 |  | CH₃ | Ph | H | I | H | 1-methoxy ethyl |  |
| 260 | 69 | CH₃ | CH₃ | H | Br | OCH₃ | OCH₃ | MS 360.9 |
| 327 |  | CH₃ | CH₃ | H | I | H | 1-methoxy ethyl |  |
| 328 |  | CH₃ | CH₃ | H | Br | H | 1-methoxy ethyl |  |
| 329 |  | CH₃ | —morpholino | H | I | 6-CH₃ | OCH₃ |  |
| 330 |  | CH₃ | Cl | H | I | 6-CH₃ | i-Pr |  |
| 261 | 67 | CH₃ | Ph | H | Br | H | i-Pr | MS 405.1 |
| 331 |  | CH₃ | —NHEt | H | Br | H | i-Pr |  |
| 332 |  | CH₃ | —NHC(=O)CH₃ | H | Br | H | i-Pr |  |

TABLE 8-continued

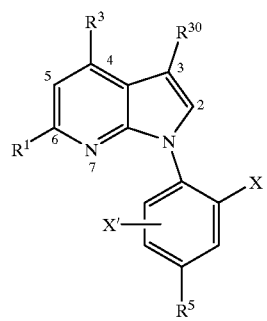

| Ex. | Synth. Ex. | $R^1$ | $R^3$ | $R^{30}$ | X | X' | $R^5$ | mp, °C. |
|---|---|---|---|---|---|---|---|---|
| 333 | | $CH_3$ | $OCH_3$ | H | Br | H | i-Pr | |
| 334 | | $CH_3$ | —$OCH_2Ph$ | H | Br | H | i-Pr | |
| 335 | | $CH_3$ | $CH_2OPh$ | H | Br | H | i-Pr | |
| 336 | | $CH_3$ | 2-thiophenylmethoxy | H | Br | H | i-Pr | |
| 337 | | $CH_3$ | —OCH(OH)Ph | H | Br | H | i-Pr | |
| 338 | | $CH_3$ | —n-propoxy | H | Br | H | i-Pr | |
| 339 | | $CH_3$ | —C(=O)N(Me)$_2$ | H | Br | H | i-Pr | |
| 340 | | $CH_3$ | —NHCH$_2$Ph | H | Br | H | i-Pr | |
| 262 | 70 | Cl | $CH_3$ | CN | Br | H | i-Pr | 123.8 |
| 341 | | N—Me$_2$ | $CH_3$ | H | Br | H | i-Pr | |
| 342 | | $CH_3$ | —CH$_2$OCH$_3$ | H | Br | H | i-Pr | |
| 263 | 71 | Cl | $CH_3$ | H | Br | H | i-Pr | MS 363.0 |
| 343 | | $CH_3$ | $CH_3$ | Et | Br | H | i-Pr | |
| 344 | | $CH_3$ | $CH_3$ | —CCH | Br | H | i-Pr | |

TABLE 9

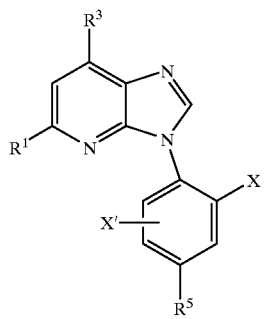

| Ex. | $R^1$ | $R^3$ | X | X' | $R^5$ |
|---|---|---|---|---|---|
| 345 | $CH_3$ | $CH_3$ | Br | H | i-Pr |
| 346 | $CH_3$ | $CH_3$ | I | H | i-Pr |
| 347 | $CH_3$ | $CH_3$ | Br | 6-$OCH_3$ | $OCH_3$ |
| 348 | $CH_3$ | —morpholino | I | 6-$CH_3$ | i-Pr |
| 349 | $CH_3$ | Ph | Br | H | i-Pr |
| 350 | $CH_3$ | $CH_3$ | SMe | H | i-Pr |

TABLE 10

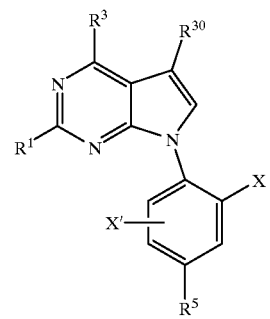

| Ex. | $R^1$ | $R^3$ | $R^{30}$ | X | X' | $R^5$ |
|---|---|---|---|---|---|---|
| 351 | $CH_3$ | $CH_3$ | H | Br | H | i-Pr |
| 352 | $CH_3$ | $CH_3$ | H | I | H | i-Pr |
| 353 | $CH_3$ | —morpholino | CN | Br | H | i-Pr |
| 354 | $CH_3$ | Ph | CN | Br | H | i-Pr |
| 355 | $CH_3$ | $CH_3$ | H | SMe | H | i-Pr |

TABLE 11

| Ex. | Synth. Ex. | R⁵ | R⁴ | R³ | X | Z | K | L | ms (m + H) |
|---|---|---|---|---|---|---|---|---|---|
| 264* | | CH₃ | ethyl | CH₃ | Br | CH | CH | CH | 321 |
| 265* | | OCH₃ | ethyl | CH₃ | Br | CH | CH | N | 337 |
| 266* | | OCH₃ | ethyl | CH₃ | H | CH | CH | N | 259 |
| 267* | | OCH₃ | ethyl | CH₃ | Br | N | CH | N | 409 |
| 356 | | i-Pr | ethyl | CH₃ | Br | N | N | N | |
| 357 | | i-Pr | allyl | CH₃ | Br | N | N | N | |
| 358 | | i-Pr | allyl | CH₃ | Br | CH | N | N | |
| 359 | | i-Pr | ethyl | CH₃ | Br | CH | N | N | |
| 360 | | i-Pr | ethyl | morpholino | Br | N | N | N | |
| 361 | | i-Pr | allyl | morpholino | Br | N | N | N | |
| 362 | | i-Pr | allyl | morpholino | Br | CH | N | N | |
| 363 | | i-Pr | ethyl | morphoiino | Br | CH | N | N | |
| 364 | | OCH₃ | ethyl | CH₃ | Br | N | N | N | |
| 365 | | OCH₃ | allyl | CH₃ | Br | N | N | N | |
| 366 | | OCH₃ | allyl | CH₃ | Br | CH | N | N | |
| 367 | | OCH₃ | ethyl | CH₃ | Br | CH | N | N | |
| 368 | | OCH₃ | ethyl | morpholino | Br | N | N | N | |
| 369 | | OCH₃ | allyl | morpholino | Br | N | N | N | |
| 370 | | OCH₃ | allyl | morpholino | Br | CH | N | N | |
| 371 | | OCH₃ | ethyl | morpholino | Br | CH | N | N | |
| 372 | | OCH₃ | ethyl | CH₃ | OCH₃ | N | N | N | |
| 373 | | OCH₃ | allyl | CH₃ | OCH₃ | N | N | N | |
| 374 | 105 | OCH₃ | allyl | CH₃ | OCH₃ | CH | N | N | 290 |
| 375 | | OCH₃ | ethyl | CH₃ | OCH₃ | CH | N | N | |
| 376 | | OCH₃ | ethyl | morpholino | OCH₃ | N | N | N | |
| 377 | | OCH₃ | allyl | morpholino | OCH₃ | N | N | N | |
| 378 | | OCH₃ | allyl | morpholino | OCH₃ | CH | N | N | |
| 379 | | OCH₃ | ethyl | morpholino | OCH₃ | CH | N | N | |
| 380 | | OCH₃ | ethyl | OCH₃ | OCH₃ | N | N | N | |
| 381 | | OCH₃ | allyl | OCH₃ | OCH₃ | N | N | N | |
| 382 | | OCH₃ | allyl | OCH₃ | OCH₃ | CH | N | N | |
| 383 | | OCH₃ | ethyl | OCH₃ | OCH₃ | CH | N | N | |
| 384 | | OCH₃ | ethyl | OCH₂CH₃ | OCH₃ | N | N | N | |
| 385 | | OCH₃ | allyl | OCH₂CH₃ | OCH₃ | N | N | N | |
| 386 | | OCH₃ | allyl | OCH₂CH₃ | OCH₃ | CH | N | N | |
| 387 | | OCH₃ | ethyl | OCH₂CH₃ | OCH₃ | CH | N | N | |

*Hydrochloride salt

TABLE 12

| Ex. | R¹ | R³ | R³⁰ | X | X' | R⁵ |
|---|---|---|---|---|---|---|
| 388 | CH₃ | CH₃ | CN | Br | H | i-Pr |
| 389 | CH₃ | CH₃ | CN | I | H | i-Pr |
| 390 | CH₃ | CH₃ | CN | Br | 6-CH₃ | i-Pr |

TABLE 12-continued

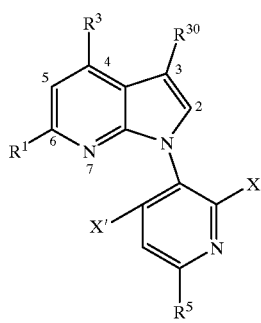

| Ex. | R¹ | R³ | R³⁰ | X | X' | R⁵ |
|---|---|---|---|---|---|---|
| 391 | CH₃ | -morpholino | CN | I | 6-CH₃ | i-Pr |
| 392 | CH₃ | Cl | CN | I | H | 1-methoxy ethyl |
| 393 | CH₃ | Ph | CN | I | H | 1-methoxy ethyl |
| 394 | CH₃ | CH₃ | CN | Cl | H | 1-methoxy ethyl |
| 395 | CH₃ | CH₃ | CN | I | H | 1-methoxy ethyl |
| 396 | CH₃ | CH₃ | CN | Br | H | 1-methoxy ethyl |
| 397 | CH₃ | -morpholino | CN | I | CH₃ | OCH₃ |
| 398 | CH₃ | Cl | CN | Br | H | i-Pr |
| 399 | CH₃ | Ph | CN | Br | H | i-Pr |
| 400 | CH₃ | Ph | CN | —SCH₃ | H | i-Pr |
| 401 | CH₃ | CH₃ | H | Cl | OCH₃ | i-Pr |
| 402 | CH₃ | CH₃ | H | Br | H | i-Pr |
| 403 | CH₃ | CH₃ | H | —SCH₃ | H | i-Pr |
| 404 | CH₃ | CH₃ | CN | Br | OCH₃ | OCH₃ |
| 405 | CH₃ | -morpholino | H | I | 6-OCH₃ | i-Pr |
| 406 | CH₃ | Cl | H | Br | H | i-Pr |
| 407 | CH₃ | Ph | H | I | H | 1-methoxy ethyl |
| 408 | CH₃ | CH₃ | H | Br | OCH₃ | OCH₃ |
| 409 | CH₃ | CH₃ | H | I | H | 1-methoxy ethyl |
| 410 | CH₃ | CH₃ | H | Br | H | 1-methoxy ethyl |
| 411 | CH₃ | -morpholino | H | I | 6-CH₃ | OCH₃ |
| 412 | CH₃ | Cl | H | I | 6-CH₃ | i-Pr |
| 413 | CH₃ | Ph | H | Br | H | i-Pr |
| 414 | CH₃ | —NHEt | H | Br | H | i-Pr |
| 415 | CH₃ | —NHC(=O)CH₃ | H | Br | H | i-Pr |
| 416 | CH₃ | OCH₃ | H | Br | H | i-Pr |
| 417 | CH₃ | —OCH₂Ph | H | Br | H | i-Pr |
| 418 | CH₃ | CH₂OPh | H | Br | H | i-Pr |
| 419 | CH₃ | 2-thiophenyl methoxy | H | Br | H | i-Pr |
| 420 | CH₃ | OCH(OH)Ph | H | Br | H | i-Pr |
| 421 | CH₃ | —n-propoxy | H | Br | H | i-Pr |
| 422 | CH₃ | —C(=O)N(Me) | H | Br | H | i-Pr |
| 423 | CH₃ | —NHCH₂Ph | H | Br | H | i-Pr |
| 424 | CH₃ | CH₃ | CN | Br | H | i-Pr |
| 425 | N—Me₂ | CH₃ | H | Br | H | i-Pr |
| 426 | CH₃ | —CH₂OCH₃ | H | Br | H | i-Pr |
| 427 | Cl | CH₃ | H | Br | H | i-Pr |
| 428 | CH₃ | CH₃ | Et | Br | H | i-Pr |
| 429 | CH₃ | CH₃ | —CCH | Br | H | i-Pr |

TABLE 13

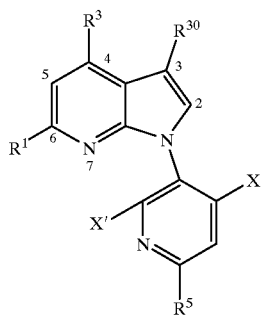

| Ex. | R¹ | R³ | R³⁰ | X | X' | R⁵ |
|---|---|---|---|---|---|---|
| 430 | CH₃ | CH₃ | CN | Br | H | i-Pr |
| 431 | CH₃ | CH₃ | CN | I | H | i-Pr |
| 432 | CH₃ | CH₃ | CN | Br | 6-CH₃ | i-Pr |
| 433 | CH₃ | -morpholino | CN | I | 6-CH₃ | i-Pr |
| 434 | CH₃ | Cl | CN | I | H | 1-methoxy ethyl |
| 435 | CH₃ | Ph | CN | I | H | 1-methoxy ethyl |
| 436 | CH₃ | CH₃ | CN | Cl | H | 1-methoxy ethyl |
| 437 | CH₃ | CH₃ | CN | I | H | 1-methoxy ethyl |
| 438 | CH₃ | CH₃ | CN | Br | H | 1-methoxy ethyl |
| 439 | CH₃ | -morpholino | CN | I | CH₃ | OCH₃ |
| 440 | CH₃ | Cl | CN | Br | H | i-Pr |
| 441 | CH₃ | Ph | CN | Br | H | i-Pr |
| 442 | CH₃ | Ph | CN | —SCH₃ | H | i-Pr |
| 443 | CH₃ | CH₃ | H | Cl | OCH₃ | i-Pr |
| 444 | CH₃ | CH₃ | H | Br | H | i-Pr |
| 445 | CH₃ | CH₃ | H | —SCH₃ | H | i-Pr |
| 446 | CH₃ | CH₃ | CN | Br | OCH₃ | OCH₃ |
| 447 | CH₃ | -morpholino | H | I | 6-OCH₃ | i-Pr |
| 448 | CH₃ | Cl | H | Br | H | i-Pr |
| 449 | CH₃ | Ph | H | I | H | 1-methoxy ethyl |
| 450 | CH₃ | CH₃ | H | Br | OCH₃ | OCH₃ |
| 451 | CH₃ | CH₃ | H | I | H | 1-methoxy ethyl |
| 452 | CH₃ | CH₃ | H | Br | H | 1-methoxy ethyl |
| 453 | CH₃ | -morpholino | H | I | 6-CH₃ | OCH₃ |
| 454 | CH₃ | Cl | H | I | 6-CH₃ | i-Pr |
| 455 | CH₃ | Ph | H | Br | H | i-Pr |
| 456 | CH₃ | —NHEt | H | Br | H | i-Pr |
| 457 | CH₃ | —NHC(=O)CH₃ | H | Br | H | i-Pr |
| 458 | CH₃ | OCH₃ | H | Br | H | i-Pr |
| 459 | CH₃ | —OCH₂Ph | H | Br | H | i-Pr |
| 460 | CH₃ | CH₂OPh | H | Br | H | i-Pr |
| 461 | CH₃ | 2-thiophenyl methoxy | H | Br | H | i-Pr |
| 462 | CH₃ | OCH(OH)Ph | H | Br | H | i-Pr |
| 463 | CH₃ | —n-propoxy | H | Br | H | i-Pr |
| 464 | CH₃ | —C(=O)N(Me)₂ | H | Br | H | i-Pr |
| 465 | CH₃ | —NHCH₂Ph | H | Br | H | i-Pr |
| 466 | Cl | CH₃ | CN | Br | H | i-Pr |
| 467 | N—Me₂ | CH₃ | H | Br | H | i-Pr |
| 468 | CH₃ | —CH₂OCH₃ | H | Br | H | i-Pr |
| 469 | Cl | CH₃ | H | Br | H | i-Pr |
| 470 | CH₃ | CH₃ | Et | Br | H | i-Pr |
| 471 | CH₃ | CH₃ | —CCH | Br | H | i-Pr |

TABLE 14

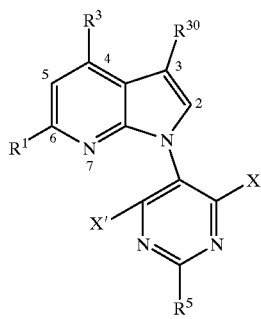

| Ex. | R¹ | R³ | R³⁰ | X | X' | R⁵ |
|---|---|---|---|---|---|---|
| 472 | CH₃ | CH₃ | CN | Br | H | i-Pr |
| 473 | CH₃ | CH₃ | CN | I | H | i-Pr |
| 474 | CH₃ | CH₃ | CN | Br | 6-CH₃ | i-Pr |
| 475 | CH₃ | -morpholino | CN | I | 6-CH₃ | i-Pr |
| 476 | CH₃ | Cl | CN | I | H | 1-methoxy ethyl |
| 477 | CH₃ | Ph | CN | I | H | 1-methoxy ethyl |
| 478 | CH₃ | CH₃ | CN | Cl | H | 1-methoxy ethyl |
| 479 | CH₃ | CH₃ | CN | I | H | 1-methoxy ethyl |
| 480 | CH₃ | CH₃ | CN | Br | H | 1-methoxy ethyl |
| 481 | CH₃ | -morpholino | CN | I | CH₃ | OCH₃ |
| 482 | CH₃ | Cl | CN | Br | H | i-Pr |
| 483 | CH₃ | Ph | CN | Br | H | i-Pr |
| 484 | CH₃ | Ph | CN | —SCH₃ | H | i-Pr |
| 485 | CH₃ | CH₃ | H | Cl | OCH₃ | i-Pr |
| 486 | CH₃ | CH₃ | H | Br | H | i-Pr |
| 487 | CH₃ | CH₃ | H | —SCH₃ | H | i-Pr |
| 488 | CH₃ | CH₃ | CN | Br | OCH₃ | OCH₃ |
| 489 | CH₃ | -morpholino | H | I | 6-OCH₃ | i-Pr |
| 490 | CH₃ | Cl | H | Br | H | i-Pr |
| 491 | CH₃ | Ph | H | I | H | 1-methoxy ethyl |
| 492 | CH₃ | CH₃ | H | Br | OCH₃ | OCH₃ |
| 493 | CH₃ | CH₃ | H | I | H | 1-methoxy ethyl |
| 494 | CH₃ | CH₃ | H | Br | H | 1-methoxy ethyl |
| 495 | CH₃ | -morpholino | H | I | 6-CH₃ | OCH₃ |
| 496 | CH₃ | Cl | H | I | 6-CH₃ | i-Pr |
| 497 | CH₃ | Ph | H | Br | H | i-Pr |
| 498 | CH₃ | —NHEt | H | Br | H | i-Pr |
| 499 | CH₃ | —NHC(=O)CH₃ | H | Br | H | i-Pr |
| 500 | CH₃ | OCH₃ | H | Br | H | i-Pr |
| 501 | CH₃ | —OCH₂Ph | H | Br | H | i-Pr |
| 502 | CH₃ | CH₂OPh | H | Br | H | i-Pr |
| 503 | CH₃ | 2-thiophenyl methoxy | H | Br | H | i-Pr |
| 504 | CH₃ | OCH(OH)Ph | H | Br | H | i-Pr |
| 505 | CH₃ | -n-propoxy | H | Br | H | i-Pr |
| 506 | CH₃ | C(=O)N(Me)₂ | H | Br | H | i-Pr |
| 507 | CH₃ | —NHCH₂Ph | H | Br | H | i-Pr |
| 508 | Cl | CH₃ | CN | Br | H | i-Pr |
| 509 | N—Me₂ | CH₃ | H | Br | H | i-Pr |
| 510 | CH₃ | —CH₂OCH₃ | H | Br | H | i-Pr |
| 511 | Cl | CH₃ | H | Br | H | i-Pr |
| 512 | CH₃ | CH₃ | Et | Br | H | i-Pr |
| 513 | CH₃ | CH₃ | —CCH | Br | H | i-Pr |

TABLE 15

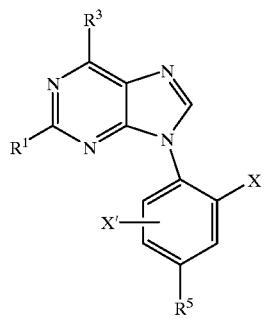

| Ex. | Synth. Ex. | R¹ | R³ | X | X' | R⁵ | Mp (° C.) |
|---|---|---|---|---|---|---|---|
| 514 | | CH₃ | CH₃ | Br | H | i-Pr | |
| 515 | | CH₃ | CH₃ | I | H | i-Pr | |
| 516 | | CH₃ | CH₃ | Br | 6-OCH₃ | OCH₃ | |
| 517 | | CH₃ | -morpholino | I | 6-CH₃ | i-Pr | |
| 518 | | CH₃ | Ph | Br | H | i-Pr | |
| 519 | | CH₃ | CH₃ | SMe | H | i-Pr | |
| 520 | 101 | CH₃ | Cl | Br | H | i-Pr | 49–52 |
| 521 | | CH₃ | CH₃ | Br | H | i-Pr | |
| 522 | | CH₃ | CH₃ | I | H | i-Pr | |
| 523 | | CH₃ | CH₃ | Br | 6-OCH₃ | OCH₃ | |
| 524 | | CH₃ | -morpholino | I | 6-CH₃ | i-Pr | |
| 525 | | CH₃ | Ph | Br | H | i-Pr | |
| 526 | | CH₃ | CH₃ | SMe | H | i-Pr | |
| 527 | 102 | CH₃ | -morpholino | Br | H | i-Pr | 132–135 |
| 528 | | CH₂CH₃ | CH₃ | Br | H | i-Pr | |
| 529 | | CH₂CH₃ | CH₃ | I | H | i-Pr | |
| 530 | | CH₂CH₃ | CH₃ | Br | 6-OCH₃ | OCH₃ | |
| 531 | | CH₂CH₃ | -morpholino | I | 6-CH₃ | i-Pr | |
| 532 | | CH₂CH₃ | Ph | Br | H | i-Pr | |
| 533 | | CH₂CH₃ | CH₃ | SMe | H | i-Pr | |
| 534 | | CH₂CH₃ | Cl | Br | H | i-Pr | |
| 535 | | CH₂CH₃ | CH | Br | H | i-Pr | |
| 536 | | CH₂CH₃ | CH₃ | I | H | i-Pr | |
| 537 | | CH₂CH₃ | CH₃ | Br | 6-OCH₃ | OCH₃ | |
| 538 | | CH₂CH₃ | -morpholino | I | 6-CH₃ | i-Pr | |
| 539 | | CH₂CH₃ | Ph | Br | H | i-Pr | |
| 540 | | CH₂CH₃ | CH₃ | SMe | H | i-Pr | |
| 541 | | CH₂CH₃ | -morpholino | Br | H | i-Pr | |

TABLE 16

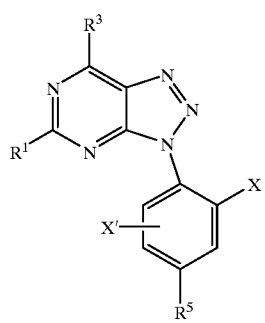

| Ex. | Synth. Ex. | R¹ | R³ | X | X' | R⁵ | Mp (° C.) |
|---|---|---|---|---|---|---|---|
| 542 | | CH₃ | CH₃ | Br | H | i-Pr | |
| 543 | | CH₃ | CH₃ | I | H | i-Pr | |
| 544 | | CH₃ | CH₃ | Br | 6-OCH₃ | OCH₃ | |
| 545 | | CH₃ | -morpholino | I | 6-CH₃ | i-Pr | |

TABLE 16-continued

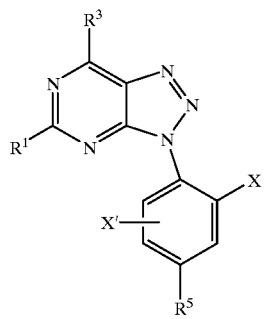

| Ex. | Synth. Ex. | R¹ | R³ | X | X' | R⁵ | Mp (° C.) |
|---|---|---|---|---|---|---|---|
| 546 | | CH₃ | Ph | Br | H | i-Pr | |
| 547 | | CH₃ | CH₃ | SMe | H | i-Pr | |
| 548 | 103 | CH₃ | Cl | Br | H | i-Pr | MS 368 |
| 549 | | CH₃ | CH₃ | Br | H | i-Pr | |
| 550 | | CH₃ | CH₃ | I | H | i-Pr | |
| 551 | | CH₃ | CH₃ | Br | 6-OCH₃ | OCH₃ | |
| 552 | | CH₃ | -morpholino | I | 6-CH₃ | i-Pr | |
| 553 | | CH₃ | Ph | Br | H | i-Pr | |
| 554 | | CH₃ | CH₃ | SMe | H | i-Pr | |
| 555 | 104 | CH₃ | -morpholino | Br | H | i-Pr | 145–148 |
| 556 | | CH₂CH₃ | CH₃ | Br | H | i-Pr | |
| 557 | | CH₂CH₃ | CH₃ | I | H | i-Pr | |
| 558 | | CH₂CH₃ | CH₃ | Br | 6-OCH₃ | OCH₃ | |
| 559 | | CH₂CH₃ | -morpholino | I | 6-CH₃ | i-Pr | |
| 560 | | CH₂CH₃ | Ph | Br | H | i-Pr | |
| 561 | | CH₂CH₃ | CH₃ | SMe | H | i-Pr | |
| 562 | | CH₂CH₃ | Cl | Br | H | i-Pr | |
| 563 | | CH₂CH₃ | CH₃ | Br | H | i-Pr | |
| 564 | | CH₂CH₃ | CH₃ | I | H | i-Pr | |
| 565 | | CH₂CH₃ | CH₃ | Br | 6-OCH₃ | OCH₃ | |
| 566 | | CH₂CH₃ | -morpholino | I | 6-CH₃ | i-Pr | |
| 567 | | CH₂CH₃ | Ph | Br | H | i-Pr | |
| 568 | | CH₂CH₃ | CH₃ | SMe | H | i-Pr | |
| 569 | | CH₂CH₃ | -morpholino | Br | H | i-Pr | |

Utility

In vitro Receptor Binding Assay

Tissue Preparation: Male Sprague Dawley rats (180–200 g) were sacrificed by decapitation and the cortex was dissected on ice, frozen whole in liquid nitrogen and stored at −70° C. until use. On the day of assay, frozen tissue was weighed and homogenized in 20 volumes of ice cold buffer containing 50 mM Tris, 10 mM MgCl₂, 2 mM EGTA, pH 7.0 at 22° C. using a Polytron (Brinkmann Instruments, Westbury, N.Y.; setting 6) for 20 s. The homogenate was centrifuged at 48,000× g for 10 min at 4° C. The supernatant was discarded, and the pellet was re-homogenized in the same volume of buffer and centrifuged at 48,000× g for 10 min at 4° C. The resulting pellet was resuspended in the above buffer to a final concentration of 20–40 mg original wet weight/mL and used in the assays described below. Protein determinations were performed according to the method of Lowry (Lowry et al., *J. Biol. Chem.* 193:265 (1951)) using bovine serum albumin as a standard.

CRF Receptor Binding: Receptor binding assays were carried out essentially as described by E. B. De Souza, *J. Neurosci.* 7:88 (1987).

Saturation Curve Analysis

In saturation studies, 100 μl $^{125}$I-ovine CRF (50 pM–10 nM final concentration), 100 μl of assay buffer (with or without 1 mM r/hCRF final concentration, to define the non-specific binding) and 100 μl of membrane suspension (as described above) were added in sequence to 1.5 mL polypropylene microfuge tubes for a final volume of 300 μl. All assays were carried out at equilibrium for 2 h at 22° C. as described by E. B. De Souza, *J. Neurosci.* 7:88 (1987). The reaction was terminated by centrifugation of the tubes in a Beckman microfuge for 5 min at 12,000× g. Aliquots of the supernatant were collected to determine the "free" radioligand concentration. The remaining supernatant was aspirated and the pellets washed gently with ice-cold PBS plus 0.01% Triton X-100; centrifuged again and monitored for bound radioactivity as described above. Data from saturation curves were analyzed using the non-linear least-squares curve-fitting program LIGAND (P. J. Munson and D. Rodbard, *Anal. Biochem.* 107:220 (1980)). This program has the distinct advantage of fitting the raw experimental data on an untransformed coordinate system where errors are most likely to be normally distributed and uncorrelated with the independent variable. LIGAND does not expect the non-specific binding to be defined arbitrarily by the investigator, rather it estimates the value as an independent variable from the entire data set. The parameters for the affinity constants ($K_D$) and receptor densities ($B_{max}$) are also provided along with statistics on the general "fit" of the estimated parameters to the raw data. This program also offers the versatility of analyzing multiple curves simultaneously, thus improving the reliability of the data analysis and hence the validity of the final estimated parameters for any saturation experiment.

Competition Curve Analysis

In competition studies, 100 µl [$^{125}$I] ovine CRF ([$^{125}$I] CRF; final concentration 200–300 pM) was incubated along with 100 µl buffer (in the presence of varying concentrations of competing ligands, typically 1 pM to 10 mM) and 100 µl of membrane suspension as prepared above to give a total reaction volume of 300 µl. The reaction was initiated by the addition of membrane homogenates, allowed to proceed to equilibrium for 2 h at 22° C. and was terminated by centrifugation (12,000× g) in a Beckman microfuge to separate the bound radioligand from free radioligand. The resulting pellets were surface washed twice by centrifugation with 1 mL of ice-cold phosphate buffered saline and 0.01% Triton X-100; the supernatants discarded and the pellets monitored for radioactivity at approximately 80% efficiency. The level of non-specific binding was defined in the presence of 1 mM unlabeled rat/humanCRF (r/hCRF). Data from competition curves were analyzed by the program LIGAND. For each competition curve, estimates of the affinity of the radiolabeled ligand for the CRF receptor ([$^{125}$I]CRF) were obtained in independent saturation experiments and these estimates were constrained during the analysis of the apparent inhibitory constants ($K_i$) for the peptides tested. Routinely, the data were analyzed using a one- and two-site model comparing the "goodness of fit" between the models in order to accurately determine the $K_i$. Statistical analyses provided by LIGAND allowed the determination of whether a single-site or multiple-site model should be used. For both peptides (α-helical CRF$_{9-41}$ and d-PheCRF$_{12-41}$), as well as for all compounds of this invention, data were fit significantly to a single site model; a two-site model was either not possible or did not significantly improve the fit of the estimated parameters to the data.

The results of the in vitro testing of the compounds of the invention are shown in Table 17. It was found, for a representative number of compounds of the invention, that either form of the compound, be it the free-base or the hydrochloride salt, produced essentially the same inhibition value in the binding assay.

A compound is considered to be active if it has an $K_i$ value of less than about 10000 nM for the inhibition of CRF. In Table 17; the $K_i$ values were determined using the assay conditions described above. The $K_i$ values are indicated as follows: +++=<500 nM; ++=501–2000 nM; +=2001–10000 nM.

TABLE 17

| Example No. | Synth. Ex. | Inhibition $K_i$ (nM) |
| --- | --- | --- |
| 1 | 1 | ++ |
| 2 |   | ++ |
| 3 |   | ++ |
| 4 | 2 | +++ |
| 5 |   | ++ |
| 6 |   | ++ |
| 7 |   | +++ |
| 8 |   | +++ |
| 9 | 3 | +++ |
| 10 |   | +++ |
| 11 |   | +++ |
| 12 |   | ++ |
| 13 |   | +++ |
| 14 |   | ++ |
| 15 |   | +++ |
| 16 | 4 | +++ |
| 17 |   | +++ |
| 18 |   | +++ |
| 19 |   | +++ |
| 20 |   | +++ |
| 21 | 5 | +++ |
| 22 |   | ++ |
| 23 |   | +++ |
| 24 |   | ++ |
| 25 |   | +++ |
| 26 |   | +++ |
| 27 |   | +++ |
| 28 |   | +++ |
| 29 | 6 | +++ |
| 30 | 7 | +++ |
| 31 | 8 | +++ |
| 32 |   | +++ |
| 33 | 9 | +++ |
| 34 | 10 | +++ |
| 37 |   | +++ |
| 49 | 12 | + |
| 50 | 13 | +++ |
| 51 |   | ++ |
| 52 |   | + |
| 53 |   | + |
| 54 |   | + |
| 55 |   | +++ |
| 56 | 14 | +++ |
| 57 | 15 | +++ |
| 58 | 16 | +++ |
| 59 | 17 | +++ |
| 60 |   | ++ |
| 61 | 18 | +++ |
| 62 |   | ++ |
| 63 | 19 | + |
| 64 | 20 | + |
| 65 | 21 | + |
| 66 |   | + |
| 68 |   | + |
| 69 |   | + |
| 70 |   | + |
| 71 |   | + |
| 72 |   | + |
| 73 | 22 | +++ |
| 74 |   | +++ |
| 78 |   | + |
| 95 |   | ++ |
| 130 |   | ++ |
| 131 |   | + |
| 132 |   | + |
| 133 |   | ++ |
| 134 | 23 | +++ |
| 135 |   | +++ |
| 136 |   | +++ |
| 137 |   | +++ |
| 138 | 24 | +++ |
| 139 | 25 | +++ |
| 140 | 26 | +++ |
| 141 |   | +++ |
| 142 |   | +++ |
| 143 |   | +++ |
| 145 |   | + |
| 146 |   | + |
| 147 |   | +++ |
| 148 |   | +++ |
| 149 |   | +++ |
| 150 |   | +++ |
| 151 |   | +++ |
| 152 |   | +++ |
| 153 |   | +++ |
| 154 |   | +++ |
| 155 |   | +++ |
| 156 |   | +++ |
| 157 |   | +++ |
| 158 |   | +++ |
| 159 | 27 | +++ |
| 160 | 28 | +++ |
| 161 |   | +++ |
| 162 |   | +++ |

TABLE 17-continued

| Example No. | Synth. Ex. | Inhibition $K_i$ (nM) |
|---|---|---|
| 163 |  | ++ |
| 165 | 31 | +++ |
| 166 | 34 | +++ |
| 167 | 32 | +++ |
| 168 | 35 | +++ |
| 170 | 36 | +++ |
| 171 | 38 | +++ |
| 172 | 39 | +++ |
| 173 | 40 | ++ |
| 174 | 41 | +++ |
| 175 | 42 | ++ |
| 176 | 43 | +++ |
| 177 | 33 | ++ |
| 178 | 44 | +++ |
| 179 | 45 | + |
| 180 | 46 | +++ |
| 181 | 47 | +++ |
| 182 | 48 | +++ |
| 183 | 49 | + |
| 184 |  | ++ |
| 185 | 51 | +++ |
| 186 | 52 | +++ |
| 187 |  | +++ |
| 188 | 54 | +++ |
| 189 | 55 | +++ |
| 190 | 56 | +++ |
| 191 | 57 | +++ |
| 192 |  | +++ |
| 193 |  | +++ |
| 194 |  | +++ |
| 195 |  | +++ |
| 196 |  | +++ |
| 197 |  | ++ |
| 201 |  | +++ |
| 203 |  | ++ |
| 204 |  | + |
| 205 |  | +++ |
| 206 |  | +++ |
| 207 |  | +++ |
| 208 |  | +++ |
| 209 |  | +++ |
| 210 |  | ++ |
| 211 |  | +++ |
| 212 |  | +++ |
| 213 |  | +++ |
| 214 |  | ++ |
| 215 |  | ++ |
| 216 |  | +++ |
| 217 |  | +++ |
| 218 |  | +++ |
| 219 |  | +++ |
| 221 |  | +++ |
| 222 | 58 | ++ |
| 223 |  | ++ |
| 224 | 63 | +++ |
| 225 | 59 | +++ |
| 226 |  | +++ |
| 227 |  | +++ |
| 228 |  | ++ |
| 229 |  | + |
| 230 | 60 | +++ |
| 231 |  | + |
| 232 |  | +++ |
| 236 |  | +++ |
| 237 |  | +++ |
| 238 |  | +++ |
| 239 |  | +++ |
| 240 |  | +++ |
| 241 |  | +++ |
| 242 | 29 | ++ |
| 243 |  | + |
| 244 |  | + |
| 245 |  | + |
| 246 |  | +++ |
| 247 |  | +++ |
| 248 |  | +++ |
| 249 | 30 | + |
| 250 |  | ++ |
| 251 | 62 | ++ |
| 252 |  | + |
| 253 | 61 | ++ |
| 254 | 64 | +++ |
| 255 | 74 | ++ |
| 256 | 66 | +++ |
| 257 | 65 | +++ |
| 258 | 68 | +++ |
| 259 | 75 | +++ |
| 260 | 69 | +++ |
| 261 | 67 | +++ |
| 262 | 70 | +++ |
| 263 | 71 | +++ |
| 264 | 77 | + |
| 265 | 76 | +++ |
| 266 | 78 | ++ |
| 267 | 79 | +++ |
| 268 |  | +++ |
| 269 |  | +++ |
| 270 |  | + |
| 271 |  | +++ |
| 272 |  | + |
| 273 |  | ++ |
| 274 |  | + |
| 275 |  | +++ |
| 276 |  | +++ |
| 277 |  | +++ |
| 278 |  | +++ |
| 279 |  | +++ |
| 280 |  | +++ |
| 281 |  | +++ |
| 282 |  | +++ |
| 283 |  | + |
| 284 |  | +++ |
| 285 |  | +++ |
| 286 |  | +++ |
| 287 |  | ++ |
| 288 |  | +++ |
| 289 |  | +++ |
| 290 |  | +++ |
| 291 |  | +++ |
| 292 |  | +++ |
| 293 |  | +++ |
| 294 |  | +++ |
| 295 |  | +++ |
| 296 |  | +++ |
| 297 | 80 | +++ |
| 298 | 82 | +++ |
| 299 | 83 | +++ |
| 300 | 84 | +++ |
| 301 | 85 | +++ |
| 302 | 86 | +++ |
| 303 | 87 | +++ |
| 304 | 88 | +++ |
| 305 | 89 | +++ |
| 307 | 91 | +++ |
| 308 | 92 | +++ |
| 309 | 93 | +++ |
| 310 | 94 | ++ |
| 311 | 95 | +++ |
| 312 | 96 | +++ |

Inhibition of CRF-Stimulated Adenylate Cyclase Activity

Inhibition of CRF-stimulated adenylate cyclase activity was performed as described by G. Battaglia et al., *Synapse* 1:572 (1987). Briefly, assays were carried out at 37° C. for 10 min in 200 mL of buffer containing 100 mM Tris-HCl (pH 7.4 at 37° C.), 10 mM $MgCl_2$, 0.4 mM EGTA, 0.1% BSA, 1 mM isobutylmethylxanthine (IBMX), 250 units/mL phosphocreatine kinase, 5 mM creatine phosphate, 100 mM guanosine 5'-triphosphate, 100 nM oCRF, antagonist peptides (concentration range $10^{-9}$ to $10^{-6m}$) and 0.8 mg original wet weight tissue (approximately 40–60 mg protein). Reactions were initiated by the addition of 1 mM ATP/[$^{32}$P] ATP (approximately 2–4 mCi/tube) and terminated by the addition of 100 mL of 50 mM Tris-HCl, 45 mM ATP and 2% sodium dodecyl sulfate. In order to monitor the recovery of cAMP, 1 µl of [$^3$H]cAMP (approximately 40,000 dpm) was added to each tube prior to separation. The separation of [$^{32}$P]cAMP from [$^{32}$P]ATP was performed by sequential elution over Dowex and alumina columns. Recovery was consistently greater than 80%.

Representative compounds of this invention were found to be active in this assay. $IC_{50} < 10,000$ nanomolar.

In Vivo Biological Assay

The in vivo activity of the compounds of the present invention can be assessed using any one of the biological assays available and accepted within the art. Illustrative of these tests include the Acoustic Startle Assay, the Stair Climbing Test, and the Chronic Administration Assay. These and other models useful for the testing of compounds of the present invention have been outlined in C. W. Berridge and A. J. Dunn *Brain Research Reviews* 15:71 (1990).

Compounds may be tested in any species of rodent or small mammal. Disclosure of the assays herein is not intended to limit the enablement of the invention.

The foregoing tests results demonstrate that compounds of this invention have utility in the treatment of imbalances associated with abnormal levels of corticotropin releasing factor in patients suffering from depression, affective disorders, and/or anxiety. The foregoing tests also demonstrate that compounds of this invention have utility in the treatment of uterine contraction disorders.

Compounds of this invention can be administered to treat said abnormalities by means that produce contact of the active agent with the agent's site of action in the body of a mammal. The compounds can be administered by any conventional means available for use in conjunction with pharmaceuticals either as individual therapeutic agents or in a combination of therapeutic agents. They can be administered alone, but are generally administered with a pharmaceutical carrier selected on the basis of the chosen route of administration and standard pharmaceutical practice.

The dosage administered will vary depending on the use and known factors such as the pharmacodynamic character of the particular agent, and its mode and route of administration; the recipient's age, weight, and health; nature and extent of symptoms; kind of concurrent treatment; frequency of treatment; and desired effect. For use in the treatment of said diseases or conditions, the compounds of this invention can be orally administered daily at a dosage of the active ingredient of 0.002 to 200 mg/kg of body weight. Ordinarily, a dose of 0.01 to 10 mg/kg in divided doses one to four times a day, or in sustained release formulation is effective in obtaining the desired pharmacological effect.

Dosage forms (compositions) suitable for administration contain from about 1 mg to about 100 mg of active ingredient per unit. In these pharmaceutical compositions, the active ingredient will ordinarily be present in an amount of about 0.5 to 95% by weight based on the total weight of the composition.

The active ingredient can be administered orally in solid dosage forms, such as capsules, tablets and powders; or in liquid forms such as elixirs, syrups, and/or suspensions. The compounds of this invention can also be administered parenterally in sterile liquid dose formulations.

Gelatin capsules can be used to contain the active ingredient and a suitable carrier, such as, but not limited to, lactose, starch, magnesium stearate, steric acid, or cellulose derivatives. Similar diluents can be used to make compressed tablets. Both tablets and capsules can be manufactured as sustained release products to provide for continuous release of medication over a period of time. Compressed tablets can be sugar-coated or film-coated to mask any unpleasant taste, or used to protect the active ingredients from the atmosphere, or to allow selective disintegration of the tablet in the gastrointestinal tract.

Liquid dose forms for oral administration can contain coloring or flavoring agents to increase patient acceptance.

In general, water, pharmaceutically acceptable oils, saline, aqueous dextrose (glucose), and related sugar solutions and glycols, such as propylene glycol or polyethylene glycol, are suitable carriers for parenteral solutions. Solutions for parenteral administration preferably contain a water soluble salt of the active ingredient, suitable stabilizing agents, and if necessary, buffer substances. Antioxidizing agents, such as sodium bisulfite, sodium sulfite, or ascorbic acid, either alone or in combination, are suitable stabilizing agents. Also used are citric acid and its salts, and EDTA. In addition, parenteral solutions can contain preservatives such as benzalkonium chloride, methyl- or propyl-paraben, and chlorobutanol.

Suitable pharmaceutical carriers are described in "Remington's Pharmaceutical Sciences", A. Osol, a standard reference in the field.

Useful pharmaceutical dosage-forms for administration of the compounds of this invention can be illustrated as follows:

Capsules

A large number of units in the form of capsules are prepared by filling standard two-piece hard gelatin capsules each with 100 mg of powdered active ingredient, 150 mg lactose, 50 mg cellulose, and 6 mg magnesium stearate.

Soft Gelatin Capsules

A mixture of active ingredient in a digestible oil such as soybean, cottonseed oil, or olive oil is prepared and injected by means of a positive displacement into gelatin to form soft gelatin capsules containing 100 mg of the active ingredient. The capsules are washed and dried.

Tablets

A large number of tablets are prepared by conventional procedures so that the dosage unit is 100 mg active ingredient, 0.2 mg of colloidal silicon dioxide, 5 mg of magnesium stearate, 275 mg of microcrystalline cellulose, 11 mg of starch, and 98.8 mg lactose. Appropriate coatings may be applied to increase palatability or delayed adsorption.

The compounds of this invention may also be used as reagents or standards in the biochemical study of neurological function, dysfunction, and disease.

What is claimed is:
1. A compound of formula (I):

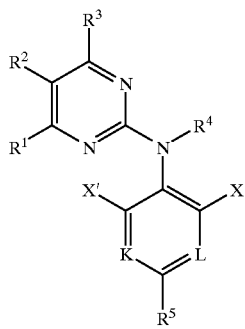

or a pharmaceutically acceptable salt thereof, wherein:

$R^1$ is independently selected, at each occurrence from the group consisting of $C_1$–$C_4$ alkyl, $C_2$–$C_4$ alkenyl, $C_2$–$C_4$ alkynyl, and $C_1$–$C_2$ haloalkyl;

$R^3$ is $C_1$–$C_4$ alkyl, $C_3$–$C_6$ cycloalkyl, $C_1$–$C_2$ haloalkyl, nitro, $NR^6R^7$, $OR^8$, $S(O)_nR^8$, $C(=O)R^9$, $C(=O)NR^6R^7$, $C(=S)NR^6R^7$, —$(CHR^{16})_kNR^6R^7$, $(CH_2)_kOR^8$, $C(=O)NR^{10}CH(R^{11})CO_2R^{12}$, —$C(OH)(R^{25})(R^{25a})$, —$(CH_2)_sS(O)_n$-alkyl, —$(CHR^{16})R^{25}$, —$C(CN)(R^{25})(R^{16})$, —$C(=O)R^{25}$, —$CH(CO_2R^{16})_2$, $NR^{10}C(=O)CH(R^{11})NR^{10}R^{12}$, $NR^{10}CH(R^{11})CO_2R^{12}$;

K and L are each independently CX';

$R^2$ is independently selected at each occurrence from the group consisting of hydrogen, halo, halomethyl, $C_1$–$C_3$ alkyl, and cyano;

$R^4$ is $(CH_2)_mOR^{16}$, $C_1$–$C_4$ alkyl, allyl, propargyl, $(CH_2)_mR^{13}$, or —$(CH_2)_mOC(O)R^{16}$;

X is halogen, $S(O)_2R^8$, $SR^8$, halomethyl, —$(CH_2)_pOR^8$, cyano, —$(CHR^{16})_pNR^{14}R^{15}$, —$C(=O)R^8$, $C_1$–$C_6$ alkyl, $C_4$–$C_{10}$ cycloalkylalkyl, $C_2$–$C_{10}$ alkenyl, $C_2$–$C_{10}$ alkynyl, $C_1$–$C_{10}$ alkoxy, $C_3$–$C_6$ cycloalkyl, nitro, thio-$(C_1$–$C_{10})$-alkyl, —$C(=NOR^{16})$—$C_1$–$C_4$-alkyl, —$C(=NOR^{16})H$, or —$C(=O)NR^{14}R^{15}$ where substitution by $R^{18}$ can occur on any carbon containing substituents;

X' is independently selected at each occurrence from the group consisting of hydrogen, halogen, $S(O)_nR^8$, halomethyl, —$(CHR^{16})_pOR^8$, cyano, —$(CHR^{16})_pNR^{14}R^{15}$, $C(=O)R^8$, $C_1$–$C_6$ alkyl, $C_2$–$C_{10}$ alkenyl, $C_2$–$C_{10}$ alkynyl, $C_1$–$C_{10}$ alkoxy, $C_3$–$C_6$ cycloalkyl, nitro, thio-$(C_1$–$C_{10})$-alkyl, —$C(=NOR^{16})$—$C_1$–$C_4$-alkyl, —$C(=NOR^{16})H$, or —$C(=O)NR^{14}R^{15}$ where substitution by $R^{18}$ can occur on any carbon containing substituents;

$R^5$ is halo, —$C(=NOR^{16})$—$C_1$–$C_4$-alkyl, $C_1$–$C_6$ alkyl, $C_1$–$C_3$ haloalkyl, $C_1$–$C_6$ alkoxy, —$(CHR^{16})_pOR^8$, $(CHR^{16})_pS(O)_nR^8$, —$(CHR^{16})_pNR^{14}R^{15}$, $C_3$–$C_6$ cycloalkyl, $C_2$–$C_{10}$ alkenyl, $C_2$–$C_{10}$ alkynyl, cyano, $C_3$–$C_6$ cycloalkoxy, nitro, amino-$(C_2$–$C_{10})$-alkyl, thio-$(C_2$–$C_{10})$-alkyl, $SO_n(R^8)$, $C(=O)R^8$, —$C(=NOR^{16})H$, or $C(=O)NR^{14}R^{15}$, where substitution by $R^{18}$ can occur on any carbon containing substituents;

$R^6$ and $R^7$ are independently selected at each occurrence from the group consisting of hydrogen, $C_1$–$C_6$ alkyl, $C_3$–$C_{10}$ cycloalkyl, $C_1$–$C_6$ alkoxy, $(C_4$–$C_{12})$-cycloalkylalkyl, —$(CH_2)_kR^{13}$, $(CHR^{16})_pOR^8$, —$(C_1$–$C_6$ alkyl)-aryl, phenyl, heteroaryl, —$S(O)_z$-aryl or —$(C_1$–$C_6$ alkyl)-heteroaryl, wherein the aryl or heteroaryl groups are optionally substituted with 1–3 groups selected from the group consisting of hydrogen, halogen, $C_1$–$C_6$ alkyl, $C_1$–$C_6$ alkoxy, amino, NHC$(=O)(C_1$–$C_6$ alkyl), NH$(C_1$–$C_6$ alkyl), N$(C_1$–$C_6$ alkyl$)_2$, nitro, carboxy, $CO_2(C_1$–$C_6$ alkyl), cyano, $S(O)_z$—$(C_1$–$C_6$ alkyl); or can be taken together to form —$(CH_2)_qA(CH_2)_r$—, optionally substituted with 0–3 $R^{17}$;

A is $CH_2$, O, $NR^{25}$, $C(=O)$, $S(O)_n$, $N(C(=O)R^{17})$, $N(R^{19})$, $C(H)(NR^{14}R^{15})$, $C(H)(OR^{20})$, $C(H)(C(=O)R^{21})$, $N(S(O)_nR^{21})$;

$R^8$ is independently selected at each occurrence from the group consisting of hydrogen; $C_1$–$C_6$ alkyl; —$(C_4$–$C_{12})$ cycloalkylalkyl; $(CH_2)_kR^{22}$; $C_3$–$C_{10}$ cycloalkyl; —$NR^6R^7$; aryl; heteroaryl; —$NR^{16}(CH_2)_nNR^6R^7$; —$(CH_2)_kR^{25}$; and $(CH_2)_k$heteroaryl or $(CH_2)_t$aryl, either of which can be optionally substituted with 1–3 groups selected from the group consisting of hydrogen, halogen, $C_1$–$C_6$ alkyl, $C_1$–$C_6$ alkoxy, amino, NHC$(=O)(C_1$–$C_6$ alkyl), NH$(C_1$–$C_6$ alkyl) N$(C_1$–$C_6$ alkyl$)_2$, nitro, carboxy, $CO_2(C_1$–$C_6$ alkyl), cyano, and $S(O)_z(C_1$–$C_6$-alkyl);

$R^9$ is independently selected at each occurrence from $R^{10}$, hydroxy, $C_1$–$C_4$ alkoxy, $C_3$–$C_6$ cycloalkyl, $C_2$–$C_4$ alkenyl, phenyl substituted with 0–3 $R^{18}$, and —$(C_1$–$C_6$ alkyl)-aryl substituted with 0–3 $R^{18}$;

$R^{10}$, $R^{16}$, $R^{23}$, and $R^{24}$ are independently selected at each occurrence from hydrogen or $C_1$–$C_4$ alkyl;

$R^{11}$ is $C_1$–$C_4$ alkyl substituted with 0–3 groups chosen from the following: keto, amino, sulfhydryl, hydroxyl, guanidinyl, p-hydroxyphenyl, imidazolyl, phenyl, indolyl, and indolinyl, or, when taken together with an adjacent $R^{10}$, are $(CH_2)_r$;

$R^{12}$ is hydrogen or an appropriate amine protecting group for nitrogen or an appropriate carboxylic acid protecting group for carboxyl;

$R^{13}$ is independently selected at each occurrence from the group consisting of CN, $OR^{19}$, $SR^{19}$, and $C_3$–$C_6$ cycloalkyl;

$R^{14}$ and $R^{15}$ are independently selected at each occurrence from the group consisting of hydrogen, $C_4$–$C_{10}$ cycloalkyl-alkyl, and $R^{19}$;

$R^{17}$ is independently selected at each occurrence from the group consisting of $R^{10}$, $C_1$–$C_4$ alkoxy, halo, $OR^{23}$, $SR^{23}$, $NR^{23}R^{24}$, and $(C_1$–$C_6)$ alkyl $(C_1$–$C_4)$ alkoxy;

$R^{18}$ is independently selected at each occurrence from the group consisting of $R^{10}$, hydroxy, halogen, $C_1$–$C_2$ haloalkyl, $C_1$–$C_4$ alkoxy, $C(=O)R^{24}$, and cyano;

$R^{19}$ is independently selected at each occurrence from the group consisting of $C_1$–$C_6$ alkyl, $C_3$–$C_6$ cycloalkyl, $(CH_2)_wR^{22}$, and phenyl substituted with 0–3 $R^{18}$;

$R^{20}$ is independently selected at each occurrence from the group consisting of $R^{10}$, $C(=O)R^{31}$, and $C_2$–$C_4$ alkenyl;

$R^{21}$ is independently selected at each occurrence from the group consisting of $R^{10}$, $C_1$–$C_4$ alkoxy, $NR^{23}R^{24}$, and hydroxyl;

$R^{22}$ is independently selected at each occurrence from the group consisting of cyano, $OR^{24}$, $SR^{24}$, $NR^{23}R^{24}$, $C_1$–$C_6$ alkyl, $C_3$–$C_6$ cycloalkyl, —$S(O)_nR^{31}$, and —$C(=O)R^{25}$;

$R^{25}$, which can be optionally substituted with 0–3 $R^{17}$, is independently selected at each occurrence from the group consisting of phenyl, and pyridyl;

$R^{25a}$, which can be optionally substituted with 0–3 $R^{17}$, is independently selected at each occurrence from the group consisting of H and $R^{25}$;

$R^{27}$ is independently selected at each occurrence from the group consisting of $C_1$–$C_3$ alkyl, $C_2$–$C_4$ alkenyl, $C_{2-4}$ alkynl, $C_{2-4}$ alkoxy, aryl, nitro, cyano, halogen, and phenyloxy;

$R^{31}$ is independently selected at each occurrence from the group consisting of $C_1$–$C_4$ alkyl, $C_3$–$C_7$ cycloalkyl, $C_4$–$C_{10}$ cycloalkyl-alkyl, and aryl-($C_1$–$C_4$) alkyl;

k, m, and r are independently selected at each occurrence from 1–4;

n is independently selected at each occurrence from 0–2;

p, q, and z are independently selected at each occurrence from 0–3;

t and w are independently selected at each occurrence from 1–6; provided that when K and L are both CH, then (A) when $R^2$ is H and $R^1$ and $R^3$ are methyl,
  (1) and $R^4$ is methyl, then
    (a) $R^5$ can not be $C_1$–$C_6$ alkyl when X is OH and X' is H;
    (b) $R^5$ can not be $(CHR^{16})_p NR^{14}R^{15}$ wherein p is 0 when X and X' are —$OCH_3$; and
    (c) $R^5$ can not be $(CHR^{16})_p NR^{14}R^{15}$ when X and X' are —$OCH_2CH_3$; and
  (2) and $R^4$ is ethyl, then
    (a) $R^5$ can not be $(CHR^{16})_p NR^{14}R^{15}$ when X and X' are —$OCH_3$;
    (b) $R^5$ can not be $(CHR^{16})_p OR^{18}$ with p=0 and $R^{18}$=H when X is Br and X' is OH; and
    (c) $R^5$ can not be C1–C6 alkyl substituted with OH; or $(CHR^{16})_p NR^{14}R^{15}$ wherein $R^{16}$=H and p=1–3 and $R^{14}$ and $R^{15}$ are H or $C_1$–$C_6$ alkyl when X is —$SCH_3$ and X' is H;

(B) when $R^2$ is H, $R^4$ is ethyl, $R^5$ is iso-propyl, X is Br, X' is H, and
  (1) $R^1$ is $CH_3$; then
    (a) $R^3$ can not be $OR^8$, $CO_2R^{12}$, $C(=O)NR^6R^7$, $(CH_2)_k OR_8$; $(CHR^{16})_k NR^6R^7$;
  (2) $R^1$ is —$CH_2CH_2CH_3$ then $R^3$ can not be $C_1$–$C_6$ alkyl;

further provided that when X' is H, and K and L are both CH, then (D) when $R^2$ is H or $C_1$–$C_3$ alkyl; $R^4$ is $C_1$–$C_4$ alkyl; $R^5$, X and/or X' are OH, halo, $CF_3$, $C_1$–$C_4$ alkyl, $C_1$–$C_4$ alkoxy, $C_1$–$C_4$ alkylthio, cyano, amino, carbamoyl, or $C_1$–$C_4$ alkanoyl; and $R^1$ is $C_1$–$C_4$ alkyl, then $R^3$ can not be —NH(substituted phenyl) or —N ($C_1$–$C_4$ alkyl) (substituted phenyl) and further provided that when $R^3$ is $S(O)_n R^8$, $R^8$ is not hydrogen;

and when $R^3$ is —$C(CN)(R^{25})(R^{16})$, $R^{25}$ is not pyridyl and when $R^3$ is $S(O)_n R^8$, $R^8$ is not H;

wherein the term "heterocycle" is defined as pyridyl, pyridinyl, furanyl, thienyl, pyrrolyl, pyrazolyl, imidazolyl, tetrazolyl, benzofuranyl, benzothiophenyl, indolyl, indolenyl, quinolinyl, isoquinolinyl or benzimidazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl or octahydroisoquinolinyl, azocinyl, 6H-1,2,5-thiadiazinyl, 2H,6H-1,5,2-dithiazinyl, thiophenyl, thianthrenyl, furanyl, pyranyl, isobenzofuranyl, chromenyl, xanthenyl, phenoxathiinyl, 2H-pyrrolyl, pyrrole, imidazolyl, pyrazolyl, isothiazolyl, isoxazole, pyridinyl, pyrazinyl, pyrimidinyl, pyridazinyl, indolizinyl, isoindole, 3H-indolyl, indolyl, 1H-indazolyl, purinyl, 4H-quinolizinyl, isoquinolinyl, quinolinyl, phthalazinyl, naphthyridinyl, quinoxalinyl, quinazolinyl, cinnolinyl, pteridinyl, 4aH-carbazolyl, carbazolyl, β-carbolinyl, phenanthridinyl, acridinyl, perimidinyl, phenanthrolinyl, phenazinyl, phenothiazinyl, furazanyl, phenoxazinyl, isochromanyl, chromanyl, pyrrolidinyl, pyrrolinyl, imidazolidinyl, imidazolinyl, pyrazolidinyl, pyrazolinyl, piperidinyl, piperazinyl, indolinyl, isoindolinyl, quinuclidinyl, morpholinyl or oxazolidinyl;

wherein the term "aryl" is defined as phenyl, biphenyl or naphthyl; and wherein the term "heteroaryl" is defined as 2-, or 3-, or 4-pyridyl; 2- or 3-furyl; 2- or 3-benzofuranyl; 2-, or 3-, or 3-thiophenyl; 2- or 3-benzo[b]thiophenyl; 2-, or 3-, or 4-quinolinyl; 1-, or 3-, or 4-isoquinolinyl; 2- or 3-pyrrolyl; 1- or 2- or 3-indolyl; 2-, or 4-, or 5-oxazolyl; 2-benzoxazolyl; 2- or 4- or 5-imidazolyl; 1- or 2-benzimidazolyl; 2- or 4- or 5-thiazolyl; 2-benzothiazolyl; 3- or 4- or 5-isoxazolyl; 3- or 4- or 5-pyrazolyl; 3- or 4- or 5-isothiazolyl; 3- or 4-pyridazinyl; 2- or 4- or 5-pyrimidinyl; 2-pyrazinyl; 2-triazinyl; 3- or 4- cinnolinyl; 1-phthalazinyl; 2- or 4-quinazolinyl; or 2-quinoxalinyl ring.

2. A compound of claim 1 wherein:

$R^1$ is $C_1$–$C_4$ alkyl;

$R^3$ is $C_1$–$C_4$ alkyl, $C_3$–$C_6$ cycloalkyl, $C_1$–$C_2$ haloalkyl, $NR^6R^7$, $OR^8$, $C(=O)R^9$, $C(=O)NR^6R^7$, —$(CHR^{16})_k NR^6R^7$, $(CH_2)_k OR^8$, —$(CHR^{16})R^{25}$, substituted $C_1$–$C_4$ alkyl, substituted $C_1$–$C_4$ alkenyl, substituted $C_2$–$C_4$ alkynyl, substituted $C_1$–$C_4$ alkoxy, substituted $C_3$–$C_6$ cycloalkyl or substituted $C_1$–$C_4$ alkylamino, where substitution by one or two $R^{27}$ can occur on any carbon-containing substituent;

$R^4$ is $C_1$–$C_4$ alkyl, allyl, or propargyl;

X is halogen, $S(O)_2 R^8$, $SR^8$, halomethyl, —$(CH_2)_p OR^8$, cyano, —$(CHR^{16})_p NR^{14}R^{15}$, —$C(=O)R^8$, $C_1$–$C_6$ alkyl, $C_4$–$C_{10}$ cycloalkylalkyl, $C_2$–$C_{10}$ alkenyl, $C_2$–$C_{10}$ alkynyl, $C_1$–$C_{10}$ alkoxy, aryl-($C_2$–$C_{10}$)-alkyl, $C_3$–$C_6$ cycloalkyl, aryl-($C_1$–$C_{10}$)-alkoxy, nitro, thio-($C_1$–$C_{10}$)-alkyl, —$C(=NOR^{16})$—$C_1$–$C_4$-alkyl, —$C(=NOR^{16})$H, or —$C(=O)NR^{14}R^{15}$;

X' is independently selected at each occurrence from the group consisting of hydrogen, halogen except when M is N, $S(O)_n R^8$, halomethyl, —$(CHR^{16})_p OR^8$, cyano, —$(CHR^{16})_p NR^{14}R^{15}$, $C(=O)R^8$, $C_1$–$C_6$ alkyl, $C_2$–$C_{10}$ alkenyl, $C_2$–$C_{10}$ alkynyl, $C_1$–$C_{10}$ alkoxy, aryl-($C_1$–$C_{10}$)-alkyl, $C_3$–$C_6$ cycloalkyl, aryl-($C_1$–$C_{10}$)-alkoxy, nitro, thio-($C_1$–$C_{10}$)-alkyl, —$C(=NOR^{16})$—$C_1$–$C_4$-alkyl, —$C(=NOR^{16})$H, or —$C(=O)NR^{14}R^{15}$;

$R^5$ is halo, —$C(=NOR^{16})$—$C_1$–$C_4$-alkyl, $C_1$–$C_6$ alkyl, $C_1$–$C_3$ haloalkyl, $C_1$–$C_6$ alkoxy, —$(CHR^{16})_p OR^8$, $(CHR^{16})_p S(O)_n R^8$, —$(CHR^{16})_p NR^{14}R^{15}$, $C_3$–$C_6$ cycloalkyl, $C_2$–$C_{10}$ alkenyl, $C_2$–$C_{10}$ alkynyl, cyano, $C_3$–$C_6$ cycloalkoxy, nitro, amino-($C_2$–$C_{10}$)-alkyl, thio-($C_2$–$C_{10}$)-alkyl, $SO_n(R^8)$, $C(=O)R^8$, —$C(=NOR^{16})$H, or $C(=O)NR^{14}R^{15}$;

$R^6$ and $R^7$ are independently selected at each occurrence from the group consisting of hydrogen, $C_1$–$C_6$ alkyl, $C_3$–$C_{10}$ cycloalkyl, $C_1$–$C_6$ alkoxy, ($C_4$–$C_{12}$)-cycloalkylalkyl, —$(CH_2)_k R^{13}$, $(CHR^{16})_p OR^8$, phenyl, or —$S(O)_z$-aryl; or can be taken together to form —$(CH_2)_q A(CH_2)_r$—, optionally substituted with 0–3 $R^{17}$;

$R^8$ is independently selected at each occurrence from the group consisting of hydrogen; $C_1$–$C_6$ alkyl; —($C_4$–$C_{12}$) cycloalkylalkyl; $(CH_2)_rR^{22}$; $C_3$–$C_{10}$ cycloalkyl; or —$NR^6R^7$; and $R^9$ is independently selected at each occurrence from $R^{10}$, $C_1$–$C_4$ alkoxy, $C_3$–$C_6$ cycloalkyl, or $C_2$–$C_4$ alkenyl.

3. A compound of claim 1 selected from the group consisting of:

N-(2,4-dimethoxyphenyl)-N-4,6-dimethyl-2-pyrimidinamine;
N-(2-bromophenyl)-N-allyl-4,6-dimethyl-2-pyrimidinamine;
N-(2-bromo-4-(1-methylethyl)phenyl)-N-methyl-4,6-dimethyl-2-pyrimidinamine;
N-(2-bromophenyl)-N-ethyl-4,6-dimethyl-2-pyrimidinamine;
N-(2,4-dimethoxyphenyl)-N-ethyl-4,6-dimethyl-2-pyrimidinamine;
N-(2,4-dibromophenyl)-N-methyl-4,6-dimethyl-2-pyrimidinamine;
N-(2-bromo-4-ethylphenyl)-N-methyl-4,6-dimethyl-2-pyrimidinamine;
N-(2-bromo-4-tert-butylphenyl)-N-ethyl-4,6-dimethyl-2-pyrimidinamine;
N-(2-bromo-4-tert-butylphenyl)-N-methyl-4,6-dimethyl-2-pyrimidinamine;
N-(2-bromo-4-trifluoromethylphenyl)-N-methyl-4,6-dimethyl-2-pyrimidinamine;
N-(2-bromo-4-trifluoromethylphenyl)-N-ethyl-4,6-dimethyl-2-pyrimidinamine;
N-(2,4,6-trimethoxyphenyl)-N-methyl-4,6-dimethyl-2-pyrimidinamine;
N-(2,4,6-trimethoxyphenyl)-N-ethyl-4,6-dimethyl-2-pyrimidinamine;
N-(2-bromo-4-n-butylphenyl)-N-allyl-4,6-dimethyl-2-pyrimidinamine;
N-(2-bromo-4-n-butylphenyl)-N-ethyl-4,6-dimethyl-2-pyrimidinamine;
N-(2-bromo-4-n-butylphenyl)-N-propyl-4,6-dimethyl-2-pyrimidinamine;
N-(2-bromo-4-(1-methylethyl)phenyl)-N-ethyl-4,6-dimethyl-2-pyrimidinamine;
N-(2-bromo-4-cyclohexylethyl)-N-ethyl-4,6-dimethyl-2-pyrimidinamine;
N-(2-bromo-4-(1-methylethyl)phenyl)-N-ethyl-4,6-diethyl-2-pyrimidinamine;
N-(2-bromo-4-n-butylphenyl)-N-ethyl-4,6-diethyl-2-pyrimidinamine;
N-(2-bromo-4-(1-methylethyl)phenyl)-N-ethyl-4-(4-formyl-piperazino)-6-methyl-2-pyrimidinamine;
N-(2-bromo-4-(1-methylethyl)phenyl)-N-allyl-4,6-dimethyl-2-pyrimidinamine;
N-(2-iodo-4-(1-methylethyl)phenyl)-N-ethyl-4,6-dimethyl-2-pyrimidinamine;
N-(2-bromo-4-(1-methylethyl)phenyl)-N-ethyl-4-methyl-6-trifluoromethyl-2-pyrimidinamine;
N-(2-bromo-4-methoxyethyl)-N-ethyl-4,6-dimethyl-2-pyrimidinamine;
N-(2-bromo-4-(1-methylethyl)phenyl)-N-ethyl-4-methyl-6-(2-thiopheno)-2-pyrimidinamine;
N-(2-bromo-4-(1-methylethyl)phenyl)-N-cyanomethyl-4,6-dimethyl-2-pyrimidinamine;
N-(2-bromo-4-(1-methylethyl)phenyl)-N-cyclopropylmethyl-4,6-dimethyl-2-pyrimidinamine;
N-(2-bromo-4-(1-methylethyl)phenyl)-N-propargyl-4,6-dimethyl-2-pyrimidinamine;
N-(2-iodo-4-methoxyethylphenyl)-N-ethyl-4,6-dimethyl-2-pyrimidinamine;
N-(2-iodo-4-methoxymethylphenyl)-N-ethyl-4,6-dimethyl-2-pyrimidinamine;
N-(2-methylthio-4-methoxymethylphenyl)-N-ethyl-4,6-dimethyl-2-pyrimidinamine;
N-(2-dimethylamino-4-methoxymethylphenyl)-N-ethyl-4,6-dimethyl-2-pyrimidinamine;
N-(2-methylthio-4-methoxymethylphenyl)-N-ethyl-4,6-dimethyl-2-pyrimidinamine;
N-(2-methylthio-4-(1-methylethyl)phenyl)-N-ethyl-4,6-dimethyl-2-pyrimidinamine;
N-(2-dimethylamino-4-(1-methylethyl)phenyl)-N-ethyl-4,6-dimethyl-2-pyrimidinamine;
N-(2,4-dimethylthiophenyl)-N-ethyl-4,6-dimethyl-2-pyrimidinamine;
N-(2-methylthio-4-methylthiomethylphenyl)-N-ethyl-4,6-dimethyl-2-pyrimidinamine;
N-(2,6-dibromo-4-(1-methylethyl)phenyl)-N-ethyl-4,6-dimethyl-2-pyrimidinamine;
N-(2,4-diiodophenyl)-N-ethyl-4,6-dimethyl-2-pyrimidinamine;
N-(2-Bromo-4-(1-methylethyl)phenyl)-N-ethyl-4-methyl-2-pyrimidinamine;
N-(2-Bromo-4-(1-methylethyl)phenyl)-N-ethyl-4-methyl-6-(N-methyl-2-hydroxyethylamino)-2-pyrimidinamine;
N-(2,6-dimethoxy-4-methylphenyl)-N-ethyl-4,6-dimethyl-2-pyrimidinamine;
N-(2-bromo-4-(1-methylethyl)phenyl)-N-ethyl-2,4-dimethoxy-6-pyrimidinamine;
N-(2-bromo-4-(1-methylethyl)phenyl)-N-ethyl-6-methyl-4-(1-piperidinylcarbonyl)-2-pyrimidinamine;
methyl 2-((2-bromo-4-(1-methylethyl)phenyl)ethylamino)-6-methyl-4-pyrimidinecarboxylate;
2-((2-bromo-4-(1-methylethyl)phenyl)ethylamino)-N-cyclohexyl-6-methyl-4-pyrimidinecarboxamide;
N-(2-bromo-4-(1-methylethyl)phenyl)-N-ethyl-6-methyl-4-(4-methyl-1-piperazinylcarbonyl)-2-pyrimidinamine;
N-(2-bromo-4-(1-methylethyl)phenyl)-N-ethyl-4-methyl-6-(thiomethyl)-2-pyrimidinamine;
N-(2-bromo-4-(1-methylethyl)phenyl)-N-ethyl-4-methyl-6-(methylsulfinyl)-2-pyrimidinamine;
N-(2-bromo-4-(1-methylethyl)phenyl)-N-ethyl-4-methyl-6-(methylsulfonyl)-2-pyrimidinamine;
N-(2-methylthio-4-(1-methylethyl)phenyl)-N-ethyl-4(S)-(N-methyl-2'-pyrrolidinomethoxy)-6-methyl-2-pyrimidinamine;
N-(2-methylthio-4-(1-methylethyl)phenyl)-N-ethyl-4,6-dimethyl-2-pyrimidinamine;
N-(2-methylthio-4-(1-methylethyl)phenyl)-N-ethyl-4,6-dimethyl-2-pyrimidinamine;
N-(2-methylsulfinyl-4-(1-methylethyl)phenyl)-N-ethyl-4,6-dimethyl-2-pyrimidinamine;
N-(2-iodo-4-(1-methylethyl)phenyl)-N-ethyl-4-thiazolidino-6-methyl-2-pyrimidinamine;
N-(2-iodo-4-methoxymethylphenyl)-N-ethyl-4,6-dimethyl-2-pyrimidinamine;
N-(2-methylsulfonyl-4-(1-methylethyl)phenyl)-N-ethyl-4,6-dimethyl-2-pyrimidinamine;
N-(2-ethylthio-4-(1-methylethyl)phenyl)-N-ethyl-4,6-dimethyl-2-pyrimidinamine;
N-(2-ethylthio-4-methoxyiminoethylphenyl)-N-ethyl-4,6-dimethyl-2-pyrimidinamine;
N-(2-methylthio-4-methoxyiminoethylphenyl)-N-ethyl-4,6-dimethyl-2-pyrimidinamine;
N-(2-methylsulfonyl-4-methoxyiminoethylphenyl)-N-ethyl-4,6-dimethyl-2-pyrimidinamine;
N-(4-bromo-2-methylthiophenyl)-N-ethyl-4,6-dimethyl-2-pyrimidinamine;

N-(4-ethyl-2-methylthiophenyl)-N-(1-methylethyl)-4,6-dimethyl-2-pyrimidinamine;
N-(4-ethyl-2-methylthiophenyl)-N-ethyl-4,6-dimethyl-2-pyrimidinamine;
N-(2-methylthio-4-(N-acetyl-N-methylamino)phenyl)-N-ethyl-4,6-dimethyl-2-pyrimidinamine;
N-(4-carboethoxy-2-methylthiophenyl)-N-ethyl-4,6-dimethyl-2-pyrimidinamine;
N-(4-methoxy-2-methylthiophenyl)-N-ethyl-4,6-dimethyl-2-pyrimidinamine;
N-(4-cyano-2-methylthiophenyl)-N-ethyl-4,6-dimethyl-2-pyrimidinamine;
N-(4-acetyl-2-methylthiophenyl)-N-ethyl-4,6-dimethyl-2-pyrimidinamine;
N-(4-propionyl-2-methylthiophenyl)-N-ethyl-4,6-dimethyl-2-pyrimidinamine;
N-(4-(1-methoxyethyl)-2-methylthiophenyl)-N-ethyl-4,6-dimethyl-2-pyrimidinamine;
N-(4-(N-methylamino)-2-methylthiophenyl)-N-ethyl-4,6-dimethyl-2-pyrimidinamine;
N-(4-(N,N-dimethylamino)-2-methylthiophenyl)-N-ethyl-4,6-dimethyl-2-pyrimidinamine;
N-(2-Bromo-4-(1-methylethyl)phenyl)-N-ethyl-4-formyl-6-methyl-2-pyrimidinamine;
N-(2-Bromo-4-(1-methylethyl)phenyl)-N-ethyl-4-hydroxyethoxymethyl-6-methyl-2-pyrimidinamine;
N-(2-Bromo-6-hydroxy-4-methoxyphenyl)-N-ethyl-4,6-dimethyl-2-pyrimidinamine;
N-(3-Bromo-4,6-dimethoxyphenyl)-N-ethyl-4,6-dimethyl-2-pyrimidinamine;
N-(2,3-Dibromo-4,6-dimethoxyphenyl)-N-ethyl-4,6-dimethyl-2-pyrimidinamine;
N-(2,6-Dibromo-4-(ethoxy)phenyl)-N-ethyl-4,6-dimethyl-2-pyrimidinamine;
N-(2-bromo-4-(1-methylethyl)phenyl)-N-ethyl-4-(N-(2-furylmethyl)-N-methylamino)carbonyl-6-methylpyrimidinamine;
N-(2-bromo-4-(1-methylethyl)phenyl)-N-ethyl-4-((4,4-ethylenedioxypiperidino)carbonyl)-6-methylpyrimidinamine;
N-(2-bromo-4-(1-methylethyl)phenyl)-N-ethyl-4-(4-oxopiperidino)carbonyl-6-methylpyrimidinamine;
N-(2-bromo-4-(1-methylethyl)phenyl)-N-ethyl-4-(4-oxopiperidino)methyl-6-methylpyrimidinamine, hydrochloride salt;
N-(2-bromo-4-(1-methylethyl)phenyl)-N-ethyl-4-(imidazol-1-yl)methyl-6-methylpyrimidinamine;
N-(2-bromo-4-(1-methylethyl)phenyl)-N-ethyl-4-(3-(methoxyphenyl)methoxymethyl)-6-methylpyrimidinamine;
N-(2-bromo-4-(1-methylethyl)phenyl)-N-ethyl-4-(2-thiazolyl)carbonyl-6-methylpyrimidinamine;
N-(2-bromo-4-(1-methylethyl)phenyl)-N-ethyl-4-(2-imidazolyl)carbonyl-6-methylpyrimidinamine;
N-(2-bromo-4-(1-methylethyl)phenyl)-N-ethyl-4-(5-indolylcarbonyl)-6-methylpyrimidinamine;
N-(2-bromo-4-(1-methylethyl)phenyl)-N-ethyl-4-(4-fluorophenyl)carbonyl-6-methylpyrimidinamine;
N-(2-bromo-4-(1-methylethyl)phenyl)-N-ethyl-4-carboxy-6-methylpyrimidinamine;
N-(2-bromo-4-(1-methylethyl)phenyl)-N-ethyl-4-acetyl-6-methylpyrimidinamine;
N-(2-bromo-4-(1-methylethyl)phenyl)-N-ethyl-4-(hydroxy-3-pyridyl-methyl)-6-methylpyrimidinamine;
N-(2-bromo-4-(1-methylethyl)phenyl)-N-ethyl-4-(4-(methoxyphenyl)-3-pyridyl-hydroxymethyl)-6-methylpyrimidinamine;
N-(2-bromo-4-(1-methylethyl)phenyl)-N-ethyl-4-(3-pyrazolyl)-6-methylpyrimidinamine, hydrochloride salt;
N-(2-bromo-4-(1-methylethyl)phenyl)-N-ethyl-4-(1-aminoethyl)-6-methylpyrimidinamine;
N-(2-bromo-4-(1-methylethyl)phenyl)-N-ethyl-4-(2-(4-tetrazolyl)-1-methylethyl)-6-methylpyrimidinamine;
2-(N-(2-bromo-4-(2-propyl)phenyl)amino)-4-carbomethoxy-6-methylpyrimidine; and
2-(N-(2-bromo-4-(2-propyl)phenyl)-N-ethylamino)-4-carbomethoxy-6-methylpyrimidine.

4. A compound of claim 1 selected from the group consisting of:
N-(2,4-dimethoxyphenyl)-N-4,6-dimethyl-2-pyrimidinamine;
N-(2-bromophenyl)-N-allyl-4,6-dimethyl-2-pyrimidinamine;
N-(2-bromo-4-(1-methylethyl)phenyl)-N-methyl-4,6-dimethyl-2-pyrimidinamine;
N-(2-bromophenyl)-N-ethyl-4,6-dimethyl-2-pyrimidinamine;
N-(2,4-dimethoxyphenyl)-N-ethyl-4,6-dimethyl-2-pyrimidinamine;
N-(2,4-dibromophenyl)-N-methyl-4,6-dimethyl-2-pyrimidinamine;
N-(2-bromo-4-ethylphenyl)-N-methyl-4,6-dimethyl-2-pyrimidinamine;
N-(2-bromo-4-tert-butylphenyl)-N-ethyl-4,6-dimethyl-2-pyrimidinamine;
N-(2-bromo-4-tert-butylphenyl)-N-methyl-4,6-dimethyl-2-pyrimidinamine;
N-(2-bromo-4-trifluoromethylphenyl)-N-methyl-4,6-dimethyl-2-pyrimidinamine;
N-(2-bromo-4-trifluoromethylphenyl)-N-ethyl-4,6-dimethyl-2-pyrimidinamine;
N-(2,4,6-trimethoxyphenyl)-N-methyl-4,6-dimethyl-2-pyrimidinamine;
N-(2,4,6-trimethoxyphenyl)-N-ethyl-4,6-dimethyl-2-pyrimidinamine;
N-(2-bromo-4-n-butylphenyl)-N-allyl-4,6-dimethyl-2-pyrimidinamine;
N-(2-bromo-4-n-butylphenyl)-N-ethyl-4,6-dimethyl-2-pyrimidinamine;
N-(2-bromo-4-n-butylphenyl)-N-propyl-4,6-dimethyl-2-pyrimidinamine;
N-(2-bromo-4-(1-methylethyl)phenyl)-N-ethyl-4,6-dimethyl-2-pyrimidinamine;
N-(2-bromo-4-cyclohexylphenyl)-N-ethyl-4,6-dimethyl-2-pyrimidinamine;
N-(2-bromo-4-(1-methylethyl)phenyl)-N-allyl-4,6-dimethyl-2-pyrimidinamine;
N-(2-iodo-4-(1-methylethyl)phenyl)-N-ethyl-4,6-dimethyl-2-pyrimidinamine;
N-(2-bromo-4-methoxyethyl)-N-ethyl-4,6-dimethyl-2-pyrimidinamine;
N-(2-bromo-4-(1-methylethyl)phenyl)-N-cyanomethyl-4,6-dimethyl-2-pyrimidinamine;
N-(2-bromo-4-(1-methylethyl)phenyl)-N-cyclopropylmethyl-4,6-dimethyl-2-pyrimidinamine;
N-(2-bromo-4-(1-methylethyl)phenyl)-N-propargyl-4,6-dimethyl-2-pyrimidinamine;
N-(2-iodo-4-methoxyethylphenyl)-N-ethyl-4,6-dimethyl-2-pyrimidinamine;
N-(2-iodo-4-methoxymethylphenyl)-N-ethyl-4,6-dimethyl-2-pyrimidinamine;
N-(2-methylthio-4-methoxymethylphenyl)-N-ethyl-4,6-dimethyl-2-pyrimidinamine;
N-(2-dimethylamino-4-methoxymethylphenyl)-N-ethyl-4,6-dimethyl-2-pyrimidinamine;

N-(2-methylthio-4-methoxymethylphenyl)-N-ethyl-4,6-dimethyl-2-pyrimidinamine;
N-(2-methylthio-4-(1-methylethyl)phenyl)-N-ethyl-4,6-dimethyl-2-pyrimidinamine;
N-(2-dimethylamino-4-(1-methylethyl)phenyl)-N-ethyl-4,6-dimethyl-2-pyrimidinamine;
N-(2,4-dimethylthiophenyl)-N-ethyl-4,6-dimethyl-2-pyrimidinamine;
N-(2-methylthio-4-methylthiomethylphenyl)-N-ethyl-4,6-dimethyl-2-pyrimidinamine;
N-(2,6-dibromo-4-(1-methylethyl)phenyl)-N-ethyl-4,6-dimethyl-2-pyrimidinamine;
N-(2,4-diiodophenyl)-N-ethyl-4,6-dimethyl-2-pyrimidinamine;
N-(2,6-dimethoxy-4-methylphenyl)-N-ethyl-4,6-dimethyl-2-pyrimidinamine;
N-(2-methylthio-4-(1-methylethyl)phenyl)-N-ethyl-4,6-dimethyl-2-pyrimidinamine;
N-(2-methylthio-4-(1-methylethyl)phenyl)-N-ethyl-4,6-dimethyl-2-pyrimidinamine;
N-(2-methylsulfinyl-4-(1-methylethyl)phenyl)-N-ethyl-4,6-dimethyl-2-pyrimidinamine;
N-(2-iodo-4-methoxymethylphenyl)-N-ethyl-4,6-dimethyl-2-pyrimidinamine;
N-(2-methylsulfonyl-4-(1-methylethyl)phenyl)-N-ethyl-4,6-dimethyl-2-pyrimidinamine;
N-(2-ethylthio-4-(1-methylethyl)phenyl)-N-ethyl-4,6-dimethyl-2-pyrimidinamine;
N-(2-ethylthio-4-methoxyiminoethylphenyl)-N-ethyl-4,6-dimethyl-2-pyrimidinamine;
N-(2-methylthio-4-methoxyiminoethylphenyl)-N-ethyl-4,6-dimethyl-2-pyrimidinamine;
N-(2-methylsulfonyl-4-methoxyiminoethylphenyl)-N-ethyl-4,6-dimethyl-2-pyrimidinamine;
N-(4-bromo-2-methylthiophenyl)-N-ethyl-4,6-dimethyl-2-pyrimidinamine;
N-(4-ethyl-2-methylthiophenyl)-N-(1-methylethyl)-4,6-dimethyl-2-pyrimidinamine;
N-(4-ethyl-2-methylthiophenyl)-N-ethyl-4,6-dimethyl-2-pyrimidinamine;
N-(2-methylthio-4-(N-acetyl-N-methylamino)phenyl)-N-ethyl-4,6-dimethyl-2-pyrimidinamine;
N-(4-carboethoxy-2-methylthiophenyl)-N-ethyl-4,6-dimethyl-2-pyrimidinamine;
N-(4-methoxy-2-methylthiophenyl)-N-ethyl-4,6-dimethyl-2-pyrimidinamine;
N-(4-cyano-2-methylthiophenyl)-N-ethyl-4,6-dimethyl-2-pyrimidinamine;
N-(4-acetyl-2-methylthiophenyl)-N-ethyl-4,6-dimethyl-2-pyrimidinamine;
N-(4-propionyl-2-methylthiophenyl)-N-ethyl-4,6-dimethyl-2-pyrimidinamine;
N-(4-(1-methoxyethyl)-2-methylthiophenyl)-N-ethyl-4,6-dimethyl-2-pyrimidinamine;
N-(4-(N-methylamino)-2-methylthiophenyl)-N-ethyl-4,6-dimethyl-2-pyrimidinamine;
N-(4-(N,N-dimethylamino)-2-methylthiophenyl)-N-ethyl-4,6-dimethyl-2-pyrimidinamine;
N-(2-Bromo-6-hydroxy-4-methoxyphenyl)-N-ethyl-4,6-dimethyl-2-pyrimidinamine;
N-(3-Bromo-4,6-dimethoxyphenyl)-N-ethyl-4,6-dimethyl-2-pyrimidinamine;
N-(2,3-Dibromo-4,6-dimethoxyphenyl)-N-ethyl-4,6-dimethyl-2-pyrimidinamine; and
N-(2,6-Dibromo-4-(ethoxy)phenyl)-N-ethyl-4,6-dimethyl-2-pyrimidinamine.

5. A compound of claim 1 selected from the group consisting of:

N-(2-bromo-4-(1-methylethyl)phenyl)-N-ethyl-4,6-diethyl-2-pyrimidinamine;
N-(2-bromo-4-(1-methylethyl)phenyl)-N-ethyl-4-(4-formyl-piperazino)-6-methyl-2-pyrimidinamine;
N-(2-bromo-4-(1-methylethyl)phenyl)-N-ethyl-4-methyl-6-trifluoromethyl-2-pyrimidinamine;
N-(2-bromo-4-(1-methylethyl)phenyl)-N-ethyl-4-methyl-6-(2-thiopheno)-2-pyrimidinamine;
N-(2-Bromo-4-(1-methylethyl)phenyl)-N-ethyl-4-methyl-2-pyrimidinamine;
N-(2-Bromo-4-(1-methylethyl)phenyl)-N-ethyl-4-methyl-6-(N-methyl-2-hydroxyethylamino)-2-pyrimidinamine;
N-(2-bromo-4-(1-methylethyl)phenyl)-N-ethyl-2,4-dimethoxy-6-pyrimidinamine;
N-(2-bromo-4-(1-methylethyl)phenyl)-N-ethyl-6-methyl-4-(1-piperidinylcarbonyl)-2-pyrimidinamine;
methyl 2-((2-bromo-4-(1-methylethyl)phenyl)ethylamino)-6-methyl-4-pyrimidinecarboxylate;
2-((2-bromo-4-(1-methylethyl)phenyl)ethylamino)-N-cyclohexyl-6-methyl-4-pyrimidinecarboxamide;
N-(2-bromo-4-(1-methylethyl)phenyl)-N-ethyl-6-methyl-4-(4-methyl-1-piperazinylcarbonyl)-2-pyrimidinamine;
N-(2-bromo-4-(1-methylethyl)phenyl)-N-ethyl-4-methyl-6-(thiomethyl)-2-pyrimidinamine;
N-(2-bromo-4-(1-methylethyl)phenyl)-N-ethyl-4-methyl-6-(methylsulfinyl)-2-pyrimidinamine;
N-(2-bromo-4-(1-methylethyl)phenyl)-N-ethyl-4-methyl-6-(methylsulfonyl)-2-pyrimidinamine;
N-(2-Bromo-4-(1-methylethyl)phenyl)-N-ethyl-4-formyl-6-methyl-2-pyrimidinamine;
N-(2-Bromo-4-(1-methylethyl)phenyl)-N-ethyl-4-hydroxyethoxymethyl-6-methyl-2-pyrimidinamine;
N-(2-bromo-4-(1-methylethyl)phenyl)-N-ethyl-4-(N-(2-furylmethyl)-N-methylamino)carbonyl-6-methylpyrimidinamine;
N-(2-bromo-4-(1-methylethyl)phenyl)-N-ethyl-4-((4,4-ethylenedioxypiperidino)carbonyl)-6-methylpyrimidinamine;
N-(2-bromo-4-(1-methylethyl)phenyl)-N-ethyl-4-(4-oxopiperidino)carbonyl-6-methylpyrimidinamine;
N-(2-bromo-4-(1-methylethyl)phenyl)-N-ethyl-4-(4-oxopiperidino)methyl-6-methylpyrimidinamine, hydrochloride salt;
N-(2-bromo-4-(1-methylethyl)phenyl)-N-ethyl-4-(imidazol-1-yl)methyl-6-methylpyrimidinamine;
N-($_2$-bromo-4-(1-methylethyl)phenyl)-N-ethyl-4-(3-(methoxyphenyl)methoxymethyl)-6-methylpyrimidinamine;
N-(2-bromo-4-(1-methylethyl)phenyl)-N-ethyl-4-(2-thiazolyl)carbonyl-6-methylpyrimidinamine;
N-(2-bromo-4-(1-methylethyl)phenyl)-N-ethyl-4-(2-imidazolyl)carbonyl-6-methylpyrimidinamine;
N-($_2$-bromo-4-(1-methylethyl)phenyl)-N-ethyl-4-(5-indolylcarbonyl)-6-methylpyrimidinamine;
N-(2-bromo-4-(1-methylethyl)phenyl)-N-ethyl-4-(4-fluorophenyl)carbonyl-6-methylpyrimidinamine;
N-(2-bromo-4-(1-methylethyl)phenyl)-N-ethyl-4-carboxy-6-methylpyrimidinamine;
N-(2-bromo-4-(1-methylethyl)phenyl)-N-ethyl-4-acetyl-6-methylpyrimidinamine;
N-(2-bromo-4-(1-methylethyl)phenyl)-N-ethyl-4-(hydroxy-3-pyridyl-methyl)-6-methylpyrimidinamine;
N-(2-bromo-4-(1-methylethyl)phenyl)-N-ethyl-4-(4-(methoxyphenyl)-3-pyridyl-hydroxymethyl)-6-methylpyrimidinamine;
N-(2-bromo-4-(1-methylethyl)phenyl)-N-ethyl-4-(3-pyrazolyl)-6-methylpyrimidinamine, hydrochloride salt;

N-(2-bromo-4-(1-methylethyl)phenyl)-N-ethyl-4-(1-aminoethyl)-6-methylpyrimidinamine;

N-(2-bromo-4-(1-methylethyl)phenyl)-N-ethyl-4-(2-(4-tetrazolyl)-1-methylethyl)-6-methylpyrimidinamine;

2-(N-(2-bromo-4-(2-propyl)phenyl)amino)-4-carbomethoxy-6-methylpyrimidine; and 2-(N-(2-bromo-4-(2-propyl)phenyl)-N-ethylamino)-4-carbomethoxy-6-methylpyrimidine.

6. A pharmaceutical composition comprising a pharmaceutically acceptable carrier and a therapeutically effective amount of a compound of claim 1.

7. A method of treating affective disorders, anxiety, or depression in mammals in need of such treatment comprising administering to the mammals a therapeutically effective amount of a compound of claim 1.

\* \* \* \* \*